(12) United States Patent
Hoveyda et al.

(10) Patent No.: US 10,544,150 B2
(45) Date of Patent: *Jan. 28, 2020

(54) NK-3 RECEPTOR SELECTIVE ANTAGONIST COMPOUNDS, PHARMACEUTICAL COMPOSITION AND METHODS FOR USE IN NK-3 RECEPTORS MEDIATED DISORDERS

(71) Applicant: Ogeda SA, Gosselies (BE)

(72) Inventors: Hamid R. Hoveyda, Brussels (BE); Marie-Odile Roy, Paris (FR); Graeme Lovat Fraser, Bousval (BE); Guillaume Dutheuil, Vedrin (BE)

(73) Assignee: Ogeda SA, Gosselies (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/906,268

(22) Filed: Feb. 27, 2018

(65) Prior Publication Data

US 2018/0194772 A1    Jul. 12, 2018

Related U.S. Application Data

(60) Division of application No. 14/473,147, filed on Aug. 29, 2014, now Pat. No. 9,926,325, which is a division of application No. 13/627,091, filed on Sep. 26, 2012, now Pat. No. 8,871,761, which is a continuation of application No. PCT/EP2011/055218, filed on Apr. 4, 2011.

(60) Provisional application No. 61/379,028, filed on Sep. 1, 2010.

(30) Foreign Application Priority Data

Apr. 2, 2010 (EP) ................................. 10305343

(51) Int. Cl.
  *A61K 31/4985* (2006.01)
  *A61K 31/407* (2006.01)
  *C07D 487/04* (2006.01)

(52) U.S. Cl.
  CPC .......... *C07D 487/04* (2013.01); *A61K 31/407* (2013.01); *A61K 31/4985* (2013.01)

(58) Field of Classification Search
  CPC ......................... A61K 31/407; A61K 31/4985
  See application file for complete search history.

(56) References Cited

U.S. PATENT DOCUMENTS

| | | | |
|---|---|---|---|
| 6,414,149 | B1 | 7/2002 | Chu-Moyer et al. |
| 2007/0219181 | A1 | 9/2007 | Kimura et al. |
| 2008/0275052 | A1 | 11/2008 | Dhar et al. |
| 2008/0318935 | A1 | 12/2008 | Beckett et al. |
| 2011/0046096 | A1 | 2/2011 | Pouzet et al. |
| 2012/0142672 | A1 | 6/2012 | Koike et al. |
| 2013/0023530 | A1 | 1/2013 | Hoveyda et al. |
| 2014/0275097 | A1 | 9/2014 | Hoveyda et al. |
| 2015/0232471 | A1 | 8/2015 | Hoveyda et al. |
| 2015/0315199 | A1 | 11/2015 | Hoveyda et al. |

FOREIGN PATENT DOCUMENTS

| | | |
|---|---|---|
| EP | 2085398 A1 | 8/2009 |
| JP | H06128261 A | 5/1994 |
| WO | 200043008 A1 | 7/2000 |
| WO | 03/082817 A2 | 10/2003 |
| WO | 2004/014914 A1 | 2/2004 |
| WO | 2004/021984 A2 | 3/2004 |
| WO | 2004/080958 A2 | 9/2004 |
| WO | 2005/032464 A2 | 4/2005 |
| WO | 2005/080397 A2 | 9/2005 |
| WO | 2006120478 A2 | 11/2006 |
| WO | 2007138351 A2 | 12/2007 |
| WO | 2009/072643 A1 | 6/2009 |
| WO | 2009/089462 A1 | 7/2009 |
| WO | 2009/090055 A1 | 7/2009 |
| WO | 2009/095253 A1 | 8/2009 |
| WO | 2009/095254 A1 | 8/2009 |
| WO | 2010125101 A1 | 11/2010 |
| WO | 2010125102 A1 | 11/2010 |
| WO | 2011/121137 A1 | 10/2011 |
| WO | 2013/050424 A1 | 4/2013 |
| WO | 2014154896 A1 | 10/2014 |
| WO | 2014154897 A1 | 10/2014 |

OTHER PUBLICATIONS

Chemical Abstract—Registry No. 1065517-25-0, Document No. XP002597353, entered on Oct. 24, 2008.
Chemical Abstract—Registry No. 1185694-78-3, Document No. XP002597356, entered on Sep. 18, 2009.
Chemical Abstract—Registry No. 1060453-21-5, Document No. XP002597351, entered on Oct. 13, 2008.

(Continued)

*Primary Examiner* — Karen Cheng
(74) *Attorney, Agent, or Firm* — Locke Lord LLP; Nicholas J. DiCeglie, Jr.

(57) ABSTRACT

The present invention is directed to novel compounds of formula I

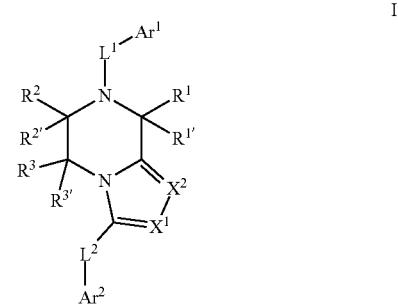

and their use as therapeutic compounds.

12 Claims, 3 Drawing Sheets

(56) References Cited

OTHER PUBLICATIONS

Chemical Abstract—Registry No. 1060482-62-3, Document No. XP002597354, entered on Oct. 13, 2008.
Chemical Abstract—Registry No. 1066941-41-0, Document No. XP002597357, entered on Oct. 27, 2008.
Chemical Abstract—Registry No. 1185553-59-6, Document No. XP002597352, entered on Sep. 18, 2009.
Chemical Abstract—Registry No. 1065547-14-9, Document No. XP-002597355, entered on Oct. 24, 2008.
M. J. Bottomley et al., "Structural and Functional Analysis of the Human HDAC4 Catalytic Domain Reveals a Regulatory Structural Zinc-binding Domain." The Journal of Biological Chemistry, vol. 283, No. 39, pp. 26694-26704 (2008).
T. G. Murali Dhar et al., "Synthesis and SAR of p38a MAP kinase inhibitors based on heterobicyclic scaffolds." Bioorganic & Medicinal Chemistry Letters 17, 5019-5024, (2007).
L. A. Dawson et al., "Therapeutic Utility of NK3 Recepto Antagonists for the Treatment of Schizophrenia." Current Pharmaceutical Design 16, 344-357, (2010).
G. A. M. Giardina et al., "Recent advances in neurokinin-3 recepto antagonists." Exp. Opin. Ther. Patents 10(6), 939-960, (2000).
R. L. Goodman et al., "Evidence That Dynorphin Plays a Major Role in Mediating Progesterone Negative Feedback on Gonadotropin-Releasing Hormone Neurons in Sheep." Endocrinology 145(6), 2959-2967, (2004).
S. J. Krajewski et al., "Morphologic Evidence That Neurokinin B Modulates Gonadotropin-Releasing Hormone Secretion via Neurokinin 3 Receptors in the Rat Median Eminence." The Journal of Comparitive Neurology 498, 372-386, (2005).
H. Y. Meltzer et al., "Placebo-Controlled Evaluation of Four Novel Compounds for the Treatment of Schizophrenia and Schizoaffective Disorder." Am. J. Psychiatry 161, 975-984, (2004).
V. M. Navarro et al., "Regulation of Gonadotropin-Releasing Hormone Secretion by Kisspeptin/Dynorphin/Neurokinin B Neurons in the Arcuate Nucleus of the Mouse." The Journal of Neuroscience 23(38), 11859-11866, (2009).
M. C. Burke et al. "Coexpression of Dynorphin and Neurokinin B Immunoreactivity in the Rat Hypothalamus: Morphologic Evidence of Interrelated Function Within the Arcuate Nucleus." The Journal of Comparative Neurology 498, 712-726, (2006).
Jeffrey A.S., "Neurokinin antagonists and their potential role in treating depression and other stress disorders", Expert Opinion on Therapeutics Patents, Informa Healthcare, vol. 14, N° 10., 2004, pp. 1421-1433.
Granik, V. et al. "Properties of lactim aster of 3-carbomethoxy-4-acetyl-2-piperazinone and the synthesis of 3-oxo-5-acetyl-1,2,3,4,5,6,7,8-octahydropyrazino[2,3-c]pyridazine", Kimiko-Farmatsevticheskii Zhumal, vol. 2, N° 2., 1968, pp. 16-18. [XP002663277].
McCort, G.A. et al., "A rapid and efficient synthesis of imidazo [1,2-a] and [1,2,4]triazolo[4,3-a]piperazine carboxylic acids", Tetrahedron Letters, vol. 33, N° 31., Feb. 1992, pp. 4443-4446.
Fioramonti, J. et al., "Intestinal anti-nociceptive behaviour of NK3 receptor antagonism in conscious rats: evidence to support a peripheral mechanism of action", Neurogastroenterol Motil, vol. 15, Mar. 2003, pp. 363-369.
Shafton, A.D. et al., "Effects of the peripherally acting NK3 receptor antagonist, SB-235375, on intestinal and somatic nociceptive responses and on intestinal motility in anaesthetized rats", Neurogastroenterol Motil, vol. 16, Oct. 2003, pp. 223-231.
Nelson, P.J. et al., "1,2,4-Triazoles. V1.I The Synthesis of Some s-Triazolo[4,3-a]pyrazines", J. Org. Chem., vol. 27, Mar. 1962, pp. 3243-3248.
Hansen, K. B. et al. "First Generation Process for the Preparation of the DPP-IV Inhibitor Sitagliptin", Org. Process Res. Dev., vol. 9, N° 5., Aug. 2005, pp. 634-639.
Kowalchick, J. E. et al., "Design, synthesis, and biological evaluation of triazolopiperazine-based b-amino amides as potent, orally active dipeptidyl peptidase IV (DPP-4) inhibitors", Bioorg. Med. Chem. Lett., vol. 17, Jul. 2007, pp. 5934-5939.
Balsells, J. et al., "Synthesis of [1,2,4]Triazolo[4,3-alpha]piperazines via Highly Reactive Chloromethyloxadiazoles", Org. Lett., vol. 7, N° 6., Feb. 2005, pp. 1039-1042.
Houghton, L.A. et al., "Effect of the NK3 receptor antagonist, talnetant, on rectal sensory function and compliance in healthy humans", Neurogastroenterol Motil, vol. 19, Feb. 2007, pp. 732-743.
Scolnick, M.D. et al., "Comparative Study of Experimentally Induced Benign and Atypical Hyperplasia in the Ventral Prostate of Differents Rat Strains", J. Andrology, vol. 15, N° 4., Jul./Aug. 1994, pp. 287-297.
Rick, F.G. et al., "Combining Growth Hormone-Releasing Hormone AntagonistWith Luteinizing Hormone-Releasing Hormone Antagonist Greatly Augments Benign Prostatic Hyperplasia Shrinkage", J. Urol., vol. 187, Apr. 2012, pp. 1498-1504.
Lomax, A.E. et al., "Neurochemical classification of enteric neurons in the guinea-pig distal colon", Cell Tissue Res, vol. 302, Aug. 2000, pp. 59-72.
Copel, C. et al.,"Activation of neurokinin 3 receptor increases Nav 1.9 current in enteric neurons", J. Physiol., vol. 587, Feb. 2009, pp. 1461-1479.
International Search Report of PCT/EP2012/069546.
International Search Report of PCT/EP2011/055218 (published as WO2013/050424).
S. Daoui et al. "Involvement of Tachykinin NK3 Receptors in Citric Acis-induced Cough and Brronchial Responses in Guinea Pigs," AM J Respir Crit Care Med (1998); 152:42-48.
G. Sanger, "Neurokinin NK1 and NK3 receptos as targets for drugs to treat gastrointestinal motility disorders and pain," British Journal of Pharmacology (2004) 141, 1303-1312.
J. E. Phillips et al., "Tachykinin NK3 and NK1 receptor activation elicits secretion from porcine airway submucosal glands," British Journal of Pharmacology (2003) 138. 254-260.
K. Marshall, "Polycystic Ovary Syndrome Clinical Considerations," Alternative Medicine Review, vol. 6, No. 3, (2001).
K. L. Herbst, "Gonadotropin-releasing hormone antagonists," Current Opinion in Pharmacology (2003), 3:1-7.
W. P. Dmowski, "Advances in the Treatment of Endometriosis—The Potential of Elagolix (NBI-56418)," Obstetrics and Gynecology (2008), 21-23.

Statistics: One-Way ANOVA and Dunnett's post hoc
* $p<0.01$ et  $p<0.05$

NK-3 RECEPTOR SELECTIVE ANTAGONIST COMPOUNDS, PHARMACEUTICAL COMPOSITION AND METHODS FOR USE IN NK-3 RECEPTORS MEDIATED DISORDERS

This application is a Divisional Application of U.S. patent application Ser. No. 14/473,147 filed Aug. 29, 2014 which application is a Divisional Application of U.S. patent application Ser. No. 13/627,091, filed Sep. 26, 2012, which application is a Continuation of PCT international application Ser. No. PCT/EP2011/055218, filed Apr. 4, 2011, designating the United States, which claims the benefit of European Application No. 10305343.5, filed on Apr. 2, 2010, and also claims the benefit of U.S. Provisional Application 61/379,028, filed Sep. 1, 2010. The entire contents of the aforementioned patent applications are incorporated herein by this reference.

The present invention relates to novel compounds including their pharmaceutically acceptable salts and solvates, which are selective antagonists of neurokinin 3 receptor (NK-3) and are useful as therapeutic compounds, particularly in the treatment and/or prevention of a broad array of CNS and peripheral diseases or disorders.

BACKGROUND OF THE INVENTION

Tachykinin receptors are the targets of a family of structurally related peptides which include substance P (SP), neurokinin A (NKA) and neurokinin B (NKB), named collectively "tachykinins". Tachykinins are synthesized in the central nervous system (CNS) and peripheral tissues, where they exert a variety of biological activities. Three tachykinin receptors are known which are named neurokinin-1 (NK-1), neurokinin-2 (NK-2) and neurokinin-3 (NK-3) receptors. Tachykinin receptors belong to the rhodopsin-like seven membrane G-protein coupled receptors. SP has the highest affinity and is believed to be the endogenous ligand of NK-1, NKA for NK-2 receptor and NKB for NK-3 receptor, although some crossreactivity probably exists. The NK-1, NK-2 and NK-3 receptors have been identified in different species. NK-1 and NK-2 receptors are expressed in a wide variety of peripheral tissues and NK-1 receptors are also expressed in the CNS; whereas NK-3 receptors are primarily expressed in the CNS.

The neurokinin receptors mediate a variety of tachykinin-stimulated biological effects that include transmission of excitatory neuronal signals in the CNS and periphery (e.g. pain), modulation of smooth muscle contractile activity, modulation of immune and inflammatory responses, induction of hypotensive effects via dilatation of the peripheral vasculature and stimulation of endocrine and exocrine gland secretions.

In the CNS, the NK-3 receptor is expressed in regions including the medial prefrontal cortex, the hippocampus, the thalamus and the amygdala. Moreover, NK-3 receptors are expressed on dopaminergic neurons. Activation of NK-3 receptors has been shown to modulate dopamine, acetylcholine and serotonin release suggesting a therapeutic utility for NK-3 receptor modulators for the treatment of a variety of disorders including psychotic disorders, anxiety, depression, schizophrenia as well as obesity, pain or inflammation (Exp. Opinion Ther. Patents (2000), 10(6); 939-960 Current Opinion in Investigational Drugs, 2001, 2(7), 950-956 and Current Pharmaceutical Design, 2010, 16, 344-357).

Schizophrenia is classified into subgroups. The paranoid type is characterized by delusions and hallucinations and absence of thought disorder, disorganized behavior, and affective flattening. In the disorganized type, which is also named 'hebephrenic schizophrenia' in the International Classification of Diseases (ICD), thought disorder and flat affect are present together. In the catatonic type, prominent psychomotor disturbances are evident, and symptoms may include catatonic stupor and waxy flexibility. In the undifferentiated type, psychotic symptoms are present but the criteria for paranoid, disorganized, or catatonic types have not been met. The symptoms of schizophrenia normally manifest themselves in three broad categories, i.e. positive, negative and cognitive symptoms. Positive symptoms are those, which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as a lack of sustained attention and deficits in decision making. The current antipsychotic drugs (APDs) are fairly successful in treating the positive symptoms but fare less well for the negative and cognitive symptoms. Contrary to that, NK3 antagonists have been shown clinically to improve on both positive and negative symptoms in schizophrenics (Meltzer et al, Am. J. Psychiatry, 161, 975-984, 2004) and ameliorate cognitive behavior of schizophrenics (Curr. Opion. Invest. Drug, 6, 717-721, 2005).

In rat, morphological studies provide evidence for putative interactions between NKB neurons and the hypothalamic reproductive axis (Krajewski et al, J. Comp. Neurol., 489(3), 372-386, 2005). In arcuate nucleus neurons, NKB expression co-localizes with estrogen receptor α and dynorphin, implicated in progesterone feedback to Gonadotropin Releasing Hormone (GnRH) secretion (Burke et al., J. Comp. Neurol., 498(5), 712-726, 2006; Goodman et al., Endocrinology, 145, 2959-2967, 2004). Moreover, NK-3 receptor is highly expressed in the hypothalamic arcuate nucleus in neurons which are involved in the regulation of GnRH release.

WO 00/43008 discloses a method of suppressing gonadotropin and/or androgen production with specific NK-3 receptor antagonists. More particularly, the WO 00/43008 application relates to lowering luteinizing hormone (LH) blood level by administering an NK-3 receptor antagonist. Concurrently or alternatively with gonadotropin suppression, WO 00/43008 also relates to suppression of androgen production with NK-3 receptor antagonists. Recently it has been postulated that NKB acts autosynaptically on kisspeptin neurons in the arcuate nucleus to synchronize and shape the pulsatile secretion of kisspeptin and drive the release of GnRH from fibers in the median eminence (Navarro et al., J. of Neuroscience, 23, 2009—pp 11859-11866). All these observations suggest a therapeutic utility for NK-3 receptor modulators for sex hormone-dependent diseases.

Non-peptide ligands have been developed for each of the tachykinin receptors. Some of them have been described as dual modulators able to modulate both NK-2 and NK-3 receptors (WO 06/120478). However known non-peptide NK-3 receptor antagonists suffer from a number of limitations such as poor drug bioavailability, poor CNS penetration and weak potency particularly at mouse/rat ortholog receptors, all aspects which limit the potential to evaluate these compounds in preclinical models and/or clinical development. On this basis, new potent and selective antagonists of NK-3 receptor may be of therapeutic value for the preparation of drugs useful in the treatment and/or prevention of CNS and peripheral diseases or disorders in which NKB and the NK-3 receptors are involved.

SUMMARY OF THE INVENTION

The invention encompasses compounds of general Formula I, their pharmaceutically acceptable salts and solvates as well as methods of use of such compounds or compositions comprising such compounds as antagonists of NK-3 receptor activity.

In a general aspect, the invention provides compounds of general formula I:

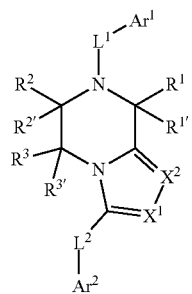

and pharmaceutically acceptable salts and solvates thereof, wherein $Ar^1$ is a 5- to 6-membered aryl or heteroaryl group, 3- to 6-membered cycloalkyl group a 3- to 6-membered heterocyclyl group or a C3-C6 alkyl group, each of the aryl, heteroaryl, cycloalkyl or heterocyclyl groups being optionally substituted by one or more group(s) selected from halo, cyano, alkyl, haloalkyl, cycloalkyl, heteroalkyl, heterocyclyl, aryl, aralkyl, heteroaryl, hydroxyl, alkoxy, haloalkoxy, alkoxyalkoxy, alkylamino, carboxy, alkoxycarbonyl, alkylcarbonyloxy, alkylcarbonylamino, haloalkylcarbonylamino, carbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or two substituents form an alkylenedioxy group or a haloalkylenedioxy group, or two substituents form a cycloalkyl or heterocycloalkyl moiety together with the cycloalkyl or heterocycloalkyl group they are attached to, or fused to the aryl, heteroaryl, cycloalkyl or heterocycloalkyl group may be one or more aryl moiety, each of said substituents being optionally substituted by one or more further substituent(s) selected from halo, cyano, alkyl, haloalkyl, cyclopropyl, alkoxy, haloalkoxy, heterocyclyl, aryl, heteroaryl, aryloxy or heteroaryloxy;

$L^1$ is $C_1$-$C_2$ alkylene optionally being substituted by one or more group(s) selected from halo, methyl or ethyl under the condition that $R^{2'}$ together with $R^2$ form an oxo substituent, or $L^1$ is carbonyl or sulfonyl, or $L^1$ is —(C═O)—$CH_2$— where the C═O is linked to the piperazine nitrogen and the $CH_2$ to $Ar^1$;

$R^1$ is H, a $C_1$-$C_4$ alkyl, aryl or aralkyl group, each of said alkyl, aryl or aralkyl groups being optionally substituted by one or more group(s) selected from halo or hydroxyl;

$R^{1'}$ is H or a $C_1$-$C_4$ alkyl group;

$R^2$ is H or a $C_1$-$C_4$ alkyl group;

$R^{2'}$ is H or a $C_1$-$C_4$ alkyl group, or, when $L^1$ is $C_1$-$C_2$ alkylene optionally being substituted by one or more group(s) selected from halo, methyl or ethyl, $R^{2'}$ together with $R^2$ form an oxo substituent;

$R^3$ is H or a $C_1$-$C_4$ alkyl group optionally substituted by one hydroxy;

$R^{3'}$ is H or a $C_1$-$C_4$ alkyl group;

$X^1$ and $X^2$ are independently selected from N or C—Z wherein Z is H or $C_1$-$C_2$ alkyl under the condition that $X^1$ and $X^2$ cannot be both C—Z;

$L^2$ is a single bond or carbonyl;

$Ar^2$ is a 5- to 6-membered aryl or heteroaryl group, each of the aryl, or heteroaryl groups being optionally substituted by one or more group(s) selected from halo, cyano, alkyl, hydroxyalkyl, haloalkyl, cycloalkyl, heteroalkyl, heterocyclyl, aryl, heteroaryl, aralkyl, heteroarylalkyl, hydroxyl, alkoxy, haloalkoxy, alkylamino, carboxy, alkoxycarbonyl, alkylcarbonyloxy, alkylcarbonylamino, haloalkylcarbonylamino, acylamino, carbamoyl, alkylcarbamoyl, carbamoylalkyl, carbamoylamino, alkylcarbamoylamino, alkylsulfonyl, haloalkylsulfonyl, arylsulfonylalkyl, sulfamoyl, alkylsulfamoyl, alkylsulfonylamino, haloalkylsulfonylamino, or two substituents form an alkylenedioxy group or a haloalkylenedioxy group, or fused to the aryl or heteroaryl group may be one or more cycloalkyl, aryl, heterocyclyl or heteroaryl moiety, each of said substituents being optionally substituted by one or more further substituent(s) selected from halo, cyano, alkyl, haloalkyl, alkoxy, haloalkoxy, cycloalkyl, heterocyclyl optionally substituted by alkyl, aryl, heteroaryl, hydroxyl, alkoxyalkyl, hydroxyalkoxy, alkylamino, alkylsulfonylamino, alkoxycarbonylamino, aminoalkoxy, or alkoxycarbonylaminoalkoxy;

and wherein, when:

$R^1$, $R^{1'}$, $R^2$, $R^{2'}$, $R^3$, $R^{3'}$ are H, and
$L^1$ is carbonyl, and
$L^2$ is single bond, and
$X^2$ is N, and
$Ar^1$ is a 6-membered aryl optionally substituted by one or more group(s) selected from halo, cyano, C1-C3 alkyl, C1 haloalkyl, and
$Ar^2$ is a 5- to 6-membered aryl or heteroaryl group optionally substituted by one or more group(s) selected from halo, C1-C3 alkyl, hydroxyl, methoxy, or fused to an aryl or heteroaryl group optionally substituted by one or more further halo, C1-C3 alkyl, hydroxyl, methoxy, then, $Ar^1$ is phenyl, 3-halophenyl, 4-halophenyl, 2,3-dichlorophenyl, 2,4-difluorophenyl, 2,4-dichlorophenyl, 2,5-dihalophenyl, 2,6-difluorophenyl, 2,6-dichlorophenyl, 3,4-dihalophenyl, 3,5-dihalophenyl, 3,4,5-trihalophenyl, 2-cyanophenyl, 3-cyanophenyl, 4-cyanophenyl, 2,3-dicyanophenyl, 2,4-dicyanophenyl, 3,5-dicyanophenyl, 3-cyano-4-halophenyl, 4-(C1-C3 alkyl)phenyl, 3,4-di(C1-C3 alkyl)phenyl, 3,5-di (C1-C3 alkyl)phenyl, 4-(C1 haloalkyl)phenyl, and $Ar^2$ is 2-(C1-C3 alkyl)thiazol-4-yl, 5-(C1-C3 alkyl)thiazol-4-yl, pyridin-2-yl, 4-halopyridin-2-yl, 4-(C1-C3 alkyl)pyridin-2-yl, 5-(C1-C3 alkyl)pyridin-2-yl, 6-(C1-C3 alkyl)pyridin-2-yl, quinolin-2-yl, isoquinolin-3-yl, 8-haloquinolin-2-yl, benzothiazol-2-yl, 4,5,6,7-tetrahydro-1,3-benzothiazol-2-yl;

with the following provisos:
compounds wherein $L^1$ is CO, $L^2$ is a single bond, $X^1$ is N, $X^2$ is CH and $Ar^2$ is a substituted phenyl are excluded; and
$Ar^1$ is neither a substituted or unsubstituted pyrazolo[1,5-a]pyridin-2yl nor a substituted or unsubstituted pyrazolo[1,5-a]pyrimidin-2yl moiety; and
the compound of formula I is none of:
1-methyl-7-[(3-phenyl-5-isoxazolyl)carbonyl]-3-(4-pyridinyl)-5,6,7,8-tetrahydroimidazo[1,5-a]pyrazine,
7-[(2-benzyl-1,3-thiazol-4-yl)carbonyl]-1-methyl-3-(4-pyridinyl)-5,6,7,8-tetrahydroimidazo[1,5-a]pyrazine, 3-{[1-methyl-3-(1-phenyl-1H-pyrazol-4-yl)-5,6-dihydroimidazo[1,5-a]pyrazin-7(8H)-yl]carbonyl}-1-indanone,
7-[5-(4-methoxyphenyl)-2-furoyl]-1-methyl-3-(4-pyridinyl)-5,6,7,8-tetrahydroimidazo[1,5-a]pyrazine,
1-methyl-3-(4-pyridinyl)-7-(4,5,6,7-tetrahydro-1-benzothien-3-ylcarbonyl)-5,6,7,8-tetrahydroimidazo[1,5-a]pyrazine,
2-{2-[1-methyl-3-(2-methyl-1,3-thiazol-4-yl)-5,6-dihydroimidazo[1,5-a]pyrazin-7(8H)-yl]-2-oxoethyl}-1,2,3,4-tetrahydroisoquinoline,
7-[(1,3-diphenyl-1H-pyrazol-5-yl)carbonyl]-1-methyl-3-(4-pyridinyl)-5,6,7,8-tetrahydroimidazo[1,5-a]pyrazine,
8-fluoro-2-{[1-methyl-3-(4-pyridinyl)-5,6-dihydroimidazo[1,5-a]pyrazin-7(8H)-yl]carbonyl}quinoline,
1-methyl-3-(2-methyl-1,3-thiazol-4-yl)-7-{[2-(2-thienyl)-1,3-thiazol-4-yl]carbonyl}-5,6,7,8-tetrahydroimidazo[1,5-a]pyrazine,
7-(3-fluoro-4-methoxybenzoyl)-1-methyl-3-(4-pyridinyl)-5,6,7,8-tetrahydroimidazo[1,5-a]pyrazine,
7-[(3-ethyl-5-methyl-4-isoxazolyl)carbonyl]-1-methyl-3-(4-pyridinyl)-5,6,7,8-tetrahydroimidazo[1,5-a]pyrazine,
3-{2-[1-methyl-3-(1-phenyl-1H-pyrazol-4-yl)-5,6-dihydroimidazo[1,5-a]pyrazin-7(8H)-yl]-2-oxoethyl}-4(3H)-quinazolinone,
3-{[1-methyl-3-(1-phenyl-1H-pyrazol-4-yl)-5,6-dihydroimidazo[1,5-a]pyrazin-7(8H)-yl]carbonyl}-6,7-dihydro-1-benzofuran-4(5H)-one,
7-{[3-(2-methoxyphenyl)-1H-pyrazol-5-yl]carbonyl}-1-methyl-3-(4-pyridinyl)-5,6,7,8-tetrahydroimidazo[1,5-a]pyrazine,
3-{[1-methyl-3-(1-phenyl-1H-pyrazol-4-yl)-5,6-dihydroimidazo[1,5-a]pyrazin-7(8H)-yl]carbonyl}-4H-pyrido[1,2-a]pyrimidin-4-one,
1-ethyl-3-(2-methoxyphenyl)-7-[3-(1H-pyrazol-1-yl)benzoyl]-5,6,7,8-tetrahydroimidazo[1,5-a]pyrazine,
1-methyl-7-[(3-phenyl-1-piperidinyl)acetyl]-3-(4-pyridinyl)-5,6,7,8-tetrahydroimidazo[1,5-a]pyrazine,
1-methyl-3-(2-methyl-1,3-thiazol-4-yl)-7-(1,2,5-thiadiazol-3-ylcarbonyl)-5,6,7,8-tetrahydroimidazo[1,5-a]pyrazine,
(2,3-dihydrobenzo[b][1,4]dioxin-6-yl)(1-methyl-3-(pyridin-4-yl)-5,6-dihydroimidazo[1,5-a]pyrazin-7(8H)-yl)methanone,
3-(1-methyl-3-(pyridin-4-yl)-5,6,7,8-tetrahydroimidazo[1,5-a]pyrazine-7-carbonyl)-5,6,7,8-tetrahydroquinolin-2(1H)-one,
(2,3-dihydrobenzofuran-2-yl)(1-methyl-3-(pyridin-4-yl)-5,6-dihydroimidazo[1,5-a]pyrazin-7(8H)-yl)methanone,
(1-methyl-3-(1-phenyl-1H-pyrazol-4-yl)-5,6-dihydroimidazo[1,5-a]pyrazin-7(8H)-yl)(8-methylimidazo[1,2-a]pyridin-2-yl)methanone,
(2,3-dihydrothieno[3,4-b][1,4]dioxin-5-yl)(1-methyl-3-(pyridin-4-yl)-5,6-dihydroimidazo[1,5-a]pyrazin-7(8H)-yl)methanone,
2-methyl-6-(1-methyl-3-(pyridin-4-yl)-5,6,7,8-tetrahydroimidazo[1,5-a]pyrazine-7-carbonyl)-4,5-dihydropyridazin-3(2H)-one
(3-(2-methoxyphenyl)-1H-pyrazol-5-yl)(1-methyl-3-(pyridin-4-yl)-5,6-dihydroimidazo[1,5-a]pyrazin-7(8H)-yl)methanone,
(2,3-dihydrobenzofuran-2-yl)(1-methyl-3-(pyridin-4-yl)-5,6-dihydroimidazo[1,5-a]pyrazin-7(8H)-yl)methanone,
(1-methyl-3-(2-methylthiazol-4-yl)-5,6-dihydroimidazo[1,5-a]pyrazin-7(8H)-yl)(2-(thiophen-2-yl)thiazol-4-yl)methanone,
(3,5-dimethyl-1H-pyrrol-2-yl)(1-methyl-3-(pyridin-4-yl)-5,6-dihydroimidazo[1,5-a]pyrazin-7(8H)-yl)methanone,
(1-methyl-3-(pyridin-4-yl)-5,6-dihydroimidazo[1,5-a]pyrazin-7(8H)-yl)(4,5,6,7-tetrahydrobenzo[b]thiophen-3-yl)methanone;
(2,4-dichlorophenyl)(3-(pyridin-2-yl)-5,6-dihydro-[1,2,4]triazolo[4,3-a]pyrazin-7(8H)-yl)methanone;
(2,4-difluorophenyl)(3-(pyridin-2-yl)-5,6-dihydro-[1,2,4]triazolo[4,3-a]pyrazin-7(8H)-yl)methanone;
(3-chlorophenyl)(3-(pyridin-2-yl)-5,6-dihydro-[1,2,4]triazolo[4,3-a]pyrazin-7(8H)-yl)methanone;
2-(3-(pyridin-2-yl)-5,6,7,8-tetrahydro-[1,2,4]triazolo[4,3-a]pyrazine-7-carbonyl)benzonitrile;
(2,6-dichlorophenyl)(3-(pyridin-2-yl)-5,6-dihydro-[1,2,4]triazolo[4,3-a]pyrazin-7(8H)-yl)methanone,
(2,3-dichlorophenyl)(3-(pyridin-2-yl)-5,6-dihydro-[1,2,4]triazolo[4,3-a]pyrazin-7(8H)-yl)methanone,
(2,3-dichlorophenyl)(3-(5-methylpyridin-2-yl)-5,6-dihydro-[1,2,4]triazolo[4,3-a]pyrazin-7(8H)-yl)methanone,
(2,3-dichlorophenyl)(3-(6-methylpyridin-2-yl)-5,6-dihydro-[1,2,4]triazolo[4,3-a]pyrazin-7(8H)-yl)methanone.

In another aspect, the present invention provides a pharmaceutical composition comprising at least one compound according to the invention or a pharmaceutically acceptable salt or solvate thereof.

The invention also relates to the use of the above compounds or their pharmaceutically acceptable salts and solvates as modulators of NK-3 receptors, preferably as antagonists of NK-3 receptors.

The invention further provides methods of treatment and/or prevention of depression, anxiety, pyschosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome and inflammatory bowel disorders, emesis, pre-eclampsia, airway related diseases including chronic obstructive pulmonary disease, asthma, airway hyperresponsiveness, bronchoconstriction and cough, reproduction disorders and sex hormone-dependent diseases including but not limited to benign prostatic hyperplasia (BPH), metastatic prostatic carninoma, testicular cancer, breast cancer, androgen dependent acne, male pattern baldness, endometriosis, abnormal puberty, uterine fibrosis, hormone-dependent cancers, hyperandrogenism, hirsutism, virilization, polycystic ovary syndrome (PCOS), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility) and androgen-producing tumor (virilizing ovarian or adrenal tumor) comprising the administration of a therapeutically effective amount of a compound or pharmaceutically acceptable salt or solvate of formula (I), to a patient in need thereof. Preferably the patient is a warm-blooded animal, more preferably a human.

The invention further provides methods of treatment for gynecological disorders and infertility. In particular, the invention provides methods to suppress the LH-surge in assisted conception comprising the administration of a therapeutically effective amount of a compound or pharmaceutically acceptable salt or solvate of formula (I), to a patient in need thereof. Preferably the patient is a warm-blooded animal, more preferably a woman.

The invention further provides methods to affect androgen production to cause male castration and to inhibit the sex drive in male sexual offenders comprising the administration of a therapeutically effective amount of a compound or pharmaceutically acceptable salt or solvate of formula (I), to a patient in need thereof. Preferably the patient is a warm-blooded animal, more preferably a man.

The invention also provides the use of a compound of formula (I) or a pharmaceutically acceptable salt or solvate thereof as a medicament. Preferably, the medicament is used for the treatment and/or prevention of depression, anxiety, pyschosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome and inflammatory bowel disorders, emesis, pre-eclampsia, airway related diseases including chronic obstructive pulmonary disease, asthma, airway hyperresponsiveness, bronchoconstriction and cough, reproduction disorders and sex hormone-dependent diseases including but not limited to benign prostatic hyperplasia (BPH), metastatic prostatic carninoma, testicular cancer, breast cancer, androgen dependent acne, male pattern baldness, endometriosis, abnormal puberty, uterine fibrosis, hormone-dependent cancers, hyperandrogenism, hirsutism, virilization, polycystic ovary syndrome (PCOS), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility) and androgen-producing tumor (virilizing ovarian or adrenal tumor). The medicament may also be used for the treatment of gynecologic disorder, infertility and to affect androgen production to cause male castration.

DETAILED DESCRIPTION OF THE INVENTION

As noted above, the invention relates to compounds of formula I, as well as their pharmaceutically acceptable salts and solvates.

Preferred compounds of formula I and pharmaceutically acceptable salts and solvates thereof are those wherein
$Ar^1$ is a 5- to 6-membered aryl or heteroaryl group, 5- to 6-membered cycloalkyl group, C3-C6 alkyl group, each of the aryl or heteroaryl groups being optionally substituted by one or more group(s) selected from halo, cyano, alkyl, haloalkyl, C3-C6 cycloalkyl, heteroalkyl, heterocyclyl, aryl, heteroaryl, hydroxyl, alkoxy, haloalkoxy, alkylamino, carboxy, alkoxycarbonyl, alkylcarbonyloxy, alkylcarbonylamino, haloalkylcarbonylamino, carbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or two substituents form an alkylenedioxy group or a haloalkylenedioxy group, or fused to the aryl, heteroaryl, cycloalkyl or heterocycloalkyl group may be one aryl moiety, each of said substituents being optionally substituted by one or more further substituent(s) selected from halo, cyano, alkyl, haloalkyl, cyclopropyl, alkoxy, haloalkoxy, heterocyclyl, aryl, heteroaryl, aryloxy or heteroaryloxy, preferably $Ar^1$ is a 5- to 6-membered aryl, preferably phenyl, heteroaryl group preferably pyridinyl, isopropyl, isobutyl, each of the aryl or heteroaryl groups being optionally substituted by one or more group(s) selected from halo, cyano, alkyl, haloalkyl, C3-C6 cycloalkyl, aryl, heteroaryl, or fused to the aryl or heteroaryl group may be one aryl, preferably phenyl, moiety, each of said substituents being optionally substituted by one or more further substituent(s) selected from halo, alkyl, haloalkyl, cyclopropyl, haloalkoxy, or aryloxy, more preferably $Ar^1$ is a phenyl, a biaryl, preferably 4-biphenyl, heterobiaryl preferably 4-(thiophen-2-yl)phenyl, 3-phenyl-1H-pyrazol-5-yl, 5-phenylpyridin-2-yl, 2-phenylpyridin-5-yl, more preferably 4-(thiophen-2-yl)phenyl, each of said biaryl or heterobiaryl being optionally substituted by one or more further substituent(s) selected from halo, alkyl, cyclopropyl, haloalkyl, haloalkoxy or aryloxy; and/or
$L^1$ is carbonyl; and/or
$R^1$ is H, a $C_1$-$C_4$ alkyl, aryl or aralkyl group, each of said alkyl, aryl or aralkyl groups being optionally substituted by one or more group(s) selected from halo or hydroxyl, preferably $R^1$ is H, a $C_1$-$C_3$ alkyl, preferably methyl or isopropyl, hydroxyethyl, phenyl or benzyl group, each of said phenyl or benzyl groups being optionally substituted by one or more group(s) selected from halo, preferably fluoro or chloro, more preferably $R^1$ is H, methyl or 2-hydroxyethyl; and/or
$R^{1'}$ is H or methyl preferably $R^{1'}$ is H; and/or
$R^2$, $R^{2'}$, $R^3$ and $R^{3'}$ are H; and/or
$X^1$ and $X^2$ are independently selected from N or C—Z wherein Z is H or methyl, under the condition that $X^1$ and $X^2$ cannot be both C—Z, preferably $X^1$ and $X^2$ are independently selected from N or CH under the condition that $X^1$ and $X^2$ cannot be both CH, more preferably $X^1$ and $X^2$ are both N; and/or
$L^2$ is a single bond; and/or
$Ar^2$ is a 5- to 6-membered heteroaryl group optionally substituted by one or more group(s) selected from halo, cyano, alkyl, haloalkyl, C3-C6 cycloalkyl heterocyclyl, aryl, heteroaryl, aralkyl, heteroarylalkyl, arylsulfonylalkyl, alkoxy, or fused to the heteroaryl group may be one cycloalkyl, aryl, heterocyclyl or heteroaryl moiety, each of said substituents being optionally substituted by one or more further substituent(s) selected from halo, cyano, alkyl, haloalkyl, cyclopropyl, alkoxy, heterocyclyl optionally substituted by alkyl aryl, hydroxyl, alkoxyalkyl, hydroxyalkoxy, alkylamino, alkylsulfonylamino, alkoxycarbonylamino, aminoalkoxy, or alkoxycarbonylaminoalkoxy preferably $Ar^2$ is a fused heteroaryl, preferably quinolin-2-yl, benzo[d]thiazol-2-yl, 4,5,6,7-tetrahydrobenzo[d]thiazol-2-yl, heterocyclylheteroaryl, preferably 2-(pyrrolidin-1-yl) thiazol-4-yl, 2-(piperidin-1-yl)thiazol-4-yl, 2-(morpholin-4-yl)thiazol-4-yl, 2-(piperazin-1-yl)thiazol-4-yl, heterobiaryl preferably 2-phenylthiazol-4-yl, 2-phenyloxazol-4-yl, 2-phenylthiazol-5-yl, 2-phenyloxazol-5-yl, 2-phenylimidazol-4-yl, 3-phenylpyrazol-5-yl, 5-phenylpyrazol-3-yl, 3-phenyl-1,2,4-oxadiazol-5-yl, 3-phenyl-1,2,4-thiadiazol-5-yl, 5-phenyl-1,2,4-oxadiazol-3-yl, 5-phenyl-1,2,4-triazol-3-yl, 2-(thiophen-2-yl)thiazol-4-yl, 2-(pyridin-2-yl)thiazol-4-yl, 2-(pyridin-4-yl)thiazol-4-yl, 2-(quinolin-2-yl)thiazol-4-yl, 2-(pyrazin-2-yl)thiazol-4-yl, each of said fused heteroaryl, heterocyclylheteroaryl and heterobiaryl being optionally substituted by one or more further substituent(s) selected from halo, cyano, alkyl, haloalkyl, cyclopropyl, alkoxy, heterocyclyl optionally substituted by alkyl, aryl, hydroxyl, alkoxyalkyl, hydroxyalkoxy, alkylamino, alkylsulfonylamino, aminoalkoxy, or alkoxycarbonylaminoalkoxy; and/or
wherein, when:
$R^1$, $R^{1'}$, $R^2$, $R^{2'}$, $R^3$, $R^{3'}$ are H, and
$L^1$ is carbonyl, and
$L^2$ is single bond, and
$X^2$ is N, and Ar¹ is a 6-membered aryl optionally substituted by one or more group(s) selected from halo, cyano, C1-C3 alkyl, C1 haloalkyl, and
Ar² is a 5- to 6-membered aryl or heteroaryl group optionally substituted by one or more group(s) selected from halo, C1-C3 alkyl, hydroxyl, methoxy, or fused to an aryl or heteroaryl group optionally substituted by one or more further halo, C1-C3 alkyl, hydroxyl, methoxy,
then,
Ar¹ is phenyl, 3-halophenyl, 4-halophenyl, 2,3-dichlorophenyl 3,4-dihalophenyl, 3,4,5-trihalophenyl, 4-cyanophenyl, 4-(C1-C3 alkyl)phenyl, 4-(C1 haloalkyl)phenyl, preferably Ar¹ is phenyl, 3-fluorophenyl, 3-chlorophenyl, 4-fluorophenyl, 4-chlorophenyl, 3,4-difluorophenyl, 3,4-dichlorophenyl, 4-chloro-3-fluorophenyl, 3-chloro-4-fluorophenyl, 3,4,5-trifluorophenyl, 4-cyanophenyl, 4-tolyl, 4-trifluoromethylphenyl, and
Ar² is 2-(C1-C3 alkyl)thiazol-4-yl, 5-(C1-C3 alkyl)thiazol-4-yl, pyridin-2-yl, 4-halopyridin-2-yl, 4-(C1-C3 alkyl)pyridin-2-yl, 5-(C1-C3 alkyl)pyridin-2-yl, 6-(C1-C3 alkyl)pyridin-2-yl, quinolin-2-yl, isoquinolin-3-yl, 8-haloquinolin-2-yl, benzothiazol-2-yl, 4,5,6,7-tetrahydro-1,3-benzothiazol-2-yl, preferably, Ar² is 2-isopropylthiazol-4-yl, 5-methylthiazol-4-yl, pyridin-2-yl, 4-chloropyridin-2-yl, 4-methylpyridin-2-yl, 5-methylpyridin-2-yl, 6-methylpyridin-2-yl, quinolin-2-yl, isoquinolin-3-yl, 8-fluoroquinolin-2-yl, 8-chloroquinolin-2-yl, benzothiazol-2-yl, 4,5,6,7-tetrahydro-1,3-benzothiazol-2-yl.

In one embodiment, preferred compounds of Formula I are those of formula Ia:

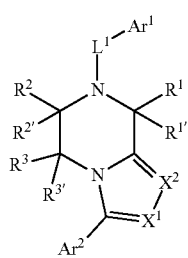

Ia and pharmaceutically acceptable salts and solvates thereof, wherein
Ar¹, Ar², L¹, R¹, R¹', R², R²', R³, R³', X¹ and X² are as defined above in respect to formula I.

Preferred compounds of formula Ia are those of formula Ib:

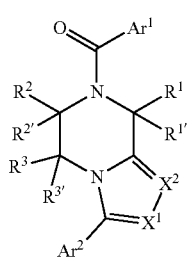

Ib and pharmaceutically acceptable salts and solvates thereof, wherein
Ar¹ is as defined above in respect to formula I, preferably Ar¹ is a 5- to 6-membered aryl or heteroaryl group, 5- to 6-membered cycloalkyl group, or a C3-C6 alkyl group each of the aryl, heteroaryl or cycloalkyl groups being optionally substituted by one or more group(s) selected from halo, cyano, alkyl, haloalkyl, 3- to 6-membered cycloalkyl, heteroalkyl, heterocyclyl, aryl, heteroaryl, alkoxy, haloalkoxy, alkylamino, carboxy, alkoxycarbonyl, alkylcarbonyloxy, alkylcarbonylamino, carbamoyl, alkylcarbamoyl, alkylsulfonyl, sulfamoyl, alkylsulfamoyl, alkylsulfonylamino, or two substituents form an alkylenedioxy group, or fused to the aryl or heteroaryl group may be one or more aryl moiety, each of said substituents being optionally substituted by one or more further substituent(s) selected from halo, cyano, alkyl, haloalkyl, cyclopropyl, alkoxy, haloalkoxy, heterocyclyl, aryloxy or heteroaryloxy, more preferably Ar¹ is a 5- to 6-membered aryl group preferably phenyl, or 5- to 6-membered heteroaryl group preferably pyrazolyl, pyridinyl, more preferably pyrazolyl, C3-C6 alkyl group, each of the aryl or heteroaryl group being optionally substituted by one or more group(s) selected from halo, cyano, alkyl, haloalkyl, C3-C6 cycloalkyl, heteroalkyl, heterocyclyl, aryl, heteroaryl, alkoxy, haloalkoxy, alkylamino, carboxy, alkoxycarbonyl, alkylcarbonyloxy, alkylcarbonylamino, carbamoyl, alkylcarbamoyl, alkylsulfonyl, sulfamoyl, alkylsulfamoyl, alkylsulfonylamino, or two substituents form an alkylenedioxy group, or fused to the aryl or heteroarylgroup may be one aryl moiety, each of said substituents being optionally substituted by one or more further substituent(s) selected from halo, cyano, alkyl, haloalkyl, cyclopropyl, alkoxy, haloalkoxy, heterocyclyl, aryloxy, or heteroaryloxy, even more preferably Ar¹ is a 5- to 6-membered aryl preferably phenyl, or heteroaryl preferably pyrrolyl, oxazolyl, thiazolyl, pyrazolyl, triazolyl, oxadiazolyl, thiadiazolyl, pyridinyl, pyrimidinyl, pyrazinyl, pyridazinyl, more preferably pyrazolyl group, isobutyl, each of the aryl or heteroaryl groups being optionally substituted by one or more group(s) selected from halo preferably chloro or fluoro, cyano, alkyl preferably methyl, haloalkyl preferably —CF₃ or —CHF₂, cycloalkyl preferably cyclopropyl, cyclohexyl, aryl preferably phenyl, heteroaryl preferably furanyl, thiophenyl, thiazolyl, isothiazolyl, more preferably thiophen-2-yl, thiophen-3-yl, thiazol-2-yl, thiazol-5-yl, isothiazol-5-yl, even more preferably thiophen-2-yl, thiophen-2-yl, furan-2-yl, or fused to the aryl or heteroaryl group may be one phenyl moiety, each of said substituents being optionally substituted by one or more further substituent(s) selected from halo preferably chloro or fluoro, alkyl preferably methyl, haloalkyl preferably —CF₃ or —CHF₂, cyclopropyl, haloalkoxy preferably —OCF₃ or —OCHF₂, or aryloxy preferably phenoxy; and
R¹ is as defined above in respect to formula I, preferably R¹ is H, C₁-C₄ alkyl preferably isopropyl, methyl, aryl preferably phenyl, or aralkyl preferably benzyl, each of which being optionally substituted by one or more group(s) selected from halo, preferably chloro, fluoro, or hydroxyl, more preferably R¹ is H, methyl, isopropyl, 2-hydroxyethyl, 4-fluorophenyl or benzyl, still more preferably R¹ is H, methyl or 2-hydroxyethyl, even more preferably R¹ is methyl; and
R¹' is as defined above in respect to formula I, preferably R¹' is H or methyl, more preferably R¹' is H;
R², R²', R³ and R³' are as defined above in respect to formula I, preferably R², R²', R³ and R³' are H; and
X¹ and X² are as defined above in respect to formula I, preferably X¹ and X² are independently selected from N or C—Z wherein Z is H or methyl under the condition that X¹ and X² cannot be both C—Z, more preferably X¹ and X² are independently selected from N or CH under the condition that X¹ and X² cannot be both CH, even more preferably X¹ and X² are N; and Ar² is as defined above in respect to formula I, preferably, Ar² is a 5- to 6-membered heteroaryl group optionally substituted by one or more group(s) selected from halo, cyano, alkyl, hydroxyalkyl, haloalkyl, C3-C6 cycloalkyl, heteroalkyl, heterocyclyl, aryl, aralkyl, heteroaryl, heteroarylalkyl, hydroxyl, alkoxy, alkylamino, carboxy, alkoxycarbonyl, alkylcarbonyloxy, alkylcarbonylamino, acylamino, carbamoyl, alkylcarbamoyl, alkylsulfonyl, arylsulfonylalkyl, sulfamoyl, alkylsulfamoyl, alkylsulfonylamino, or two substituents form an alkylenedioxy group, or fused to the heteroaryl group may be one or more cycloalkyl, aryl, heterocyclyl or heteroaryl moiety, each of said substituents being optionally substituted by one or more further substituent(s) selected from halo, cyano, alkyl, haloalkyl, cyclopropyl, alkoxy, haloalkoxy, alkoxyalkyl, cycloalkyl, aryl, heterocyclyl optionally substituted by alkyl, heteroaryl, hydroxyl, alkoxy, alkoxyalkyl, hydroxyalkoxy, alkylamino, alkylsulfonylamino, alkoxycarbonylamino, aminoalkoxy or alkoxycarbonylaminoalkoxy, more preferably Ar² is a 5- to 6-membered heteroaryl preferably imidazolyl, pyrazolyl, oxazolyl, thiazolyl, oxadiazolyl, triazolyl, thiadiazolyl or pyridyl group, each of the heteroaryl groups being optionally substituted by one or more group(s) selected from halo preferably chloro or fluoro, cyano, alkyl preferably methyl, isopropyl, isobutyl, haloalkyl preferably —CF₃ or —CHF₂, C3-C6 cycloalkyl preferably cyclopropyl, heterocyclyl preferably pyrrolidinyl, piperidinyl, morpholinyl, piperazinyl, aryl preferably phenyl, aralkyl preferably benzyl, heteroarylalkyl preferably (imidazol-3-yl)methyl, arylsulfonylalkyl preferably phenylsulfonylmethyl, heteroaryl preferably thiophen-2-yl, pyridin-2-yl, pyridin-4-yl, pyrimidin-2-yl, pyrazin-2-yl, quinolin-2-yl, alkoxy preferably methoxy, or fused to the heteroaryl group may be one or more cycloalkyl, aryl, heterocyclyl or heteroaryl moiety, each of said substituents being optionally substituted by one or more further substituent(s) selected from halo preferably bromo, chloro or fluoro, cyano, alkyl preferably methyl, haloalkyl preferably —CF₃ or —CHF₂, cyclopropyl, alkoxy preferably methoxy heterocyclyl optionally substituted by alkyl, preferably pyrrolidin-1yl, piperidin-1-yl, morpholin-4-yl, 4-methylpiperazin-1-yl, aryl preferably phenyl, hydroxyl, alkoxy preferably methoxy, alkoxyalkyl preferably methoxymethyl, methoxyethyl, hydroxyalkoxy preferably hydroxyethoxy, alkylamino preferably dimethylamino, alkylsulfonylamino preferably methylsulfonylamino, alkoxycarbonylamino preferably tert-butoxycarbonylamino, aminoalkoxy preferably aminoethyloxy, or alkoxycarbonylaminoalkoxy preferably tert-butoxycarbonylaminoethoxy, more preferably Ar² is a pyrazolyl, oxazolyl, thiazolyl, oxadiazolyl triazolyl, thiadiazolyl or pyridyl group, each of which being optionally substituted by one or more groups selected chloro, fluoro, cyano, methyl, isobutyl, C3-C6 cycloalkyl preferably cyclopropyl, heterocyclyl preferably pyrrolidinyl, piperidinyl, morpholinyl, piperazinyl, aryl preferably phenyl, heteroaryl preferably thiophen-2-yl, pyridin-2-yl, pyridin-4-yl, or fused to the oxazolyl, thiazolyl or pyridyl group may be one cyclohexyl or phenyl moiety, each of said substituents being optionally substituted by one or more further substituent(s) selected from bromo, chloro, fluoro, cyano, haloalkyl preferably —CF₃, methoxy, cyclopropyl, heterocyclyl optionally substituted by methyl, preferably pyrrolidin-1yl, piperidin-1-yl, morpholin-4-yl, 4-methylpiperazin-1-yl, phenyl, hydroxyl, alkoxy preferably methoxy, alkoxyalkyl preferably methoxyethyl, hydroxy-alkoxy preferably hydroxyethoxy, alkylamino preferably dimethylamino, alkylsulfonylamino preferably methylsulfonylamino, aminoalkoxy preferably aminoethyloxy, even more preferably Ar² is a pyrazolyl, oxazolyl, thiazolyl, oxadiazolyl, thiadiazolyl or pyridyl group, each of which being optionally substituted by one or more groups selected chloro, fluoro, cyano, methyl, isobutyl, heterocyclyl preferably pyrrolidin-1-yl, piperidin-1-yl, morpholin-4-yl, 4-phenylpiperazin-1-yl, aryl preferably phenyl, heteroaryl preferably thiophen-2-yl, pyridin-2-yl, or fused to the oxazolyl, thiazolyl or pyridyl group may be one cyclohexyl or phenyl moiety, each of said substituents being optionally substituted by one or more further substituent(s) selected from chloro, fluoro, cyano, methyl, cyclopropyl, phenyl, hydroxyl, alkoxy preferably methoxy, or methoxyethyl.

Preferred compounds of formula Ib are those of formula Ic:

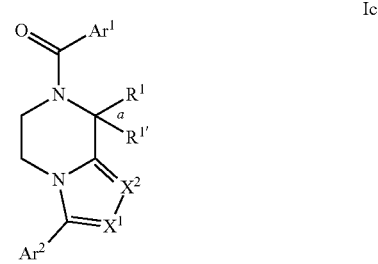

Ic and pharmaceutically acceptable salts and solvates thereof, wherein a depicts the bond linking R¹ to the piperazine moiety, and Ar¹, Ar², R¹, R¹', X¹, and X² are as defined above in respect to formula Ib.

In one embodiment, compounds of formula Ic are those wherein R¹' is H, and/or X¹ and X² are N.

In another embodiment, compounds of formula Ic are those wherein bond a is drawn as a dotted wedge, R¹ is selected from the group consisting of $C_1$-$C_4$ alkyl, aryl or aralkyl group, each of said alkyl, aryl or aralkyl groups being optionally substituted by one or more group(s) selected from halo or hydroxyl, R¹' is H, and/or X¹ and X² are N.

In yet another embodiment, compounds of formula Ic are those wherein bond a is drawn as a solid wedge, R¹ is selected from the group consisting of $C_1$-$C_4$ alkyl, aryl or aralkyl group, each of said alkyl, aryl or aralkyl groups being optionally substituted by one or more group(s) selected from halo or hydroxyl, R¹' is H, and/or X¹ and X² are N.

Preferred compounds of formula Ic are those of formulae Id-1, Id-2, Id-3 and Id-4:

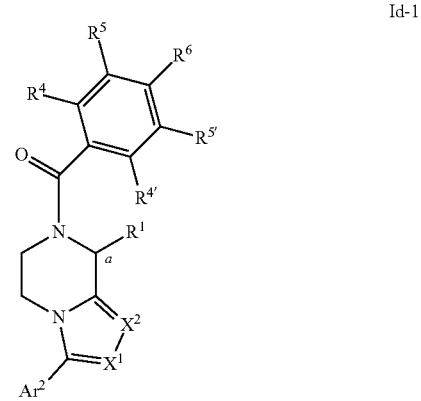

Id-1

-continued

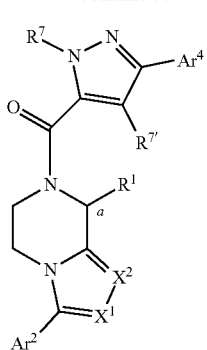

Id-2

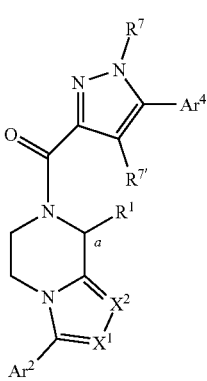

Id-3

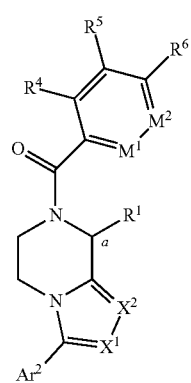

Id-4 and pharmaceutically acceptable salts and solvates thereof, wherein a depicts the bond linking $R^1$ to the piperazine moiety; and $Ar^2$, $R^1$, $X^1$ and $X^2$ are as defined above in respect to formula Ib; and $R^4$, $R^{4'}$, $R^5$, $R^{5'}$ and $R^6$ are independently selected from H, halo, cyano, alkyl, haloalkyl, C3-C6 cycloalkyl, heteroalkyl, heterocyclyl, aryl, heteroaryl, hydroxyl, alkoxy, haloalkoxy, alkoxyalkoxy, alkylamino, carboxy, alkoxycarbonyl, alkylcarbonyloxy, alkylcarbonylamino, haloalkylcarbonylamino, carbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or $R^5$ together with $R^4$ or $R^6$, or $R^{5'}$ together with $R^{4'}$ or $R^6$ forms an alkylenedioxy group or a haloalkylenedioxy group, or $R^5$ together with $R^4$ or $R^6$, or $R^{5'}$ together with $R^{4'}$ or $R^6$ forms an aryl moiety fused to the phenyl group to which they are attached, each of said substituents being optionally substituted by one or more further substituent(s) selected from halo, cyano, alkyl, haloalkyl, cyclopropyl, preferably $R^4$ and $R^{4'}$ are H and at least one of $R^5$, $R^{5'}$, $R^6$ is independently selected from halo preferably chloro or fluoro, cyano, alkyl preferably methyl, haloalkyl preferably —$CF_3$ or —$CHF_2$, more preferably —$CF_3$, cyclopropyl, aryl preferably phenyl, heteroaryl preferably thiophen-2-yl, thiophen-3-yl, or furan-2-yl, the others, if applicable, being H, each of said aryl and heteroaryl group being optionally substituted by one or more further substituent(s) selected from halo preferably chloro or fluoro, alkyl preferably methyl, cyclopropyl, or $R^5$ together with $R^4$ or $R^6$, or $R^{5'}$ together with $R^{4'}$ or $R^6$ forms a phenyl moiety fused to the phenyl group to which they are attached, more preferably $R^4$, $R^{4'}$, $R^5$, and $R^{5'}$ are H and $R^6$ is selected from cyano, phenyl, thiophen-2-yl, thiophen-3-yl, or furan-2-yl, each of said group being optionally substituted by one or more further substituent(s) selected from chloro, fluoro or methyl, or $R^4$, $R^{4'}$, $R^5$ are H and $R^{5'}$, $R^6$ are independently selected from fluoro or chloro, or $R^4$ and $R^{4'}$ are H and $R^5$, $R^{5'}$, $R^6$ are fluoro; and $R^7$ is H or methyl, preferably $R^7$ is H; and $R^{7'}$ is H or methyl, preferably $R^{7'}$ is H; and $Ar^4$ is a cycloalkyl preferably cyclohexyl or an aryl preferably phenyl group, each of said cycloalkyl or aryl groups being optionally substituted by one or more group(s) selected from halo preferably chloro or fluoro, alkyl preferably methyl, haloalkyl preferably —$CF_3$ or —$CHF_2$, more preferably —$CF_3$, cyclopropyl, haloalkoxy preferably —$OCF_3$ or —$OCHF_2$, more preferably —$OCF_3$, aryloxy preferably phenoxy; and $M^1$ is N or C—$R^{4''}$ wherein $R^{4''}$ is selected from H, halo, cyano, alkyl, haloalkyl, C3-C6 cycloalkyl, heteroalkyl, heterocyclyl, aryl, heteroaryl, hydroxyl, alkoxy, haloalkoxy, alkoxyalkoxy, alkylamino, carboxy, alkoxycarbonyl, alkylcarbonyloxy, alkylcarbonylamino, haloalkylcarbonylamino, carbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, each of said substituents being optionally substituted by one or more further substituent(s) selected from halo, cyano, alkyl, haloalkyl, cyclopropyl, preferably $R^{4''}$ is H; and $M^2$ is N or $M^2$ is C—$R^{5''}$ under the condition that $M^1$ is N, wherein $R^{5''}$ is selected from H, halo, cyano, alkyl, haloalkyl, C3-C6 cycloalkyl, heteroalkyl, heterocyclyl, aryl, heteroaryl, hydroxyl, alkoxy, haloalkoxy, alkoxyalkoxy, alkylamino, carboxy, alkoxycarbonyl, alkylcarbonyloxy, alkylcarbonylamino, haloalkylcarbonylamino, carbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or $R^{5''}$ together with $R^6$ forms an alkylenedioxy group or a haloalkylenedioxy group, or an aryl moiety fused to the pyridinyl group to which they are attached, each of said substituents being optionally substituted by one or more further substituent(s) selected from halo, cyano, alkyl, haloalkyl, cyclopropyl, preferably $R^{5''}$ is selected from H, halo preferably chloro or fluoro, alkyl preferably methyl, haloalkyl preferably —$CF_3$ or —$CHF_2$, more preferably —$CF_3$, more preferably $R^{5''}$ is H; and wherein, in formula Id-1 when:

$R^1$ is H, and $X^2$ is N, and $R^4$, $R^{4'}$, $R^5$, $R^{5'}$ and $R^6$ are independently selected from H, halo, cyano, C1-C3 alkyl, C1 haloalkyl, and $Ar^2$ is a 5- to 6-membered aryl or heteroaryl group optionally substituted by one or more group(s) selected from halo, C1-C3 alkyl, hydroxyl, alkoxy, or fused to an aryl group optionally substituted by one or more further halo, C1-C3 alkyl, hydroxyl, methoxy, then, $R^4$, $R^{4'}$, $R^5$, $R^{5'}$ and $R^6$ are H, or $R^4$, $R^{4'}$, $R^{5'}$, $R^6$ are H and $R^5$ is halo, or $R^4$, $R^{4'}$, $R^5$, $R^{5'}$ are H and $R^6$ is halo, cyano, C1-C3 alkyl, C1 haloalkyl, or $R^{4'}$, $R^{5'}$, $R^6$ are H and $R^4$, $R^5$ are halo, or $R^4$, $R^{4'}$, $R^{5'}$ are H and $R^5$, $R^6$ are independently halo, or $R^4$, $R^{4'}$ are H and $R^5$, $R^{5'}$, $R^6$ are halo, preferably, $R^4$, $R^{4'}$, $R^5$, $R^{5'}$ and $R^6$ are H, or $R^4$, $R^{4'}$, $R^{5'}$, $R^6$ are H and $R^5$ is fluoro, chloro, or $R^4$, $R^{4'}$, $R^5$, $R^{5'}$ are H and $R^6$ is fluoro, chloro, cyano, methyl, trifluoromethyl, or $R^4$, $R^{4'}$, $R^{5'}$ are H and $R^5$, $R^6$ are independently fluoro, chloro, or $R^4$, $R^{4'}$ are H and $R^5$, $R^{5'}$, $R^6$ are fluoro, and $Ar^2$ is 2-(C1-C3 alkyl)thiazol-4-yl, 5-(C1-C3 alkyl)thiazol-4-yl, pyridin-2-yl, 4-halopyridin-2-yl, 4-(C1-C3 alkyl)pyridin-2-yl, 5-(C1-C3 alkyl)pyridin-2-yl, 6-(C1-C3 alkyl)pyridin-2-yl, quinolin-2-yl, isoquinolin-3-yl, 8-haloquinolin-2-yl, benzothiazol-2-yl, 4,5,6,7-tetrahydro-1,3-benzothiazol-2-yl, preferably $Ar^2$ is 2-isopropylthiazol-4-yl, 5-methylthiazol-4-yl pyridin-2-yl, 6-methylpyridin-2-yl, 5-methylpyridin-2-yl, 4-methylpyridin-2-yl, 4-chloropyridin-2-yl, quinolin-2-yl, isoquinolin-3-yl, 8-fluoroquinolin-2-yl, 8-chloroquinolin-2-yl, benzothiazol-2-yl, 4,5,6,7-tetrahydro-1,3-benzothiazol-2-yl.

In one embodiment, compounds of formulae Id-1, Id-2, Id-3 and Id-4 are those wherein $X^1$ and $X^2$ are N.

In another embodiment, compounds of formulae Id-1, Id-2, Id-3 and Id-4 are those wherein bond a is drawn as a dotted wedge, $R^1$ is selected from the group consisting of $C_1$-$C_4$ alkyl, aryl or aralkyl group, each of said alkyl, aryl or aralkyl groups being optionally substituted by one or more group(s) selected from halo or hydroxyl, and/or $X^1$ and $X^2$ are N.

In yet another embodiment, compounds of formulae Id-1, Id-2, Id-3 and Id-4 are those wherein bond a is drawn as a solid wedge, $R^1$ is selected from the group consisting of $C_1$-$C_4$ alkyl, aryl or aralkyl group, each of said alkyl, aryl or aralkyl groups being optionally substituted by one or more group(s) selected from halo or hydroxyl, and/or $X^1$ and $X^2$ are N.

Preferred compounds of formulae Id-1, Id-2, Id-3 and Id-4 are those of formulae Ie-1, Ie-2 and Ie-3:

Ie-1
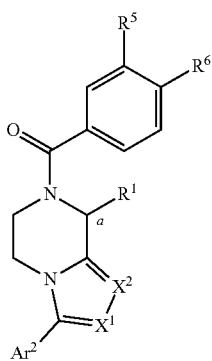

Ie-2
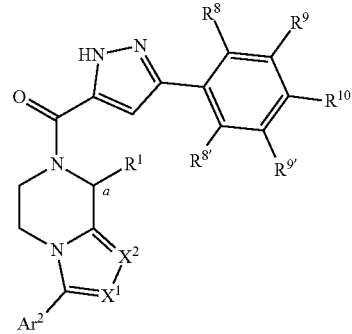

Ie-3
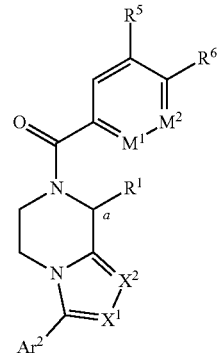

and pharmaceutically acceptable salts and solvates thereof, wherein a depicts the bond linking $R^1$ to the piperazine moiety; and $Ar^2$, $R^1$, $X^1$ and $X^2$ are as defined above in respect to formula Ib; and $R^5$ and $R^6$ are independently selected from H, halo preferably chloro or fluoro, cyano, alkyl preferably methyl, cyclopropyl, aryl preferably phenyl, heteroaryl, preferably thiophen-2-yl, thiophen-2-yl, furan-2-yl, each of said aryl and heteroaryl groups being optionally substituted by one or more group(s) selected from halo, preferably chloro or fluoro, alkyl preferably methyl, cyclopropyl, or $R^5$ and $R^6$ together form a phenyl moiety fused to the phenyl ring they are attached to, preferably $R^5$ is H and $R^6$ is selected from H, chloro, fluoro, cyano, methyl, cyclopropyl, phenyl, 4-fluorophenyl, 4-chlorophenyl, 4-cyanophenyl, 4-tolyl, 3-tolyl, 2-tolyl, 2-fluorophenyl, 3,4-difluorophenyl, 3,4-dichlorophenyl, 3-fluoro-4-chlorophenyl, 3,5-difluorophenyl, thiophen-2-yl, 5-methylthiophen-2-yl, 2-methylthiophen-3-yl, furan-2-yl, or $R^6$ is H and $R^5$ is selected from chloro, fluoro, methyl, cyclopropyl or phenyl, or $R^5$ and $R^6$ are both chloro, more preferably $R^5$ is H and $R^6$ is selected from H, chloro, fluoro, phenyl, 4-fluorophenyl, 4-chlorophenyl, 4-cyanophenyl, 4-tolyl, 2-fluorophenyl, 3,4-difluorophenyl, thiophen-2-yl, 5-methylthiophen-2-yl, 2-methylthiophen-3-yl, or $R^6$ is H and $R^5$ is selected from chloro, fluoro, methyl or phenyl, or $R^5$ and $R^6$ are both chloro, even more preferably $R^5$ is H and $R^6$ is selected from phenyl, 4-fluorophenyl, thiophen-2-yl, 5-methylthiophen-2-yl, 2-methylthiophen-3-yl, or $R^5$ and $R^6$ are both chloro; and $R^8$, $R^{8'}$, $R^9$, $R^{9'}$ and $R^{10}$ are independently selected from H, halo preferably fluoro or chloro, haloalkyl preferably —$CF_3$ or —$CHF_2$, more preferably —$CF_3$, cyclopropyl or haloalkoxy preferably —$OCF_3$ or —$OCHF_2$ more preferably —$OCF_3$, or $R^8$, $R^{8'}$, $R^9$, $R^{9'}$ are H and $R^{10}$ is phenoxy, preferably $R^{8'}$, $R^9$, $R^{9'}$, $R^{10}$ are H and $R^8$ is —$CF_3$, or $R^8$, $R^{8'}$, $R^{9'}$, $R^{10}$ are H and $R^9$ is selected from chloro or fluoro, or $R^8$, $R^{8'}$, $R^9$, $R^{9'}$ are H and $R^{10}$ is selected from chloro, fluoro, —$CF_3$, —$OCF_3$ or —$OCHF_2$, phenoxy, or $R^8$, $R^9$, $R^{9'}$ are H, $R^{8'}$ is selected from chloro, fluoro —$CF_3$, and $R^{10}$ is selected from fluoro or chloro, or $R^8$, $R^{8'}$, $R^{9'}$ are H and $R^9$, $R^{10}$ are independently selected from fluoro or chloro, more preferably $R^8$, $R^{8'}$, $R^9$, $R^{9'}$ are H and $R^{10}$ is selected from chloro, fluoro or phenoxy, or $R^8$, $R^9$, $R^{9'}$ are H and $R^{8'}$, $R^{10}$ are both chloro, or $R^8$, $R^{8'}$, $R^{9'}$ are H and $R^9$, $R^{10}$ are both chloro; and $M^1$ and $M^2$ are as defined above in respect to formula Id-4; and wherein, in formula Ie-1 when:

$R^1$ is H, and $X^2$ is N, and $R^5$ and $R^6$ are independently selected from H, halo, cyano, C1-C3 alkyl, and $Ar^2$ is a 5- to 6-membered aryl or heteroaryl group optionally substituted by one or more group(s) selected from halo, C1-C3 alkyl, hydroxyl, alkoxy, or fused to an aryl group optionally substituted by one or more further halo, C1-C3 alkyl, hydroxyl, methoxy, then, $R^6$ is H and $R^5$ is H, halo, or $R^5$ is H and $R^6$ is halo, cyano, C1-C3 alkyl, C1 haloalkyl, or $R^5$ and $R^6$ are independently halo, preferably $R^6$ is H and $R^5$ is fluoro, chloro, or $R^5$ is H and $R^6$ is fluoro, chloro, cyano, methyl, trifluoromethyl or $R^5$ and $R^6$ are independently fluoro, chloro, and $Ar^2$ is 2-(C1-C3 alkyl)thiazol-4-yl, 5-(C1-C3 alkyl)thiazol-4-yl, pyridin-2-yl, 4-halopyridin-2-yl, 4-(C1-C3 alkyl)pyridin-2-yl, 5-(C1-C3 alkyl)pyridin-2-yl, 6-(C1-C3 alkyl)pyridin-2-yl, quinolin-2-yl, isoquinolin-3-yl, 8-haloquinolin-2-yl, benzothiazol-2-yl, 4,5,6,7-tetrahydro-1,3-benzothiazol-2-yl, preferably $Ar^2$ is 2-isopropylthiazol-4-yl, 5-methylthiazol-4-yl, pyridin-2-yl, 6-methylpyridin-2-yl, 5-methylpyridin-2-yl, 4-methylpyridin-2-yl, 4-chloropyridin-2-yl, quinolin-2-yl, isoquinolin-3-yl, 8-fluoroquinolin-2-yl, 8-chloroquinolin-2-yl, benzothiazol-2-yl, 4,5,6,7-tetrahydro-1,3-benzothiazol-2-yl.

In one embodiment, compounds of formulae Ie-1, Ie-2 and Ie-3 are those wherein $X^1$ and $X^2$ are N.

In another embodiment, compounds of formulae Ie-1, Ie-2 and Ie-3 are those wherein bond a is drawn as a dotted wedge, $R^1$ is selected from the group consisting of $C_1$-$C_4$ alkyl, aryl or aralkyl group, each of said alkyl, aryl or aralkyl groups being optionally substituted by one or more group(s) selected from halo or hydroxyl, and/or $X^1$ and $X^2$ are N.

In yet another embodiment, compounds of formulae Ie-1, Ie-2 and Ie-3 are those wherein bond a is drawn as a solid wedge, $R^1$ is selected from the group consisting of $C_1$-$C_4$ alkyl, aryl or aralkyl group, each of said alkyl, aryl or aralkyl groups being optionally substituted by one or more group(s) selected from halo or hydroxyl, and/or $X^1$ and $X^2$ are N.

Other preferred compounds of formula Ic are those of formulae If-1, If-2, If-3, If-4, If-5, If-6, If-7 and If-8:

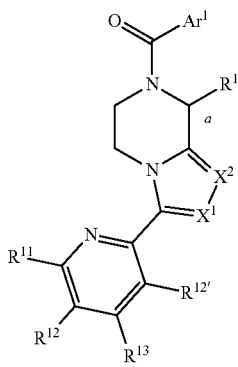

If-1

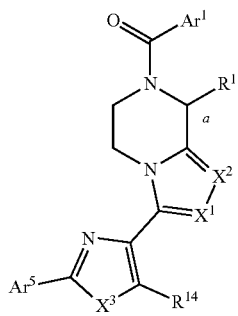

If-2

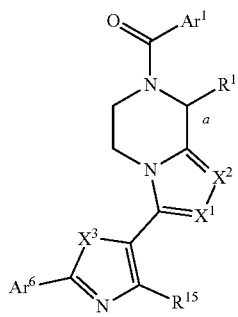

If-3

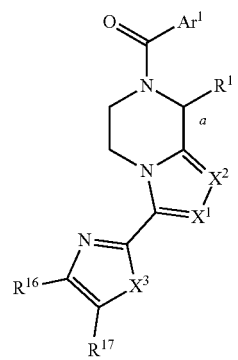

If-4

If-5
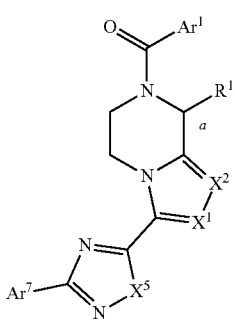

If-6
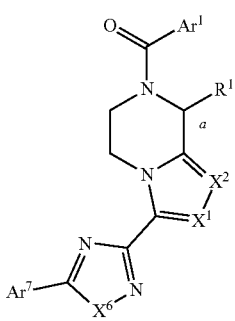

If-7
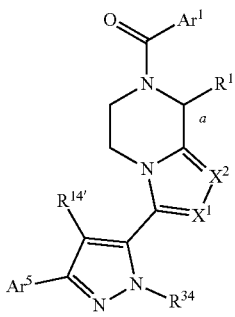

If-8
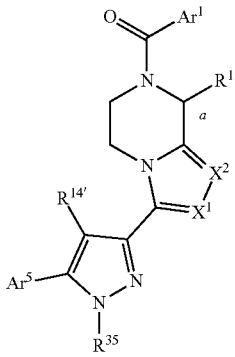

and pharmaceutically acceptable salts and solvates thereof, wherein
a designates the bond linking $R^1$ to the piperazine moiety; and
$Ar^1$, $R^1$, $X^1$ and $X^2$ are as defined above in respect to formula Ib; and
$R^{11}$, $R^{12}$, $R^{12'}$ and $R^{13}$ are independently selected from H, halo, cyano, alkyl, hydroxyalkyl, haloalkyl, C3-C6 cycloalkyl, heteroalkyl, heterocyclyl, aryl, heteroaryl, hydroxyl, alkoxy, haloalkoxy, alkylamino, carboxy, alkoxycarbonyl, alkylcarbonyloxy, alkylcarbonylamino, haloalkylcarbonylamino, acylamino, carbamoyl, alkylcarbamoyl, carbamoylalkyl, carbamoylamino, alkylcarbamoylamino, alkylsulfonyl, haloalkylsulfonyl, sulfamoyl, alkylsulfamoyl, alkylsulfonylamino, haloalkylsulfonylamino, or $R^{12}$ together with $R^{11}$ or $R^{13}$, or $R^{13}$ together with $R^{12'}$ forms an alkylenedioxy group or a haloalkylenedioxy group, or $R^{12}$ together with $R^{11}$ or $R^{13}$ forms a cycloalkyl, aryl, heterocyclyl or heteroaryl moiety fused to the pyridyl group to which they are attached, each of said groups being optionally substituted by one or more group(s) selected from halo, cyano, alkyl, haloalkyl, cyclopropyl, alkoxy, haloalkoxy or hydroxyl, preferably $R^{11}$, $R^{12}$, $R^{12'}$ and $R^{13}$ are independently selected from H, halo preferably chloro or fluoro, alkyl preferably methyl, haloalkyl preferably —$CF_3$ or —$CHF_2$, more preferably —$CF_3$, C3-C6 cycloalkyl, preferably cyclopropyl, heterocyclyl preferably pyrrolidin-1-yl, morpholin-4-yl, aryl preferably phenyl, or $R^{12}$ together with $R^{11}$ or $R^{13}$ forms an aryl preferably phenyl moiety fused to the pyridyl group to which they are attached, each of said groups being optionally substituted by one or more group(s) selected from halo, cyano, alkyl, haloalkyl, alkoxy or haloalkoxy more preferably $R^{12}$, $R^{12'}$ and $R^{13}$ are H and $R^{11}$ is selected from methyl, —$CF_3$, cyclopropyl, pyrrolidin-1-yl, morpholin-4-yl or phenyl, or $R^{11}$, $R^{12'}$, $R^{13}$ are H and $R^{12}$ is methyl, cyclopropyl, or $R^{11}$, $R^{12}$, $R^{12'}$ are H and $R^{13}$ is selected from chloro or methyl, cyclopropyl, or $R^{12}$ together with $R^{11}$ or $R^{13}$ forms an aryl preferably phenyl moiety fused to the pyridyl group to which they are attached, thus forming a fused ring system, each of said phenyl and fused ring system being optionally substituted by one or more halo preferably chloro or fluoro, still more preferably $R^{12}$, $R^{12'}$ and $R^{13}$ are H and $R^{11}$ is selected from methyl, pyrrolidin-1-yl or morpholin-4-yl, or $R^{12}$ together with $R^{11}$ forms a phenyl moiety fused to the pyridyl group to which they are attached, thus forming a quinoline moiety, each of said phenyl and quinoline groups being optionally substituted by one or more group(s) selected from halo preferably chloro or fluoro, even more preferably $R^{12}$, $R^{12'}$ and $R^{13}$ are H and $R^{11}$ is methyl, or $R^{12}$ together with $R^{11}$ forms a phenyl moiety fused to the pyridyl group to which they are attached, thus forming a quinoline moiety; and
$Ar^5$ is a heterocyclyl, aryl, heteroaryl, aralkyl, heteroarylalkyl, or arylsulfonylalkyl group, each of which being optionally substituted by one or more group(s) selected from halo, cyano, alkyl, haloalkyl, cyclopropyl, alkoxy, haloalkoxy, heterocyclyl optionally substituted by alkyl, aryl, hydroxyl, alkoxy, alkoxyalkyl, hydroxyalkyl, alkylamino, alkylsulfonylamino, aminoalkoxy, or alkoxycarbonylaminoalkoxy preferably tert-butyloxycarbonylaminoethoxy, preferably $Ar^5$ is pyrrolidin-1-yl, morpholin-4-yl, piperidin-1-yl, 4-methylpiperazin-1-yl, each of which being optionally substituted by one or more halo preferably fluoro, alkyl preferably methyl, alkoxyalkyl preferably methoxymethyl, methoxyethyl, or $Ar^5$ is 4-phenyl-piperazin-1-yl or a phenyl group optionally substituted by one or more group(s) selected from halo preferably bromo, chloro or fluoro, cyano, haloalkyl preferably —$CF_3$ or —$CHF_2$, more preferably —$CF_3$, cyclopropyl, hydroxyl, alkoxy preferably methoxy, heterocyclyl optionally substituted by alkyl, preferably pyrrolidin-1-yl, piperidin-1-yl, morpholin-4-yl, 4-methylpiperazin-1-yl, hydroxyalkoxy preferably hydroxyethoxy, alkylamino preferably dimethylamino, alkylsulfonylamino preferably methylsulfonylamino, aminoalkoxy preferably aminoethoxy, or $Ar^5$ is thiophen-2-yl, pyridin-2-yl, pyridin-4-yl, pyrimidin-2-yl, pyrazin-2-yl, quinolin-2-yl, 4-chlorobenzyl, 4,5-dichloro(imidazol-3-yl)methyl, 4-chlorophenylsulfonylmethyl more preferably $Ar^5$ is a phenyl optionally substituted by one or more group(s) selected from chloro or fluoro, cyano, —$CF_3$, hydroxyl, methoxy, 4-methylpiperazin-1-yl hydroxyethoxy or Ar⁵ is thiophen-2-yl, pyridin-2-yl even more preferably Ar⁵ is phenyl, 2-fluorophenyl, 4-fluorophenyl, 4-chlorophenyl, 3-fluorophenyl, 3-chlorophenyl, 2-chlorophenyl, 2,4-difluorophenyl or 2,4-dichlorophenyl, 4-cyanophenyl; and $X^3$ is O or S, preferably $X^3$ is S; and $R^{14}$ is H or methyl, preferably $R^{14}$ is H; and $Ar^6$ is a heterocyclyl, aryl or heteroaryl group, each of which being optionally substituted by one or more group(s) selected from halo, cyano, alkyl, haloalkyl, cyclopropyl, alkoxy, haloalkoxy, aryl or hydroxyl, preferably $Ar^6$ is a phenyl group optionally substituted by one or more group(s) selected from halo preferably chloro or fluoro, haloalkyl preferably —CF₃ or —CHF₂, cyclopropyl, more preferably —CF₃, or alkoxy preferably methoxy, more preferably $Ar^6$ is phenyl, 4-fluorophenyl, 2,4-difluorophenyl; and $R^{15}$ is H or methyl, preferably $R^{15}$ is methyl; and $R^{16}$ is a heterocyclyl, aryl or heteroaryl group, each of said groups being optionally substituted by one or more group(s) selected from halo, cyano, alkyl, haloalkyl, cyclopropyl, alkoxy, haloalkoxy or hydroxyl, preferably $R^{16}$ is a phenyl group optionally substituted by one or more group(s) selected from halo preferably chloro or fluoro, haloalkyl preferably —CF₃ or —CHF₂, more preferably —CF₃, alkoxy preferably methoxy, more preferably $R^{16}$ is phenyl; and $R^{17}$ is H, methyl or $R^{17}$ together with $R^{16}$ forms a cycloalkyl or aryl moiety fused to the thiazolyl group to which they are attached, thus forming a fused ring system, said fused ring system being optionally substituted by one or more group(s) selected from halo, cyano, alkyl, haloalkyl, cyclopropyl, alkoxy, haloalkoxy or hydroxyl, preferably $R^{17}$ is H or $R^{17}$ together with $R^{16}$ forms a cyclohexyl or phenyl moiety fused to the thiazolyl group to which they are attached, more preferably $R^{17}$ together with $R^{16}$ forms a cyclohexyl or phenyl moiety fused to the thiazolyl group to which they are attached; and $X^5$ is O or S, or N—$R^{36}$ wherein $R^{36}$ is H or C1-C3 alkyl, preferably $X^5$ is O or S, more preferably $X^5$ is O; and $Ar^7$ is a heterocyclyl, aryl or heteroaryl group, each of which being optionally substituted by one or more group(s) selected from halo, cyano, alkyl, haloalkyl, cyclopropyl, alkoxy, haloalkoxy, aryl or hydroxyl, preferably $Ar^7$ is a phenyl group optionally substituted by one or more group(s) selected from halo preferably chloro or fluoro, haloalkyl preferably —CF₃ or —CHF₂, more preferably —CF₃, or alkoxy preferably methoxy, more preferably $Ar^7$ is phenyl, 4-fluorophenyl, 2,4-difluorophenyl; and $X^6$ is O, S or N—$R^{36'}$ wherein $R^{36'}$ is H or C1-C3 alkyl, preferably $X^6$ is O or NH, more preferably $X^6$ is O; and $R^{14'}$ is H or methyl, preferably $R^{14'}$ is H; and $R^{34}$ is H, alkyl, alkoxyalkyl, hydroxyalkyl, alkoxycarbonylaminoalkyl, preferably $R^{34}$ is H, methyl, ethyl, hydroxyethyl, methoxyethyl, tert-butoxycarbonylaminoethyl, more preferably $R^{34}$ is H, methyl, hydroxyethyl, methoxyethyl; and $R^{35}$ is H, alkyl, alkoxyalkyl, hydroxyalkyl, alkoxycarbonylaminoalkyl, preferably $R^{35}$ is H, methyl, ethyl, hydroxyethyl, methoxyethyl, tert-butoxycarbonylaminoethyl, more preferably $R^{35}$ is H, methyl, hydroxyethyl; and wherein, in formula If-1 when:
$R^1$ is H, and
$X^2$ is N, and
$Ar^1$ is a 6-membered aryl optionally substituted by one or more group(s) selected from halo, cyano, C1-C3 alkyl, C1-haloalkyl, and $R^{11}$, $R^{12}$, $R^{12'}$ and $R^{13}$ are independently selected from H, halo, C1-C3 alkyl, hydroxyl, methoxy, or $R^{12}$ together with $R^{11}$ or $R^{13}$ forms an aryl or heterocyclyl or heteroaryl moiety fused to the pyridyl group to which they are attached and being optionally substituted by one or more group(s) selected from halo, C1-C3 alkyl, methoxy or hydroxyl, then, $Ar^1$ is phenyl, 3-halophenyl, 4-halophenyl, 2,3-dichlorophenyl, 3,4-dihalophenyl, 3,4,5-trihalophenyl, 4-cyanophenyl, 4-(C1-C3 alkyl)phenyl, 4-(C1 haloalkyl)phenyl, preferably $Ar^1$ is phenyl, 4-fluorophenyl, 4-chlorophenyl, 3-chlorophenyl, 3-fluorophenyl, 3,4-dichlorophenyl, 3,4-difluorophenyl, 3,4,5-trifluorophenyl, 4-chloro-3-fluorophenyl, 3-chloro-4-fluorophenyl, 4-cyanophenyl, 4-tolyl, 4-trifluoromethylphenyl, and $R^{11}$, $R^{12}$, $R^{12'}$ and $R^{13}$ are H, or $R^{11}$, $R^{12}$, $R^{12'}$ are H and $R^{13}$ is halo, C1-C3 alkyl, or $R^{11}$, $R^{12'}$, $R^{13}$ are H and $R^{12}$ is C1-C3 alkyl, or $R^{12}$, $R^{12'}$, $R^{13}$ are H and $R^{11}$ is C1-C3 alkyl, or $R^{11}$, $R^{12}$, $R^{12'}$ and $R^{13}$ together with the pyridyl group they are attached form a quinolin-2-yl, isoquinolin-3-yl or 8-haloquinolin-2-yl moiety, preferably $R^{11}$, $R^{12}$, $R^{12'}$ and $R^{13}$ are H, or $R^{11}$, $R^{12}$, $R^{12'}$ are H and $R^{13}$ is chloro, methyl, or $R^{11}$, $R^{12'}$, $R^{13}$ are H and $R^{12}$ is methyl, or $R^{12}$, $R^{12'}$, $R^{13}$ are H and $R^{11}$ is methyl, or $R^{11}$, $R^{12}$, $R^{12'}$ and $R^{13}$ together with the pyridyl group they are attached form a quinolin-2-yl, isoquinolin-3-yl, 8-fluoroquinolin-2-yl or 8-chloroquinolin-2-yl moiety; and in formula If-4 when:
$R^1$ is H, and
$X^2$ is N, and
$Ar^1$ is a 6-membered aryl optionally substituted by one or more group(s) selected from halo, cyano, C1-C3 alkyl, C1-haloalkyl, and $R^{17}$ together with $R^{16}$ forms a cycloalkyl or aryl moiety fused to the thiazolyl group to which they are attached, thus forming a fused ring system, said fused ring system being optionally substituted by one or more group(s) selected from halo, C1-3 alkyl, methoxy or hydroxyl, then $Ar^1$ is phenyl, 3-halophenyl, 4-halophenyl, 2,3-dichlorophenyl, 3,4-dihalophenyl, 3,4,5-trihalophenyl, 4-cyanophenyl, 4-(C1-C3 alkyl)phenyl, 4-(C1 haloalkyl)phenyl, preferably $Ar^1$ is phenyl, 4-fluorophenyl, 4-chlorophenyl, 3-chlorophenyl, 3-fluorophenyl, 3,4-dichlorophenyl, 3,4-difluorophenyl, 3,4,5-trifluorophenyl, 4-chloro-3-fluorophenyl, 3-chloro-4-fluorophenyl, 4-cyanophenyl, 4-tolyl, 4-trifluoromethylphenyl, and $R^{17}$ and $R^{16}$ form together with the thiazolyl group to which they are attached a benzothiazol-2-yl or 4,5,6,7-tetrahydro-1,3-benzothiazol-2-yl moiety.

In one embodiment, compounds of formulae If-1, If-2, If-3, If-4, If-5, If-6, If-7 and If-8 are those wherein $X^1$ and $X^2$ are N.

In another embodiment, compounds of formulae If-1, If-2, If-3, If-4, If-5, If-6, If-7 and If-8 are those wherein bond a is drawn as a dotted wedge, $R^1$ is selected from the group consisting of $C_1$-$C_4$ alkyl, aryl or aralkyl group, each of said alkyl, aryl or aralkyl groups being optionally substituted by one or more group(s) selected from halo or hydroxyl, and/or $X^1$ and $X^2$ are N.

In yet another embodiment, compounds of formulae If-1, If-2, If-3, If-4, If-5, If-6, If-7 and If-8 are those wherein bond a is drawn as a solid wedge, $R^1$ is selected from the group consisting of $C_1$-$C_4$ alkyl, aryl or aralkyl group, each of said alkyl, aryl or aralkyl groups being optionally substituted by one or more group(s) selected from halo or hydroxyl, and/or $X^1$ and $X^2$ are N.
Preferred compounds of formulae If-1, If-2, If-3, If-4, If-5, If-6, If-7 and If-8 are those of formulae Ig-1, Ig-2, Ig-3, Ig-4, Ig-5, Ig-6, Ig-7 and Ig-8 respectively:
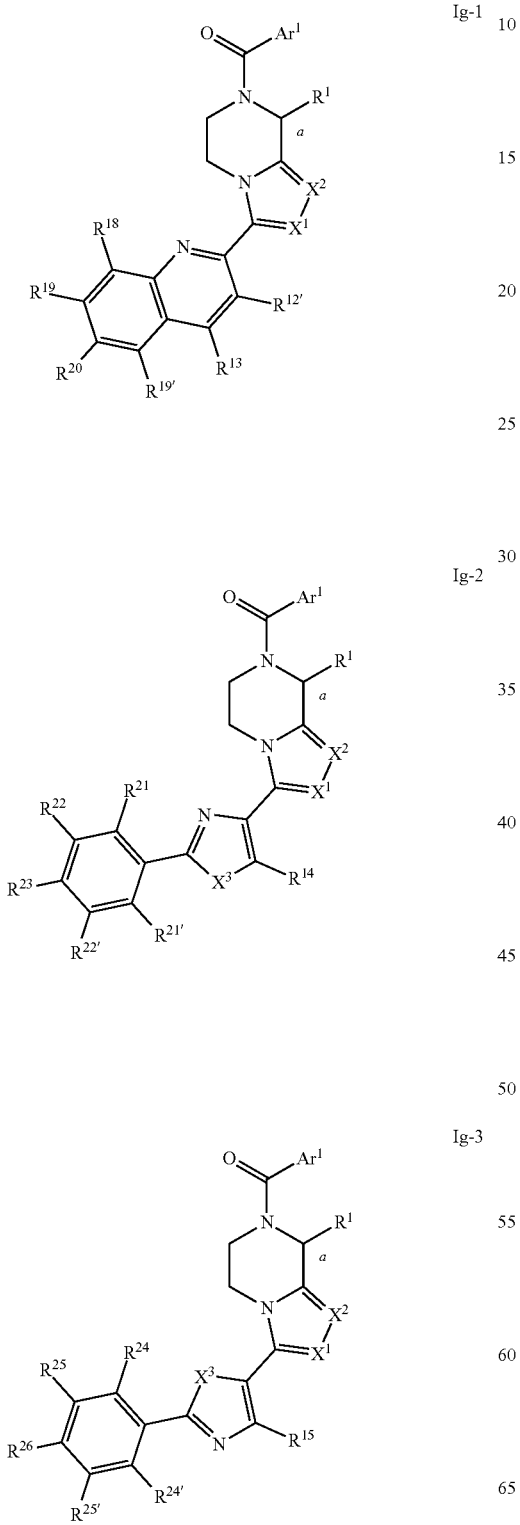
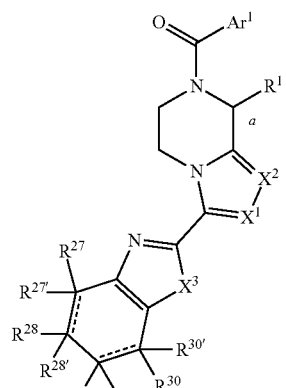
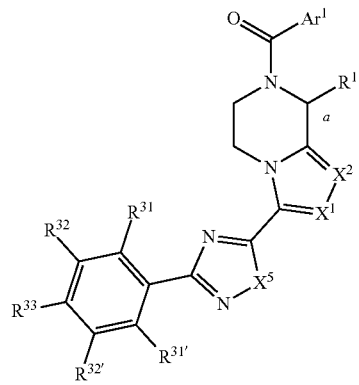
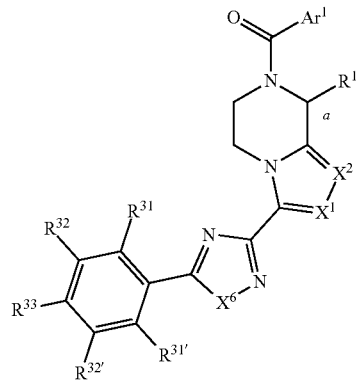
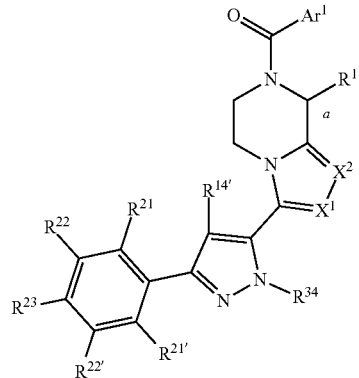

-continued

Ig-8

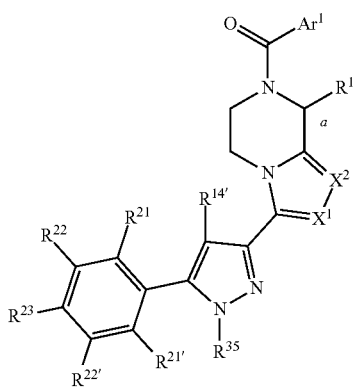

and pharmaceutically acceptable salts, and solvates thereof, wherein
a depicts the bond linking $R^1$ to the piperazine moiety; and
$Ar^1$, $R^1$, $X^1$ and $X^2$ are as defined above in respect to formula Ib; and
$R^{12'}$ and $R^{13}$ are independently selected from H, halo, cyano, alkyl, hydroxyalkyl, haloalkyl, cycloalkyl, heteroalkyl, hydroxyl, alkoxy, haloalkoxy, carboxy, alkoxycarbonyl, alkylcarbonyloxy, alkylcarbonylamino, haloalkylcarbonylamino, acylamino, carbamoyl, alkylcarbamoyl, carbamoylalkyl, carbamoylamino, alkylcarbamoylamino, alkylsulfonyl, haloalkylsulfonyl, sulfamoyl, alkylsulfamoyl, alkylsulfonylamino, haloalkylsulfonylamino, or $R^{13}$ together with $R^{12'}$ forms an alkylenedioxy group or a haloalkylenedioxy group, each of said groups being optionally substituted by one or more group(s) selected from halo, cyano, alkyl, haloalkyl, alkoxy, haloalkoxy, hydroxyl or oxo, preferably, $R^{12'}$ and $R^{13}$ are independently selected from H, halo preferably chloro or fluoro, alkyl preferably methyl, haloalkyl preferably —$CF_3$ or —$CHF_2$, more preferably —$CF_3$, more preferably $R^{12'}$ and $R^{13}$ are H; and
$X^3$ is as defined above in respect to formula If-2, preferably $X^3$ is S; and
$R^{18}$, $R^{19}$, $R^{19'}$ and $R^{20}$ are independently selected from H, halo, cyano, alkyl, haloalkyl, cyclopropyl, alkoxy, haloalkoxy, preferably $R^{19}$, $R^{19'}$ and $R^{20}$ are H and $R^{18}$ is selected from H, fluoro or chloro, more preferably $R^{18}$, $R^{19}$, $R^{19'}$ and $R^{20}$ are H; and
$R^{14}$ is as defined above in respect to formula If-2; and
$R^{21}$, $R^{21'}$, $R^{22}$, $R^{22'}$ and $R^{23}$ are independently selected from H, halo preferably bromo, chloro or fluoro, cyano, alkyl, haloalkyl preferably —$CF_3$ or —$CHF_2$, more preferably —$CF_3$, cyclopropyl, heterocyclyl optionally substituted by alkyl, preferably pyrrolidin-1-yl, piperidin-1-yl, morpholin-4-yl, 4-methylpiperazin-1-yl, hydroxyl, alkoxy preferably methoxy, haloalkoxy, hydroxyalkoxy preferably hydroxyethoxy, alkylamino preferably dimethylamino, alkylsulfonylamino preferably methylsulfonylamino, aminoalkoxy preferably aminoethoxy, alkoxycarbonylaminoalkoxy preferably tert-butyloxycarbonylaminoethoxy, preferably $R^{21}$, $R^{21'}$, $R^{22}$ and $R^{22'}$ are H and $R^{23}$ is selected from bromo, fluoro, chloro, cyano, methyl —$CF_3$, pyrrolidin-1-yl, piperidin-1-yl, morpholin-4-yl, 4-methylpiperazin-1-yl methoxy, dimethylamino or methylsulfonylamino, or $R^{21}$, $R^{21'}$, $R^{22'}$ and $R^{23}$ are H and $R^{22}$ is selected from fluoro, chloro, bromo, cyano, —$CF_3$, dimethylamino or methylsulfonylamino or $R^{21'}$, $R^{22}$, $R^{22'}$ and $R^{23}$ are H and $R^{21}$ is fluoro, chloro, bromo, cyano, hydroxyl, methoxy, hydroxyethoxy, dimethylamino, methylsulfonylamino, aminoethoxy or tert-butoxycarbonylaminoethoxy or $R^{21'}$, $R^{22}$, $R^{22'}$ are H and $R^{21}$ and $R^{23}$ are independently selected from H, chloro or fluoro, or $R^{21'}$, $R^{22'}$, and $R^{23}$ are H and $R^{21}$ and $R^{22}$ are chloro, or $R^{21}$, $R^{21'}$ and $R^{23}$ are H and $R^{22}$ and $R^{22'}$ are chloro, more preferably $R^{21}$, $R^{21'}$, $R^{22}$ and $R^{22'}$ are H and $R^{23}$ is selected from fluoro or chloro, cyano, or $R^{21}$, $R^{21'}$, $R^{22'}$ and $R^{23}$ are H and $R^{22}$ is chloro, or $R^{21'}$, $R^{22}$, $R^{22'}$ and $R^{23}$ are H and $R^{21}$ is chloro, or $R^{21'}$, $R^{22}$, $R^{22'}$ are H and $R^{21}$ and $R^{23}$ are independently selected from H, chloro or fluoro, even more preferably $R^{21}$, $R^{21'}$, $R^{22}$ and $R^{22'}$ are H and $R^{23}$ is selected from H, fluoro, chloro, cyano, or $R^{21}$, $R^{22}$, $R^{22'}$ are H and $R^{21}$ and $R^{23}$ are independently selected from H, chloro or fluoro; and
$R^{15}$ is as defined above in respect to formula If-3, preferably $R^{15}$ is methyl; and
$R^{24}$, $R^{24'}$, $R^{25}$, $R^{25'}$ and $R^{26}$ are independently selected from H, halo preferably chloro or fluoro, haloalkyl preferably —$CF_3$ or —$CHF_2$, more preferably —$CF_3$, cyclopropyl, preferably $R^{24}$, $R^{24'}$, $R^{25}$, $R^{25'}$ are H and $R^{26}$ is selected from H, chloro or fluoro, more preferably $R^{24}$, $R^{24'}$, $R^{25}$, $R^{25'}$ and $R^{26}$ are H; and
$R^{27}$, $R^{28}$, $R^{29}$ and $R^{30}$ are independently selected from H, halo, cyano, alkyl, haloalkyl, cyclopropyl, alkoxy, haloalkoxy, preferably $R^{28}$, $R^{29}$ and $R^{30}$ are H and $R^{27}$ is selected from H, fluoro or chloro, more preferably $R^{27}$, $R^{28}$, $R^{29}$ and $R^{30}$ are H; and
$R^{27'}$, $R^{28'}$, $R^{29'}$ and $R^{30'}$ are absent, or $R^{27'}$, $R^{28'}$, $R^{29'}$ and $R^{30'}$ are H under the condition that $R^{28}$, $R^{29}$ and $R^{30}$ are H and that $R^{27}$ is selected from H, chloro or fluoro preferably $R^{27'}$, $R^{28'}$, $R^{29'}$ and $R^{30'}$ are absent or H under the condition that $R^{27}$, $R^{28}$, $R^{29}$ and $R^{30}$ are H; and
the two bonds represented by the dotted lines in formula Ig-4 are both absent, or both present under the condition that $R^{27'}$, $R^{28'}$, $R^{29'}$ and $R^{30'}$ are absent; and
$X^5$ is as defined above in respect to formula If-5, preferably $X^5$ is O; and
$R^{31}$, $R^{31'}$, $R^{32}$, $R^{32'}$ and $R^{33}$ are independently selected from H, halo preferably chloro or fluoro, cyano, alkyl, haloalkyl preferably —$CF_3$ or —$CHF_2$, more preferably —$CF_3$, cyclopropyl, alkoxy preferably methoxy, haloalkoxy, preferably $R^{31}$, $R^{31'}$, $R^{32}$ and $R^{32'}$ are H and $R^{33}$ is selected from fluoro, chloro, cyano, —$CF_3$ or methoxy, or $R^{31}$, $R^{31'}$, $R^{32'}$ and $R^{33}$ are H and $R^{32}$ is selected from chloro or —$CF_3$, or $R^{31'}$, $R^{32}$, $R^{32'}$ and $R^{33}$ are H and $R^{31}$ is chloro, or $R^{31'}$, $R^{32}$, $R^{32'}$ are H and $R^{31}$ and $R^{33}$ are independently selected from H, chloro or fluoro, or $R^{31'}$, $R^{32'}$, and $R^{33}$ are H and $R^{31}$, and $R^{32}$ are chloro, or $R^{31}$, $R^{31'}$ and $R^{33}$ are H and $R^{32}$ and $R^{32'}$ are chloro, more preferably $R^{31}$, $R^{31'}$, $R^{32}$ and $R^{32'}$ are H and $R^{33}$ is selected from fluoro, chloro or cyano or $R^{31}$, $R^{31'}$, $R^{32'}$ and $R^{33}$ are H and $R^{32}$ is chloro, or $R^{31'}$, $R_{32}$, $R^{32'}$ and $R^{33}$ are H and $R^{31}$ is chloro, or $R^{31'}$, $R^{32}$, $R^{32'}$ are H and $R^{31}$ and $R^{33}$ are independently selected from H, chloro or fluoro, even more preferably $R^{31}$, $R^{31'}$, $R^{32}$ and $R^{32'}$ are H and $R^{33}$ is selected from H, fluoro or chloro, or $R^{31'}$, $R^{32}$, $R^{32'}$ are H and $R^{31}$ and $R^{33}$ are fluoro; and
$X^6$ is as defined above in respect to formula If-6; and
$R^{14'}$ is as defined above in respect to formulae If-7 and If-8, preferably $R^{14'}$ is H; and
$R^{34}$ and $R^{35}$ are as defined above in respect to formula If-7; and
wherein,
  in formula Ig-1 when:
    $R^1$ is H, and
    $X^2$ is N, and
    $Ar^1$ is a 6-membered aryl optionally substituted by one or more group(s) selected from halo, cyano, C1-C3 alkyl, C1-haloalkyl, and $R^{12'}$, $R^{13}$, $R^{18}$, $R^{19}$, $R^{19'}$ and $R^{20}$ are independently selected from H, halo, C1-3 alkyl, hydroxyl, methoxy, then, $Ar^1$ is phenyl, 3-halophenyl, 4-halophenyl, 2,3-dichlorophenyl, 3,4-dihalophenyl, 3,4,5-trihalophenyl, 4-cyanophenyl, 4-(C1-C3 alkyl)phenyl, 4-(C1 haloalkyl) phenyl, preferably $Ar^1$ is phenyl, 4-fluorophenyl, 4-chlorophenyl, 4-trifluoromethylphenyl, 3-chlorophenyl, 3-fluorophenyl, 3,4-dichlorophenyl, 3,4-difluorophenyl, 3,4,5-trifluorophenyl, 4-chloro-3-fluorophenyl, 3-chloro-4-fluorophenyl, 4-cyanophenyl, 4-tolyl, 4-trifluoromethylphenyl, and $R^{12'}$, $R^{13}$, $R^{18}$, $R^{19}$, $R^{19'}$ and $R^{20}$ are H, or $R^{12'}$, $R^{13}$, $R^{19}$, $R^{19'}$, $R^{20}$ are H and $R^{18}$ is fluoro, chloro, and in formula Ig-4 when $R^1$ is H, and $X^2$ is N, and $Ar^1$ is a 6-membered aryl optionally substituted by one or more group(s) selected from halo, cyano, C1-C3 alkyl, C1-haloalkyl, and $R^{27}$, $R^{28}$, $R^{29}$ and $R^{30}$ are independently selected from H, halo, C1-3 alkyl, methoxy, and $R^{27'}$, $R^{28'}$, $R^{29'}$ and $R^{30'}$ are absent or H under the condition that $R^{28}$, $R^{29}$ and $R^{30}$ are H and $R^{27}$ is selected from H, chloro or fluoro, then $Ar^1$ is phenyl, 3-halophenyl, 4-halophenyl, 2,3-dichlorophenyl, 3,4-dihalophenyl, 3,4,5-trihalophenyl, 4-cyanophenyl, 4-(C1-C3 alkyl)phenyl, 4-(C1 haloalkyl) phenyl, preferably $Ar^1$ is phenyl, 4-fluorophenyl, 4-chlorophenyl, 3-chlorophenyl, 3-fluorophenyl, 3,4-dichlorophenyl, 3,4-difluorophenyl, 3,4,5-trifluorophenyl, 4-chloro-3-fluorophenyl, 3-chloro-4-fluorophenyl, 4-cyanophenyl, 4-tolyl, 4-trifluoromethylphenyl, and $R^{27}$, $R^{28}$, $R^{29}$ and $R^{30}$ are H, and $R^{27'}$, $R^{28'}$, $R^{29'}$ and $R^{30'}$ are absent or H under the condition that $R^{27}$, $R^{28}$, $R^{29}$ and $R^{30}$ are H.

In one embodiment, compounds of formulae Ig-1, Ig-2, Ig-3, Ig-4, Ig-5, Ig-6, Ig-7 and Ig-8 are those wherein $X^1$ and $X^2$ are N.

In another embodiment, compounds of formulae Ig-1, Ig-2, Ig-3, Ig-4, Ig-5, Ig-6, Ig-7 and Ig-8 are those wherein bond a is drawn as a dotted wedge, $R^1$ is selected from the group consisting of $C_1$-$C_4$ alkyl, aryl or aralkyl group, each of said alkyl, aryl or aralkyl groups being optionally substituted by one or more group(s) selected from halo or hydroxyl, and/or $X^1$ and $X^2$ are N.

In yet another embodiment, compounds of formulae Ig-1, Ig-2, Ig-3, Ig-4, Ig-5, Ig-6, Ig-7 and Ig-8 are those wherein bond a is drawn as a solid wedge, $R^1$ is selected from the group consisting of $C_1$-$C_4$ alkyl, aryl or aralkyl group, each of said alkyl, aryl or aralkyl groups being optionally substituted by one or more group(s) selected from halo or hydroxyl, and/or $X^1$ and $X^2$ are N.

Other preferred compounds of formulae If-1 and If-2, are those of formulae Ih-1 and Ih-2 respectively:

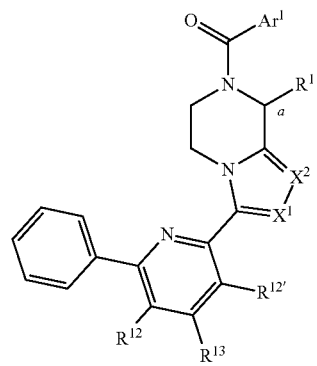

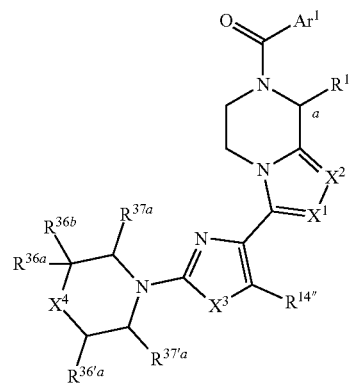

and pharmaceutically acceptable salts and solvates thereof, wherein a designates the bond linking $R^1$ to the piperazine moiety; and $Ar^1$, $R^1$, $X^1$ and $X^2$ are as defined above in respect to formula Ib; and $R^{12}$, $R^{12'}$ and $R^{13}$ are as defined above in respect to formula If-1, preferably $R^{12}$, $R^{12'}$ and $R^{13}$ are H; and $R^{14''}$ is H or methyl; and $X^3$ is as defined above in respect to formula If-2, preferably $X^3$ is S; and $X^4$ is O, $CH_2$, $CF_2$, $C(CH_3)_2$, N—(C1-C3 alkyl) N-phenyl, preferably $X^4$ is O, $CH_2$, $CF_2$, N-methyl or N-phenyl; and $R^{36a}$, $R^{36b}$, $R^{36'a}$, $R^{37a}$ and $R^{37'a}$ are independently selected from H, C1-C3 alkyl, alkoxyC1-C3 alkyl, preferably $R^{36a}$, $R^{36b}$, $R^{37a}$ and $R^{37'a}$ are H and $R^{36'a}$ is H, methyl, methoxyethyl, or $R^{36a}$, $R^{36b}$, $R^{37'a}$ are H and $R^{37a}$ and $R^{36'a}$ are methyl, or $R^{36b}$, $R^{37a}$, $R^{37'a}$ are H and $R^{36a}$ and $R^{36'a}$ are methyl, or $R^{36'a}$, $R^{37a}$, $R^{37'a}$ are H and $R^{36a}$ and $R^{36b}$ are methyl, or $R^{36a}$, $R^{36b}$, $R^{36'a}$, $R^{37a}$ are H and and $R^{37'a}$ is methoxymethyl.

In one embodiment, compounds of formula Ih-1 are those wherein $X^1$ and $X^2$ are N.

In another embodiment, compounds of formula Ih-1 are those wherein bond a is drawn as a dotted wedge and/or $X^1$ and $X^2$ are N.

In another embodiment, compounds of formula Ih-1 are those wherein bond a is drawn as a solid wedge and/or $X^1$ and $X^2$ are N.

In another embodiment, compounds of formula Ih-2 are those wherein $X^1$ and $X^2$ are N.

In another embodiment, compounds of formula Ih-2 are those wherein bond a is drawn as a dotted wedge and/or $X^1$ and $X^2$ are N. In one variant of this embodiment, compounds of formula Ih-2 are those wherein bond a is drawn as a dotted wedge, $X^1$ and $X^2$ are N and $R^{36a}$, $R^{36b}$, $R^{36'a}$, $R^{37a}$ and $R^{37'a}$ are H.

In yet another embodiment, compounds of formula Ih-2 are those wherein bond a is drawn as a solid wedge and/or $X^1$ and $X^2$ are N. In one variant of this embodiment, compounds of formula Ih-2 are those wherein bond a is drawn as a solid wedge, $X^1$ and $X^2$ are N and $R^{36a}$, $R^{36b}$, $R^{36'a}$, $R^{37a}$ and $R^{37'a}$ are H.

Other preferred compounds of formula Ic are those of formulae Ii-1, Ii-2, Ii-3, Ii-4, Ii-5, Ii-6, Ii-7, Ii-8, Ij-1, Ij-2, Ij-3, Ij-4, Ij-5, Ij-6, Ij-7, Ij-8, Ik-1, Ik-2, Ik-3, Ik-4 Ik-5, Ik-6, Ik-7, Ik-8, Ii'-1, Ii'-2, Ii'-3, Ii'-4, Ii'-5, Ii'-6, Ii'-7 and Ii'-8,

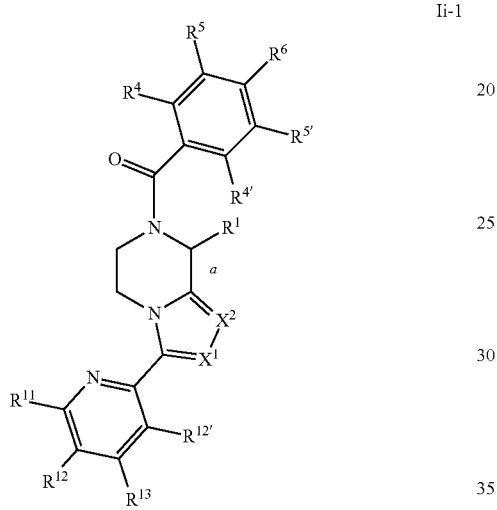

Ii-1

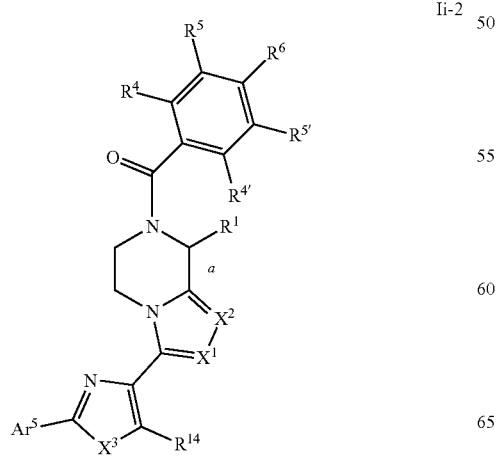

Ii-2

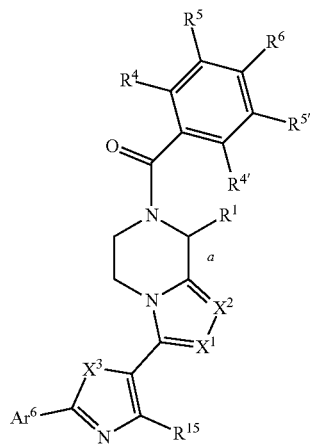

Ii-3

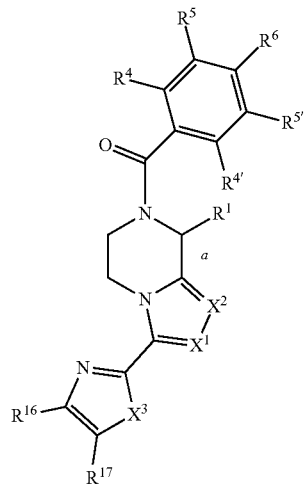

Ii-4

Ii-5

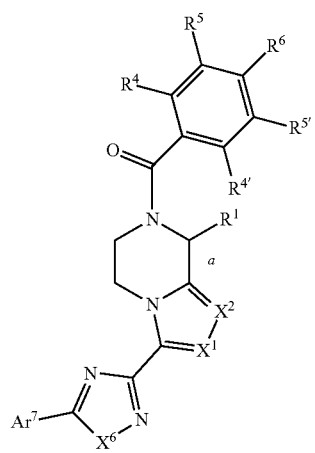
Ii-6
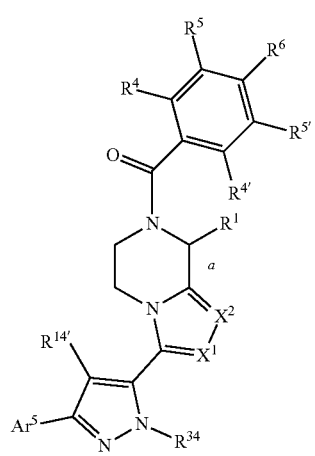
Ii-7
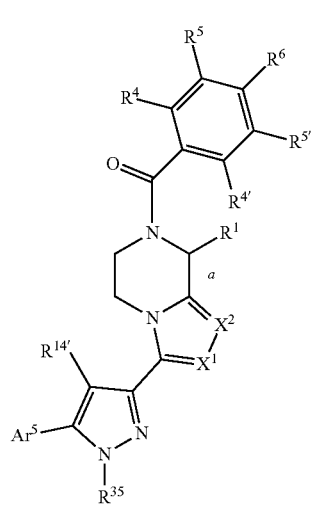
Ii-8
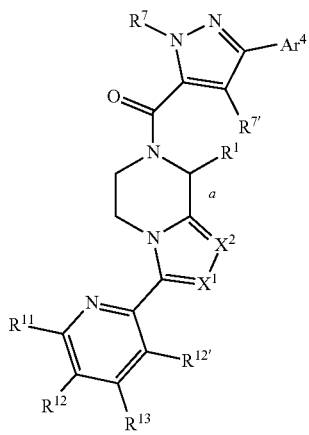
Ij-1
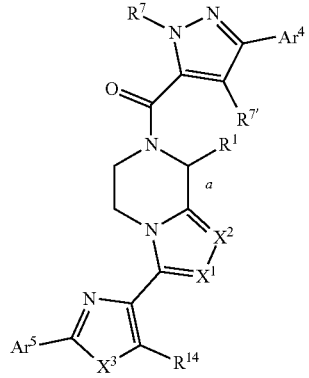
Ij-2
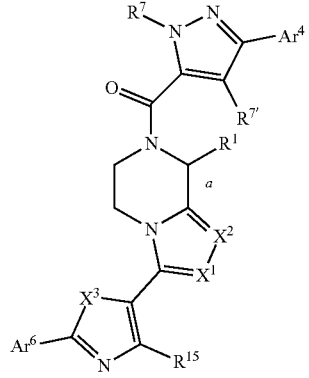
Ij-3
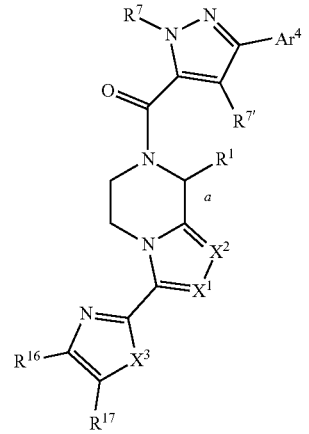
Ij-4

Ij-5
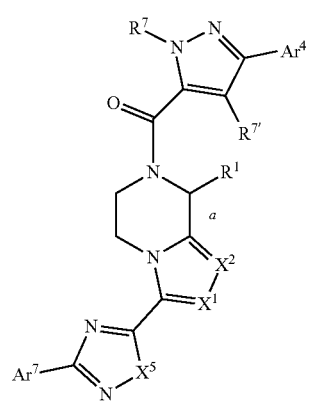
Ij-6
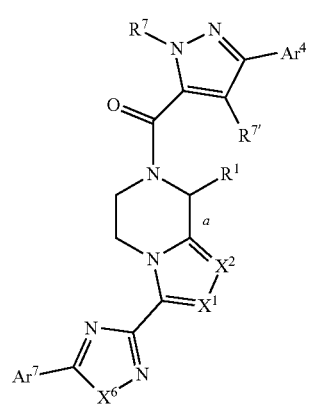
Ij-7
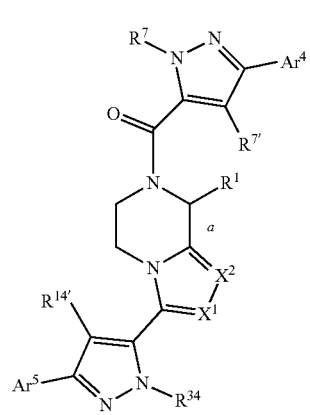
Ij-8
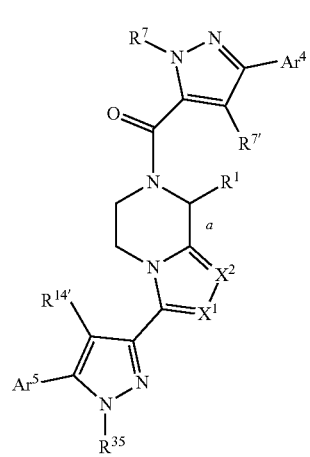
Ik-1
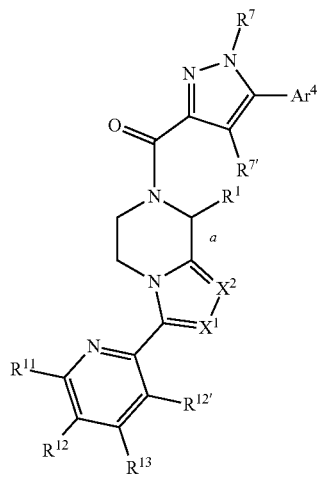
Ik-2
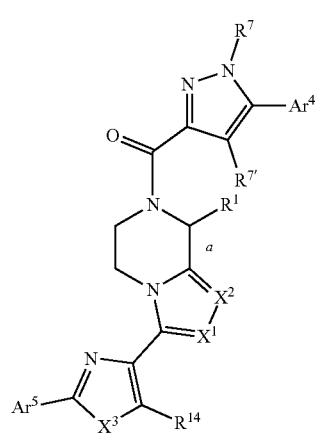
Ik-3
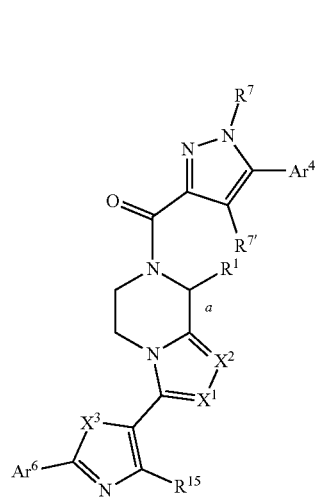

Ik-4
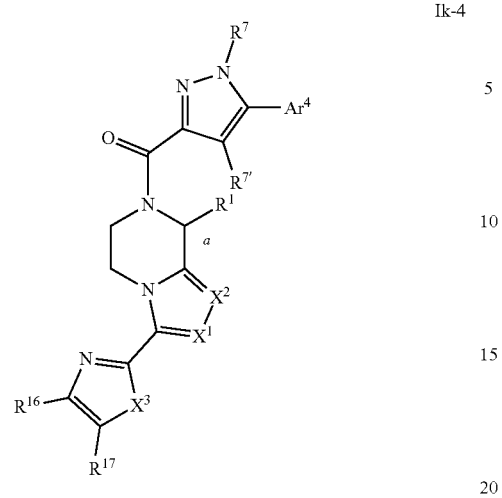
Ik-5
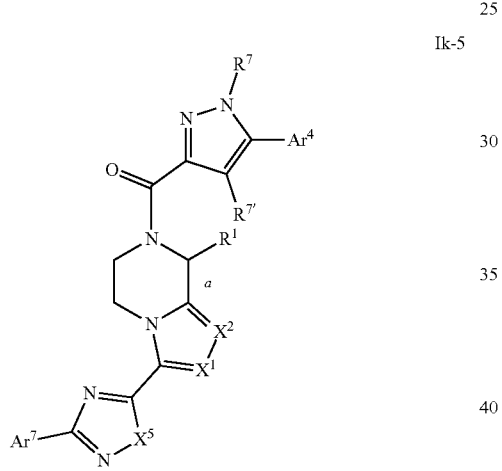
Ik-6
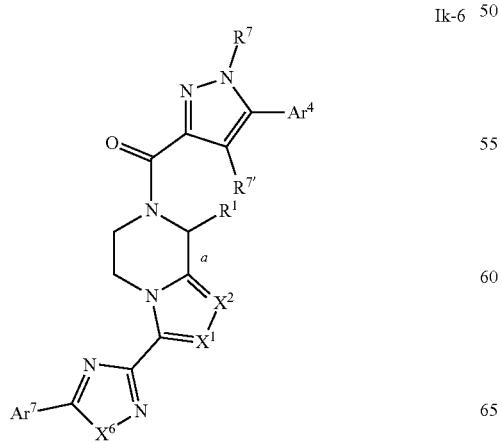
Ik-7
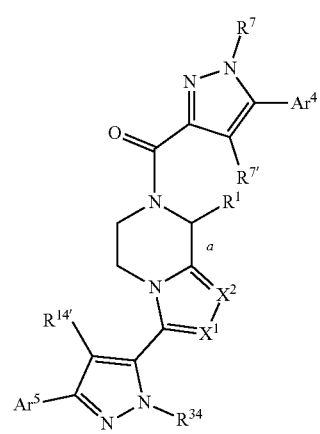
Ik-8
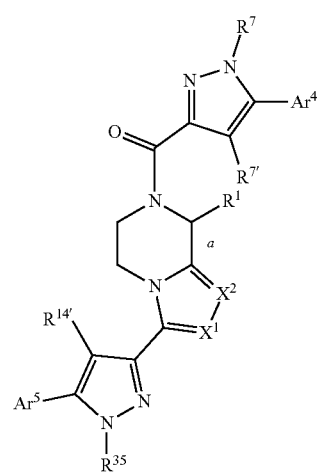
Ii'-1
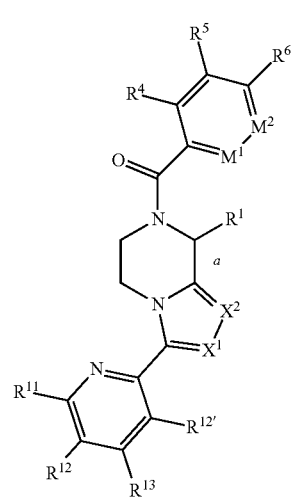

Ii'-2
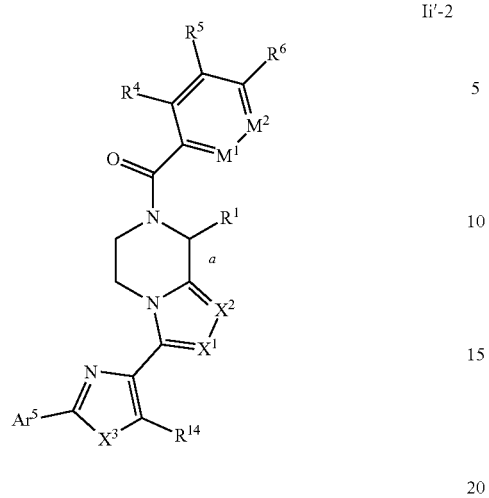
Ii'-5
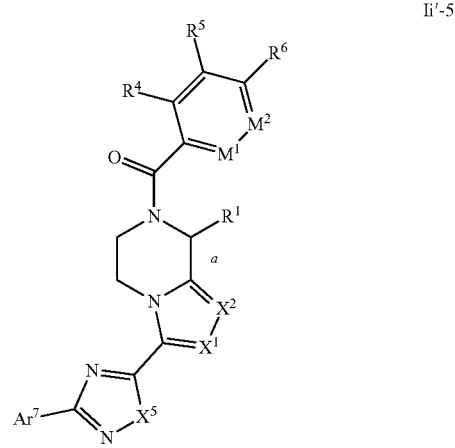
Ii'-3
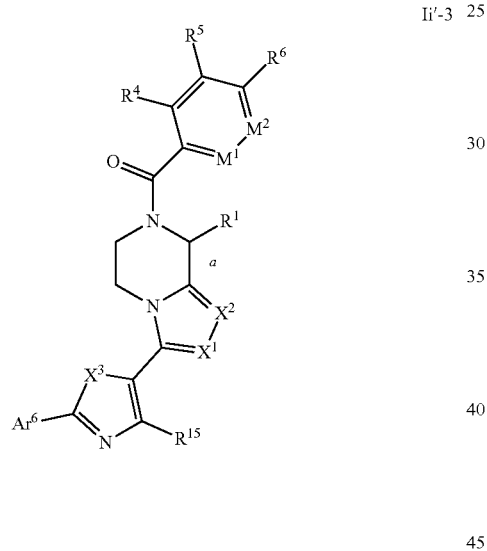
Ii'-6
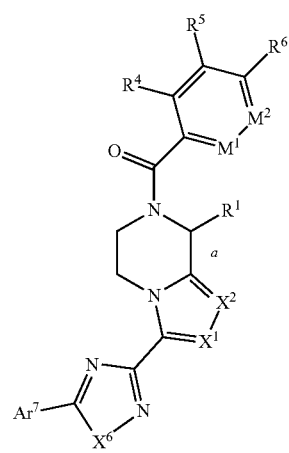
Ii'-4
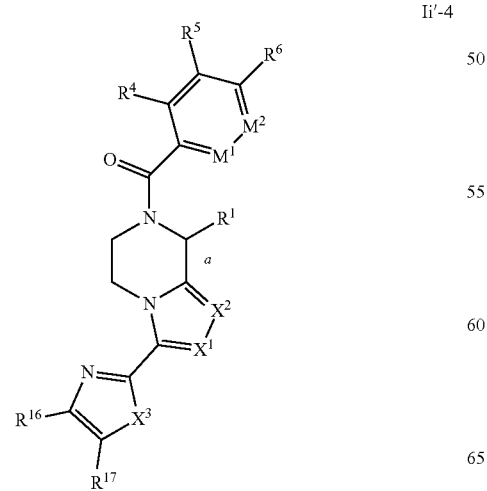
Ii'-7
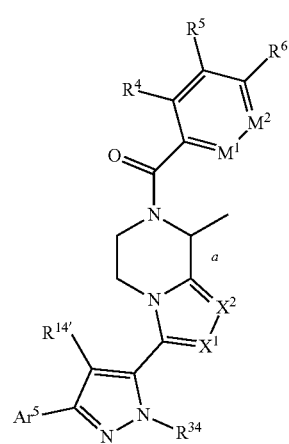

-continued

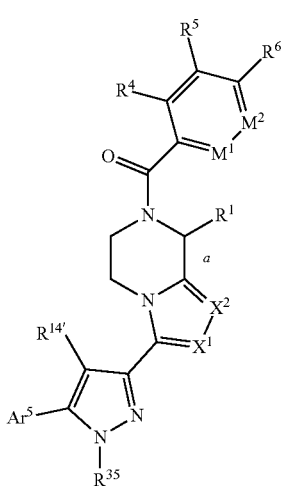

Ii'-8 and pharmaceutically acceptable salts and solvates thereof, wherein
a depicts the bond linking $R^1$ to the piperazine moiety; and
$R^1$, $X^1$ and $X^2$ are as defined above in respect to formula Ib; and
$R^4$, $R^{4'}$, $R^5$, $R^{5'}$ and $R^6$ are as defined above in respect to formula Id-1; and
$Ar^4$, $R^7$ and $R^{7'}$ are as defined above in respect to formulae Id-2 and Id-3; and
$M^1$ and $M^2$ are as defined above in respect to formula Id-4; and
$R^{11}$, $R^{12}$, $R^{12'}$ and $R^{13}$ are as defined above in respect to formula If-1; and
$Ar^5$, $R^{14}$ and $X^3$ are as defined above in respect to formula If-2; and
$Ar^6$ and $R^{15}$ are as defined above in respect to formula If-3; and
$R^{16}$ and $R^{17}$ are as defined above in respect to formula If-4; and
$Ar^7$ and $X^5$ are are as defined above in respect to formula If-5; and
$X^6$ is as defined above in respect to formula If-6; and
$R^{14'}$, $R^{34}$ and $R^{35}$ are as defined above in respect to formulae If-7 and If-8.

Among the compounds of formulae Ii-1, Ii-2, Ii-3, Ii-4, Ii-5, Ii-6, Ii-7, Ii-8, Ij-1, Ij-2, Ij-3, Ij-4, Ij-5, Ij-6, Ij-7, Ij-8, Ik-1, Ik-2, Ik-3, Ik-4 Ik-5, Ik-6, Ik-7, Ik-8, Ii'-1, Ii'-2, Ii'-3, Ii'-4, Ii'-5, Ii-6, Ii'-7 and Ii'-8, compounds of formulae Ii-1, Ii-2, Ii-3, Ii-4, Ii-5, Ii-6, Ii-7, Ii-8, Ii'-1, Ii'-2, Ii'-3, Ii'-4, Ii'-5, Ii-6, Ii'-7 and Ii'-8 are preferred.
In one embodiment, compounds of Ii-1, Ii-2, Ii-3, Ii-4, Ii-5, Ii-6, Ii-7, Ii-8, Ij-1, Ij-2, Ij-3, Ij-4, Ij-5, Ij-6, Ij-7, Ij-8, Ik-1, Ik-2, Ik-3, Ik-4 Ik-5, Ik-6, Ik-7, Ik-8, Ii'-1, Ii'-2, Ii'-3, Ii'-4, Ii'-5, Ii-6, Ii'-7 and Ii'-8 are those wherein $X^1$ and $X^2$ are N.
In another embodiment, compounds of formulae Ii-1, Ii-2, Ii-3, Ii-4, Ii-5, Ii-6, Ii-7, Ii-8, Ij-1, Ij-2, Ij-3, Ij-4, Ij-5, Ij-6, Ij-7, Ij-8, Ik-1, Ik-2, Ik-3, Ik-4 Ik-5, Ik-6, Ik-7, Ik-8, Ii'-1, Ii'-2, Ii'-3, Ii'-4, Ii'-5, Ii-6, Ii-7 and Ii-8 are those wherein bond a is drawn as a dotted wedge, $R^1$ is selected from the group consisting of $C_1$-$C_4$ alkyl, aryl or aralkyl group, each of said alkyl, aryl or aralkyl groups being optionally substituted by one or more group(s) selected from halo or hydroxyl, and/or $X^1$ and $X^2$ are N.
In yet another embodiment, compounds of formulae Ii-1, Ii-2, Ii-3, Ii-4, Ii-5, Ii-6, Ii-7, Ii-8, Ij-1, Ij-2, Ij-3, Ij-4, Ij-5, Ij-6, Ij-7, Ij-8, Ik-1, Ik-2, Ik-3, Ik-4 Ik-5, Ik-6, Ik-7, Ik-8, Ii'-1, Ii'-2, Ii'-3, Ii'-4, Ii'-5, Ii-6, Ii-7 and Ii-8 are those wherein bond a is drawn as a solid wedge, $R^1$ is selected from the group consisting of $C_1$-$C_4$ alkyl, aryl or aralkyl group, each of said alkyl, aryl or aralkyl groups being optionally substituted by one or more group(s) selected from halo or hydroxyl, and/or $X^1$ and $X^2$ are N.

Preferred compounds of formulae Ii-1, Ii-2, Ii-3, Ii-4, Ii-5, Ii-6, Ii-7, Ii-8, Ii'-1, Ii'-2, Ii'-3, Ii'-4, Ii'-5, Ii'-6, Ii'-7 and Ii'-8 are those of formulae Il-1, Il-2, Il-3, Il-4, Il-5, Il-6, Il-7, Il-8, Il'-1, Il'-2, Il'-3, Il'-4, Il'-5, Il'-6, Il'-7 and Il'-8 respectively:

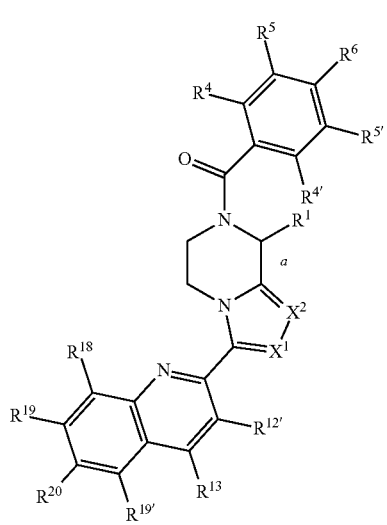

Il-1

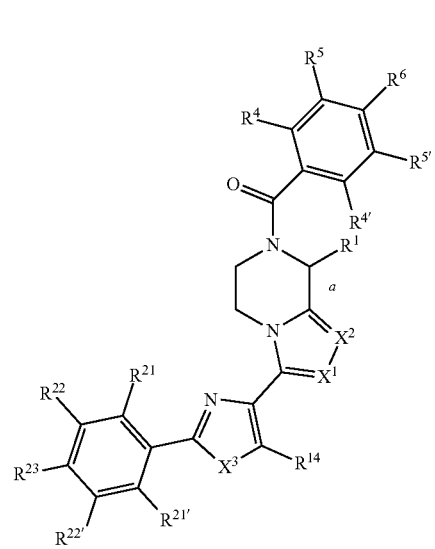

Il-2

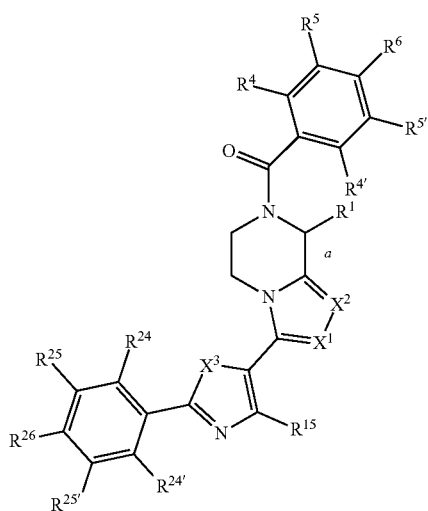
II-3
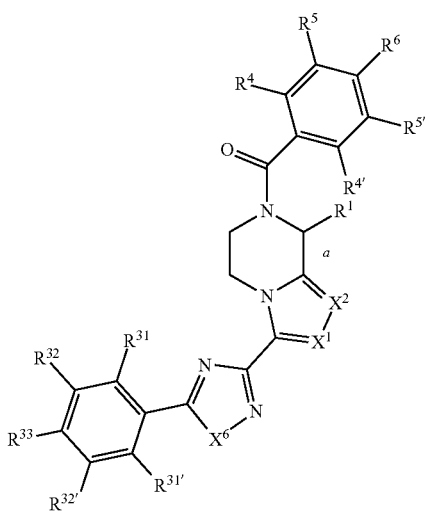
II-6
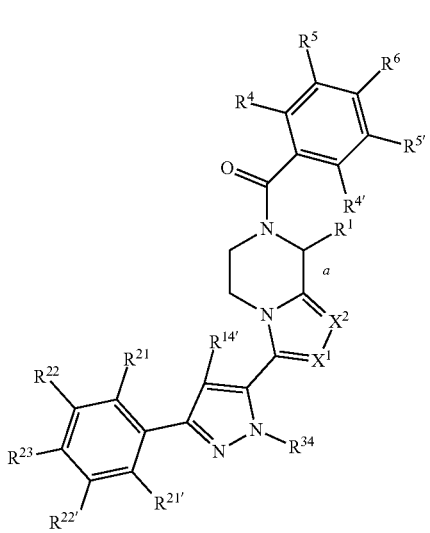
II-4
II-7
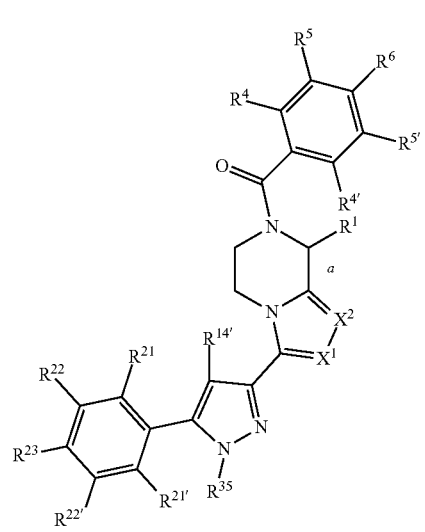
II-5
II-8

II'-1
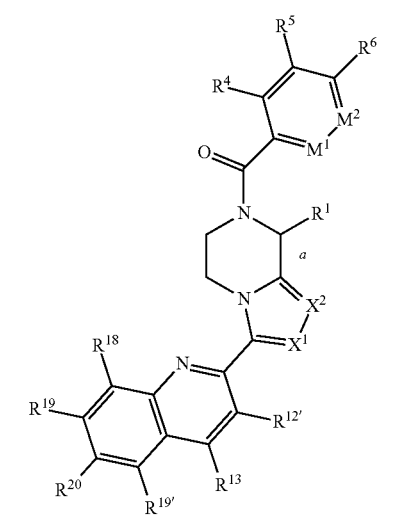
II'-2
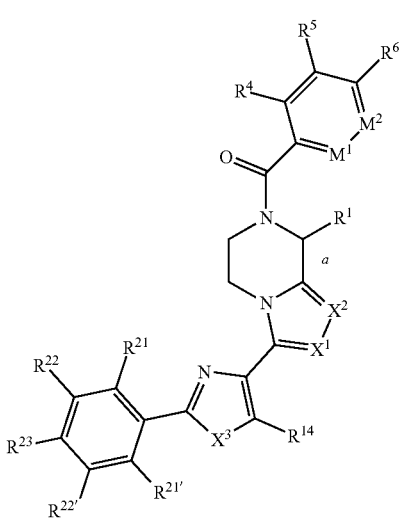
II'-3
II'-4
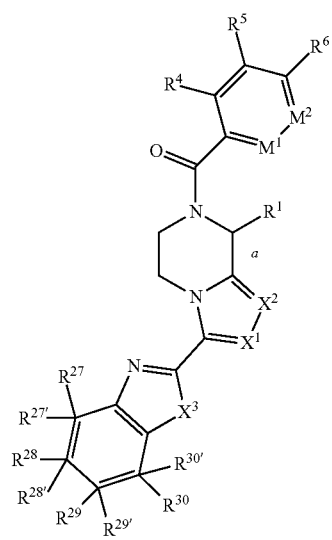
II'-5
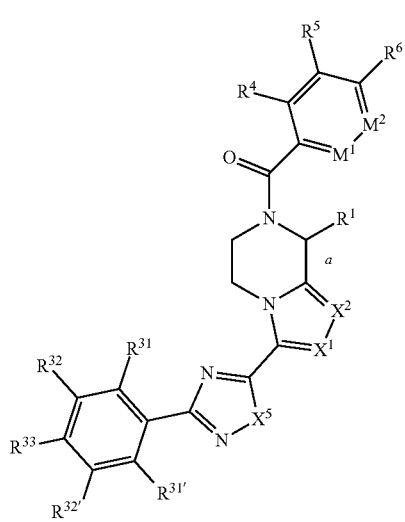
II'-6
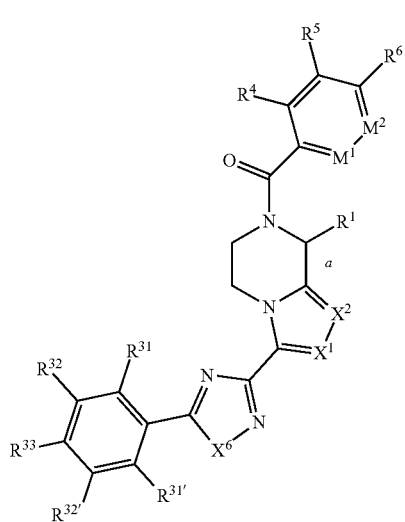

-continued

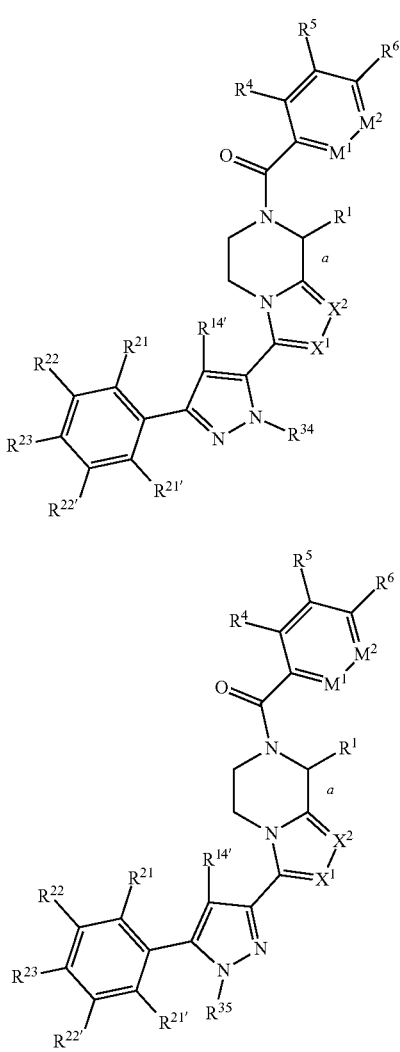

Il'-7

Il'-8 and pharmaceutically acceptable salts and solvates thereof, wherein
a depicts the bond linking $R^1$ to the piperazine moiety; and
$R^1$, $X^1$ and $X^2$ are as defined above in respect to formula Ib; and
$R^4$, $R^{4'}$, $R^5$, $R^{5'}$ and $R^6$ are as defined above in respect to formula Id-1; and
$M^1$ and $M^2$ are as defined above in respect to formula Id-4; and
$R^{12'}$, $R^{13}$, $R^{14}$, $R^{14'}$, $R^{15}$, $R^{18}$, $R^{19}$, $R^{19'}$, $R^{20}$, $R^{21}$, $R^{21'}$, $R^{22}$, $R^{22'}$, $R^{23}$, $R^{24}$, $R^{24'}$, $R^{25}$, $R^{25'}$, $R^{26}$, $R^{27}$, $R^{27'}$, $R^{28}$, $R^{28'}$, $R^{29}$, $R^{29'}$, $R^{30}$, $R^{30'}$, $R^{31}$, $R^{31'}$, $R^{32}$, $R^{32'}$, $R^{33}$, $R^{34}$, $R^{35}$, $X^3$, $X^5$; $X^6$; and the two bonds represented by the dotted lines are as defined above in respect of formulae Ig-1, Ig-2, Ig-3, Ig-4, Ig-5, Ig-6, Ig-7 and Ig-8.

In one embodiment, compounds of formulae Il-1, Il-2, Il-3, Il-4, Il-5, Il-6, Il-7, Il-8, Il'-1, Il'-2, Il'-3, Il'-4, Il'-5, Il'-6, Il'-7 and Il'-8 are those wherein $X^1$ and $X^2$ are N.

In another embodiment, compounds of formulae Il-1, Il-2, Il-3, Il-4, Il-5, Il-6, Il-7, Il-8, Il'-1, Il'-2, Il'-3, Il'-4, Il'-5, Il'-6, Il'-7 and Il'-8 are those wherein bond a is drawn as a dotted wedge, $R^1$ is selected from the group consisting of $C_1$-$C_4$ alkyl, aryl or aralkyl group, each of said alkyl, aryl or aralkyl groups being optionally substituted by one or more group(s) selected from halo or hydroxyl, and/or $X^1$ and $X^2$ are N.

In yet another embodiment, compounds of formulae Il-1, Il-2, Il-3, Il-4, Il-5, Il-6, Il-7, Il-8, Il'-1, Il'-2, Il'-3, Il'-4, Il'-5, Il'-6, Il'-7 and Il'-8 are those wherein bond a is drawn as a solid wedge, $R^1$ is selected from the group consisting of $C_1$-$C_4$ alkyl, aryl or aralkyl group, each of said alkyl, aryl or aralkyl groups being optionally substituted by one or more group(s) selected from halo or hydroxyl, and/or $X^1$ and $X^2$ are N.

Preferred compounds of formulae Il-1, Il-2, Il-3, Il-4, Il-5, Il-6, Il-7, Il-8, Il'-1, Il'-2, Il'-3, Il'-4, Il'-5, Il'-6, Il'-7 and Il'-8 are those of formulae Im-1, Im-2, Im-3, Im-4, Im-5, Im-6, Im-7, Im-8, Im'-1, Im'-2, Im'-3, Im'-4, Im'-5, Im'-6, Im'-7 and Im'-8 respectively:

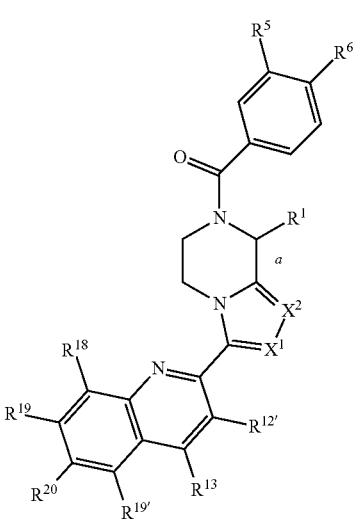

Im-1

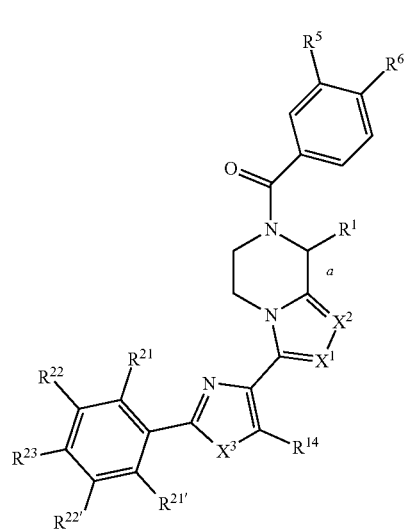

Im-2

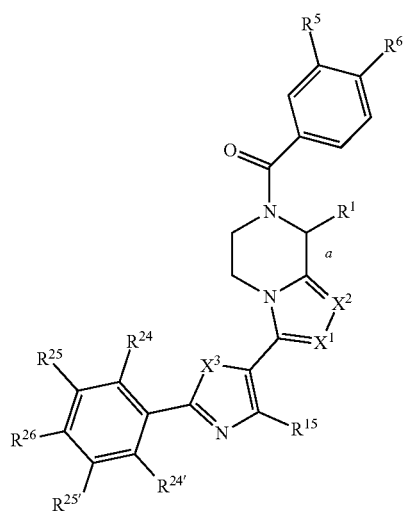
Im-3
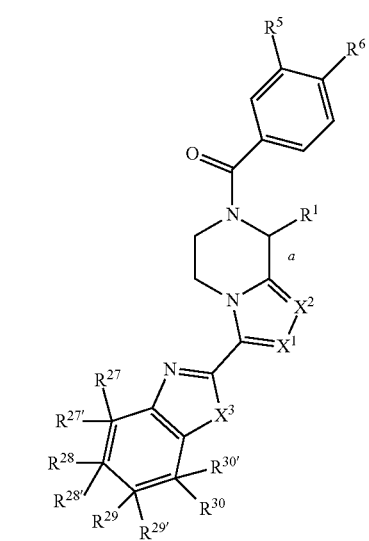
Im-4
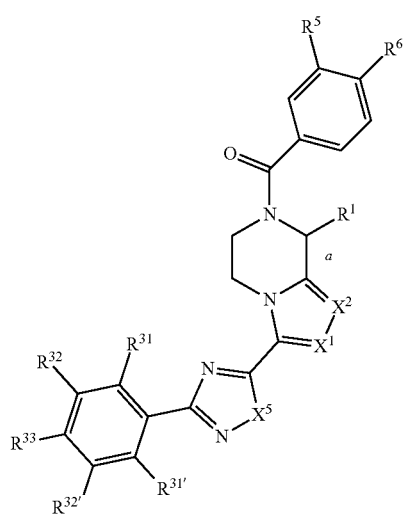
Im-5
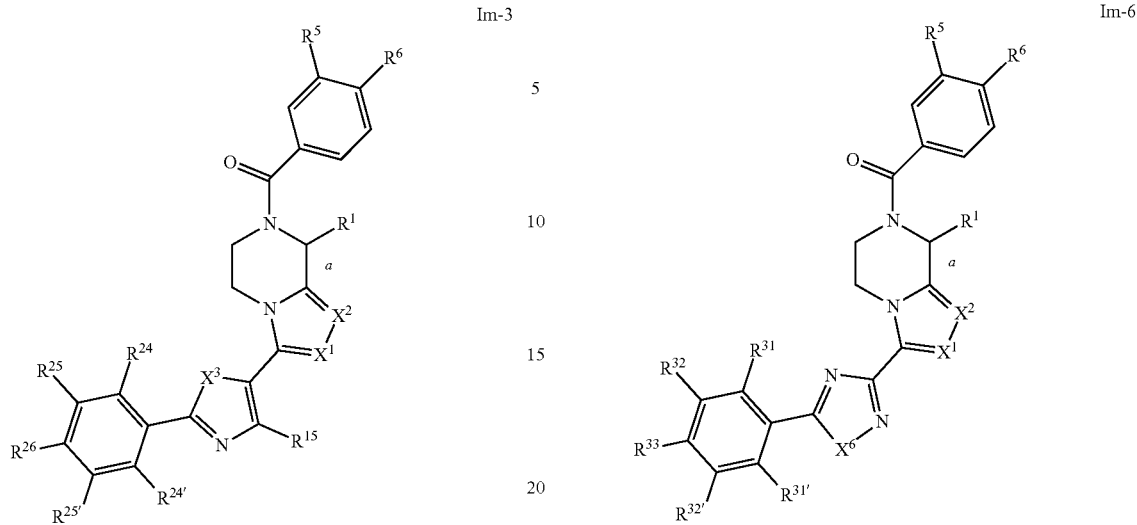
Im-6
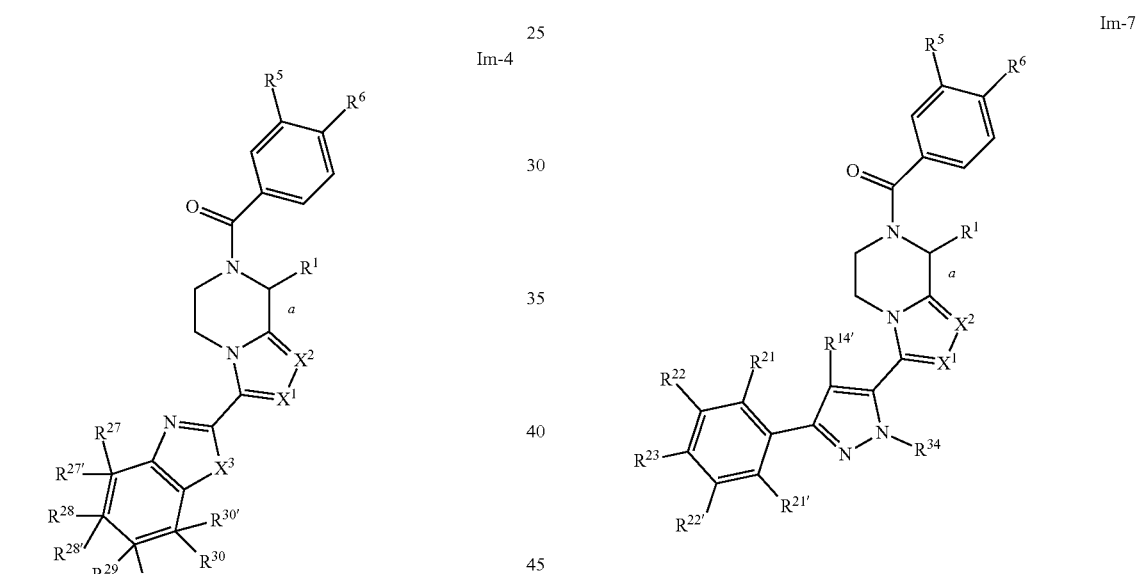
Im-7
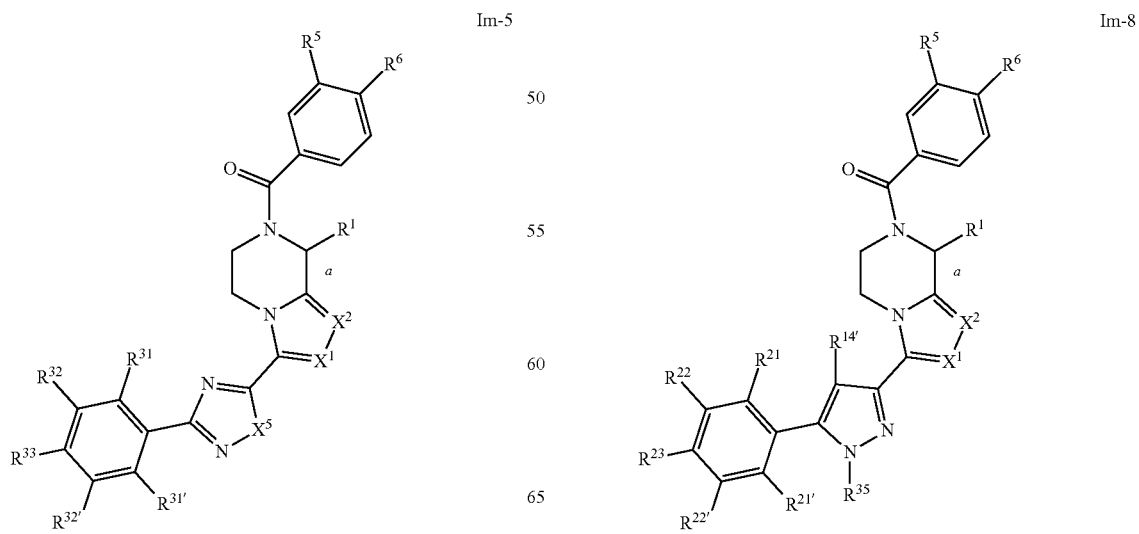
Im-8

-continued
Im'-1
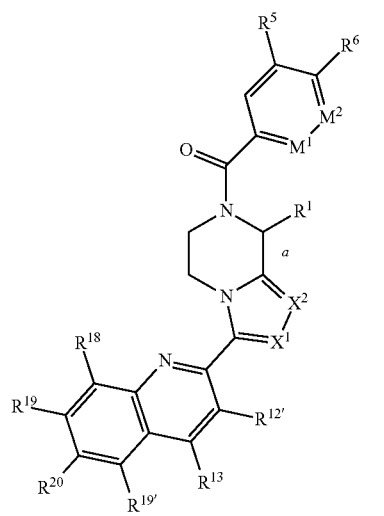
Im'-2
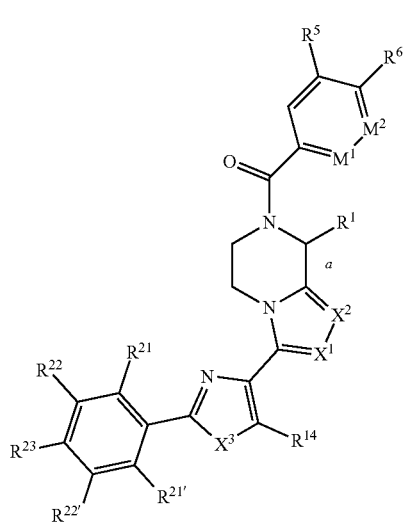
Im'-3
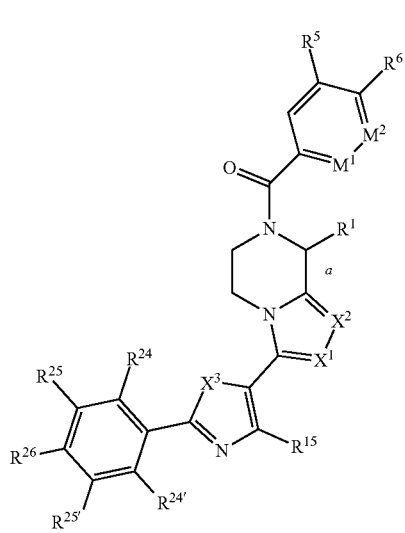
-continued
Im'-4
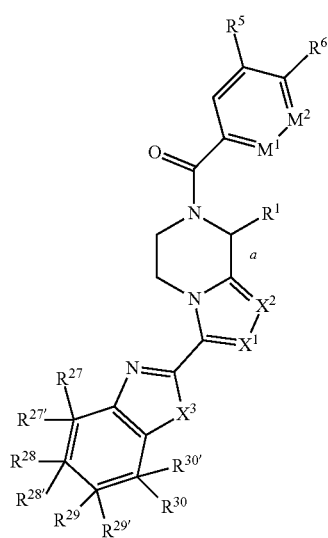
Im'-5
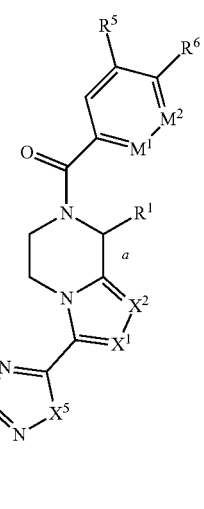
Im'-6
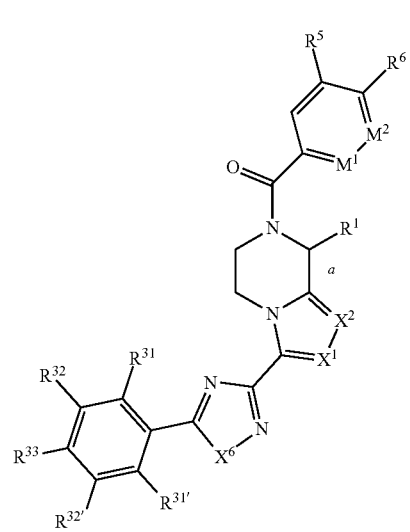

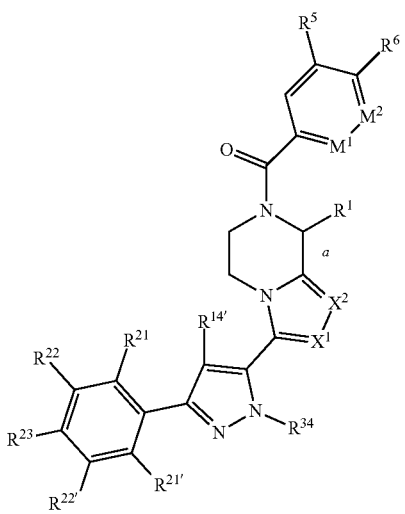

Im'-7

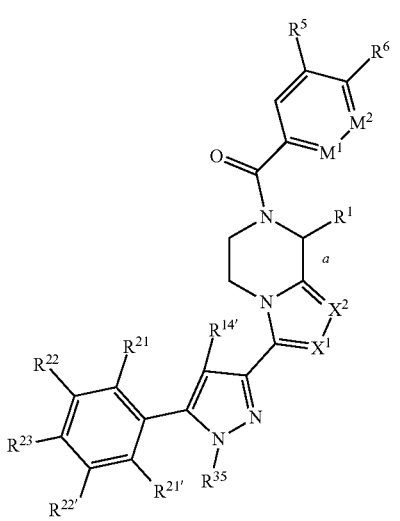

Im'-8 and pharmaceutically acceptable salts and solvates thereof, wherein:

a designates the bond linking $R^1$ to the piperazine moiety; and $R^1$, $X^1$ and $X^2$ are as defined above in respect to formula Ib; and $R^5$ and $R^6$ are as defined above in respect to formula Ie-1; and $M^1$ and $M^2$ are as defined above in respect to formula Ie-3; and $R^{12'}$, $R^{13}$, $R^{14}$, $R^{14'}$, $R^{15}$, $R^{18}$, $R^{19}$, $R^{19'}$, $R^{20}$, $R^{21}$, $R^{21'}$, $R^{22}$, $R^{22'}$, $R^{23}$, $R^{24}$, $R^{24'}$, $R^{25}$, $R^{25'}$, $R^{26}$, $R^{27}$, $R^{27'}$, $R^{28}$, $R^{28'}$, $R^{29}$, $R^{29'}$, $R^{30}$, $R^{30'}$, $R^{31}$, $R^{31'}$, $R^{32}$, $R^{32'}$, $R^{33}$, $R^{34}$, $R^{35}$, $X^3$, $X^5$, $X^6$; and the two bonds represented by the dotted lines are as defined above in respect to formulae Ig-1, Ig-2, Ig-3, Ig-4, Ig-5, Ig-6, Ig-7 and Ig-8.

In one embodiment, compounds of formulae Im-1, Im-2, Im-3, Im-4, Im-5, Im-6, Im-7, Im-8, Im'-1, Im'-2, Im'-3, Im'-4, Im'-5, Im'-6, Im'-7 and Im'-8 are those wherein $X^1$ and $X^2$ are N.

In another embodiment, compounds of formulae Im-1, Im-2, Im-3, Im-4, Im-5, Im-6, Im-7, Im-8, Im'-1, Im'-2, Im'-3, Im'-4, Im'-5, Im'-6, Im'-7 and Im'-8 are those wherein bond a is drawn as a dotted wedge, $R^1$ is selected from the group consisting of $C_1$-$C_4$ alkyl, aryl or aralkyl group, each of said alkyl, aryl or aralkyl groups being optionally substituted by one or more group(s) selected from halo or hydroxyl, and/or $X^1$ and $X^2$ are N.

In yet another embodiment, compounds of Im-1, Im-2, Im-3, Im-4, Im-5, Im-6, Im-7, Im-8, Im'-1, Im'-2, Im'-3, Im'-4, Im'-5, Im'-6, Im'-7 and Im'-8 are those wherein bond a is drawn as a solid wedge, $R^1$ is selected from the group consisting of $C_1$-$C_4$ alkyl, aryl or aralkyl group, each of said alkyl, aryl or aralkyl groups being optionally substituted by one or more group(s) selected from halo or hydroxyl, and/or $X^1$ and $X^2$ are N.

Other preferred compounds of formula I are those of formulae In, Io, Ip and In'

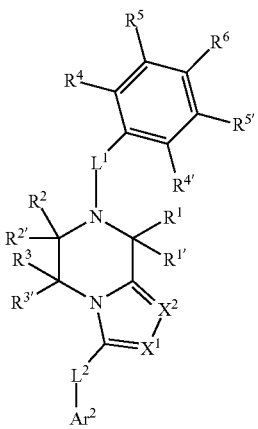

In

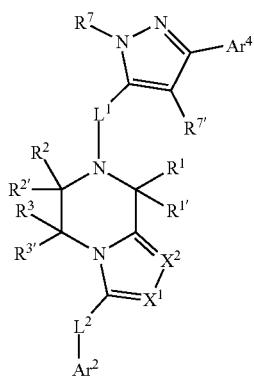

Io

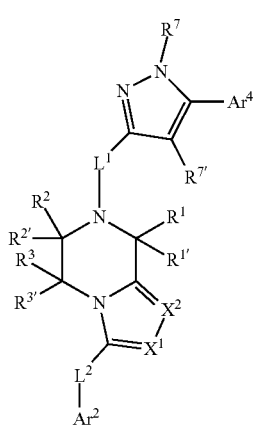

Ip

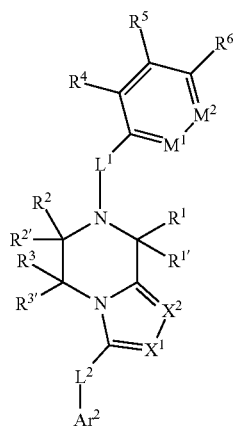

In' and pharmaceutically acceptable salts and solvates thereof, wherein:
Ar², L¹, L², R¹, R¹', R², R²', R³, R³', X¹ and X² are as defined above in respect to formula I.
R⁴, R⁴', R⁵, R⁵' and R⁶ are as defined above in respect to formula Id-1;
Ar⁴, R⁷ and R⁷' are as defined above in respect to formulae Id-2 and Id-3;
M¹ and M² are as defined above in respect to formula Id-4;
Preferred compounds of formulae In, Io and Ip are those wherein R², R²', R³ and R³' are H.

Still other preferred compounds of formula I are those of formulae Iq, Ir, Is and It

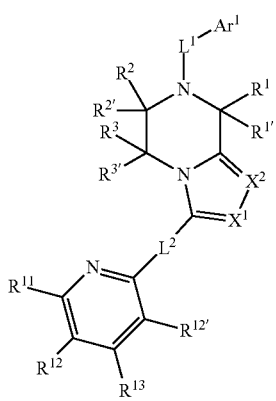

Iq

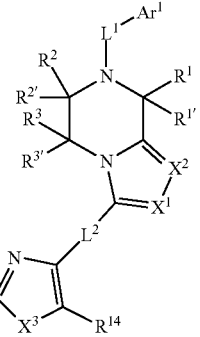

Ir

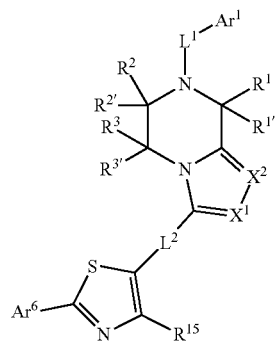

Is

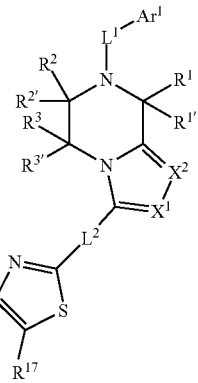

It and pharmaceutically acceptable salts and solvates thereof, wherein:
Ar¹, L¹, L², R¹, R¹', R², R²', R³, R³', X¹ and X² are as defined above in respect to formula I;
R¹¹, R¹², R¹²' and R¹³ are as defined above in respect to formula If-1;
Ar⁵, R¹⁴ and X³ are as defined above in respect to formula If-2;
Ar⁶ and R¹⁵ are as defined above in respect to formula If-3;
R¹⁶ and R¹⁷ are as defined above in respect to formula If-4.
Preferred compounds of formulae Iq, Ir, Is and It are those wherein R², R²', R³ and R³' are H.

Other preferred compounds of formula I are those of formulae Iu and Iv

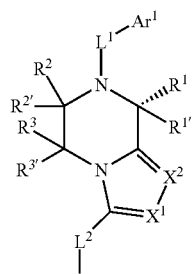

Iu

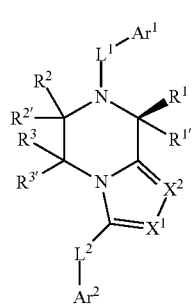

Iv and pharmaceutically acceptable salts and solvates thereof, wherein $Ar^1$, $Ar^2$, $L^1$, $L^2$, $R^1$, $R^{1'}$, $R^2$, $R^{2'}$, $R^3$, $R^{3'}$, $X^1$ and $X^2$, are as defined above in respect to formula I, and $R^1$ and $R^{1'}$ are different.

Preferred compounds of formulae Iu and Iv are those wherein $X^1$ and $X^2$ are both N.

Still other preferred compounds of formula I are those of formula Iw:

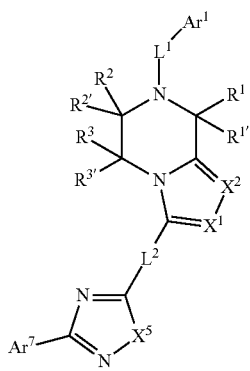

Iw and pharmaceutically acceptable salts and solvates thereof, wherein $Ar^1$, $L^1$, $L^2$, $R^1$, $R^{1'}$, $R^2$, $R^{2'}$, $R^3$, $R^{3'}$, $X^1$ and $X^2$, are as defined above in respect to formula I;
$Ar^7$ and $X^5$ are as defined above in respect to formula If-5;
Preferred compounds of formula Iw are those wherein $R^2$, $R^{2'}$, $R^3$ and $R^{3'}$ are H.

Still other preferred compounds of formula I are those of formulae Ix, Iy and Iz:

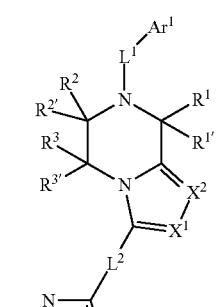

Ix

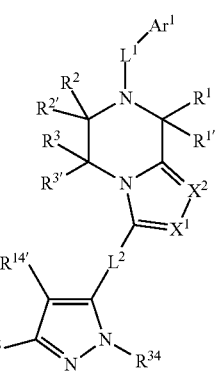

Iy

Iz and pharmaceutically acceptable salts and solvates thereof, wherein $Ar^1$, $L^1$, $L^2$, $R^1$, $R^{1'}$, $R^2$, $R^{2'}$, $R^3$, $R^{3'}$, $X^1$ and $X^2$, are as defined above in respect to formula I;
$Ar^5$, $Ar^7$, $R^{14'}$, $R^{34}$, $R^{35}$, and $X^6$ are as defined above in respect to formulae If-6, If-7 and If-8.

Preferred compounds of formula Ix, Iy and Iz are those wherein $R^2$, $R^{2'}$, $R^3$ and $R^{3'}$ are H and/or $R^{14'}$ is H.

Particularly preferred compounds of the invention are those listed in Table 1 hereafter:

TABLE 1

| Compound no | Name | $(M + H)^+$ |
|---|---|---|
| 1 | (4-fluorophenyl)(3-(pyridin-2-yl)-5,6-dihydro-[1,2,4]triazolo[4,3-a]pyrazin-7(8H)-yl)methanone | 324.3 |

TABLE 1-continued

| Compound no | Name | (M + H)+ |
|---|---|---|
| 2 | (4-chlorophenyl)(3-(pyridin-2-yl)-5,6-dihydro-[1,2,4]triazolo[4,3-a]pyrazin-7(8H)-yl)methanone | 340.8 |
| 3 | (3-(4-chlorophenyl)-1H-pyrazol-5-yl)(3-(pyridin-2-yl)-5,6-dihydro-[1,2,4]triazolo[4,3-a]pyrazin-7(8H)-yl)methanone | 406.8 |
| 4 | (3-(3,4-dichlorophenyl)-1H-pyrazol-5-yl)(3-(pyridin-2-yl)-5,6-dihydro-[1,2,4]triazolo[4,3-a]pyrazin-7(8H)-yl)methanone | 441.3 |
| 5 | (3,4-dichlorophenyl)(3-(pyridin-2-yl)-5,6-dihydro-[1,2,4]triazolo[4,3-a]pyrazin-7(8H)-yl)methanone | 375.2 |
| 6 | [1,1'-biphenyl]-4-yl(3-(pyridin-2-yl)-5,6-dihydro-[1,2,4]triazolo[4,3-a]pyrazin-7(8H)-yl)methanone | 382.4 |
| 7 | (4-fluorophenyl)(3-(quinolin-2-yl)-5,6-dihydro-[1,2,4]triazolo[4,3-a]pyrazin-7(8H)-yl)methanone | 374.4 |
| 8 | (4-fluorophenyl)(3-(2-phenylthiazol-4-yl)-5,6-dihydro-[1,2,4]triazolo[4,3-a]pyrazin-7(8H)-yl)methanone | 406.4 |
| 9 | (4-fluorophenyl)(3-(2-morpholinothiazol-4-yl)-5,6-dihydro-[1,2,4]triazolo[4,3-a]pyrazin-7(8H)-yl)methanone | 415.5 |
| 10 | (3-(5-chloropyridin-2-yl)-5,6-dihydro-[1,2,4]triazolo[4,3-a]pyrazin-7(8H)-yl)(4-fluorophenyl)methanone | 358.8 |
| 11 | (4-fluorophenyl)(3-(6-methylpyridin-2-yl)-5,6-dihydro-[1,2,4]triazolo[4,3-a]pyrazin-7(8H)-yl)methanone | 338.4 |
| 12 | (4-fluorophenyl)(8-methyl-3-(pyridin-2-yl)-5,6-dihydro-[1,2,4]triazolo[4,3-a]pyrazin-7(8H)-yl)methanone | 338.4 |
| 13 | (3-(2,4-dichlorophenyl)-1H-pyrazol-5-yl)(3-(pyridin-2-yl)-5,6-dihydro-[1,2,4]triazolo[4,3-a]pyrazin-7(8H)-yl)methanone | 441.3 |
| 14 | (3-(3,4-dichlorophenyl)-1-methyl-1H-pyrazol-5-yl)(3-(pyridin-2-yl)-5,6-dihydro-[1,2,4]triazolo[4,3-a]pyrazin-7(8H)-yl)methanone | 455.3 |
| 15 | (4-fluorophenyl)(3-(isoquinolin-3-yl)-5,6-dihydro-[1,2,4]triazolo[4,3-a]pyrazin-7(8H)-yl)methanone | 374.4 |
| 16 | (4'-fluoro-[1,1'-biphenyl]-4-yl)(3-(pyridin-2-yl)-5,6-dihydro-[1,2,4]triazolo[4,3-a]pyrazin-7(8H)-yl)methanone | 400.4 |
| 17 | (3-(pyridin-2-yl)-5,6-dihydro-[1,2,4]triazolo[4,3-a]pyrazin-7(8H)-yl)(3-(4-(trifluoromethyl)phenyl)-1H-pyrazol-5-yl)methanone | 440.4 |
| 18 | (3-(4-phenoxyphenyl)-1H-pyrazol-5-yl)(3-(pyridin-2-yl)-5,6-dihydro-[1,2,4]triazolo[4,3-a]pyrazin-7(8H)-yl)methanone | 464.5 |
| 19 | [1,1'-biphenyl]-4-yl(3-(quinolin-2-yl)-5,6-dihydro-[1,2,4]triazolo[4,3-a]pyrazin-7(8H)-yl)methanone | 432.5 |
| 20 | [1,1'-biphenyl]-4-yl(3-(2-morpholinothiazol-4-yl)-5,6-dihydro-[1,2,4]triazolo[4,3-a]pyrazin-7(8H)-yl)methanone | 473.6 |
| 21 | (3-(pyridin-2-yl)-5,6-dihydro-[1,2,4]triazolo[4,3-a]pyrazin-7(8H)-yl)(4-(thiophen-2-yl)phenyl)methanone | 388.5 |
| 22 | (4-fluorophenyl)(3-(8-fluoroquinolin-2-yl)-5,6-dihydro-[1,2,4]triazolo[4,3-a]pyrazin-7(8H)-yl)methanone | 392.4 |
| 23 | (3-(8-chloroquinolin-2-yl)-5,6-dihydro-[1,2,4]triazolo[4,3-a]pyrazin-7(8H)-yl)(4-fluorophenyl)methanone | 408.8 |
| 24 | (4-fluorophenyl)(3-(2-(4-(trifluoromethyl)phenyl)thiazol-4-yl)-5,6-dihydro-[1,2,4]triazolo[4,3-a]pyrazin-7(8H)-yl)methanone | 474.4 |
| 25 | (4-fluorophenyl)(3-(6-phenylpyridin-2-yl)-5,6-dihydro-[1,2,4]triazolo[4,3-a]pyrazin-7(8H)-yl)methanone | 400.4 |
| 26 | [1,1'-biphenyl]-4-yl(3-(2-phenylthiazol-4-yl)-5,6-dihydro-[1,2,4]triazolo[4,3-a]pyrazin-7(8H)-yl)methanone | 464.6 |
| 27 | (4-fluorophenyl)(3-(4,5,6,7-tetrahydrobenzo[d]thiazol-2-yl)-5,6-dihydro-[1,2,4]triazolo[4,3-a]pyrazin-7(8H)-yl)methanone | 384.4 |
| 28 | (4-fluorophenyl)(3-(2-(3-(trifluoromethyl)phenyl)thiazol-4-yl)-5,6-dihydro-[1,2,4]triazolo[4,3-a]pyrazin-7(8H)-yl)methanone | 474.4 |
| 29 | (3-(2-(2,4-difluorophenyl)thiazol-4-yl)-5,6-dihydro-[1,2,4]triazolo[4,3-a]pyrazin-7(8H)-yl)(4-fluorophenyl)methanone | 442.4 |
| 30 | (3-(2-(2,3-dichlorophenyl)thiazol-4-yl)-5,6-dihydro-[1,2,4]triazolo[4,3-a]pyrazin-7(8H)-yl)(4-fluorophenyl)methanone | 475.3 |
| 31 | (3-(2-(4-chlorophenyl)thiazol-4-yl)-5,6-dihydro-[1,2,4]triazolo[4,3-a]pyrazin-7(8H)-yl)(4-fluorophenyl)methanone | 440.9 |
| 32 | (4-fluorophenyl)(3-(2-(4-fluorophenyl)thiazol-4-yl)-5,6-dihydro-[1,2,4]triazolo[4,3-a]pyrazin-7(8H)-yl)methanone | 424.4 |
| 33 | (4-fluorophenyl)(3-(2-(piperidin-1-yl)thiazol-4-yl)-5,6-dihydro-[1,2,4]triazolo[4,3-a]pyrazin-7(8H)-yl)methanone | 413.5 |
| 34 | (4-fluorophenyl)(3-(2-(4-phenylpiperazin-1-yl)thiazol-4-yl)-5,6-dihydro-[1,2,4]triazolo[4,3-a]pyrazin-7(8H)-yl)methanone | 490.6 |

TABLE 1-continued

| Compound no | Name | (M + H)+ |
|---|---|---|
| 35 | (3-(2-(2,4-dichlorophenyl)thiazol-4-yl)-5,6-dihydro-[1,2,4]triazolo[4,3-a]pyrazin-7(8H)-yl)(4-fluorophenyl)methanone | 475.3 |
| 36 | (3-(2-(3,5-dichlorophenyl)thiazol-4-yl)-5,6-dihydro-[1,2,4]triazolo[4,3-a]pyrazin-7(8H)-yl)(4-fluorophenyl)methanone | 475.3 |
| 37 | (4-fluorophenyl)(3-(6-(pyrrolidin-1-yl)pyridin-2-yl)-5,6-dihydro-[1,2,4]triazolo[4,3-a]pyrazin-7(8H)-yl)methanone | 393.4 |
| 38 | (4-fluorophenyl)(3-(6-morpholinopyridin-2-yl)-5,6-dihydro-[1,2,4]triazolo[4,3-a]pyrazin-7(8H)-yl)methanone | 409.4 |
| 39 | (4-fluorophenyl)(3-(6-(trifluoromethyl)pyridin-2-yl)-5,6-dihydro-[1,2,4]triazolo[4,3-a]pyrazin-7(8H)-yl)methanone | 392.3 |
| 40 | (3-(2-(3,4-dimethoxyphenyl)thiazol-4-yl)-5,6-dihydro-[1,2,4]triazolo[4,3-a]pyrazin-7(8H)-yl)(4-fluorophenyl)methanone | 466.5 |
| 41 | (4-fluorophenyl)(8-(4-fluorophenyl)-3-(2-phenylthiazol-4-yl)-5,6-dihydro-[1,2,4]triazolo[4,3-a]pyrazin-7(8H)-yl)methanone | 500.5 |
| 42 | (3-(2-(3-chlorophenyl)thiazol-4-yl)-5,6-dihydro-[1,2,4]triazolo[4,3-a]pyrazin-7(8H)-yl)(4-fluorophenyl)methanone | 440.9 |
| 43 | (4-fluorophenyl)(8-isopropyl-3-(2-phenylthiazol-4-yl)-5,6-dihydro-[1,2,4]triazolo[4,3-a]pyrazin-7(8H)-yl)methanone | 448.5 |
| 44 | (R)-(4-fluorophenyl)(8-methyl-3-(pyridin-2-yl)-5,6-dihydro-[1,2,4]triazolo[4,3-a]pyrazin-7(8H)-yl)methanone | 338.4 |
| 45 | (R)-(4-fluorophenyl)(8-methyl-3-(2-phenylthiazol-4-yl)-5,6-dihydro-[1,2,4]triazolo[4,3-a]pyrazin-7(8H)-yl)methanone | 420.5 |
| 46 | [1,1'-biphenyl]-4-yl(8-methyl-3-(2-morpholinothiazol-4-yl)-5,6-dihydro-[1,2,4]triazolo[4,3-a]pyrazin-7(8H)-yl)methanone | 487.6 |
| 47 | (4-fluorophenyl)(3-(2-phenyloxazol-4-yl)-5,6-dihydro-[1,2,4]triazolo[4,3-a]pyrazin-7(8H)-yl)methanone | 390.4 |
| 48 | (4-fluorophenyl)(8-methyl-3-(2-phenyloxazol-4-yl)-5,6-dihydro-[1,2,4]triazolo[4,3-a]pyrazin-7(8H)-yl)methanone | 404.4 |
| 49 | [1,1'-biphenyl]-4-yl(8-methyl-3-(2-phenyloxazol-4-yl)-5,6-dihydro-[1,2,4]triazolo[4,3-a]pyrazin-7(8H)-yl)methanone | 462.5 |
| 50 | [1,1'-biphenyl]-4-yl(3-(2-phenyloxazol-4-yl)-5,6-dihydro-[1,2,4]triazolo[4,3-a]pyrazin-7(8H)-yl)methanone | 448.5 |
| 51 | (4-fluorophenyl)(8-(2-hydroxyethyl)-3-(2-phenylthiazol-4-yl)-5,6-dihydro-[1,2,4]triazolo[4,3-a]pyrazin-7(8H)-yl)methanone | 450.5 |
| 52 | (4-fluorophenyl)(8-methyl-3-(2-morpholinothiazol-4-yl)-5,6-dihydro-[1,2,4]triazolo[4,3-a]pyrazin-7(8H)-yl)methanone | 429.5 |
| 53 | (4'-fluoro-[1,1'-biphenyl]-4-yl)(8-methyl-3-(2-morpholinothiazol-4-yl)-5,6-dihydro-[1,2,4]triazolo[4,3-a]pyrazin-7(8H)-yl)methanone | 505.6 |
| 54 | (3-(2-phenylthiazol-4-yl)-5,6-dihydro-[1,2,4]triazolo[4,3-a]pyrazin-7(8H)-yl)(4-(thiophen-2-yl)phenyl)methanone | 470.6 |
| 55 | (3-(2-morpholinothiazol-4-yl)-5,6-dihydro-[1,2,4]triazolo[4,3-a]pyrazin-7(8H)-yl)(4-(thiophen-2-yl)phenyl)methanone | 479.6 |
| 56 | (8-methyl-3-(2-morpholinothiazol-4-yl)-5,6-dihydro-[1,2,4]triazolo[4,3-a]pyrazin-7(8H)-yl)(4-(thiophen-2-yl)phenyl)methanone | 493.6 |
| 57 | (4-fluorophenyl)(3-(4-phenylthiazol-2-yl)-5,6-dihydro-[1,2,4]triazolo[4,3-a]pyrazin-7(8H)-yl)methanone | 406.4 |
| 58 | (3-(2-(2-chlorophenyl)thiazol-4-yl)-5,6-dihydro-[1,2,4]triazolo[4,3-a]pyrazin-7(8H)-yl)(4-fluorophenyl)methanone | 440.9 |
| 59 | (3-(benzo[d]thiazol-2-yl)-5,6-dihydro-[1,2,4]triazolo[4,3-a]pyrazin-7(8H)-yl)(4-fluorophenyl)methanone | 380.4 |
| 60 | (8,8-dimethyl-3-(2-phenylthiazol-4-yl)-5,6-dihydro-[1,2,4]triazolo[4,3-a]pyrazin-7(8H)-yl)(4-fluorophenyl)methanone | 434.5 |
| 61 | (4-fluorophenyl)(8-methyl-3-(quinolin-2-yl)-5,6-dihydro-[1,2,4]triazolo[4,3-a]pyrazin-7(8H)-yl)methanone | 388.4 |
| 62 | (8-methyl-3-(2-phenylthiazol-4-yl)-5,6-dihydro-[1,2,4]triazolo[4,3-a]pyrazin-7(8H)-yl)(4-(thiophen-2-yl)phenyl)methanone | 484.6 |
| 63 | (3-(2-phenylthiazol-4-yl)-5,6-dihydro-[1,2,4]triazolo[4,3-a]pyrazin-7(8H)-yl)(4-(thiophen-3-yl)phenyl)methanone | 470.6 |
| 64 | (8-methyl-3-(2-phenylthiazol-4-yl)-5,6-dihydro-[1,2,4]triazolo[4,3-a]pyrazin-7(8H)-yl)(4-(thiophen-3-yl)phenyl)methanone | 484.6 |

TABLE 1-continued

| Compound no | Name | (M + H)⁺ |
|---|---|---|
| 65 | (8-methyl-3-(quinolin-2-yl)-5,6-dihydro-[1,2,4]triazolo[4,3-a]pyrazin-7(8H)-yl)(4-(thiophen-2-yl)phenyl)methanone | 452.5 |
| 66 | (3-(2-(2-chlorophenyl)thiazol-4-yl)-5,6-dihydro-[1,2,4]triazolo[4,3-a]pyrazin-7(8H)-yl)(4-(thiophen-2-yl)phenyl)methanone | 505.0 |
| 67 | [1,1'-biphenyl]-4-yl(3-(2-(2-chlorophenyl)thiazol-4-yl)-5,6-dihydro-[1,2,4]triazolo[4,3-a]pyrazin-7(8H)-yl)methanone | 499.0 |
| 68 | (R)-(3-(2-(4-chlorophenyl)thiazol-4-yl)-8-methyl-5,6-dihydro-[1,2,4]triazolo[4,3-a]pyrazin-7(8H)-yl)(4-fluorophenyl)methanone | 454.9 |
| 69 | (3-(quinolin-2-yl)-5,6-dihydro-[1,2,4]triazolo[4,3-a]pyrazin-7(8H)-yl)(4-(thiophen-2-yl)phenyl)methanone | 438.5 |
| 70 | (4-fluorophenyl)(3-(2-(4-fluorophenyl)thiazol-4-yl)-8-methyl-5,6-dihydro-[1,2,4]triazolo[4,3-a]pyrazin-7(8H)-yl)methanone | 438.5 |
| 71 | (R)-(4-fluorophenyl)(3-(2-(4-fluorophenyl)thiazol-4-yl)-8-methyl-5,6-dihydro-[1,2,4]triazolo[4,3-a]pyrazin-7(8H)-yl)methanone | 438.5 |
| 72 | [1,1'-biphenyl]-4-yl(8-methyl-3-(4-methyl-2-phenylthiazol-5-yl)-5,6-dihydro-[1,2,4]triazolo[4,3-a]pyrazin-7(8H)-yl)methanone | 492.6 |
| 73 | (3-(2-(4-fluorophenyl)thiazol-4-yl)-5,6-dihydro-[1,2,4]triazolo[4,3-a]pyrazin-7(8H)-yl)(4-(thiophen-2-yl)phenyl)methanone | 488.6 |
| 74 | (3-(2-(2-chlorophenyl)thiazol-4-yl)-8-methyl-5,6-dihydro-[1,2,4]triazolo[4,3-a]pyrazin-7(8H)-yl)(4-fluorophenyl)methanone | 454.9 |
| 75 | (4-fluorophenyl)(8-methyl-3-(4-methyl-2-phenylthiazol-5-yl)-5,6-dihydro-[1,2,4]triazolo[4,3-a]pyrazin-7(8H)-yl)methanone | 434.5 |
| 76 | [1,1'-biphenyl]-4-yl(3-(2-(4-fluorophenyl)thiazol-4-yl)-8-methyl-5,6-dihydro-[1,2,4]triazolo[4,3-a]pyrazin-7(8H)-yl)methanone | 496.6 |
| 77 | (3-(2-(2,4-difluorophenyl)thiazol-4-yl)-8-methyl-5,6-dihydro-[1,2,4]triazolo[4,3-a]pyrazin-7(8H)-yl)(4-fluorophenyl)methanone | 456.5 |
| 78 | (3-(2-(4-fluorophenyl)thiazol-4-yl)-8-methyl-5,6-dihydro-[1,2,4]triazolo[4,3-a]pyrazin-7(8H)-yl)(4-(thiophen-2-yl)phenyl)methanone | 502.6 |
| 79 | [1,1'-biphenyl]-4-yl(3-(2-(2,4-difluorophenyl)thiazol-4-yl)-8-methyl-5,6-dihydro-[1,2,4]triazolo[4,3-a]pyrazin-7(8H)-yl)methanone | 514.6 |
| 80 | (3-(2-(2,4-difluorophenyl)thiazol-4-yl)-8-methyl-5,6-dihydro-[1,2,4]triazolo[4,3-a]pyrazin-7(8H)-yl)(4-(thiophen-2-yl)phenyl)methanone | 520.6 |
| 81 | naphthalen-1-yl(3-(pyridin-2-yl)-5,6-dihydro-[1,2,4]triazolo[4,3-a]pyrazin-7(8H)-yl)methanone | 356.4 |
| 82 | (3-(4-chlorophenyl)-1-methyl-1H-pyrazol-5-yl)(3-(pyridin-2-yl)-5,6-dihydro-[1,2,4]triazolo[4,3-a]pyrazin-7(8H)-yl)methanone | 420.9 |
| 83 | (5-(4-chlorophenyl)-1-methyl-1H-pyrazol-3-yl)(3-(pyridin-2-yl)-5,6-dihydro-[1,2,4]triazolo[4,3-a]pyrazin-7(8H)-yl)methanone | 420.9 |
| 84 | (8-methyl-3-(5-phenyl-1,2,4-oxadiazol-3-yl)-5,6-dihydro-[1,2,4]triazolo[4,3-a]pyrazin-7(8H)-yl)(4-(thiophen-2-yl)phenyl)methanone | 469.5 |
| 85 | (8-methyl-3-(3-phenyl-1,2,4-oxadiazol-5-yl)-5,6-dihydro-[1,2,4]triazolo[4,3-a]pyrazin-7(8H)-yl)(4-(thiophen-2-yl)phenyl)methanone | 469.5 |
| 86 | (R)-(3-(2-(4-fluorophenyl)oxazol-4-yl)-8-methyl-5,6-dihydro-[1,2,4]triazolo[4,3-a]pyrazin-7(8H)-yl)(4-(thiophen-2-yl)phenyl)methanone | 486.5 |
| 87 | 2-(7-((4-fluorophenyl)sulfonyl)-5,6,7,8-tetrahydro-[1,2,4]triazolo[4,3-a]pyrazin-3-yl)quinoline | 410.4 |
| 89 | 2-(4-fluorophenyl)-1-(3-(quinolin-2-yl)-5,6-dihydro-[1,2,4]triazolo[4,3-a]pyrazin-7(8H)-yl)ethanone | 388.4 |
| 90 | (5-phenylpyridin-2-yl)(3-(quinolin-2-yl)-5,6-dihydro-[1,2,4]triazolo[4,3-a]pyrazin-7(8H)-yl)methanone | 433.5 |
| 91 | (6-phenylpyridin-3-yl)(3-(quinolin-2-yl)-5,6-dihydro-[1,2,4]triazolo[4,3-a]pyrazin-7(8H)-yl)methanone | 433.5 |
| 92 | (2-phenylpyrimidin-5-yl)(3-(quinolin-2-yl)-5,6-dihydro-[1,2,4]triazolo[4,3-a]pyrazin-7(8H)-yl)methanone | 434.5 |
| 93 | (4-phenylcyclohexyl)(3-(quinolin-2-yl)-5,6-dihydro-[1,2,4]triazolo[4,3-a]pyrazin-7(8H)-yl)methanone | 438.5 |
| 94 | cyclohexyl(3-(quinolin-2-yl)-5,6-dihydro-[1,2,4]triazolo[4,3-a]pyrazin-7(8H)-yl)methanone | 362.4 |

TABLE 1-continued

| Compound no | Name | (M + H)+ |
|---|---|---|
| 95 | 3-methyl-1-(3-(quinolin-2-yl)-5,6-dihydro-[1,2,4]triazolo[4,3-a]pyrazin-7(8H)-yl)butan-1-one | 336.4 |
| 96 | [1,1'-biphenyl]-2-yl(3-(quinolin-2-yl)-5,6-dihydro-[1,2,4]triazolo[4,3-a]pyrazin-7(8H)-yl)methanone | 432.5 |
| 97 | (4-(furan-3-yl)phenyl)(3-(quinolin-2-yl)-5,6-dihydro-[1,2,4]triazolo[4,3-a]pyrazin-7(8H)-yl)methanone | 422.5 |
| 98 | (4-(pyrimidin-5-yl)phenyl)(3-(quinolin-2-yl)-5,6-dihydro-[1,2,4]triazolo[4,3-a]pyrazin-7(8H)-yl)methanone | 434.5 |
| 99 | (9-methyl-9H-carbazol-2-yl)(3-(quinolin-2-yl)-5,6-dihydro-[1,2,4]triazolo[4,3-a]pyrazin-7(8H)-yl)methanone | 459.5 |
| 100 | (4-(pyrimidin-2-yl)phenyl)(3-(quinolin-2-yl)-5,6-dihydro-[1,2,4]triazolo[4,3-a]pyrazin-7(8H)-yl)methanone | 434.5 |
| 101 | (4-(pyrazin-2-yl)phenyl)(3-(quinolin-2-yl)-5,6-dihydro-[1,2,4]triazolo[4,3-a]pyrazin-7(8H)-yl)methanone | 434.5 |
| 102 | (4-(pyridazin-3-yl)phenyl)(3-(quinolin-2-yl)-5,6-dihydro-[1,2,4]triazolo[4,3-a]pyrazin-7(8H)-yl)methanone | 434.5 |
| 103 | 4'-(3-(quinolin-2-yl)-5,6,7,8-tetrahydro-[1,2,4]triazolo[4,3-a]pyrazine-7-carbonyl)-[1,1'-biphenyl]-4-carbonitrile | 457.5 |
| 104 | 1-(4-(3-(quinolin-2-yl)-5,6,7,8-tetrahydro-[1,2,4]triazolo[4,3-a]pyrazine-7-carbonyl)phenyl)piperidin-2-one | 453.5 |
| 105 | (4-morpholinophenyl)(3-(quinolin-2-yl)-5,6-dihydro-[1,2,4]triazolo[4,3-a]pyrazin-7(8H)-yl)methanone | 441.5 |
| 106 | (4-(3,5-dimethyl-1H-pyrazol-1-yl)phenyl)(3-(quinolin-2-yl)-5,6-dihydro-[1,2,4]triazolo[4,3-a]pyrazin-7(8H)-yl)methanone | 450.5 |
| 107 | (3-(2-(4-fluorophenyl)thiazol-4-yl)-6-methyl-5,6-dihydro-[1,2,4]triazolo[4,3-a]pyrazin-7(8H)-yl)(4-(thiophen-2-yl)phenyl)methanone | 502.6 |
| 108 | (3-(2-(4-fluorophenyl)thiazol-4-yl)-5-methyl-5,6-dihydro-[1,2,4]triazolo[4,3-a]pyrazin-7(8H)-yl)(4-(thiophen-2-yl)phenyl)methanone | 502.6 |
| 109 | (3,4-dichlorophenyl)(3-(2-(4-fluorophenyl)thiazol-4-yl)-8-methyl-5,6-dihydro-[1,2,4]triazolo[4,3-a]pyrazin-7(8H)-yl)methanone | 489.4 |
| 110 | (3,4-difluorophenyl)(3-(2-(4-fluorophenyl)thiazol-4-yl)-8-methyl-5,6-dihydro-[1,2,4]triazolo[4,3-a]pyrazin-7(8H)-yl)methanone | 456.5 |
| 111 | (3-chloro-4-fluorophenyl)(3-(2-(4-fluorophenyl)thiazol-4-yl)-8-methyl-5,6-dihydro-[1,2,4]triazolo[4,3-a]pyrazin-7(8H)-yl)methanone | 472.9 |
| 112 | (4-chloro-3-fluorophenyl)(3-(2-(4-fluorophenyl)thiazol-4-yl)-8-methyl-5,6-dihydro-[1,2,4]triazolo[4,3-a]pyrazin-7(8H)-yl)methanone | 472.9 |
| 113 | (3-(2-(4-fluorophenyl)thiazol-4-yl)-8-methyl-5,6-dihydro-[1,2,4]triazolo[4,3-a]pyrazin-7(8H)-yl)(3,4,5-trifluorophenyl)methanone | 474.4 |
| 114 | (8-methyl-3-(2-phenyloxazol-4-yl)-5,6-dihydro-[1,2,4]triazolo[4,3-a]pyrazin-7(8H)-yl)(4-(thiophen-2-yl)phenyl)methanone | 468.5 |
| 115 | (R)-(4-fluorophenyl)(8-methyl-3-(quinolin-2-yl)-5,6-dihydro-[1,2,4]triazolo[4,3-a]pyrazin-7(8H)-yl)methanone | 388.4 |
| 117 | (R)-[1,1'-biphenyl]-4-yl(8-methyl-3-(quinolin-2-yl)-5,6-dihydro-[1,2,4]triazolo[4,3-a]pyrazin-7(8H)-yl)methanone | 446.5 |
| 118 | (R)-[1,1'-biphenyl]-4-yl(8-methyl-3-(2-morpholinothiazol-4-yl)-5,6-dihydro-[1,2,4]triazolo[4,3-a]pyrazin-7(8H)-yl)methanone | 487.6 |
| 119 | (R)-(4-fluorophenyl)(8-methyl-3-(6-phenylpyridin-2-yl)-5,6-dihydro-[1,2,4]triazolo[4,3-a]pyrazin-7(8H)-yl)methanone | 414.4 |
| 120 | (R)-[1,1'-biphenyl]-4-yl(8-methyl-3-(2-phenylthiazol-4-yl)-5,6-dihydro-[1,2,4]triazolo[4,3-a]pyrazin-7(8H)-yl)methanone | 478.6 |
| 121 | (R)-(4-fluorophenyl)(8-methyl-3-(4,5,6,7-tetrahydrobenzo[d]thiazol-2-yl)-5,6-dihydro-[1,2,4]triazolo[4,3-a]pyrazin-7(8H)-yl)methanone | 398.5 |
| 122 | (R)-(3-(2-(2,4-difluorophenyl)thiazol-4-yl)-8-methyl-5,6-dihydro-[1,2,4]triazolo[4,3-a]pyrazin-7(8H)-yl)(4-fluorophenyl)methanone | 456.5 |
| 123 | (R)-(3-(2-(2,3-dichlorophenyl)thiazol-4-yl)-8-methyl-5,6-dihydro-[1,2,4]triazolo[4,3-a]pyrazin-7(8H)-yl)(4-fluorophenyl)methanone | 489.4 |
| 126 | (R)-(4-fluorophenyl)(8-methyl-3-(2-(4-phenylpiperazin-1-yl)thiazol-4-yl)-5,6-dihydro-[1,2,4]triazolo[4,3-a]pyrazin-7(8H)-yl)methanone | 504.6 |
| 127 | (R)-(3-(2-(2,4-dichlorophenyl)thiazol-4-yl)-8-methyl-5,6-dihydro-[1,2,4]triazolo[4,3-a]pyrazin-7(8H)-yl)(4-fluorophenyl)methanone | 489.4 |

TABLE 1-continued

| Compound no | Name | (M + H)+ |
|---|---|---|
| 128 | (R)-(3-(2-(3-chlorophenyl)thiazol-4-yl)-8-methyl-5,6-dihydro-[1,2,4]triazolo[4,3-a]pyrazin-7(8H)-yl)(4-fluorophenyl)methanone | 454.9 |
| 130 | (R)-(4-fluorophenyl)(8-methyl-3-(2-phenyloxazol-4-yl)-5,6-dihydro-[1,2,4]triazolo[4,3-a]pyrazin-7(8H)-yl)methanone | 404.4 |
| 131 | (R)-[1,1'-biphenyl]-4-yl(8-methyl-3-(2-phenyloxazol-4-yl)-5,6-dihydro-[1,2,4]triazolo[4,3-a]pyrazin-7(8H)-yl)methanone | 462.5 |
| 133 | (R)-(4-fluorophenyl)(8-(2-hydroxyethyl)-3-(2-phenylthiazol-4-yl)-5,6-dihydro-[1,2,4]triazolo[4,3-a]pyrazin-7(8H)-yl)methanone | 450.5 |
| 134 | (R)-(4'-fluoro-[1,1'-biphenyl]-4-yl)(8-methyl-3-(2-morpholinothiazol-4-yl)-5,6-dihydro-[1,2,4]triazolo[4,3-a]pyrazin-7(8H)-yl)methanone | 505.6 |
| 135 | (R)-(8-methyl-3-(2-phenylthiazol-4-yl)-5,6-dihydro-[1,2,4]triazolo[4,3-a]pyrazin-7(8H)-yl)(4-(thiophen-2-yl)phenyl)methanone | 484.6 |
| 136 | (R)-(8-methyl-3-(2-morpholinothiazol-4-yl)-5,6-dihydro-[1,2,4]triazolo[4,3-a]pyrazin-7(8H)-yl)(4-(thiophen-2-yl)phenyl)methanone | 493.6 |
| 138 | (R)-(4-fluorophenyl)(8-methyl-3-(4-phenylthiazol-2-yl)-5,6-dihydro-[1,2,4]triazolo[4,3-a]pyrazin-7(8H)-yl)methanone | 420.5 |
| 139 | (R)-(3-(2-(2-chlorophenyl)thiazol-4-yl)-8-methyl-5,6-dihydro-[1,2,4]triazolo[4,3-a]pyrazin-7(8H)-yl)(4-fluorophenyl)methanone | 454.9 |
| 142 | (R)-(8-methyl-3-(2-phenylthiazol-4-yl)-5,6-dihydro-[1,2,4]triazolo[4,3-a]pyrazin-7(8H)-yl)(4-(thiophen-3-yl)phenyl)methanone | 484.6 |
| 144 | (R)-(8-methyl-3-(quinolin-2-yl)-5,6-dihydro-[1,2,4]triazolo[4,3-a]pyrazin-7(8H)-yl)(4-(thiophen-2-yl)phenyl)methanone | 452.5 |
| 145 | (R)-(3-(2-(2-chlorophenyl)thiazol-4-yl)-8-methyl-5,6-dihydro-[1,2,4]triazolo[4,3-a]pyrazin-7(8H)-yl)(4-(thiophen-2-yl)phenyl)methanone | 519.1 |
| 146 | (R)-[1,1'-biphenyl]-4-yl(3-(2-(2-chlorophenyl)thiazol-4-yl)-8-methyl-5,6-dihydro-[1,2,4]triazolo[4,3-a]pyrazin-7(8H)-yl)methanone | 513.0 |
| 149 | (R)-[1,1'-biphenyl]-4-yl(8-methyl-3-(4-methyl-2-phenylthiazol-5-yl)-5,6-dihydro-[1,2,4]triazolo[4,3-a]pyrazin-7(8H)-yl)methanone | 492.6 |
| 150 | (R)-(3-(2-(4-fluorophenyl)thiazol-4-yl)-8-methyl-5,6-dihydro-[1,2,4]triazolo[4,3-a]pyrazin-7(8H)-yl)(4-(thiophen-2-yl)phenyl)methanone | 502.6 |
| 152 | (R)-[1,1'-biphenyl]-4-yl(3-(2-(4-fluorophenyl)thiazol-4-yl)-8-methyl-5,6-dihydro-[1,2,4]triazolo[4,3-a]pyrazin-7(8H)-yl)methanone | 496.6 |
| 155 | (R)-[1,1'-biphenyl]-4-yl(3-(2-(2,4-difluorophenyl)thiazol-4-yl)-8-methyl-5,6-dihydro-[1,2,4]triazolo[4,3-a]pyrazin-7(8H)-yl)methanone | 514.6 |
| 156 | (R)-(3-(2-(2,4-difluorophenyl)thiazol-4-yl)-8-methyl-5,6-dihydro-[1,2,4]triazolo[4,3-a]pyrazin-7(8H)-yl)(4-(thiophen-2-yl)phenyl)methanone | 520.6 |
| 157 | (8-methyl-3-(2-phenylthiazol-4-yl)-5,6-dihydroimidazo[1,5-a]pyrazin-7(8H)-yl)(4-(thiophen-2-yl)phenyl)methanone | 483.6 |
| 158 | (8-methyl-3-(2-phenylthiazol-4-yl)-5,6-dihydroimidazo[1,2-a]pyrazin-7(8H)-yl)(4-(thiophen-2-yl)phenyl)methanone | 483.6 |
| 159 | (S)-(4-fluorophenyl)(8-methyl-3-(pyridin-2-yl)-5,6-dihydro-[1,2,4]triazolo[4,3-a]pyrazin-7(8H)-yl)methanone | 338.4 |
| 160 | (S)-(4-fluorophenyl)(3-(2-(4-fluorophenyl)thiazol-4-yl)-8-methyl-5,6-dihydro-[1,2,4]triazolo[4,3-a]pyrazin-7(8H)-yl)methanone | 438.5 |
| 161 | (S)-(4'-fluoro-[1,1'-biphenyl]-4-yl)(8-methyl-3-(2-morpholinothiazol-4-yl)-5,6-dihydro-[1,2,4]triazolo[4,3-a]pyrazin-7(8H)-yl)methanone | 505.6 |
| 162 | (S)-(4-fluorophenyl)(8-methyl-3-(quinolin-2-yl)-5,6-dihydro-[1,2,4]triazolo[4,3-a]pyrazin-7(8H)-yl)methanone | 388.4 |
| 163 | (S)-(8-methyl-3-(quinolin-2-yl)-5,6-dihydro-[1,2,4]triazolo[4,3-a]pyrazin-7(8H)-yl)(4-(thiophen-2-yl)phenyl)methanone | 452.5 |
| 164 | (S)-(4-fluorophenyl)(3-(2-(4-fluorophenyl)thiazol-4-yl)-8-methyl-5,6-dihydro-[1,2,4]triazolo[4,3-a]pyrazin-7(8H)-yl)methanone | 438.5 |

TABLE 1-continued

| Compound no | Name | (M + H)+ |
|---|---|---|
| 165 | (S)-(3-(2-(2,4-difluorophenyl)thiazol-4-yl)-8-methyl-5,6-dihydro-[1,2,4]triazolo[4,3-a]pyrazin-7(8H)-yl)(4-(thiophen-2-yl)phenyl)methanone | 520.6 |
| 166 | (4-fluorophenyl)(8-methyl-3-(2-phenylthiazol-4-yl)-5,6-dihydro-[1,2,4]triazolo[4,3-a]pyrazin-7(8H)-yl)methanone | 420.5 |
| 167 | (S)-(4-fluorophenyl)(8-methyl-3-(2-phenylthiazol-4-yl)-5,6-dihydro-[1,2,4]triazolo[4,3-a]pyrazin-7(8H)-yl)methanone | 420.5 |
| 168 | (S)-(3-(3-(4-fluorophenyl)-1,2,4-oxadiazol-5-yl)-8-methyl-5,6-dihydro-[1,2,4]triazolo[4,3-a]pyrazin-7(8H)-yl)(4-(thiophen-2-yl)phenyl)methanone | 487.5 |
| 169 | (R)-(3-(3-(4-fluorophenyl)-1,2,4-oxadiazol-5-yl)-8-methyl-5,6-dihydro-[1,2,4]triazolo[4,3-a]pyrazin-7(8H)-yl)(4-(thiophen-2-yl)phenyl)methanone | 487.5 |
| 170 | (3-(2-(2,4-difluorophenyl)thiazol-4-yl)-5,6-dihydro-[1,2,4]triazolo[4,3-a]pyrazin-7(8H)-yl)(4-(thiophen-2-yl)phenyl)methanone | 506.6 |
| 171 | (3-(5-phenyl-1,2,4-oxadiazol-3-yl)-5,6-dihydro-[1,2,4]triazolo[4,3-a]pyrazin-7(8H)-yl)(4-(thiophen-2-yl)phenyl)methanone | 455.5 |
| 172 | (4-fluorophenyl)(3-(3-phenyl-1,2,4-oxadiazol-5-yl)-5,6-dihydro-[1,2,4]triazolo[4,3-a]pyrazin-7(8H)-yl)methanone | 391.4 |
| 173 | (4-fluorophenyl)(3-(5-phenyl-1,2,4-oxadiazol-3-yl)-5,6-dihydro-[1,2,4]triazolo[4,3-a]pyrazin-7(8H)-yl)methanone | 391.4 |
| 174 | (3-(3-phenyl-1,2,4-oxadiazol-5-yl)-5,6-dihydro-[1,2,4]triazolo[4,3-a]pyrazin-7(8H)-yl)(4-(thiophen-2-yl)phenyl)methanone | 455.5 |
| 175 | (4-fluorophenyl)(3-(3-(4-fluorophenyl)-1,2,4-oxadiazol-5-yl)-5,6-dihydro-[1,2,4]triazolo[4,3-a]pyrazin-7(8H)-yl)methanone | 409.4 |
| 176 | (3-(3-(4-fluorophenyl)-1,2,4-oxadiazol-5-yl)-5,6-dihydro-[1,2,4]triazolo[4,3-a]pyrazin-7(8H)-yl)(4-(thiophen-2-yl)phenyl)methanone | 473.5 |
| 177 | (3-(3-(2,4-difluorophenyl)-1,2,4-oxadiazol-5-yl)-5,6-dihydro-[1,2,4]triazolo[4,3-a]pyrazin-7(8H)-yl)(4-(thiophen-2-yl)phenyl)methanone | 491.5 |
| 178 | (4-fluorophenyl)(3-(5-phenyl-1H-1,2,4-triazol-3-yl)-5,6-dihydro-[1,2,4]triazolo[4,3-a]pyrazin-7(8H)-yl)methanone | 390.4 |
| 179 | (3-(5-phenyl-1H-1,2,4-triazol-3-yl)-5,6-dihydro-[1,2,4]triazolo[4,3-a]pyrazin-7(8H)-yl)(4-(thiophen-2-yl)phenyl)methanone | 454.5 |
| 180 | (4-fluorophenyl)(3-(2-(2-fluorophenyl)thiazol-4-yl)-5,6-dihydro-[1,2,4]triazolo[4,3-a]pyrazin-7(8H)-yl)methanone | 424.4 |
| 181 | (3-(2-(2-fluorophenyl)thiazol-4-yl)-5,6-dihydro-[1,2,4]triazolo[4,3-a]pyrazin-7(8H)-yl)(4-(thiophen-2-yl)phenyl)methanone | 488.6 |
| 182 | [1,1'-biphenyl]-4-yl(3-(2-(2-fluorophenyl)thiazol-4-yl)-5,6-dihydro-[1,2,4]triazolo[4,3-a]pyrazin-7(8H)-yl)methanone | 482.5 |
| 183 | (4'-fluoro-[1,1'-biphenyl]-4-yl)(3-(2-(2-fluorophenyl)thiazol-4-yl)-5,6-dihydro-[1,2,4]triazolo[4,3-a]pyrazin-7(8H)-yl)methanone | 500.5 |
| 185 | (3-(3-(2,4-difluorophenyl)-1,2,4-oxadiazol-5-yl)-5,6-dihydro-[1,2,4]triazolo[4,3-a]pyrazin-7(8H)-yl)(4-(thiophen-2-yl)phenyl)methanone | 491.5 |
| 186 | [1,1'-biphenyl]-4-yl(3-(2-((4,5-dichloro-1H-imidazol-1-yl)methyl)thiazol-4-yl)-5,6-dihydro-[1,2,4]triazolo[4,3-a]pyrazin-7(8H)-yl)methanone | 537.4 |
| 187 | (3-(2-((4,5-dichloro-1H-imidazol-1-yl)methyl)thiazol-4-yl)-5,6-dihydro-[1,2,4]triazolo[4,3-a]pyrazin-7(8H)-yl)(4'-fluoro-[1,1'-biphenyl]-4-yl)methanone | 555.4 |
| 188 | (3-(2-(4-chlorobenzyl)thiazol-4-yl)-5,6-dihydro-[1,2,4]triazolo[4,3-a]pyrazin-7(8H)-yl)(4-fluorophenyl)methanone | 454.9 |
| 189 | (3-(2-(4-chlorobenzyl)thiazol-4-yl)-5,6-dihydro-[1,2,4]triazolo[4,3-a]pyrazin-7(8H)-yl)(4-(thiophen-2-yl)phenyl)methanone | 519.1 |
| 190 | (4-fluorophenyl)(3-(2-(p-tolyl)thiazol-4-yl)-5,6-dihydro-[1,2,4]triazolo[4,3-a]pyrazin-7(8H)-yl)methanone | 420.5 |
| 191 | (4-(thiophen-2-yl)phenyl)(3-(2-(p-tolyl)thiazol-4-yl)-5,6-dihydro-[1,2,4]triazolo[4,3-a]pyrazin-7(8H)-yl)methanone | 484.6 |
| 192 | [1,1'-biphenyl]-4-yl(3-(2-(p-tolyl)thiazol-4-yl)-5,6-dihydro-[1,2,4]triazolo[4,3-a]pyrazin-7(8H)-yl)methanone | 478.6 |
| 193 | (4-fluorophenyl)(3-(2-(thiophen-2-yl)thiazol-4-yl)-5,6-dihydro-[1,2,4]triazolo[4,3-a]pyrazin-7(8H)-yl)methanone | 412.5 |
| 194 | (4-(thiophen-2-yl)phenyl)(3-(2-(thiophen-2-yl)thiazol-4-yl)-5,6-dihydro-[1,2,4]triazolo[4,3-a]pyrazin-7(8H)-yl)methanone | 476.6 |

TABLE 1-continued

| Compound no | Name | (M + H)+ |
|---|---|---|
| 195 | [1,1'-biphenyl]-4-yl(3-(2-(thiophen-2-yl)thiazol-4-yl)-5,6-dihydro-[1,2,4]triazolo[4,3-a]pyrazin-7(8H)-yl)methanone | 470.6 |
| 196 | (4'-fluoro-[1,1'-biphenyl]-4-yl)(3-(2-(thiophen-2-yl)thiazol-4-yl)-5,6-dihydro-[1,2,4]triazolo[4,3-a]pyrazin-7(8H)-yl)methanone | 488.6 |
| 198 | (3-(2-(((4-chlorophenyl)sulfonyl)methyl)thiazol-4-yl)-5,6-dihydro-[1,2,4]triazolo[4,3-a]pyrazin-7(8H)-yl)(4-(thiophen-2-yl)phenyl)methanone | 583.1 |
| 199 | [1,1'-biphenyl]-4-yl(3-(2-(((4-chlorophenyl)sulfonyl)methyl)thiazol-4-yl)-5,6-dihydro-[1,2,4]triazolo[4,3-a]pyrazin-7(8H)-yl)methanone | 577.1 |
| 200 | (3-(2-(((4-chlorophenyl)sulfonyl)methyl)thiazol-4-yl)-5,6-dihydro-[1,2,4]triazolo[4,3-a]pyrazin-7(8H)-yl)(4'-fluoro-[1,1'-biphenyl]-4-yl)methanone | 595.1 |
| 201 | (4-fluorophenyl)(3-(2-(2-methoxyphenyl)thiazol-4-yl)-5,6-dihydro-[1,2,4]triazolo[4,3-a]pyrazin-7(8H)-yl)methanone | 436.5 |
| 202 | (3-(2-(2-methoxyphenyl)thiazol-4-yl)-5,6-dihydro-[1,2,4]triazolo[4,3-a]pyrazin-7(8H)-yl)(4-(thiophen-2-yl)phenyl)methanone | 500.6 |
| 203 | [1,1'-biphenyl]-4-yl(3-(2-(2-methoxyphenyl)thiazol-4-yl)-5,6-dihydro-[1,2,4]triazolo[4,3-a]pyrazin-7(8H)-yl)methanone | 494.6 |
| 204 | [1,1'-biphenyl]-4-yl(3-(3-(4-fluorophenyl)-1,2,4-oxadiazol-5-yl)-5,6-dihydro-[1,2,4]triazolo[4,3-a]pyrazin-7(8H)-yl)methanone | 467.5 |
| 205 | (4'-fluoro-[1,1'-biphenyl]-4-yl)(3-(3-(4-fluorophenyl)-1,2,4-oxadiazol-5-yl)-5,6-dihydro-[1,2,4]triazolo[4,3-a]pyrazin-7(8H)-yl)methanone | 485.5 |
| 206 | (4-fluorophenyl)(3-(2-(3-fluorophenyl)thiazol-4-yl)-5,6-dihydro-[1,2,4]triazolo[4,3-a]pyrazin-7(8H)-yl)methanone | 424.4 |
| 207 | (3-(2-(3-fluorophenyl)thiazol-4-yl)-5,6-dihydro-[1,2,4]triazolo[4,3-a]pyrazin-7(8H)-yl)(4-(thiophen-2-yl)phenyl)methanone | 488.6 |
| 208 | (4-fluorophenyl)(3-(2-isopropylthiazol-4-yl)-5,6-dihydro-[1,2,4]triazolo[4,3-a]pyrazin-7(8H)-yl)methanone | 372.4 |
| 209 | (3-(3-(4-fluorophenyl)-1,2,4-oxadiazol-5-yl)-8-methyl-5,6-dihydro-[1,2,4]triazolo[4,3-a]pyrazin-7(8H)-yl)(4-(thiophen-2-yl)phenyl)methanone | 487.5 |
| 211 | (3-(3-phenyl-1,2,4-thiadiazol-5-yl)-5,6-dihydro-[1,2,4]triazolo[4,3-a]pyrazin-7(8H)-yl)(4-(thiophen-2-yl)phenyl)methanone | 471.6 |
| 212 | (4-fluorophenyl)(3-(3-phenyl-1,2,4-thiadiazol-5-yl)-5,6-dihydro-[1,2,4]triazolo[4,3-a]pyrazin-7(8H)-yl)methanone | 407.4 |
| 213 | (3-(2-(4-bromophenyl)thiazol-4-yl)-5,6-dihydro-[1,2,4]triazolo[4,3-a]pyrazin-7(8H)-yl)(4-(thiophen-2-yl)phenyl)methanone | 549.5 |
| 214 | (3-(2-(4-bromophenyl)thiazol-4-yl)-5,6-dihydro-[1,2,4]triazolo[4,3-a]pyrazin-7(8H)-yl)(4-fluorophenyl)methanone | 485.3 |
| 215 | (3-(2-(4-fluorophenyl)thiazol-4-yl)-8-methyl-5,6-dihydro-[1,2,4]triazolo[4,3-a]pyrazin-7(8H)-yl)(4-(5-methylthiophen-2-yl)phenyl)methanone | 516.6 |
| 216 | 4-(3-(2-(4-fluorophenyl)thiazol-4-yl)-8-methyl-5,6,7,8-tetrahydro-[1,2,4]triazolo[4,3-a]pyrazine-7-carbonyl)benzonitrile | 445.5 |
| 217 | [1,1'-biphenyl]-4-yl(3-(3-phenyl-1,2,4-oxadiazol-5-yl)-5,6-dihydro-[1,2,4]triazolo[4,3-a]pyrazin-7(8H)-yl)methanone | 449.5 |
| 218 | (4-fluorophenyl)(3-(2-(pyridin-4-yl)thiazol-4-yl)-5,6-dihydro-[1,2,4]triazolo[4,3-a]pyrazin-7(8H)-yl)methanone | 407.4 |
| 219 | (3-(2-(quinolin-2-yl)thiazol-4-yl)-5,6-dihydro-[1,2,4]triazolo[4,3-a]pyrazin-7(8H)-yl)(4-(thiophen-2-yl)phenyl)methanone | 521.6 |
| 220 | (3-(1-methyl-3-phenyl-1H-pyrazol-5-yl)-5,6-dihydro-[1,2,4]triazolo[4,3-a]pyrazin-7(8H)-yl)(4-(thiophen-2-yl)phenyl)methanone | 467.6 |
| 221 | (3-(2-(4-(dimethylamino)phenyl)thiazol-4-yl)-5,6-dihydro-[1,2,4]triazolo[4,3-a]pyrazin-7(8H)-yl)(4-fluorophenyl)methanone | 449.5 |
| 222 | (3-(1-methyl-5-phenyl-1H-pyrazol-3-yl)-5,6-dihydro-[1,2,4]triazolo[4,3-a]pyrazin-7(8H)-yl)(4-(thiophen-2-yl)phenyl)methanone | 467.6 |
| 223 | (4'-fluoro-[1,1'-biphenyl]-4-yl)(3-(3-phenyl-1,2,4-oxadiazol-5-yl)-5,6-dihydro-[1,2,4]triazolo[4,3-a]pyrazin-7(8H)-yl)methanone | 467.5 |
| 224 | (3-(2-(pyridin-2-yl)thiazol-4-yl)-5,6-dihydro-[1,2,4]triazolo[4,3-a]pyrazin-7(8H)-yl)(4-(thiophen-2-yl)phenyl)methanone | 471.6 |

TABLE 1-continued

| Compound no | Name | (M + H)+ |
|---|---|---|
| 225 | (4-fluorophenyl)(3-(1-methyl-3-phenyl-1H-pyrazol-5-yl)-5,6-dihydro-[1,2,4]triazolo[4,3-a]pyrazin-7(8H)-yl)methanone | 403.4 |
| 226 | (3-(2-(pyrimidin-2-yl)thiazol-4-yl)-5,6-dihydro-[1,2,4]triazolo[4,3-a]pyrazin-7(8H)-yl)(4-(thiophen-2-yl)phenyl)methanone | 472.6 |
| 227 | (S)-(8-methyl-3-(2-morpholinothiazol-4-yl)-5,6-dihydro-[1,2,4]triazolo[4,3-a]pyrazin-7(8H)-yl)(4-(thiophen-2-yl)phenyl)methanone | 493.6 |
| 228 | (3-(2-(pyridin-4-yl)thiazol-4-yl)-5,6-dihydro-[1,2,4]triazolo[4,3-a]pyrazin-7(8H)-yl)(4-(thiophen-2-yl)phenyl)methanone | 471.6 |
| 229 | (3-(2-(4-(dimethylamino)phenyl)thiazol-4-yl)-5,6-dihydro-[1,2,4]triazolo[4,3-a]pyrazin-7(8H)-yl)(4-(thiophen-2-yl)phenyl)methanone | 513.6 |
| 230 | (4-fluorophenyl)(3-(2-(pyridin-2-yl)thiazol-4-yl)-5,6-dihydro-[1,2,4]triazolo[4,3-a]pyrazin-7(8H)-yl)methanone | 407.4 |
| 231 | phenyl(3-(pyridin-2-yl)-5,6-dihydro-[1,2,4]triazolo[4,3-a]pyrazin-7(8H)-yl)methanone | 306.3 |
| 232 | (3-(pyridin-2-yl)-5,6-dihydro-[1,2,4]triazolo[4,3-a]pyrazin-7(8H)-yl)(p-tolyl)methanone | 320.4 |
| 233 | (S)-(3-(2-(4-fluorophenyl)thiazol-4-yl)-8-methyl-5,6-dihydro-[1,2,4]triazolo[4,3-a]pyrazin-7(8H)-yl)(4-(2-methylthiophen-3-yl)phenyl)methanone | 516.6 |
| 234 | (R)-(3-(2-(4-fluorophenyl)thiazol-4-yl)-8-methyl-5,6-dihydro-[1,2,4]triazolo[4,3-a]pyrazin-7(8H)-yl)(4-(2-methylthiophen-3-yl)phenyl)methanone | 516.6 |
| 235 | (3-(2-(pyrazin-2-yl)thiazol-4-yl)-5,6-dihydro-[1,2,4]triazolo[4,3-a]pyrazin-7(8H)-yl)(4-(thiophen-2-yl)phenyl)methanone | 472.6 |
| 236 | 4-(4-(7-(4-(thiophen-2-yl)benzoyl)-5,6,7,8-tetrahydro-[1,2,4]triazolo[4,3-a]pyrazin-3-yl)thiazol-2-yl)benzonitrile | 495.6 |
| 237 | (4-fluorophenyl)(3-(2-(pyrazin-2-yl)thiazol-4-yl)-5,6-dihydro-[1,2,4]triazolo[4,3-a]pyrazin-7(8H)-yl)methanone | 408.4 |
| 238 | (4-fluorophenyl)(3-(1-methyl-5-phenyl-1H-pyrazol-3-yl)-5,6-dihydro-[1,2,4]triazolo[4,3-a]pyrazin-7(8H)-yl)methanone | 403.4 |
| 239 | (3-(2-(4-morpholinophenyl)thiazol-4-yl)-5,6-dihydro-[1,2,4]triazolo[4,3-a]pyrazin-7(8H)-yl)(4-(thiophen-2-yl)phenyl)methanone | 555.7 |
| 240 | (4-fluorophenyl)(3-(2-(4-morpholinophenyl)thiazol-4-yl)-5,6-dihydro-[1,2,4]triazolo[4,3-a]pyrazin-7(8H)-yl)methanone | 491.6 |
| 241 | (3-(2-(4-(4-methylpiperazin-1-yl)phenyl)thiazol-4-yl)-5,6-dihydro-[1,2,4]triazolo[4,3-a]pyrazin-7(8H)-yl)(4-(thiophen-2-yl)phenyl)methanone | 568.7 |
| 242 | (4-fluorophenyl)(3-(2-(4-(4-methylpiperazin-1-yl)phenyl)thiazol-4-yl)-5,6-dihydro-[1,2,4]triazolo[4,3-a]pyrazin-7(8H)-yl)methanone | 504.6 |
| 243 | (3-(2-(4-(piperidin-1-yl)phenyl)thiazol-4-yl)-5,6-dihydro-[1,2,4]triazolo[4,3-a]pyrazin-7(8H)-yl)(4-(thiophen-2-yl)phenyl)methanone | 553.7 |
| 244 | (4-fluorophenyl)(3-(2-(4-(piperidin-1-yl)phenyl)thiazol-4-yl)-5,6-dihydro-[1,2,4]triazolo[4,3-a]pyrazin-7(8H)-yl)methanone | 489.6 |
| 245 | (3-(2-(4-(pyrrolidin-1-yl)phenyl)thiazol-4-yl)-5,6-dihydro-[1,2,4]triazolo[4,3-a]pyrazin-7(8H)-yl)(4-(thiophen-2-yl)phenyl)methanone | 539.7 |
| 246 | (4-fluorophenyl)(3-(2-(4-(pyrrolidin-1-yl)phenyl)thiazol-4-yl)-5,6-dihydro-[1,2,4]triazolo[4,3-a]pyrazin-7(8H)-yl)methanone | 475.6 |
| 247 | (3-(2-(piperidin-1-yl)thiazol-4-yl)-5,6-dihydro-[1,2,4]triazolo[4,3-a]pyrazin-7(8H)-yl)(4-(thiophen-2-yl)phenyl)methanone | 477.6 |
| 248 | (3-(2-(pyrrolidin-1-yl)thiazol-4-yl)-5,6-dihydro-[1,2,4]triazolo[4,3-a]pyrazin-7(8H)-yl)(4-(thiophen-2-yl)phenyl)methanone | 463.6 |
| 249 | (4-fluorophenyl)(3-(2-(pyrrolidin-1-yl)thiazol-4-yl)-5,6-dihydro-[1,2,4]triazolo[4,3-a]pyrazin-7(8H)-yl)methanone | 399.5 |
| 250 | (3-(2-(4-methylpiperazin-1-yl)thiazol-4-yl)-5,6-dihydro-[1,2,4]triazolo[4,3-a]pyrazin-7(8H)-yl)(4-(thiophen-2-yl)phenyl)methanone | 492.6 |
| 251 | (4-fluorophenyl)(3-(2-(4-methylpiperazin-1-yl)thiazol-4-yl)-5,6-dihydro-[1,2,4]triazolo[4,3-a]pyrazin-7(8H)-yl)methanone | 428.5 |
| 252 | (3-(1-methyl-2-phenyl-1H-imidazol-4-yl)-5,6-dihydro-[1,2,4]triazolo[4,3-a]pyrazin-7(8H)-yl)(4-(thiophen-2-yl)phenyl)methanone | 467.6 |

TABLE 1-continued

| Compound no | Name | (M + H)+ |
|---|---|---|
| 253 | (4-(dimethylamino)phenyl)(3-(2-(4-fluorophenyl)thiazol-4-yl)-5,6-dihydro-[1,2,4]triazolo[4,3-a]pyrazin-7(8H)-yl)methanone | 449.5 |
| 254 | (3-(1-(2-methoxyethyl)-3-phenyl-1H-pyrazol-5-yl)-5,6-dihydro-[1,2,4]triazolo[4,3-a]pyrazin-7(8H)-yl)(4-(thiophen-2-yl)phenyl)methanone | 511.6 |
| 255 | (4-fluorophenyl)(3-(1-(2-methoxyethyl)-3-phenyl-1H-pyrazol-5-yl)-5,6-dihydro-[1,2,4]triazolo[4,3-a]pyrazin-7(8H)-yl)methanone | 447.5 |
| 256 | (3-(2-isobutylthiazol-4-yl)-5,6-dihydro-[1,2,4]triazolo[4,3-a]pyrazin-7(8H)-yl)(4-(thiophen-2-yl)phenyl)methanone | 450.6 |
| 257 | (3-(2-(2-(2-methoxyethyl)morpholino)thiazol-4-yl)-5,6-dihydro-[1,2,4]triazolo[4,3-a]pyrazin-7(8H)-yl)(4-(thiophen-2-yl)phenyl)methanone | 537.7 |
| 258 | (3-(2-(4,4-difluoropiperidin-1-yl)thiazol-4-yl)-5,6-dihydro-[1,2,4]triazolo[4,3-a]pyrazin-7(8H)-yl)(4-fluorophenyl)methanone | 449.5 |
| 259 | (4-fluorophenyl)(3-(2-isobutylthiazol-4-yl)-5,6-dihydro-[1,2,4]triazolo[4,3-a]pyrazin-7(8H)-yl)methanone | 386.5 |
| 260 | (4-fluorophenyl)(3-(2-(4-fluorophenyl)thiazol-4-yl)-5,6-dihydroimidazo[1,5-a]pyrazin-7(8H)-yl)methanone | 423.5 |
| 261 | (3-(2-(2,5-dimethylmorpholino)thiazol-4-yl)-5,6-dihydro-[1,2,4]triazolo[4,3-a]pyrazin-7(8H)-yl)(4-(thiophen-2-yl)phenyl)methanone | 507.6 |
| 262 | (3-(2-(2-hydroxyphenyl)thiazol-4-yl)-5,6-dihydro-[1,2,4]triazolo[4,3-a]pyrazin-7(8H)-yl)(4-(thiophen-2-yl)phenyl)methanone | 486.6 |
| 263 | (3-(2-(4,4-difluoropiperidin-1-yl)thiazol-4-yl)-5,6-dihydro-[1,2,4]triazolo[4,3-a]pyrazin-7(8H)-yl)(4-(thiophen-2-yl)phenyl)methanone | 513.6 |
| 265 | (3-(2-(2,6-dimethylmorpholino)thiazol-4-yl)-5,6-dihydro-[1,2,4]triazolo[4,3-a]pyrazin-7(8H)-yl)(4-(thiophen-2-yl)phenyl)methanone | 507.6 |
| 266 | (3-(2-(2,2-dimethylmorpholino)thiazol-4-yl)-5,6-dihydro-[1,2,4]triazolo[4,3-a]pyrazin-7(8H)-yl)(4-(thiophen-2-yl)phenyl)methanone | 507.6 |
| 267 | (3-(3-phenyl-1H-pyrazol-5-yl)-5,6-dihydro-[1,2,4]triazolo[4,3-a]pyrazin-7(8H)-yl)(4-(thiophen-2-yl)phenyl)methanone | 453.5 |
| 268 | (3-(2-(4-fluorophenyl)thiazol-4-yl)-8-methyl-5,6-dihydro-[1,2,4]triazolo[4,3-a]pyrazin-7(8H)-yl)(4-(3-methylthiophen-2-yl)phenyl)methanone | 516.6 |
| 269 | (4-fluorophenyl)(3-(3-phenyl-1H-pyrazol-5-yl)-5,6-dihydro-[1,2,4]triazolo[4,3-a]pyrazin-7(8H)-yl)methanone | 389.4 |
| 270 | (R)-(3-(2-(4-fluorophenyl)thiazol-4-yl)-8-methyl-5,6-dihydro-[1,2,4]triazolo[4,3-a]pyrazin-7(8H)-yl)(4-(3-methylthiophen-2-yl)phenyl)methanone | 516.6 |
| 271 | (4-fluorophenyl)(3-(2-(2-hydroxyphenyl)thiazol-4-yl)-5,6-dihydro-[1,2,4]triazolo[4,3-a]pyrazin-7(8H)-yl)methanone | 422.4 |
| 272 | (S)-(3-(2-(4-fluorophenyl)thiazol-4-yl)-8-methyl-5,6-dihydro-[1,2,4]triazolo[4,3-a]pyrazin-7(8H)-yl)(4-(3-methylthiophen-2-yl)phenyl)methanone | 516.6 |
| 273 | (3-(2-(2-methylmorpholino)thiazol-4-yl)-5,6-dihydro-[1,2,4]triazolo[4,3-a]pyrazin-7(8H)-yl)(4-(thiophen-2-yl)phenyl)methanone | 493.6 |
| 274 | (3-(2-(4,4-dimethylpiperidin-1-yl)thiazol-4-yl)-5,6-dihydro-[1,2,4]triazolo[4,3-a]pyrazin-7(8H)-yl)(4-(thiophen-2-yl)phenyl)methanone | 505.7 |
| 275 | (3-(5-methylthiazol-4-yl)-5,6-dihydro-[1,2,4]triazolo[4,3-a]pyrazin-7(8H)-yl)(4-(thiophen-2-yl)phenyl)methanone | 408.5 |
| 276 | (3-(2-(4,4-dimethylpiperidin-1-yl)thiazol-4-yl)-5,6-dihydro-[1,2,4]triazolo[4,3-a]pyrazin-7(8H)-yl)(4-fluorophenyl)methanone | 441.5 |
| 277 | (4-fluorophenyl)(3-(2-(2-(methoxymethyl)piperidin-1-yl)thiazol-4-yl)-5,6-dihydro-[1,2,4]triazolo[4,3-a]pyrazin-7(8H)-yl)methanone | 457.5 |
| 278 | (4-fluorophenyl)(8-methyl-3-(6-methylpyridin-2-yl)-5,6-dihydro-[1,2,4]triazolo[4,3-a]pyrazin-7(8H)-yl)methanone | 352.4 |
| 279 | (3-(2-(2-(methoxymethyl)piperidin-1-yl)thiazol-4-yl)-5,6-dihydro-[1,2,4]triazolo[4,3-a]pyrazin-7(8H)-yl)(4-(thiophen-2-yl)phenyl)methanone | 521.7 |
| 280 | tert-butyl(2-(2-(4-(7-(4-(thiophen-2-yl)benzoyl)-5,6,7,8-tetrahydro-[1,2,4]triazolo[4,3-a]pyrazin-3-yl)thiazol-2-yl)phenoxy)ethyl)carbamate | 629.8 |
| 281 | (3-(2-(2-(2-hydroxyethoxy)phenyl)thiazol-4-yl)-5,6-dihydro-[1,2,4]triazolo[4,3-a]pyrazin-7(8H)-yl)(4-(thiophen-2-yl)phenyl)methanone | 530.6 |

TABLE 1-continued

| Compound no | Name | (M + H)⁺ |
|---|---|---|
| 282 | (3-(2-(2-(2-aminoethoxy)phenyl)thiazol-4-yl)-5,6-dihydro-[1,2,4]triazolo[4,3-a]pyrazin-7(8H)-yl)(4-(thiophen-2-yl)phenyl)methanone | 529.6 |
| 283 | N-(4-(4-(7-(4-(thiophen-2-yl)benzoyl)-5,6,7,8-tetrahydro-[1,2,4]triazolo[4,3-a]pyrazin-3-yl)thiazol-2-yl)phenyl)methanesulfonamide | 563.7 |
| 284 | (3-(1-(2-hydroxyethyl)-3-phenyl-1H-pyrazol-5-yl)-5,6-dihydro-[1,2,4]triazolo[4,3-a]pyrazin-7(8H)-yl)(4-(thiophen-2-yl)phenyl)methanone | 497.6 |
| 285 | (3-(1-(2-hydroxyethyl)-5-phenyl-1H-pyrazol-3-yl)-5,6-dihydro-[1,2,4]triazolo[4,3-a]pyrazin-7(8H)-yl)(4-(thiophen-2-yl)phenyl)methanone | 497.6 |
| 286 | [1,1'-biphenyl]-4-yl(8-methyl-3-(6-methylpyridin-2-yl)-5,6-dihydro-[1,2,4]triazolo[4,3-a]pyrazin-7(8H)-yl)methanone | 410.5 |
| 287 | (8-methyl-3-(6-methylpyridin-2-yl)-5,6-dihydro-[1,2,4]triazolo[4,3-a]pyrazin-7(8H)-yl)(4-(thiophen-2-yl)phenyl)methanone | 416.5 |
| 288 | (3-(2-(2,4-difluorophenyl)-5-methylthiazol-4-yl)-5,6-dihydro-[1,2,4]triazolo[4,3-a]pyrazin-7(8H)-yl)(4-(thiophen-2-yl)phenyl)methanone | 520.6 |
| 289 | (3-(2-(3-(dimethylamino)phenyl)thiazol-4-yl)-5,6-dihydro-[1,2,4]triazolo[4,3-a]pyrazin-7(8H)-yl)(4-(thiophen-2-yl)phenyl)methanone | 513.6 |
| 290 | (3-(2-(3-(dimethylamino)phenyl)thiazol-4-yl)-5,6-dihydro-[1,2,4]triazolo[4,3-a]pyrazin-7(8H)-yl)(4-fluorophenyl)methanone | 449.5 |
| 291 | N-(3-(4-(7-(4-(thiophen-2-yl)benzoyl)-5,6,7,8-tetrahydro-[1,2,4]triazolo[4,3-a]pyrazin-3-yl)thiazol-2-yl)phenyl)methanesulfonamide | 563.7 |
| 292 | N-(2-(4-(7-(4-(thiophen-2-yl)benzoyl)-5,6,7,8-tetrahydro-[1,2,4]triazolo[4,3-a]pyrazin-3-yl)thiazol-2-yl)phenyl)methanesulfonamide | 563.7 |
| 293 | (3-(quinolin-2-yl)-5,6-dihydroimidazo[1,2-a]pyrazin-7(8H)-yl)(4-(thiophen-2-yl)phenyl)methanone | 437.5 |
| 294 | (3-(4-chlorophenyl)-1H-pyrazol-5-yl)(3-(2-(4-fluorophenyl)thiazol-4-yl)-5,6-dihydro-[1,2,4]triazolo[4,3-a]pyrazin-7(8H)-yl)methanone | 507.0 |
| 295 | (3-(4-chlorophenyl)-1-methyl-1H-pyrazol-5-yl)(3-(2-(4-fluorophenyl)thiazol-4-yl)-5,6-dihydro-[1,2,4]triazolo[4,3-a]pyrazin-7(8H)-yl)methanone | 521.0 |
| 296 | (3-(3,4-dichlorophenyl)-1-methyl-1H-pyrazol-5-yl)(3-(2-(4-fluorophenyl)thiazol-4-yl)-5,6-dihydro-[1,2,4]triazolo[4,3-a]pyrazin-7(8H)-yl)methanone | 555.4 |
| 297 | (5-(4-chlorophenyl)-1-methyl-1H-pyrazol-3-yl)(3-(2-(4-fluorophenyl)thiazol-4-yl)-5,6-dihydro-[1,2,4]triazolo[4,3-a]pyrazin-7(8H)-yl)methanone | 521.0 |
| 298 | tert-butyl(2-(3-phenyl-5-(7-(4-(thiophen-2-yl)benzoyl)-5,6,7,8-tetrahydro-[1,2,4]triazolo[4,3-a]pyrazin-3-yl)-1H-pyrazol-1-yl)ethyl)carbamate | 596.7 |
| 299 | tert-butyl(2-(5-phenyl-3-(7-(4-(thiophen-2-yl)benzoyl)-5,6,7,8-tetrahydro-[1,2,4]triazolo[4,3-a]pyrazin-3-yl)-1H-pyrazol-1-yl)ethyl)carbamate | 596.7 |
| 300 | (3-(2-(2-bromophenyl)thiazol-4-yl)-5,6-dihydro-[1,2,4]triazolo[4,3-a]pyrazin-7(8H)-yl)(4-(thiophen-2-yl)phenyl)methanone | 549.5 |
| 301 | (3-(2-(3-bromophenyl)thiazol-4-yl)-5,6-dihydro-[1,2,4]triazolo[4,3-a]pyrazin-7(8H)-yl)(4-(thiophen-2-yl)phenyl)methanone | 549.5 |
| 302 | 2-(4-(7-(4-(thiophen-2-yl)benzoyl)-5,6,7,8-tetrahydro-[1,2,4]triazolo[4,3-a]pyrazin-3-yl)thiazol-2-yl)benzonitrile | 495.6 |
| 303 | 3-(4-(7-(4-(thiophen-2-yl)benzoyl)-5,6,7,8-tetrahydro-[1,2,4]triazolo[4,3-a]pyrazin-3-yl)thiazol-2-yl)benzonitrile | 495.6 |
| 304 | (3-(2-(4-fluorophenyl)thiazol-4-yl)-8-methyl-5,6-dihydro-[1,2,4]triazolo[4,3-a]pyrazin-7(8H)-yl)(4-(2-methylthiophen-3-yl)phenyl)methanone | 516.6 |

The compounds of table 1 were named using ChemDraw Ultra 12 purchased from CambridgeSoft (Cambridge, Mass., USA).

The compounds of formula I can be prepared by different ways with reactions known by the person skilled in the art. Reaction schemes as described in the example section illustrate by way of example different possible approaches.

The invention further provides the use of the compounds of the invention or pharmaceutically acceptable salts, or solvates thereof as antagonists of NK-3 receptor.

Accordingly, in a particularly preferred embodiment, the invention relates to the use of compounds of formula I and subformulae in particular those of table 1 above, or pharmaceutically acceptable salts and solvates thereof, as NK-3 receptor antagonists.

[Applications]

The compounds of the invention are therefore useful as medicaments, in particular in the prevention and/or treatment of depression, anxiety, pyschosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome and inflammatory bowel disorders, emesis, pre-eclampsia, airway related diseases including chronic obstructive pulmonary disease, asthma, airway hyperresponsiveness, bronchoconstriction and cough, reproduction disorders and sex hormone-dependent diseases including but not limited to benign prostatic hyperplasia (BPH), metastatic prostatic carninoma, testicular cancer, breast cancer, androgen dependent acne, male pattern baldness, endometriosis, abnormal puberty, uterine fibrosis, hormone-dependent cancers, hyperandrogenism, hirsutism, virilization, polycystic ovary syndrome (PCOS), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility) and androgen-producing tumor (virilizing ovarian or adrenal tumor).

The invention also provides for a method for delaying in patient the onset of depression, anxiety, pyschosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome and inflammatory bowel disorders, emesis, pre-eclampsia, airway related diseases including chronic obstructive pulmonary disease, asthma, airway hyperresponsiveness, bronchoconstriction and cough, reproduction disorders and sex hormone-dependent diseases including but not limited to benign prostatic hyperplasia (BPH), metastatic prostatic carninoma, testicular cancer, breast cancer, androgen dependent acne, male pattern baldness, endometriosis, abnormal puberty, uterine fibrosis, hormone-dependent cancers, hyperandrogenism, hirsutism, virilization, polycystic ovary syndrome (PCOS), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility) and androgen-producing tumor (virilizing ovarian or adrenal tumor) comprising the administration of a pharmaceutically effective amount of a compound of formula (I) or pharmaceutically acceptable salt thereof to a patient in need thereof.

Preferably, the patient is a warm-blooded animal, more preferably a human.

The compounds of the invention are also useful in the treatment of gynecological disorders and infertility. In particular, the invention provides methods to suppress the LH-surge in assisted conception.

The compounds of the invention are also useful to cause male castration and to inhibit the sex drive in men. This of particular interest in the treatment of male sexual offenders.

The invention further provides the use of a compound of formula (I) or a pharmaceutically acceptable salt or solvate thereof for the manufacture of a medicament for treating and/or preventing depression, anxiety, pyschosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome and inflammatory bowel disorders, emesis, pre-eclampsia, airway related diseases including chronic obstructive pulmonary disease, asthma, airway hyperresponsiveness, bronchoconstriction and cough, reproduction disorders and sex hormone-dependent diseases including but not limited to benign prostatic hyperplasia (BPH), metastatic prostatic carninoma, testicular cancer, breast cancer, androgen dependent acne, male pattern baldness, endometriosis, abnormal puberty, uterine fibrosis, hormone-dependent cancers, hyperandrogenism, hirsutism, virilization, polycystic ovary syndrome (PCOS), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility) and androgen-producing tumor (virilizing ovarian or adrenal tumor) in a patient.

Preferably, the patient is a warm-blooded animal, more preferably a human.

The invention further provides the use of a compound of formula (I) or a pharmaceutically acceptable salt or solvate thereof for the manufacture of a medicament to suppress the LH-surge in assisted conception in a patient. Preferably the patient is a warm-blooded animal, more preferably a woman.

The invention further provides the use of a compound of formula (I) or a pharmaceutically acceptable salt or solvate thereof for the manufacture of a medicament to cause male castration and to inhibit the sex drive in men. This is of particular interest in the treatment of male sexual offenders.

According to a further feature of the present invention there is provided a method for modulating NK-3 receptor activity, in a patient, preferably a warm blooded animal, and even more preferably a human, in need of such treatment, which comprises administering to said patient an effective amount of compound of the present invention, or a pharmaceutically acceptable salt or solvate thereof.

According to one embodiment, the compounds of the invention, their pharmaceutical acceptable salts or solvates may be administered as part of a combination therapy. Thus, are included within the scope of the present invention embodiments comprising coadministration of, and compositions and medicaments which contain, in addition to a compound of the present invention, a pharmaceutically acceptable salt or solvate thereof as active ingredient, additional therapeutic agents and/or active ingredients. Such multiple drug regimens, often referred to as combination therapy, may be used in the treatment and/or prevention of any of the diseases or conditions mediated by or associated with NK-3 receptor modulation. The use of such combinations of therapeutic agents is especially pertinent with respect to the treatment of the above-mentioned disorders within a patient in need of treatment or one at risk of becoming such a patient.

In addition to the requirement of therapeutic efficacy, which may necessitate the use of active agents in addition to the NK-3 receptor modulator compounds of Formula I or pharmaceutical acceptable salts or solvates thereof, there may be additional rationales which compel or highly recommend the use of combinations of drugs involving active ingredients which represent adjunct therapy, i.e., which complement and supplement the function performed by the NK-3 receptor modulator compounds of the present invention. Suitable supplementary therapeutic agents used for the purpose of auxiliary treatment include drugs which, instead of directly treating or preventing a disease or condition mediated by or associated with NK-3 receptor modulation, treat diseases or conditions which directly result from or indirectly accompany the basic or underlying NK-3 receptor modulated disease or condition.

According to a further feature of the present invention the compound of Formula I, a pharmaceutically acceptable salt or solvate thereof may be used in combination therapy with antipsychotic drugs (APD), to improve the efficacy and to minimize secondary effects associated to APD including but not limited to Dopamine 2/3 and 5-HT2 receptors antagonists. More particular the compound of Formula I, a pharmaceutically acceptable salt or solvate thereof may be used as an adjunct therapy in combination with an atypical antipsychotic drug, including but not limited to risperidone, clozapine, olanzapine, where the NK-3 receptor modulator may serve a role as dose-limiting for the atypical antipsychotic and therefore spare the patient from some of the side effect of those atypical antipsychotic drugs.

Thus, the methods of treatment and pharmaceutical compositions of the present invention may employ the compounds of Formula I or pharmaceutical acceptable salts or solvates thereof in the form of monotherapy, but said methods and compositions may also be used in the form of multiple therapy in which one or more compounds of Formula I or their pharmaceutically acceptable salts or solvates are coadministered in combination with one or more other therapeutic agents.

In the above-described embodiment combinations of the present invention, the compound of Formula I, a pharmaceutically acceptable salt or solvate thereof and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

The invention also provides pharmaceutical compositions comprising a compound of formula I or a pharmaceutically acceptable salt or solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable salt or solvate thereof as active ingredient, additional therapeutic agents and/or active ingredients.

Another object of this invention is a medicament comprising at least one compound of the invention, or a pharmaceutically acceptable salt or solvate thereof, as active ingredient.

According to a further feature of the present invention there is provided the use of a compound of formula I or a pharmaceutically acceptable salt or solvate thereof for the manufacture of a medicament for modulating NK-3 receptor activity in a patient, in need of such treatment, which comprises administering to said patient an effective amount of compound of the present invention, or a pharmaceutically acceptable salt or solvate thereof.

Preferably, the patient is a warm-blooded animal, more preferably a human.

As set forth above, the compounds of the invention, their pharmaceutically acceptable salts or solvates may be used in monotherapy or in combination therapy. Thus, according to one embodiment, the invention provides the use of a compound of the invention for the manufacture of a medicament for at least one of the purposes described above, wherein said medicament is administered to a patient in need thereof, preferably a warm-blooded animal, and even more preferably a human, in combination with at least one additional therapeutic agent and/or active ingredient. The benefits and advantages of such a multiple drug regimen, possible administration regimens as well as suitable additional therapeutic agents and/or active ingredients are those described above.

Generally, for pharmaceutical use, the compounds of the inventions may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 0.05 and 1000 mg, and usually between 1 and 500 mg, of the at least one compound of the invention, e.g. about 10, 25, 50, 100, 200, 300 or 400 mg per unit dosage.

Usually, depending on the condition to be prevented or treated and the route of administration, the active compound of the invention will usually be administered between 0.01 to 100 mg per kilogram, more often between 0.1 and 50 mg, such as between 1 and 25 mg, for example about 0.5, 1, 5, 10, 15, 20 or 25 mg, per kilogram body weight of the patient per day, which may be administered as a single daily dose, divided over one or more daily doses, or essentially continuously, e.g. using a drip infusion.

Definitions

The definitions and explanations below are for the terms as used throughout the entire application, including both the specification and the claims.

When describing the compounds of the invention, the terms used are to be construed in accordance with the following definitions, unless indicated otherwise.

Where groups may be substituted, such groups may be substituted with one or more substituents, and preferably with one, two or three substituents. Substituents may be selected from but not limited to, for example, the group comprising halogen, hydroxyl, oxo, nitro, amido, carboxy, amino, cyano haloalkoxy, and haloalkyl.

As used herein the terms such as "alkyl, aryl, or cycloalkyl, each being optionally substituted with . . . " or "alkyl, aryl, or cycloalkyl, optionally substituted with . . . " encompasses "alkyl optionally substituted with . . . ", "aryl optionally substituted with . . . " and "cycloalkyl optionally substituted with . . . ".

The term "halo" or "halogen" means fluoro, chloro, bromo, or iodo. Preferred halo groups are fluoro and chloro.

The term "alkyl" by itself or as part of another substituent refers to a hydrocarbyl radical of Formula $C_nH_{2n+1}$ wherein n is a number greater than or equal to 1. Generally, alkyl groups of this invention comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein.

Suitable alkyl groups include methyl, ethyl, n-propyl, i-propyl, n-butyl, i-butyl, s-butyl and t-butyl, pentyl and its isomers (e.g. n-pentyl, iso-pentyl), and hexyl and its isomers (e.g. n-hexyl, iso-hexyl). Preferred alkyl groups include methyl, ethyl, n-propyl, i-propyl, n-butyl, i-butyl, s-butyl and t-butyl. $C_{x-y}$-alkyl and Cx-Cy-alkyl refer to alkyl groups which comprise from x to y carbon atoms.

When the suffix "ene" ("alkylene") is used in conjunction with an alkyl group, this is intended to mean the alkyl group as defined herein having two single bonds as points of attachment to other groups. The term "alkylene" includes methylene, ethylene, methylmethylene, propylene, ethylethylene, and 1,2-dimethylethylene.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl and the like. $C_{x-y}$-haloalkyl and Cx-Cy-alkyl refer to alkyl groups which comprise from x to y carbon atoms. Preferred haloalkyl groups are difluoromethyl, trifluoromethyl.

The term "cycloalkyl" as used herein is a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl, with cyclopropyl being particularly preferred.

When the suffix "ene" is used in conjunction with a cyclic group, this is intended to mean the cyclic group as defined herein having two single bonds as points of attachment to other groups.

Therefore, "cycloalkylene" herein refers to a saturated homocyclic hydrocarbyl biradical of Formula $C_nH_{2n-2}$. Suitable cycloalkylene groups are $C_{3-6}$ cycloalkylene group, preferably a $C_{3-5}$ cycloalkylene (i.e. 1,2-cyclopropylene, 1,1-cyclopropylene, 1,1-cyclobutylene, 1,2-cyclobutylene, 1,3-cyclobutylene, 1,3-cyclopentylene, or 1,1-cyclopentylene), more preferably a $C_{3-4}$ cycloalkylene (i.e. 1,2-cyclopropylene, 1,1-cyclopropylene, 1,1-cyclobutylene, 1,2-cyclobutylene).

Where at least one carbon atom in a cycloalkyl group is replaced with a heteroatom, the resultant ring is referred to herein as "heterocycloalkyl" or "heterocyclyl".

The terms "heterocyclyl", "heterocycloalkyl" or "heterocyclo" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include oxetanyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, 3H-indolyl, indolinyl, isoindolinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1H-pyrrolizinyl, tetrahydro-1,1-dioxothiophenyl, N-formylpiperazinyl, and morpholin-4-yl.

The ring atoms of selected heterocyclyl and heterocyclylene moieties are numbered based on scheme below

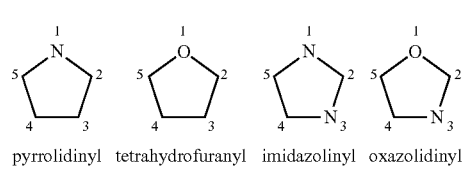

pyrrolidinyl  tetrahydrofuranyl  imidazolinyl  oxazolidinyl

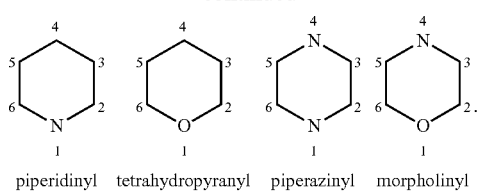

piperidinyl  tetrahydropyranyl  piperazinyl  morpholinyl

The ring atoms of fused piperazine of the invention are numbered based on scheme below

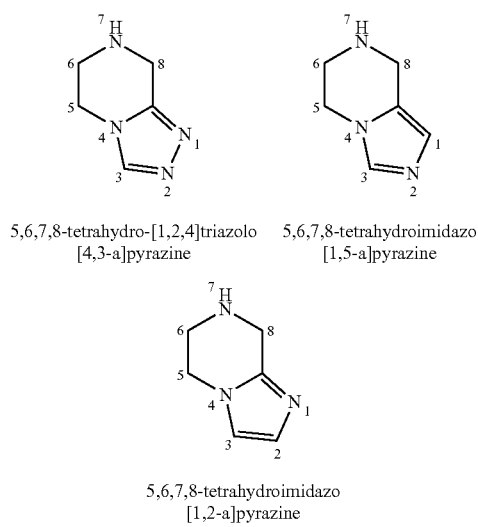

5,6,7,8-tetrahydro-[1,2,4]triazolo[4,3-a]pyrazine 5,6,7,8-tetrahydroimidazo[1,5-a]pyrazine 5,6,7,8-tetrahydroimidazo[1,2-a]pyrazine The term "aryl" as used herein refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, naphthalen-1- or -2-yl, 4-, 5-, 6 or 7-indenyl, 1- 2-, 3-, 4- or 5-acenaphthylenyl, 3-, 4- or 5-acenaphthenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

The term "arylene" as used herein is intended to include divalent carbocyclic aromatic ring systems such as phenylene, biphenylylene, naphthylene, indenylene, pentalenylene, azulenylene and the like. Arylene is also intended to include the partially hydrogenated derivatives of the carbocyclic systems enumerated above. Non-limiting examples of such partially hydrogenated derivatives are 1,2,3,4-tetrahydronaphthylene, 1,4-dihydronaphthylene and the like.

Where at least one carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxopyridazin-1 (6H)-yl, 2-oxopyridin-1 (2H)-yl, 6-oxopyridazin-1 (6H)-yl, 2-oxopyridin-1(2H)-yl, 1,3-benzodioxolyl, quinolinyl, isoquinolinyl, cinnolinyl, quinazolinyl, quinoxalinyl.

The term "heteroarylene" as used herein means divalent carbocyclic aromatic ring systems including pyridinylene and the like.

The ring atoms of selected heteroaryl or heteroarylene moieties are numbered on scheme below:

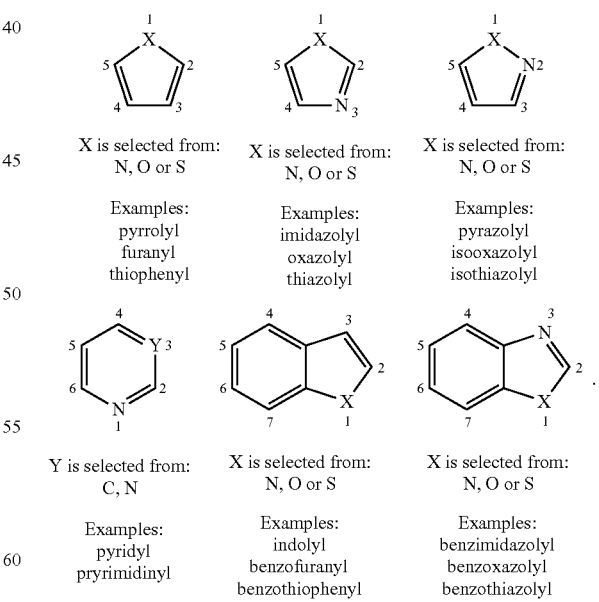

The term "biaryl" as used herein designates two aryl moieties as defined herein linked via a single bond. Non-limiting examples of such biaryl moieties include all biphenyl regioisomers 2-biphenyl, 3-biphenyl and 4-biphenyl.

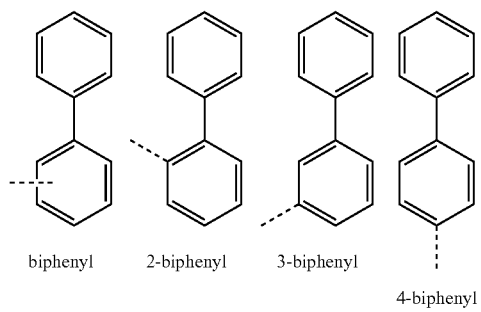

biphenyl  2-biphenyl  3-biphenyl 4-biphenyl

The term "heterobiaryl" as used herein designates two heteroaryl moieties as defined herein or a heteroaryl moiety and an aryl moiety as defined herein linked via a single bond. Non-limiting examples of such heterobiaryl moieties are given hereunder.

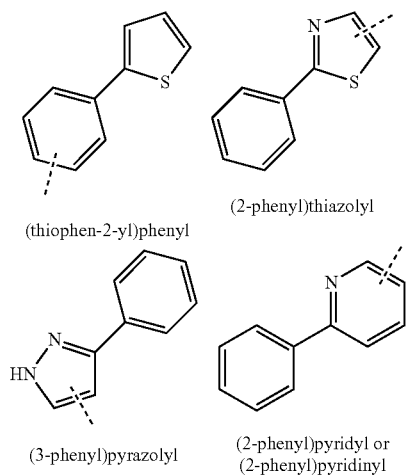

(thiophen-2-yl)phenyl (2-phenyl)thiazolyl (3-phenyl)pyrazolyl (2-phenyl)pyridyl or
(2-phenyl)pyridinyl The term "carbamoyl" as used herein means a group of formula

wherein the arrow defines the attachment point.

The term "carbamimidoyl" as used herein means a group of formula

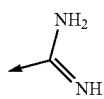

wherein the arrow defines the attachment point.

The compounds of Formula I and subformulae thereof contain at least one asymmetric center and thus may exist as different stereoisomeric forms. Accordingly, the present invention includes all possible stereoisomers and includes not only racemic compounds but the individual enantiomers and their non racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994), incorporated by reference with regard to stereochemistry.

The bonds from an asymmetric carbon in compounds of the present invention may be depicted herein using a solid line (—), a zigzag line ($\sim$), a solid wedge (━), or a dotted wedge (⋯). The use of a solid line to depict bonds from an asymmetric carbon atom is meant to indicate that all possible stereoisomers in any relative ratio are meant to be included, unless it is clear from the context that a specific stereoisomer is intended. As a non limiting example, a solid line depicting bonds from an asymmetric carbon atom in a compound containing one asymmetric carbon encompasses a racemic mixture of both enantiomers. The term racemic used herein indicated a 1/1 ratio between the two enantiomers. The use of either a solid or dotted wedge to depict bonds from an asymmetric carbon atom is meant to indicate that only the stereoisomer shown is meant to be included.

As a non limiting example, compounds of formula Ic wherein $R^{1'}$ is H, R is not H and bond a, which designates the bond linking $R^1$ to the piperazine moiety, is drawn as a dotted wedge are stereoisomers of formula A. Compounds of formula Ic wherein $R^{1'}$ is H, $R^1$ is not H and bond a is drawn as a solid wedge are stereoisomers of formula B.

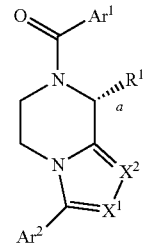

A

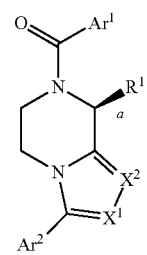

B

The compounds of the invention may also contain more than one asymmetric carbon atom. In those compounds, the use of a solid line to depict bonds from asymmetric carbon atoms is meant to indicate that all possible stereoisomers in any relative ratio are meant to be included, unless it is clear from the context that a specific stereoisomer is intended.

The compounds of the invention may be in the form of pharmaceutically acceptable salts. Pharmaceutically acceptable salts of the compounds of formula I include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of Formula I may be prepared by one or more of these methods:

(i) by reacting the compound of Formula I with the desired acid;

(ii) by reacting the compound of Formula I with the desired base;

(iii) by removing an acid- or base-labile protecting group from a suitable precursor of the compound of Formula I or by ring-opening a suitable cyclic precursor, for example, a lactone or lactam, using the desired acid; or (iv) by converting one salt of the compound of Formula I to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The term "solvate" is used herein to describe a molecular complex comprising the compound of the invention and one or more pharmaceutically acceptable solvent molecules, for example, ethanol. The term 'hydrate' is employed when said solvent is water.

All references to compounds of formula I include references to salts, solvates, multi-component complexes and liquid crystals thereof.

The compounds of the invention include compounds of formula I as hereinbefore defined, including all polymorphs and crystal habits thereof, prodrugs and isomers thereof (including optical, geometric and tautomeric isomers) and isotopically-labeled compounds of formula I.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula I above.

The invention also generally covers all pharmaceutically acceptable predrugs and prodrugs of the compounds of Formula I.

The term "prodrug" as used herein means the pharmacologically acceptable derivatives of compounds of formula I such as esters whose in vivo biotransformation product is the active drug. Prodrugs are characterized by increased bioavailability and are really metabolized into the active compounds in vivo.

The term "predrug", as used herein, means any compound that will be modified to form a drug species, wherein the modification may take place either inside or outside of the body, and either before or after the predrug reaches the area of the body where administration of the drug is indicated.

The term "patient" refers to a warm-blooded animal, more preferably a human, who/which is awaiting or receiving medical care or is or will be the object of a medical procedure.

The term "human" refers to subject of both genders and at any stage of development (i.e. neonate, infant, juvenile, adolescent, adult).

The terms "treat", "treating" and "treatment, as used herein, are meant to include alleviating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e. g. NK-3 antagonist) which is sufficient to achieve the desired therapeutic or prophylactic effect in the individual to which it is administered.

The term "administration", or a variant thereof (e.g., "administering"), means providing the active agent or active ingredient (e. g. a NK-3 antagonist), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "antagonist" as used herein means a compound which competitively or non-competitively binds to a receptor at the same site as an agonist (for example, the endogenous ligand), but does not activate an intracellular response initiated by an active form of the receptor. An antagonist thereby inhibits the intracellular response induced by an agonist.

The term "sex hormone-dependent disease" as used herein means a disease which is exacerbated by, or caused by, excessive, inappropriate or unregulated sex hormone production. Example of such diseases in men include but not limited to benign prostatic hyperplasia (BPH), metastatic prostatic carninoma, testicular cancer, breast cancer, androgen dependent acne, male pattern baldness. Example of such diseases in women include but not limited to endometriosis, abnormal puberty, uterine fibrosis, hormone-dependent cancers (ovarian cancer, breast cancer), hyperandrogenism, hirsutism, virilization, polycystic ovary syndrome (PCOS), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility) and androgen-producing tumor (virilizing ovarian or adrenal tumor).

The term "Psychotic disorders" as used herein means a group of illnesses that affect the mind. These illnesses alter a patient's ability to think clearly, make good judgments, respond emotionally, communicate effectively, understand reality, and behave appropriately. When symptoms are severe, patient with psychotic disorders have difficulty staying in touch with reality and often are unable to meet the ordinary demands of daily life. Psychotic disorders include, and are not limited to, schizophrenia, schizophreniform disorder, schizoaffective disorder, delusional disorder, brief psychotic disorder, shared psychotic disorder, psychotic disorder due to a general medical condition, substance-induced psychotic disorder or psychotic disorder not otherwise specified (Diagnostic and Statistical Manual of Mental Disorders, Ed. 4th, American Psychiatric Association, Washington, D.C. 1994).

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The present invention will be better understood with reference to the following examples. These examples are intended to representative of specific embodiments of the invention, and are not intended as limiting the scope of the invention.

Chemistry Examples

All temperatures are expressed in ° C. and all reactions were carried out at room temperature (RT) unless otherwise stated.

Analytical thin layer chromatography (TLC) was used to monitor reactions, establish flash chromatography conditions and verify purity of intermediates or final products. TLC plates used were Merck TLC aluminium sheet silica gel 60 $F_{254}$. TLC plates were revealed using ultraviolet irradiation (wavelength=254 nm) at room temperature or bromocresol green spray reagent at 0.1% in propan-2-ol purchased from VWR International upon heating at 160° C. or $KMnO_4$ revelator upon heating at 160° C. The $KMnO_4$ TLC revealing agent was prepared by dissolving 3 g of potassium permanganate, 20 g of sodium carbonate, 0.5 g of sodium hydroxide in 100 mL of distilled water.

HPLC-MS spectra were obtained on Agilent LCMS using Electropsray ionization (ESI). The Agilent instrument includes an Autosampler 1200, a binary pump 1100, a 5 wave length detector 1100 and a 6100 Single Quad. The column used was an XBridge C18, 4.6×50 mm, 3.5 µm. Eluent was a mixture of solution A (0.1% TFA in $H_2O$) and solution B (0.1% TFA in ACN). Gradient was applied at a flow rate of 2 mL $min^{-1}$ as follows: gradient A: held the initial conditions of 5% solution B for 1 min, increased linearly to 95% solution B in 4 min, held at 95% during 1 min, returned to initial conditions in 0.5 min and maintained for 1 min; gradient B: held the initial conditions of 5% solution B for 1 min, increased linearly to 60% in 10 min, increased linearly to 95% in 0.5 min, held at 95% during 3 min, returned to initial conditions in 0.5 min and maintained for 1 min.

Determination of ee was performed on an Agilent 1100 (binary pump and 5 wavelengths detector) with manual or automatic (Autosampler 1100) injection. Columns used were CHIRALPAK IA CHIRALPAK IB or CHIRALPAK IC in isocratic mode. Mixtures of eluents were selected depending on the separation obtained of enantiomers or diastereoisomers. Usual mixtures were:
hexane and ethanol (0.1% DEA)
hexane and isopropanol (0.1% DEA)
hexane and ethyl acetate (0.1% DEA)
hexane and dichloromethane (0.1% DEA)
heptane and THF (0.1% DEA)

Preparative HPLC purifications were carried out on Fractionlynx instrument, from Waters. This instrument consists of a Fraction Collector, a 2767 Sample Manager, a pump control a module II, a 515 HPLC Pump, a 2525 Binary Gradient Module, a Switching Valve, a 2996 Photodiode Array Detector and a Micromass ZQ. The column used was a Waters Sunfire C18 Eluent was a mixture of solution A (0.1% TFA in $H_2O$) and solution B (0.1% TFA in ACN). The gradient was adapted depending on impurities present in samples, to allow sufficient separation between impurities and target compound.

Chiral preparative HPLC purification were performed on an Agilent 1100 instrument (binary pump and 5 wavelengths detector) with manual injection using a CHIRALPAK IA or a CHIRALPAK IB column in isocratic mode. Mixtures of eluents were selected depending on the separation of enantiomers or diastereoisomers obtained with the analytical method. Usual mixtures were the same as those used for the determination of ee.

$^1H$ and $^{13}C$ NMR spectra were recorded on a Bruker Avance DRX 300 MHz. Chemical shifts are expressed in parts per million, (ppm, δ units). Coupling constants are expressed in Hertz units (Hz). Splitting patterns describe apparent multiplicities and are described as s (singlet), d (doublet), t (triplet), q (quadruplet), m (multiplet), or br (broad).

Solvents, reagents and starting materials were purchased from well known chemical suppliers such as for example Sigma Aldrich, Acros Organics, Fluorochem, Eurisotop, VWR International, Sopachem and Polymer labs and the following abbreviations are used:
ACN: Acetonitrile,
DCM: Dichloromethane,
DMF: N,N-dimethylformamide,
EtOAc: Ethyl acetate,
EtOH: Ethanol,
MeOH: Methanol,
IPA: isopropanol,
RT: Room temperature,
Y: Yield,
g: Gram(s),
mg: Milligram(s),
L: Liter(s),
mL: Milliliter(s),
µL: Microliter(s),
mol: Mole(s),
mmol: Millimole(s),
h: Hour(s),
mn or min: Minute(s),
TLC: Thin layer chromatography,
MW: Molecular weight,
eq: Equivalent, μW or μwave: Microwave,
THF: Tetrahydrofuran,
Ac: Acetyl,
ee: Enantiomeric excess,
tBu: tert-Butyl
P: UV purity at 254 nm or 215 nm determined by HPLC-MS,
SPE: Solid phase extraction,
rt: Retention time.
DEA: diethylamine,
HATU: O-(7-azabenzotriazol-1-yl)-N,N,N',N'-tetramethyluronium hexafluorophosphate,
TFA: trifluoroacetic acid,
DBU: 1,8-Diazabicyclo[5.4.0]undec-7-ene
TMS: trimethylsilyl,
CDI: carbonyldiimidazole,
rm or RM: reaction mixture,
dba: dibenzylideneacetone,
X-Phos: 2-Dicyclohexylphosphino-2',4',6'-triisopropylbiphenyl,
THP: tetrahydropyran,
Boc: tert-butoxycarbonyl,
DPPF: Diphenylphosphinoferrocene.

The intermediates and compounds disclosed hereunder were named using ChemDraw Ultra 12 purchased from CambridgeSoft (Cambridge, Mass., USA).

General Synthetic Scheme

Most compounds of the invention were synthesized using the methodology described in scheme 1. The chiral compounds were obtained either by purification using chiral HPLC, or by employing the appropriate chiral ketopiperazine building block.

Scheme 1: General synthetic scheme for the preparation of the majority of compounds in the present invention

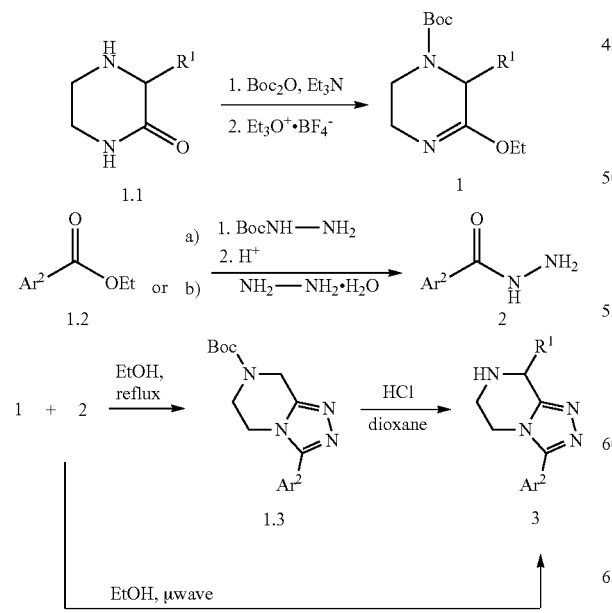

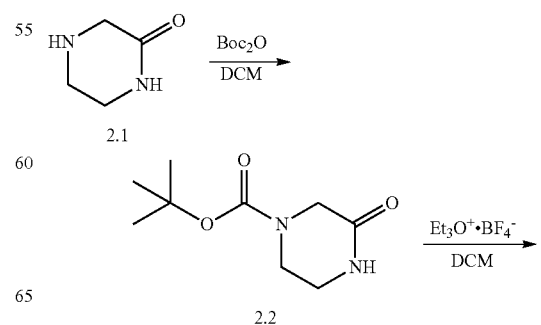

* conditions A: R = Cl: Et$_3$N, DCM
conditions B: R = OH, HATU, DIEA, MeCN

Ketopiperazine 1.1 was protected with a Boc group and converted to iminoether 1 by using Meerwein reagent (i.e., Et$_3$OBF$_4$). Ester 1.2 was subsequently converted to acyl hydrazide 2 through its reaction with hydrazine, either in N-Boc-protected form (i.e. 1.2→2, condition a), or without protection (i.e. 1.2→2, condition b). Condensation reaction between the acyl hydrazide thus generated and the iminoether aforementioned was conducted either under thermal reflux conditions, or by applying microwave irradiation. In case of reactions conducted using microwave irradiation, the N-Boc deprotection occurred during the condensation reaction, thus a deprotection step was not necessary to carry out (i.e. 1+2→3 in Scheme 1). However, when condensation reaction was carried out under thermal conditions, it was necessary to introduce a deprotection step (i.e. 1+2→1.3→3). Acylation of the amine in the triazolopiperazine intermediate 1.5, either through reaction with the appropriate acid chloride or through reaction with the appropriate activated ester, i.e. conditions A and B respectively, afforded the final target structure. This synthetic approach was used for the majority of the compounds described in the present invention.

General Method A:

General Method A is the general procedure used for the synthesis of the iminoether intermediates 1 (cf. Scheme 1) and is detailed below using the example of tert-butyl 3-ethoxy-5,6-dihydropyrazine-1(2H)-carboxylate 1a.

Scheme 2: Synthesis of tert-butyl 3-ethoxy-5,6-dihydropyrazine-1(2H)-carboxylate

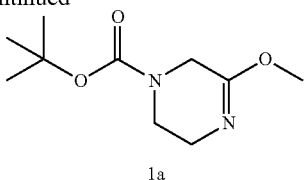

1a

Step 1: Synthesis of tert-butyl 3-oxopiperazine-1-carboxylate 2.2

Boc₂O (10.9 g, 0.05 mol) was added in portions under stirring and cooling on an ice bath to a suspension of piperazin-2-one 2.1 (5 g, 0.05 mol) in anhydrous dichloromethane (100 mL). The reaction mixture was stirred at 20° C. overnight (evolution of gas was observed at the beginning of the reaction), during which time a homogeneous solution formed. The solvent was evaporated, and the solid residue was vacuum-dried (10-15 mm Hg) at 40-50° C. to constant weight to give 2.2. Yield: 100 g (100%).

Step 2: Synthesis of tert-butyl 5-ethoxy-3,6-dihydropyrazine-1(2H)-carboxylate 1a Solid triethyloxonium tetrafluoroborate (2.3 g, 0.012 mol) was added in portions under stirring and cooling on an ice bath to a solution of 2.2 (2 g, 0.01 mol) in anhydrous dichloromethane (20 mL). After the addition was completed, the cooling was removed, and the reaction mixture was stirred at room temperature overnight. Then a 20% K₂CO₃ aqueous solution was added in portions under cooling on an ice bath to the obtained slightly muddy solution to obtain pH 8-9. The formed precipitate of potassium tetrafluoroborate was removed by filtration and washed on filter with dichloromethane. The filtrate was placed into a separatory funnel, and the organic layer was separated. The aqueous layer was extracted with dichloromethane (3×10 mL), and the combined organic extracts were washed with water (20 mL), dried over Na₂SO₄ and concentrated on a rotary evaporator. Hexane was added to the residue, and the obtained mixture was left to stand in a refrigerator for ~4 h. The formed precipitate was removed by filtration using a thin pad of Celite, and the filtrate was evaporated. The obtained viscous yellowish oil was vacuum-dried (10-15 mm Hg) at 40-50° C. for ~6 h to give title intermediate 1a. Yield: 2.03 g (88%). ¹HNMR (CDCl₃): δ: 4.1 ppm (q, 2H), 3.85 ppm (s, 2H), 3.5 ppm (m, 1H), 3.35 ppm (t, 2H), 1.45 ppm (s, 9H), 1.3 ppm (t, 3H). Alternatively, general method A was carried out as follows:

Step 1: Synthesis of tert-butyl 3-oxopiperazine-1-carboxylate 2.2

To a solution of piperazin-2-one 2.1 (5.0 g, 33.2 mmol) in commercial anhydrous CH₂Cl₂ (100 mL) under N₂ at RT was added NEt₃ (5.1 mL, 35.5 mmol). After 10 min stirring, the RM. was cooled down to 0° C. with an ice bath and Boc₂O (8.33 g, 38.2 mmol) was added in one portion. The RM. was then stirred at RT for 1 h. The mixture was diluted with 50 mL of CH₂Cl₂ and washed with HCl 0.5M (30 mL), brine (30 mL), dried over magnesium sulfate, filtered and concentrated to constant weight furnishing 2.2 as a yellow oil. Yield: 7.1 g (100%). LCMS and ¹HNMR data are consistent with those described above.

Step 2: Synthesis of tert-butyl 5-ethoxy-3,6-dihydropyrazine-1(2H)-carboxylate 1a To a pre-made solution of triethyloxonium tetrafluoroborate (2.3 g, 0.012 mol) in anhydrous dichloromethane (20 mL) was added 2.2 (2 g, 0.01 mol) at 0° C. After the addition was completed, the ice-bath was removed, and the reaction mixture was allowed to warm to room temperature and stirred for an additional hour (reaction progress monitored by LC-MS). Upon completion of the reaction, a saturated solution of NaHCO₃ (500 mL) was slowly added to the reaction mixture and it was stirred for 5 min. The organic layer was separated and the aqueous layer was further extracted with dichloromethane. The combined organic layers were subsequently washed with brine, dried over MgSO₄, filtered and further dried in vacuo to obtain the title intermediate 1a as a viscous yellow oil. Yield: 2.03 g (88%). ¹HNMR (CDCl₃): δ: 4.1 ppm (q, 2H), 3.85 (s, 2H), 3.5 ppm (m, 1H), 3.35 ppm (t, 2H), 1.45 ppm (s, 9H), 1.3 ppm (t, 3H).

The following intermediates were also prepared from the ad hoc reagents using General Method A:
intermediate 1b: (R)-tert-butyl 3-ethoxy-2-methyl-5,6-dihydropyrazine-1(2H)-carboxylate,
intermediate 1c: (S)-tert-butyl 3-ethoxy-2-methyl-5,6-dihydropyrazine-1(2H)-carboxylate,
intermediate 1d: tert-butyl 3-ethoxy-2-methyl-5,6-dihydropyrazine-1(2H)-carboxylate,
intermediate 1e: tert-butyl 3-ethoxy-2-(4-fluorophenyl)-5,6-dihydropyrazine-1(2H)-carboxylate,
intermediate 1f: tert-butyl 3-ethoxy-2-isopropyl-5,6-dihydropyrazine-1(2H)-carboxylate,
intermediate 1g: tert-butyl 3-ethoxy-2-(2-hydroxyethyl)-5,6-dihydropyrazine-1(2H)-carboxylate,
intermediate 1h: tert-butyl 3-ethoxy-2,2-dimethyl-5,6-dihydropyrazine-1(2H)-carboxylate,
intermediate 1i: tert-butyl 3-ethoxy-6-methyl-5,6-dihydropyrazine-1(2H)-carboxylate,
intermediate 1j: tert-butyl 3-ethoxy-5-methyl-5,6-dihydropyrazine-1 (2H)-carboxylate.

General Method B:

General Method B is the general procedure used for the synthesis of hydrazide intermediates 2 and is detailed below using the example of quinoline-2-carbohydrazide 2a.

Scheme 3: Synthesis of quinoline-2-carbohydrazide 2a

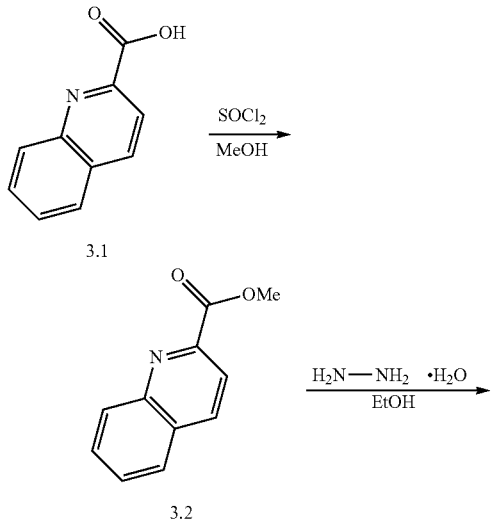

-continued

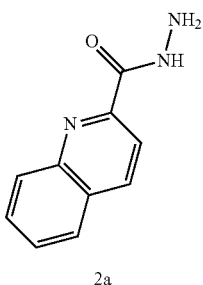

2a

Step 1: Synthesis of methyl quinoline-2-carboxylate 3.2

To an ice-cooled solution of quinoline-2-carboxylic acid 3.1 (10 g, 0.0578 mol) in 100 mL of absolute methanol was added dropwise thionyl chloride (20 g, 0.173 mol). After the addition was completed, the mixture was heated to reflux for 2 h. The solvent was then evaporated to dryness under reduced pressure and treated with 100 mL of 10% aqueous solution of $K_2CO_3$. The mixture was extracted with ethyl acetate; combined organic extracts were dried over sodium sulfate and evaporated to dryness to afford of methyl quinoline-2-carboxylate. Yield: 10.1 g (93%).

Step 2: Synthesis of quinoline-2-carbohydrazide 2a

Methyl quinoline-2-carboxylate 3.2 (10.1 g, 0.054 mol) was dissolved in 50 mL of ethanol and hydrazine hydrate (8.1 g, 0.16 mol) was added. The mixture was heated to reflux for 1 h and cooled down to RT at which point a precipitate formed. The mixture was concentrated to approximately 1/3 of the volume and the precipitate was filtered off, washed with small volumes of ethanol to afford intermediate 2a solvated by Vz equivalent of ethanol. Yield 10 g (99%). $^1$HNMR (DMSO-$d^6$): δ: 9.95 ppm (s, 1H), 8.55 (d, 1H), 8.1 ppm (d, 2H), 8.05 ppm (d, 1H), 8.85 ppm (t, 1H), 7.65 ppm (t, 1H), 4.6 ppm (s, 2H), 4.3 ppm (t, 0.5H), 4.4 ppm (q, 1H), 1.05 ppm (q, 1.5H).

In one embodiment 5 to 20 equivalents of hydrazine hydrate was used to carry out this reaction.

The following intermediates were also prepared from the ad hoc reagents using General Method B:
intermediate 2b: 6-chloropicolinylhydrazide,
intermediate 2c: 6-methylpicolinylhydrazide,
intermediate 2d: isoquinoline-3-carbohydrazide,
intermediate 2e: 8-fluoroquinoline-2-carbohydrazide,
intermediate 2f: 8-chloroquinoline-2-carbohydrazide,
intermediate 2g: 2-(4-(trifluoromethyl)phenyl)thiazole-4-carbohydrazide,
intermediate 2h: 6-phenylpicolinohydrazide,
intermediate 2i: 4,5,6,7-tetrahydrobenzo[d]thiazole-2-carbohydrazide,
intermediate 2j: benzo[d]thiazole-2-carbohydrazide,
intermediate 2k: 2-(2,4-difluorophenyl)thiazole-4-carbohydrazide,
intermediate 2l: 2-(4-chlorophenyl)thiazole-4-carbohydrazide,
intermediate 2m: 2-(4-fluorophenyl)thiazole-4-carbohydrazide,
intermediate 2n: 2-(piperidin-1-yl)thiazole-4-carbohydrazide,
intermediate 2o: 2-(4-phenylpiperazin-1-yl)thiazole-4-carbohydrazide,
intermediate 2p: 2-(2,4-dichlorophenyl)thiazole-4-carbohydrazide,
intermediate 2q: 2-(3,5-dichlorophenyl)thiazole-4-carbohydrazide,
intermediate 2r: 6-(pyrrolidin-1-yl)picolinohydrazide,
intermediate 2s: 6-morpholinopicolinohydrazide,
intermediate 2t: 6-(trifluoromethyl)picolinohydrazide,
intermediate 2u: 2-(3,4-dimethoxyphenyl)thiazole-4-carbohydrazide,
intermediate 2v: 2-(3-chlorophenyl)thiazole-4-carbohydrazide,
intermediate 2w: 2-phenyloxazole-4-carbohydrazide,
intermediate 2x: 2-(2-chlorophenyl)thiazole-4-carbohydrazide,
intermediate 2y: 5-methyl-2-phenylthiazole-4-carbohydrazide,
intermediate 2z: 3-phenyl-1,2,4-oxadiazole-5-carbohydrazide,
intermediate 2a1: 5-phenyl-1,2,4-oxadiazole-3-carbohydrazide,
intermediate 2b1: 3-(4-fluorophenyl)-1,2,4-oxadiazole-5-carbohydrazide,
intermediate 2c1 3-(2,4-difluorophenyl)-1,2,4-oxadiazole-5-carbohydrazide, was synthesized from intermediate 5a obtained using General Method E,
intermediate 2d1: 5-phenyl-1H-1,2,4-triazole-3-carbohydrazide, was synthesized from methyl 5-phenyl-1H-1,2,4-triazole-3-carboxylate whose preparation is disclosed in J. Med. Chem. 1995, 38, 2196,
intermediate 2e1: 2-((4,5-dichloro-1H-imidazol-1-yl)methyl)thiazole-4-carbohydrazide,
intermediate 2f1: 2-(4-chlorobenzyl)thiazole-4-carbohydrazide
intermediate 2g1: 2-(p-tolyl)thiazole-4-carbohydrazide,
intermediate 2h1: 2-(2-methoxyphenyl)thiazole-4-carbohydrazide,
intermediate 2i1: 2-(3-fluorophenyl)thiazole-4-carbohydrazide,
intermediate 2j1: 3-(4-fluorophenyl)-1,2,4-oxadiazole-5-carbohydrazide,
intermediate 2k1: 3-phenyl-1,2,4-thiadiazole-5-carbohydrazide,
intermediate 2l1: 2-(4-bromophenyl)thiazole-4-carbohydrazide,
intermediate 2m1: 2-(pyridin-4-yl)thiazole-4-carbohydrazide, was synthesized from intermediate 6b obtained using the General Method F,
intermediate 2n1: 2-(quinolin-2-yl)thiazole-4-carbohydrazide,
intermediate 2o1: 1-methyl-3-phenyl-1H-pyrazole-5-carbohydrazide,
intermediate 2p1: 2-(4-(dimethylamino)phenyl)thiazole-4-carbohydrazide,
intermediate 2q1: 1-methyl-5-phenyl-1H-pyrazole-3-carbohydrazide,
intermediate 2r1: 2-(pyridin-2-yl)thiazole-4-carbohydrazide,
intermediate 2s1: 2-(pyrimidin-2-yl)thiazole-4-carbohydrazide, was synthesized from intermediate 6d obtained using General Method F
intermediate 2t1: 2-(pyrazin-2-yl)thiazole-4-carbohydrazide, was synthesized from intermediate 6e obtained using General Method F,
intermediate 2u1: 2-(4-morpholinophenyl)thiazole-4-carbohydrazide, was synthesized from intermediate 7b obtained using General Method G, intermediate 2v1: 2-(4-(4-methylpiperazin-1-yl)phenyl)thiazole-4-carbohydrazide,
intermediate 2w1: 2-(4-(piperidin-1-yl)phenyl)thiazole-4-carbohydrazide, was synthesized from intermediate 7c obtained using General Method G,
intermediate 2x1: 2-(4-(pyrrolidin-1-yl)phenyl)thiazole-4-carbohydrazide, was synthesized from intermediate 7d obtained using General Method G,
intermediate 2y1: 2-(piperidin-1-yl)thiazole-4-carbohydrazide, was synthesized from intermediate 7e obtained using General Method G,
intermediate 2z1: 2-(pyrrolidin-1-yl)thiazole-4-carbohydrazide, was synthesized from intermediate 7f obtained using General Method G,
intermediate 2a2: 2-(4-methylpiperazin-1-yl)thiazole-4-carbohydrazide, was synthesized from intermediate 7g obtained using General Method G,
intermediate 2b2: 1-methyl-2-phenyl-1H-imidazole-4-carbohydrazide,
intermediate 2c2: 1-(2-methoxyethyl)-3-phenyl-1H-pyrazole-5-carbohydrazide, was synthesized from intermediate 8a obtained using General Method H,
intermediate 2d2: 2-isobutylthiazole-4-carbohydrazide, was synthesized from ethyl 2-isobutylthiazole-4-carboxylate, which was obtained from 3-methylbutanethioamide using the methodology reported by Ciufolini, et al. in *Journal of Organic Chemistry*, 1997, vol. 62, issue 12, p. 3804-3805,
intermediate 2e2: 2-(2-(2-methoxyethyl)morpholino)thiazole-4-carbohydrazide, was synthesized from intermediate 7h obtained using General Method G,
intermediate 2f2: 2-(4,4-difluoropiperidin-1-yl)thiazole-4-carbohydrazide, was synthesized from intermediate 7i obtained using General Method G,
intermediate 2g2: 2-(2,5-dimethylmorpholino)thiazole-4-carbohydrazide, was synthesized from intermediate 7j obtained using General Method G,
intermediate 2h2: 2-(2-hydroxyphenyl)thiazole-4-carbohydrazide, was synthesized from ethyl 2-(2-hydroxyphenyl)thiazole-4-carboxylate, which was obtained from 2-hydroxybenzothioamide using the methodology reported by Ciufolini, et al. in *Journal of Organic Chemistry*, 1997, vol. 62, issue 12, p. 3804-3805,
intermediate 2i2: 2-(2,6-dimethylmorpholino)thiazole-4-carbohydrazide, was synthesized from intermediate 7k obtained using General Method G,
intermediate 2j2: 2-(2,2-dimethylmorpholino)thiazole-4-carbohydrazide, was synthesized from intermediate 7l obtained using General Method G,
intermediate 2k2: 3-phenyl-1H-pyrazole-5-carbohydrazide,
intermediate 2l2: 2-(2-methylmorpholino)thiazole-4-carbohydrazide, was synthesized from intermediate 7m obtained using General Method G,
intermediate 2m2: 2-(4,4-dimethylpiperidin-1-yl)thiazole-4-carbohydrazide, was synthesized from intermediate 7n obtained using General Method G,
intermediate 2n2: 5-methylthiazole-4-carbohydrazide,
intermediate 2o2: 2-(2-(methoxymethyl)piperidin-1-yl)thiazole-4-carbohydrazide, was synthesized from intermediate 7o obtained using General Method G,
intermediate 2p2: 2-(2-bromophenyl)thiazole-4-carbohydrazide, was synthesized from ethyl 2-(2-bromophenyl)thiazole-4-carboxylate, which was obtained from 2-bromobenzothioamide using the methodology reported by Ciufolini, et al. in *Journal of Organic Chemistry*, 1997, vol. 62, issue 12, p. 3804-3805,
intermediate 2q2: 2-(3-bromophenyl)thiazole-4-carbohydrazide, was synthesized from ethyl 2-(3-bromophenyl)thiazole-4-carboxylate, which was obtained from 3-bromobenzothioamide using the methodology reported by Ciufolini, et al. in *Journal of Organic Chemistry*, 1997, vol. 62, issue 12, p. 3804-3805, General Method C:

General Method C is the general procedure used for the synthesis of triazolopiperazine intermediates 3 and is detailed below with the synthesis of (R)-4-(8-methyl-5,6,7,8-tetrahydro-[1,2,4]triazolo[4,3-a]pyrazin-3-yl)-2-phenylthiazole hydrochloride 3a.

Scheme 4: Synthesis of (R)-4-(8-methyl-5,6,7,8-tetrahydro-[1,2,4]triazolo[4,3-a]pyrazin-3-yl)-2-phenylthiazole hydrochloride salt

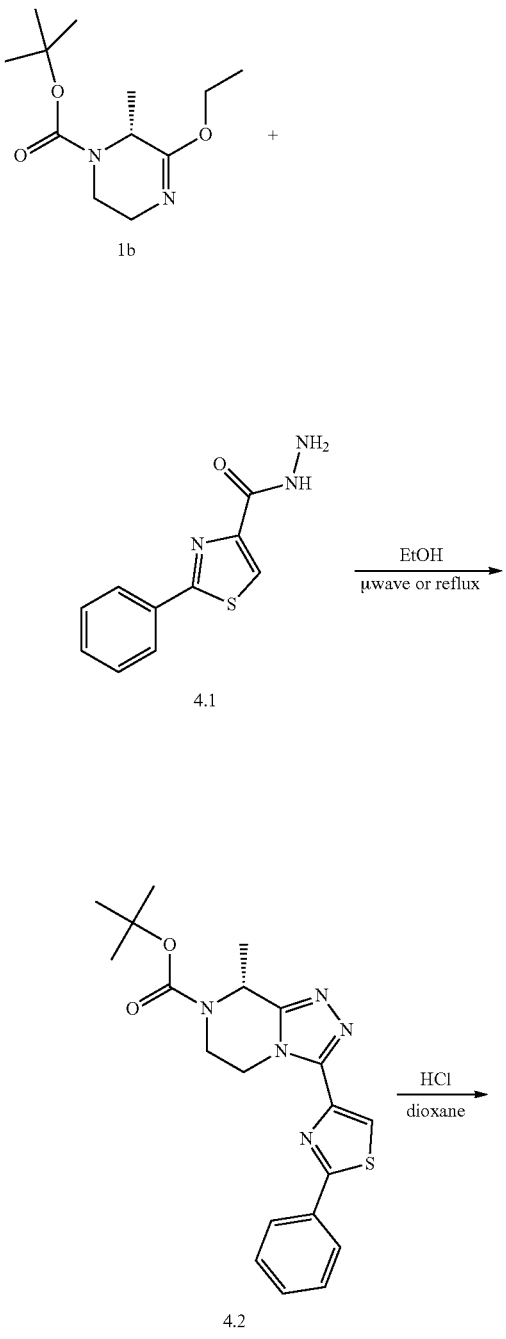

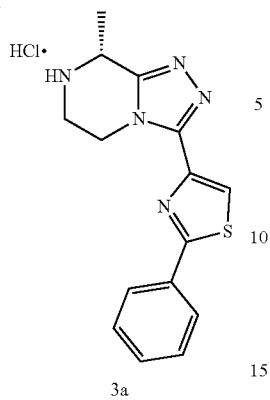

3a

Step 1: Synthesis of (R)-tert-butyl 8-methyl-3-(2-phenylthiazol-4-yl)-5,6-dihydro-[1,2,4]triazolo[4,3-a]pyrazine-7(8H)-carboxylate 4.2

To a solution of hydrazide 2-phenylthiazole-4-carbohydrazide 4.1 (100 mg, 0.4 mmol) in ethanol (7 mL) was added (2R)-tert-butyl 3-ethoxy-2-methyl-5,6-dihydropyrazine-1(2H)-carboxylate 1b (75 mg, 0.34 mmol). To this reaction mixture was applied microwave radiation (110° C., 220 psi) for 25 h. The solvent was then evaporated to dryness and the residue was purified on silica gel using $CH_2Cl_2$-Ethyl acetate (5:1→5:2+MeOH from 1% to 5%). Yield: 50 mg of 4.2+40 mg of de-Boc product 3a. Combined yield: 76%. %. LCMS: P=96%, rt=1.86 mn, m/z=398, 298.

Step 2: Synthesis of (R)-4-(8-methyl-5,6,7,8-tetrahydro-[1,2,4]triazolo[4,3-a]pyrazin-3-yl)-2-phenylthiazole Hydrochloride 3a Compound 4.2 (50 mg, 0.125 mmol) obtained in the previous step was dissolved in isopropyl alcohol (10 mL) to which was added 0.3 mL of HCl 4M in dioxane. The mixture was stirred at 50° C. overnight. After cooling down to RT, 10 mL of diethyl ether was added. The precipitate was filtered to afford title intermediate. Yield: 42 mg, 99%. LCMS: P=100%, rt=1.08 mn, m/z=298. $^1$H NMR (DMSO-$d^6$): δ: 8.3 ppm (s, 1H), 8.05 ppm (m, 2H), 7.55 ppm (m, 3H), 4.5 ppm (m, 1H), 4.25-4.05 ppm (m, 2H), 3.3 ppm (m, 1H), 2.95-3.1 ppm (m, 1H), 2.8 ppm (br s, 1H), 1.95 ppm (d, 3H).

Variant of General Method C is detailed below using the example of 2-(4-fluorophenyl)-4-(8-methyl-5,6,7,8-tetrahydro-[1,2,4]triazolo[4,3-a]pyrazin-3-yl)thiazole 3q1.

Scheme 4′: Synthesis of 2-(4-fluorophenyl)-4-(8-methyl-5,6,7,8-tetrahydro-[1,2,4]triazolo[4,3-a]pyrazin-3-yl)thiazole

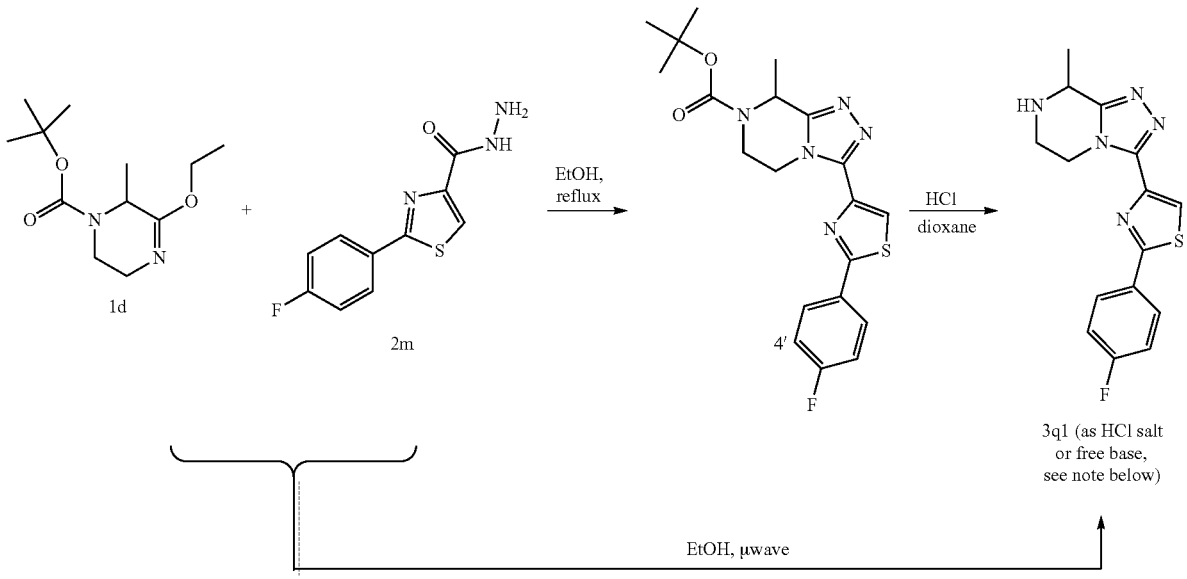

NB: When HCl/dioxane deprotection was applied, 3q1 was obtained as HCl salt. When μwave conditions were used, the Boc deprotection occurred during the cyclization, and no HCl deprotection step was required; thus, 3q1 was obtained in free-base form under the latter condition.

Step 1: Synthesis of tert-butyl 3-(2-(4-fluorophenyl) thiazol-4-yl)-8-methyl-5,6-dihydro-[1,2,4]triazolo[4, 3-a]pyrazine-7(8H)-carboxylate 4

To a solution of hydrazide 2m (1.65 g, 6.95 mmol) in anhydrous ethanol (15 mL, ~0.5M) was added iminoether 1d (1.69 g, 6.95 mmol) in one portion. The reaction mixture was then stirred under reflux. After 45 h (nearly complete conversion by LC-MS), the solvent was evaporated to dryness and the residue was purified on silica gel using a $CH_2Cl_2$/MeOH mixture (0% to 4% MeOH) as eluent, furnishing 4' as a yellow solid. Yield: 2.1 g (73%). LCMS: P=92%, rt=4.4 mn, m/z=416. $^1$HNMR (CDCl$_3$): δ: 8.11 ppm (s, 1H), 7.97 ppm (t, 2H), 7.20 ppm (t, 2H), 4.75 (m, 1H), 4.52 (m, 1H), 4.23 (dt, 1H), 4.17 (m, 1H), 3.48 (dt, 1H), 1.64 ppm (d, 3H), 1.51 ppm (s, 9H).

Step 2 Synthesis of 2-(4-fluorophenyl)-4-(8-methyl-5,6,7,8-tetrahydro-[1,2,4]triazolo[4,3-a]pyrazin-3-yl) thiazole 3q1

To a solution of Boc-triazolo-piperazine 4' (2.17 g, 5.22 mmol) in iso-propanol (150 mL) was added HCl 4M solution in 1,4-dioxane (26.1 mL, 104 mmol) in one portion. The reaction mixture was stirred at 60° C. and the reaction progress was monitored by LC-MS.
After 1 h (complete conversion by LC-MS), the reaction mixture was allowed to cool to room temperature and then further cooled to 0° C. with an ice bath. Thereupon, 150 mL of Et$_2$O was added. After 15 min stirring, the precipitate was filtered off and dried in vacuo to afford 3q1 as an off-white solid. Yield: 1.313 g (72%). LCMS: P=98%, rt=3.3 mn, m/z=316. $^1$HNMR (CD$_3$OD): δ: 8.57 ppm (s, 1H), 8.15 ppm (t, 2H), 7.30 ppm (t, 2H), 5.22 (m, 1H), 5.08 (q, 1H), 4.13 (m, 1H), 3.77 (m, 1H), 3.12 (m, 1H), 1.94 ppm (d, 3H).
As noted in Scheme 4' above, an alternative procedure to thermal reflux to effect the condensation step to form the triazolopiperazine intermediate entailed use of microwave irradiation. Such reactions were run in anhydrous ethanol and the following conditions were typically applied (CEM Discover): 300 W μwave (143° C.) with air-cooling.

The following intermediates were also prepared from the ad hoc reagents and intermediates using General Method C:

intermediate 3b: 3-(pyridin-2-yl)-5,6,7,8-tetrahydro-[1,2,4] triazolo[4,3-a]pyrazine dihydrochloride salt, intermediate 3c: 4-(4-(5,6,7,8-tetrahydro-[1,2,4]triazolo[4,3-a]pyrazin-3-yl)thiazol-2-yl)morpholine dihydrochloride salt, intermediate 3d: 3-(5-chloropyridin-2-yl)-5,6,7,8-tetrahydro-[1,2,4]triazolo[4,3-a]pyrazine dihydrochloride salt, intermediate 3e: 3-(6-methylpyridin-2-yl)-5,6,7,8-tetrahydro-[1,2,4]triazolo[4,3-a]pyrazine dihydrochloride salt, intermediate 3f: 8-methyl-3-(pyridin-2-yl)-5,6,7,8-tetrahydro-[1,2,4]triazolo[4,3-a]pyrazine dihydrochloride salt, intermediate 3g: 3-(5,6,7,8-tetrahydro-[1,2,4]triazolo[4,3-a]pyrazin-3-yl)isoquinoline hydrochloride salt, intermediate 3h: 2-(5,6,7,8-tetrahydro-[1,2,4]triazolo[4,3-a]pyrazin-3-yl)quinoline hydrochloride salt, intermediate 3i: 8-fluoro-2-(5,6,7,8-tetrahydro-[1,2,4]triazolo[4,3-a]pyrazin-3-yl)quinoline hydrochloride salt, intermediate 3j: 8-chloro-2-(5,6,7,8-tetrahydro-[1,2,4]triazolo[4,3-a]pyrazin-3-yl)quinoline hydrochloride salt, intermediate 3k: 4-(5,6,7,8-tetrahydro-[1,2,4]triazolo[4,3-a]pyrazin-3-yl)-2-(4-(trifluoromethyl)phenyl)thiazole hydrochloride salt, intermediate 3l: 3-(6-phenylpyridin-2-yl)-5,6,7,8-tetrahydro-[1,2,4]triazolo[4,3-a]pyrazine dihydrochloride salt, intermediate 3m: 2-(5,6,7,8-tetrahydro-[1,2,4]triazolo[4,3-a]pyrazin-3-yl)-4,5,6,7-tetrahydrobenzo[d]thiazole hydrochloride salt, intermediate 3n: 2-(5,6,7,8-tetrahydro-[1,2,4]triazolo[4,3-a]pyrazin-3-yl)benzo[d]thiazole hydrochloride salt, intermediate 3o: 2-phenyl-4-(5,6,7,8-tetrahydro-[1,2,4]triazolo[4,3-a]pyrazin-3-yl)thiazole hydrochloride salt, intermediate 3p: 4-(5,6,7,8-tetrahydro-[1,2,4]triazolo[4,3-a]pyrazin-3-yl)-2-(3-(trifluoromethyl)phenyl)thiazole hydrochloride salt, intermediate 3q: 2-(2,4-difluorophenyl)-4-(5,6,7,8-tetrahydro-[1,2,4]triazolo[4,3-a]pyrazin-3-yl)thiazole hydrochloride salt, intermediate 3r: 2-(2,3-dichlorophenyl)-4-(5,6,7,8-tetrahydro-[1,2,4]triazolo[4,3-a]pyrazin-3-yl)thiazole hydrochloride salt, intermediate 3s: 2-(4-chlorophenyl)-4-(5,6,7,8-tetrahydro-[1,2,4]triazolo[4,3-a]pyrazin-3-yl)thiazole hydrochloride salt, intermediate 3t: 2-(4-fluorophenyl)-4-(5,6,7,8-tetrahydro-[1,2,4]triazolo[4,3-a]pyrazin-3-yl)thiazole hydrochloride salt, intermediate 3u: 2-(piperidin-1-yl)-4-(5,6,7,8-tetrahydro-[1,2,4]triazolo[4,3-a]pyrazin-3-yl)thiazole dihydrochloride salt, intermediate 3v: 2-(4-phenylpiperazin-1-yl)-4-(5,6,7,8-tetrahydro-[1,2,4]triazolo[4,3-a]pyrazin-3-yl)thiazole dihydrochloride salt, intermediate 3w: 2-(2,4-dichlorophenyl)-4-(5,6,7,8-tetrahydro-[1,2,4]triazolo[4,3-a]pyrazin-3-yl)thiazole hydrochloride salt, intermediate 3x: 2-(3,5-dichlorophenyl)-4-(5,6,7,8-tetrahydro-[1,2,4]triazolo[4,3-a]pyrazin-3-yl)thiazole hydrochloride salt, intermediate 3y: 3-(6-(pyrrolidin-1-yl)pyridin-2-yl)-5,6,7,8-tetrahydro-[1,2,4]triazolo[4,3-a]pyrazine dihydrochloride salt, intermediate 3z: 4-(6-(5,6,7,8-tetrahydro-[1,2,4]triazolo[4,3-a]pyrazin-3-yl)pyridin-2-yl)morpholine dihydrochloride salt, intermediate 3a1: 3-(6-(trifluoromethyl)pyridin-2-yl)-5,6,7,8-tetrahydro-[1,2,4]triazolo[4,3-a]pyrazine dihydrochloride salt, intermediate 3b1: 2-(3,4-dimethoxyphenyl)-4-(5,6,7,8-tetrahydro-[1,2,4]triazolo[4,3-a]pyrazin-3-yl)thiazole hydrochloride salt, intermediate 3c1: 4-(8-(4-fluorophenyl)-5,6,7,8-tetrahydro-[1,2,4]triazolo[4,3-a]pyrazin-3-yl)-2-phenylthiazole hydrochloride salt, intermediate 3d1: 2-(3-chlorophenyl)-4-(5,6,7,8-tetrahydro-[1,2,4]triazolo[4,3-a]pyrazin-3-yl)thiazole hydrochloride salt, intermediate 3e1: 4-(8-isopropyl-5,6,7,8-tetrahydro-[1,2,4]triazolo[4,3-a]pyrazin-3-yl)-2-phenylthiazole hydrochloride salt, intermediate 3f1: (R)-8-methyl-3-(pyridin-2-yl)-5,6,7,8-tetrahydro-[1,2,4]triazolo[4,3-a]pyrazine dihydrochloride salt, intermediate 3g1: 4-(4-(8-methyl-5,6,7,8-tetrahydro-[1,2,4]triazolo[4,3-a]pyrazin-3-yl)thiazol-2-yl)morpholine dihydrochloride salt, intermediate 3h1: 2-phenyl-4-(5,6,7,8-tetrahydro-[1,2,4]triazolo[4,3-a]pyrazin-3-yl)oxazole hydrochloride salt, intermediate 3i1: 4-(8-methyl-5,6,7,8-tetrahydro-[1,2,4]triazolo[4,3-a]pyrazin-3-yl)-2-phenyloxazole, intermediate 3j1: 2-(3-(2-phenylthiazol-4-yl)-5,6,7,8-tetrahydro-[1,2,4]triazolo[4,3-a]pyrazin-8-yl)ethanol hydrochloride salt,
intermediate 3k1: 4-phenyl-2-(5,6,7,8-tetrahydro-[1,2,4]triazolo[4,3-a]pyrazin-3-yl)thiazole hydrochloride salt,
intermediate 3l1: 2-(2-chlorophenyl)-4-(5,6,7,8-tetrahydro-[1,2,4]triazolo[4,3-a]pyrazin-3-yl)thiazole hydrochloride salt,
intermediate 3m1: 4-(8,8-dimethyl-5,6,7,8-tetrahydro-[1,2,4]triazolo[4,3-a]pyrazin-3-yl)-2-phenylthiazole hydrochloride salt,
intermediate 3n1: 2-(8-methyl-5,6,7,8-tetrahydro-[1,2,4]triazolo[4,3-a]pyrazin-3-yl)quinoline hydrochloride salt,
intermediate 3o1: 4-(8-methyl-5,6,7,8-tetrahydro-[1,2,4]triazolo[4,3-a]pyrazin-3-yl)-2-phenylthiazole hydrochloride salt,
intermediate 3p1: (R)-2-(4-chlorophenyl)-4-(8-methyl-5,6,7,8-tetrahydro-[1,2,4]triazolo[4,3-a]pyrazin-3-yl)thiazole hydrochloride salt,
intermediate 3q1: 2-(4-fluorophenyl)-4-(8-methyl-5,6,7,8-tetrahydro-[1,2,4]triazolo[4,3-a]pyrazin-3-yl)thiazole hydrochloride salt,
intermediate 3r1: (R)-2-(4-fluorophenyl)-4-(8-methyl-5,6,7,8-tetrahydro-[1,2,4]triazolo[4,3-a]pyrazin-3-yl)thiazole hydrochloride salt,
intermediate 3s1: 5-methyl-4-(8-methyl-5,6,7,8-tetrahydro-[1,2,4]triazolo[4,3-a]pyrazin-3-yl)-2-phenylthiazole hydrochloride salt,
intermediate 3t1: 2-(2-chlorophenyl)-4-(8-methyl-5,6,7,8-tetrahydro-[1,2,4]triazolo[4,3-a]pyrazin-3-yl)thiazole hydrochloride salt,
intermediate 3u1: 2-(2,4-difluorophenyl)-4-(8-methyl-5,6,7,8-tetrahydro-[1,2,4]triazolo[4,3-a]pyrazin-3-yl)thiazole hydrochloride salt,
intermediate 3v1: 5-(8-methyl-5,6,7,8-tetrahydro-[1,2,4]triazolo[4,3-a]pyrazin-3-yl)-3-phenyl-1,2,4-oxadiazole hydrochloride salt,
intermediate 3w1: 2-(4-fluorophenyl)-4-(6-methyl-5,6,7,8-tetrahydro-[1,2,4]triazolo[4,3-a]pyrazin-3-yl)thiazole hydrochloride salt,
intermediate 3x1: 2-(4-fluorophenyl)-4-(5-methyl-5,6,7,8-tetrahydro-[1,2,4]triazolo[4,3-a]pyrazin-3-yl)thiazole hydrochloride salt,
intermediate 3y1: (S)-8-methyl-3-(pyridin-2-yl)-5,6,7,8-tetrahydro-[1,2,4]triazolo[4,3-a]pyrazine,
intermediate 3z1: (S)-2-(4-fluorophenyl)-4-(8-methyl-5,6,7,8-tetrahydro-[1,2,4]triazolo[4,3-a]pyrazin-3-yl)thiazole,
intermediate 3a2: (S)-4-(4-(8-methyl-5,6,7,8-tetrahydro-[1,2,4]triazolo[4,3-a]pyrazin-3-yl)thiazol-2-yl)morpholine,
intermediate 3b2: 5-phenyl-3-(5,6,7,8-tetrahydro-[1,2,4]triazolo[4,3-a]pyrazin-3-yl)-1,2,4-oxadiazole hydrochloride salt,
intermediate 3c2: 3-phenyl-5-(5,6,7,8-tetrahydro-[1,2,4]triazolo[4,3-a]pyrazin-3-yl)-1,2,4-oxadiazole hydrochloride salt,
intermediate 3d2 3-(4-fluorophenyl)-5-(5,6,7,8-tetrahydro-[1,2,4]triazolo[4,3-a]pyrazin-3-yl)-1,2,4-oxadiazole hydrochloride salt,
intermediate 3e2: 3-(2,4-difluorophenyl)-5-(5,6,7,8-tetrahydro-[1,2,4]triazolo[4,3-a]pyrazin-3-yl)-1,2,4-oxadiazole hydrochloride salt,
intermediate 3f2: 3-(5-phenyl-1H-1,2,4-triazol-3-yl)-5,6,7,8-tetrahydro-[1,2,4]triazolo[4,3-a]pyrazine hydrochloride salt,
intermediate 3g2: 2-(2-fluorophenyl)-4-(5,6,7,8-tetrahydro-[1,2,4]triazolo[4,3-a]pyrazin-3-yl)thiazole hydrochloride salt,
intermediate 3h2: 2-((4,5-dichloro-1H-imidazol-1-yl)methyl)-4-(5,6,7,8-tetrahydro-[1,2,4]triazolo[4,3-a]pyrazin-3-yl)thiazole dihydrochloride salt,
intermediate 3i2: 2-(4-chlorobenzyl)-4-(5,6,7,8-tetrahydro-[1,2,4]triazolo[4,3-a]pyrazin-3-yl)thiazole hydrochloride salt,
intermediate 3j2: 4-(5,6,7,8-tetrahydro-[1,2,4]triazolo[4,3-a]pyrazin-3-yl)-2-(p-tolyl)thiazole hydrochloride salt,
intermediate 3k2: 4-(5,6,7,8-tetrahydro-[1,2,4]triazolo[4,3-a]pyrazin-3-yl)-2-(thiophen-2-yl)thiazole hydrochloride salt,
intermediate 3l2: 2-(((4-chlorophenyl)sulfonyl)methyl)-4-(5,6,7,8-tetrahydro-[1,2,4]triazolo[4,3-a]pyrazin-3-yl)thiazole hydrochloride salt,
intermediate 3m2: 2-(2-methoxyphenyl)-4-(5,6,7,8-tetrahydro-[1,2,4]triazolo[4,3-a]pyrazin-3-yl)thiazole hydrochloride salt,
intermediate 3n2: 2-(3-fluorophenyl)-4-(5,6,7,8-tetrahydro-[1,2,4]triazolo[4,3-a]pyrazin-3-yl)thiazole hydrochloride salt,
intermediate 3o2: 2-isopropyl-4-(5,6,7,8-tetrahydro-[1,2,4]triazolo[4,3-a]pyrazin-3-yl)thiazole hydrochloride salt,
intermediate 3p2: 3-(4-fluorophenyl)-5-(8-methyl-5,6,7,8-tetrahydro-[1,2,4]triazolo[4,3-a]pyrazin-3-yl)-1,2,4-oxadiazole hydrochloride salt,
intermediate 3q2: 3-phenyl-5-(5,6,7,8-tetrahydro-[1,2,4]triazolo[4,3-a]pyrazin-3-yl)-1,2,4-thiadiazole hydrochloride salt,
intermediate 3r2: 2-(4-bromophenyl)-4-(5,6,7,8-tetrahydro-[1,2,4]triazolo[4,3-a]pyrazin-3-yl)thiazole hydrochloride salt,
intermediate 3s2: 2-(pyridin-4-yl)-4-(5,6,7,8-tetrahydro-[1,2,4]triazolo[4,3-a]pyrazin-3-yl)thiazole dihydrochloride salt,
intermediate 3t2: 2-(quinolin-2-yl)-4-(5,6,7,8-tetrahydro-[1,2,4]triazolo[4,3-a]pyrazin-3-yl)thiazole dihydrochloride salt,
intermediate 3u2: 3-(1-methyl-3-phenyl-1H-pyrazol-5-yl)-5,6,7,8-tetrahydro-[1,2,4]triazolo[4,3-a]pyrazine hydrochloride salt,
intermediate 3v2: N,N-dimethyl-4-(4-(5,6,7,8-tetrahydro-[1,2,4]triazolo[4,3-a]pyrazin-3-yl)thiazol-2-yl)aniline dihydrochloride salt,
intermediate 3w2: 3-(1-methyl-5-phenyl-1H-pyrazol-3-yl)-5,6,7,8-tetrahydro-[1,2,4]triazolo[4,3-a]pyrazine hydrochloride salt,
intermediate 3y2: 2-(pyridin-2-yl)-4-(5,6,7,8-tetrahydro-[1,2,4]triazolo[4,3-a]pyrazin-3-yl)thiazole dihydrochloride salt,
intermediate 3z2: 2-(pyrimidin-2-yl)-4-(5,6,7,8-tetrahydro-[1,2,4]triazolo[4,3-a]pyrazin-3-yl)thiazole dihydrochloride salt,
intermediate 3a3: 2-(pyrazin-2-yl)-4-(5,6,7,8-tetrahydro-[1,2,4]triazolo[4,3-a]pyrazin-3-yl)thiazole dihydrochloride salt,
intermediate 3b3: 4-(4-(4-(5,6,7,8-tetrahydro-[1,2,4]triazolo[4,3-a]pyrazin-3-yl)thiazol-2-yl)phenyl)morpholine hydrochloride salt,
intermediate 3c3: 2-(4-(4-methylpiperazin-1-yl)phenyl)-4-(5,6,7,8-tetrahydro-[1,2,4]triazolo[4,3-a]pyrazin-3-yl)thiazole dihydrochloride salt,
intermediate 3d3: 2-(4-(piperidin-1-yl)phenyl)-4-(5,6,7,8-tetrahydro-[1,2,4]triazolo[4,3-a]pyrazin-3-yl)thiazole hydrochloride salt,
intermediate 3e3: 2-(4-(pyrrolidin-1-yl)phenyl)-4-(5,6,7,8-tetrahydro-[1,2,4]triazolo[4,3-a]pyrazin-3-yl)thiazole hydrochloride salt, intermediate 3f3: 2-(piperidin-1-yl)-4-(5,6,7,8-tetrahydro-[1,2,4]triazolo[4,3-a]pyrazin-3-yl)thiazole hydrochloride salt, intermediate 3g3: 2-(pyrrolidin-1-yl)-4-(5,6,7,8-tetrahydro-[1,2,4]triazolo[4,3-a]pyrazin-3-yl)thiazole hydrochloride salt, intermediate 3h3: 2-(4-methylpiperazin-1-yl)-4-(5,6,7,8-tetrahydro-[1,2,4]triazolo[4,3-a]pyrazin-3-yl)thiazole dihydrochloride salt, intermediate 3i3: 3-(1-methyl-2-phenyl-1H-imidazol-4-yl)-5,6,7,8-tetrahydro-[1,2,4]triazolo[4,3-a]pyrazine dihydrochloride salt, intermediate 3j3: 3-(1-(2-methoxyethyl)-3-phenyl-1H-pyrazol-5-yl)-5,6,7,8-tetrahydro-[1,2,4]triazolo[4,3-a]pyrazine hydrochloride salt, intermediate 3k3: 2-isobutyl-4-(5,6,7,8-tetrahydro-[1,2,4]triazolo[4,3-a]pyrazin-3-yl)thiazole hydrochloride salt, intermediate 3l3: 2-(2-methoxyethyl)-4-(4-(5,6,7,8-tetrahydro-[1,2,4]triazolo[4,3-a]pyrazin-3-yl)thiazol-2-yl) morpholine hydrochloride salt, intermediate 3m3: 2-(4,4-difluoropiperidin-1-yl)-4-(5,6,7,8-tetrahydro-[1,2,4]triazolo[4,3-a]pyrazin-3-yl)thiazole hydrochloride salt, intermediate 3n3: 2,5-dimethyl-4-(4-(5,6,7,8-tetrahydro-[1,2,4]triazolo[4,3-a]pyrazin-3-yl)thiazol-2-yl)morpholine hydrochloride salt, Intermediate 3o3: 2-(4-(5,6,7,8-tetrahydro-[1,2,4]triazolo[4,3-a]pyrazin-3-yl)thiazol-2-yl)phenol hydrochloride salt, intermediate 3p3: 2,6-dimethyl-4-(4-(5,6,7,8-tetrahydro-[1,2,4]triazolo[4,3-a]pyrazin-3-yl)thiazol-2-yl)morpholine hydrochloride salt, intermediate 3q3: 2,2-dimethyl-4-(4-(5,6,7,8-tetrahydro-[1,2,4]triazolo[4,3-a]pyrazin-3-yl)thiazol-2-yl)morpholine hydrochloride salt, intermediate 3r3: 3-(3-phenyl-1H-pyrazol-5-yl)-5,6,7,8-tetrahydro-[1,2,4]triazolo[4,3-a]pyrazine dihydrochloride salt, intermediate 3s3: 2-methyl-4-(4-(5,6,7,8-tetrahydro-[1,2,4]triazolo[4,3-a]pyrazin-3-yl)thiazol-2-yl)morpholine hydrochloride salt, intermediate 3t3: 2-(4,4-dimethylpiperidin-1-yl)-4-(5,6,7,8-tetrahydro-[1,2,4]triazolo[4,3-a]pyrazin-3-yl)thiazole hydrochloride salt, intermediate 3u3 5-methyl-4-(5,6,7,8-tetrahydro-[1,2,4]triazolo[4,3-a]pyrazin-3-yl)thiazole hydrochloride salt, intermediate 3v3 2-(2-(methoxymethyl)piperidin-1-yl)-4-(5,6,7,8-tetrahydro-[1,2,4]triazolo[4,3-a]pyrazin-3-yl)thiazole hydrochloride salt, intermediate 3w3: 8-methyl-3-(6-methylpyridin-2-yl)-5,6,7,8-tetrahydro-[1,2,4]triazolo[4,3-a]pyrazine dihydrochloride salt, intermediate 3x3: 2-(2-bromophenyl)-4-(5,6,7,8-tetrahydro-[1,2,4]triazolo[4,3-a]pyrazin-3-yl)thiazole, intermediate 3y3: 2-(3-bromophenyl)-4-(5,6,7,8-tetrahydro-[1,2,4]triazolo[4,3-a]pyrazin-3-yl)thiazole, General Method D:

General Method D is the general procedure used for the synthesis of 3-phenyl-pyrazole-5-carboxylic acid intermediates 4 and is exemplified below using the synthesis of 3-(3,4-dichlorophenyl)-1-methyl-1H-pyrazole-5-carboxylic acid 4a and 5-(3,4-dichlorophenyl)-1-methyl-1H-pyrazole-3-carboxylic acid 4b.

Scheme 5: Synthesis of intermediates 4a and 4b

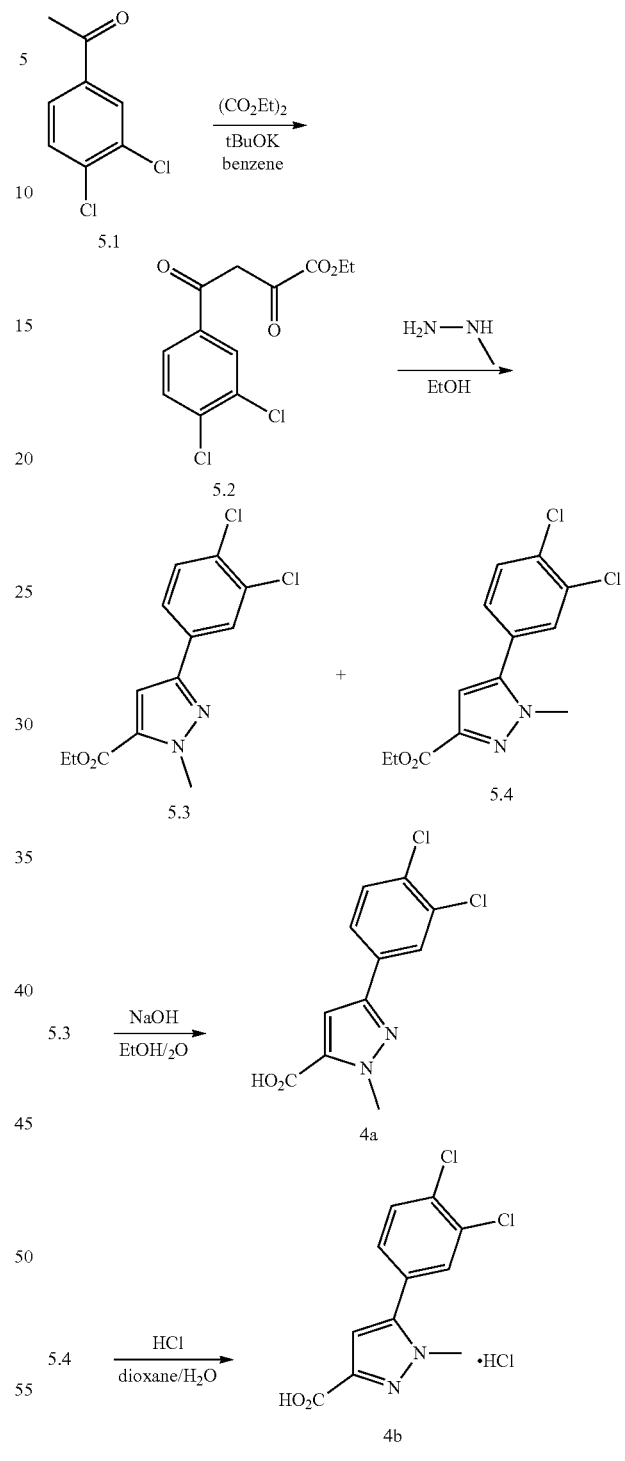

Step 1: Synthesis of ethyl 4-(3,4-dichlorophenyl)-2,4-dioxobutanoate 5.2

To a solution of t-BuOK (0.05 mol, 5.6 g) in benzene (200 mL) was added dropwise a benzene (50 mL) solution of 3,4-dichloroacetophenone 5.1 (0.05 mol, 9.45 g) and diethyloxalate (0.055 mol, 8.1 g). The resultant mixture was stirred for 8 h at room temperature, then 10% aqueous HCl solution (100 mL) was added to the mixture. The organic layer was separated and washed with brine, dried over sodium sulfate and concentrated in vacuo. The crude product was purified by column chromatography using dichloromethane as eluent to yield the title compound. Yield: 7.5 g (52%).

Step 2: Synthesis of ethyl 3-(3,4-dichlorophenyl)-1-methyl-1H-pyrazole-5-carboxylate 5.3 and ethyl 5-(3,4-dichlorophenyl)-1-methyl-1H-pyrazole-3-carboxylate 5.4

To a solution of compound 5.2 (0.035 mol, 10.2 g) in ethanol (100 mL) was added monomethyl hydrazine (0.0353 mol, 1.63 g) and the resultant mixture was refluxed for 2 h, and subsequently stirred overnight at RT. The mixture was then evaporated to dryness and the thus obtained crude product was subjected to column chromatography (eluent: ethyl acetate/hexane 2:3). This afforded 3.68 g of compound 5.3 ($R_f$=0.8) and 3.28 g of compound 5.4 ($R_f$=0.6). The structure assignment of the thus obtained regioisomers was accomplished on the basis of NOE in 2D-NOESY spectra and $^1H$-$^{13}C$ cross-coupling constants in 2D-$^1H$-$^{13}C$-HMBC spectra between N-methyl protons and quaternary carbons in the pyrazole rings.

Step 3: Synthesis of 3-(3,4-dichlorophenyl)-1-methyl-1H-pyrazole-5-carboxylic acid 4a and 5-(3,4-dichlorophenyl)-1-methyl-1H-pyrazole-3-carboxylic Acid Hydrochloride Salt 4b Synthesis of 3-(3,4-dichlorophenyl)-1-methyl-1H-pyrazole-5-carboxylate 4a Compound 5.3 (0.0123 mol, 3.68 g) and sodium hydroxide (2 g) were dissolved in water-ethanol (1:1 v/v, 300 mL) solution. The mixture was refluxed for 3 h and then most of the ethanol was evaporated. The pH of the thus obtained mixture was adjusted to pH 3 by addition of 10% HCl whereupon a precipitate formed, which was filtered, washed with water and air dried to afford compound 5.5. Yield: 3.05 g (91.6%). LCMS: P=97.5%, rt=1.86 mn, m/z=271. $^1$HNMR (DMSO-$d^6$): δ: 13.5 ppm (br s, 1H), 8.05 ppm (s, 1H), 7.8 ppm (d, 1H), 7.6 ppm (d, 1H), 7.4 ppm (s, 1H), 4.15 ppm (s, 3H).

Synthesis of 5-(3,4-dichlorophenyl)-1-methyl-1H-pyrazole-3-carboxylate 4b

Compound 5.4 (10.08 mmol, 3.24 g) was refluxed in a mixture of conc. HCl 50 mL/water 75 mL/dioxane 125 mL for 3 h. The volatiles were evaporated until the formation of a precipitate, which was filtered, washed with water and air dried to afford product 5.6 as HCl salt. Yield: 2.79 g (90%). LCMS: P=95%, rt=1.67 mn, m/z=271. $^1$H NMR (DMSO-$d^6$): δ: 7.9 ppm (s, 1H), 7.75 ppm (d, 1H), 7.6 ppm (d, 1H), 6.95 ppm (s, 1H), 3.9 ppm (s, 3H).

The following intermediates were also prepared from the ad hoc reagents and intermediates using General Method D:
Intermediate 4c: 3-(4-chlorophenyl)-1H-pyrazole-5-carboxylic acid,
Intermediate 4d: 3-(3,4-dichlorophenyl)-1H-pyrazole-5-carboxylic acid,
Intermediate 4e: 3-(2,4-dichlorophenyl)-1H-pyrazole-5-carboxylic acid,
Intermediate 4f: 3-(4-trifluoromethylphenyl)-1H-pyrazole-5-carboxylic acid,
Intermediate 4g: 3-(4-phenoxyphenyl)-1H-pyrazole-5-carboxylic acid,
Intermediate 4h: 3-(4-chlorophenyl)-1-methyl-1H-pyrazole-5-carboxylic acid,
Intermediate 4i: 5-(4-chlorophenyl)-1-methyl-1H-pyrazole-3-carboxylic acid.

General Method E:

General Method E is the general procedure used for the synthesis of ethyl 3-phenyl-1,2,4-oxadiazol-5-carboxylate intermediates 1.2 and is exemplified below with the synthesis of ethyl 3-(2,4-difluorophenyl)-1,2,4-oxadiazole-5-carboxylate 5a.

Scheme 6: synthesis of intermediate 5a

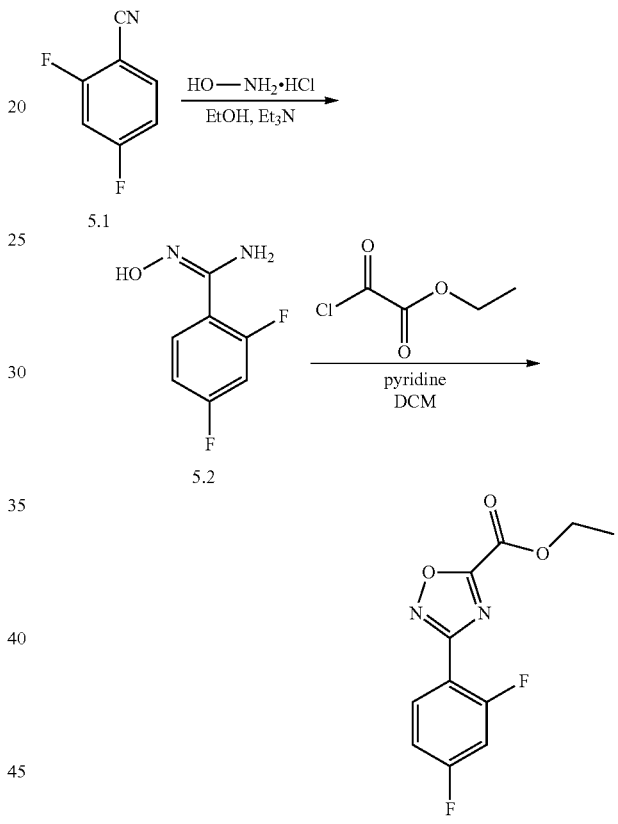

Step 1: Synthesis of 2,4-difluoro-N'-hydroxybenzimidamide 5.2

To a solution of 2,4-difluorobenzonitrile 5.1 (1 g, 7.2 mmol) and hydroxylamine hydrochloride (1 g, 14.4 mmol) in commercial dry EtOH (5 mL) under $N_2$ was added $NEt_3$ (2 mL, 14.4 mmol) dropwise over 2 min at RT. The mixture was stirred under reflux overnight. The mixture was then allowed to cool down to RT and concentrated. The white solid obtained was used crude in the next step. Yield: 3.52 g (quantitative). LCMS: P=33%, rt=0.84 mn, m/z=173.

Step 2: Synthesis of ethyl 3-(2,4-difluorophenyl)-1,2,4-oxadiazole-5-carboxylate 5a To a solution of 2,4-difluoro-N'-hydroxybenzimidamide 5.2 (3.52 g, 33% purity, max. 7.2 mmol) and pyridine (2.32 mL, 28.7 mmol) in anhydrous CH$_2$Cl$_2$ under N$_2$ was added ethyl chlorooxoacetate (1.27 g, 9.32 mmol) dropwise over 5 min at RT. The mixture was stirred under reflux. After 1 h30, the rxn mixt. was concentrated and purified on silica gel using CH$_2$Cl$_2$, furnishing 1.414 g of title product 5a as colorless oil. Yield: 1.414 g (78%). LCMS: P=94%, rt=4.21 mn, m/z=255, 277 (M+Na).

General Method F:

General Method E is the general procedure used for the synthesis of methyl 2-pyridyl-thiazol-4-carboxylate intermediates 1.2 and is exemplified below with the synthesis of methyl 2-(pyridin-2-yl)thiazole-4-carboxylate 6a.

Scheme 7: Synthesis of intermediate 6a

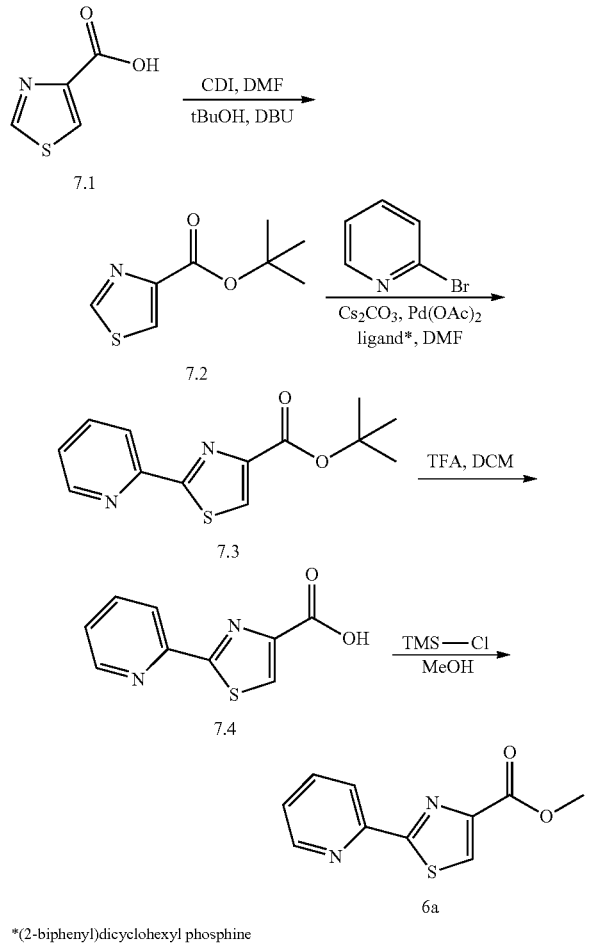

*(2-biphenyl)dicyclohexyl phosphine

Step 1: Synthesis of tert-butyl thiazole-4-carboxylate 7.2

To a solution of thiazole-4-carboxylic acid 7.1 (1 g, 7.2 mmol) and carbonyldiimidazole (6.3 g, 38.7 mmol) in commercial dry DMF (50 mL) under N$_2$ was stirred at 50° C. for 20 min. Tert-butanol (8.6 g, 116.0 mmol) and DBU (5.8 mL, 38.7 mmol) were then successively added at once and the reaction was warmed at 60° C. for 48 h. The RM was then allowed to cool down to RT and the pH was adjusted to 4 with a solution of HCl (2M, ~80 mL). The mixture was diluted with water (250 mL) and extracted with Et$_2$O (3×100 mL). The combined org. layers were washed with brine (250 mL), dried over MgSO$_4$, concentrated and purified on silica gel using DCM to afford title product as yellowish oil (47%). Yield: 3.37 g (47%). LCMS: P=98%, rt=3.65 mn, m/z=186.

Step 2: Synthesis of tert-butyl 2-(pyridin-2-yl)thiazole-4-carboxylate 7.3

To a solution of tert-butyl thiazole-4-carboxylate 7.2 (256 mg, 1.62 mmol), anhydrous cesium carbonate (1 g, 3.24 mmol) and 2-bromo-pyridine (300 mg, 1.62 mmol) sequentially added in commercial anhydrous DMF (6 mL) at RT under N$_2$ was added Pd(OAc)$_2$ (18 mg, 0.08 mmol) and (2-biphenyl)dicyclohexyl phosphine (57 mg, 0.16 mmol). The RM was heated at 110° C. overnight. The RM was then allowed to cool down to RT, filtered on Celite pad and concentrated. The residue was purified on silica gel using cyclohexane/EtOAc (5% to 20% of EtOAc), furnishing 7.3 as yellow oil. Yield: 340 mg (80%). LCMS: P=96%, rt=4.28 mn, m/z=263.

Step 3: Synthesis of 2-(pyridin-2-yl)thiazole-4-carboxylic Acid 7.4

To a solution of tert-butyl 2-(pyridin-2-yl)thiazole-4-carboxylate 7.3 (340 mg, 1.3 mmol) in commercial anhydrous CH$_2$Cl$_2$ (5 mL) at RT was added TFA (0.93 mL, 13 mmol) under N$_2$. The mixture was stirred at RT overnight. The mixture was diluted with CH$_2$Cl$_2$ (25 mL), washed with an aqueous solution of NaHSO$_3$ 10% (5×25 mL), brine (25 mL) and then water (25 mL). The organic layer was dried over MgSO$_4$ and evaporated to afford title product as a yellow oil. Yield: 250 mg (94%). LCMS: P=93%, rt=3.03 mn, m/z=207.

Step 4: Synthesis of methyl 2-(pyridin-2-yl)thiazole-4-carboxylate 6a

To a solution of 2-(pyridin-2-yl)thiazole-4-carboxylic acid 7.4 (500 mg, 2.425 mmol) in commercial anhydrous methanol (10 mL) was added TMS-Cl (0.77 mL, 6.06 mmol) at once. The RM was heated to 50° C. overnight. The RM. was concentrated under reduced pressure and the residue was used crude in next step. Yield: 649 mg (quantitative). LCMS: P=94%, rt=4.07 mn, m/z=221.

The following intermediates were also prepared from the ad hoc reagents and intermediates using General Method F:

intermediate 6b: methyl 2-(pyridin-4-yl)thiazole-4-carboxylate, intermediate 6c: methyl 2-(quinolin-2-yl)thiazole-4-carboxylate, intermediate 6d: methyl 2-(pyrimidin-2-yl)thiazole-4-carboxylate, intermediate 6e: methyl 2-(pyrazin-2-yl)thiazole-4-carboxylate.

General Method G:

General Method G is the general procedure used for the synthesis of methyl 2-(4-heterocyclylphenyl)thiazole-4-carboxylate intermediates 1.2 and is exemplified below with the synthesis of methyl 2-(4-(4-methylpiperazin-1-yl)phenyl)thiazole-4-carboxylate 7a.

Scheme 8: Synthesis of intermediate 7a

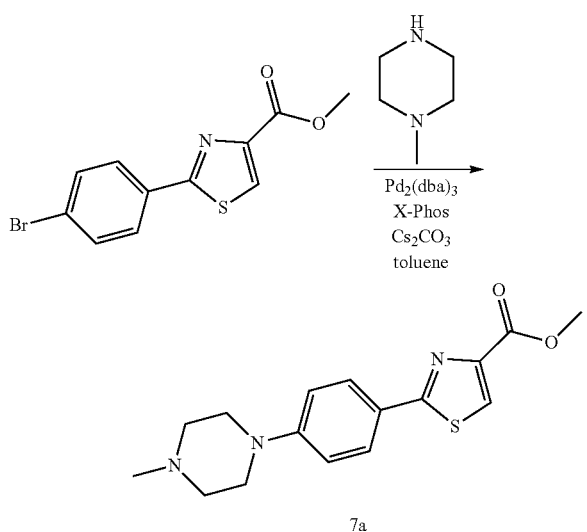

7a

In a tube previously dried in a 113° C.-heated oven overnight were introduced successively 2-(4-bromophenyl)thiazole-4-carboxylate 8.1 (500 mg, 1.6 mmol), 1-methylpiperazine (0.21 mL, 1.9 mmol) and anhydrous cesium carbonate (1.04 g, 3.0 mmol) under $N_2$. Commercial anhydrous toluene (10 mL) was then added and RM was degassed (argon bubbling for ~5 min). $Pd_2(dba)_3$ (73 mg, 0.08 mmol) and X-Phos (76 mg, 0.16 mmol) were quickly added successively and the mixture was heated under reflux overnight. The reaction mixture was then allowed to cool down to RT and EtOAc (50 mL) was added. This mixture was washed with brine (30 mL) and the aqueous layer was further extracted twice with EtOAc (30 mL). The combined organic layers were dried over $MgSO_4$, filtered and concentrated under reduced pressure. The residue was purified on silica gel using $CH_2Cl_2$/MeOH (2% of MeOH) to afford title product as a yellow solid. Yield: 374 mg (71%). LCMS: P=92%, rt=3.31 mn, m/z=332.

This General Method was also applied to the synthesis of methyl 2-heterocyclylthiazole-4-carboxylate intermediates, starting from methyl 2-bromothiazole-4-carboxylate.

The following intermediates were also prepared from the ad hoc reagents and intermediates using General Method G
intermediate 7b: methyl 2-(4-morpholinophenyl)thiazole-4-carboxylate,
intermediate 7c: methyl 2-(4-(piperidin-1-yl)phenyl)thiazole-4-carboxylate,
intermediate 7d: methyl 2-(4-(pyrrolidin-1-yl)phenyl)thiazole-4-carboxylate,
intermediate 7e: methyl 2-(piperidin-1-yl)thiazole-4-carboxylate,
intermediate 7f: methyl 2-(pyrrolidin-1-yl)thiazole-4-carboxylate,
intermediate 7g: methyl 2-(4-methylpiperazin-1-yl)thiazole-4-carboxylate,
intermediate 7h: methyl 2-(2-(2-methoxyethyl)morpholino)thiazole-4-carboxylate,
intermediate 7i: methyl 2-(4,4-difluoropiperidin-1-yl)thiazole-4-carboxylate,
intermediate 7j: methyl 2-(2,5-dimethylmorpholino)thiazole-4-carboxylate,
intermediate 7k: methyl 2-(2,6-dimethylmorpholino)thiazole-4-carboxylate,
intermediate 7l: methyl 2-(2,2-dimethylmorpholino)thiazole-4-carboxylate,
intermediate 7m: methyl 2-(2-methylmorpholino)thiazole-4-carboxylate,
intermediate 7n: methyl 2-(4,4-dimethylpiperidin-1-yl)thiazole-4-carboxylate,
intermediate 7o: methyl 2-(2-(methoxymethyl)piperidin-1-yl)thiazole-4-carboxylate, General Method H:

General Method H is the general procedure used for the synthesis of methyl 3-phenylpyrazole-5-carboxylate and methyl 5-phenylpyrazole-3-carboxylate intermediates 1.2 and is exemplified below with the synthesis of methyl 1-(2-methoxyethyl)-3-phenyl-1H-pyrazole-5-carboxylate 8a and methyl 1-(2-methoxyethyl)-5-phenyl-1H-pyrazole-3-carboxylate 8b.

Scheme 9: Synthesis of intermediates 8a and 8b

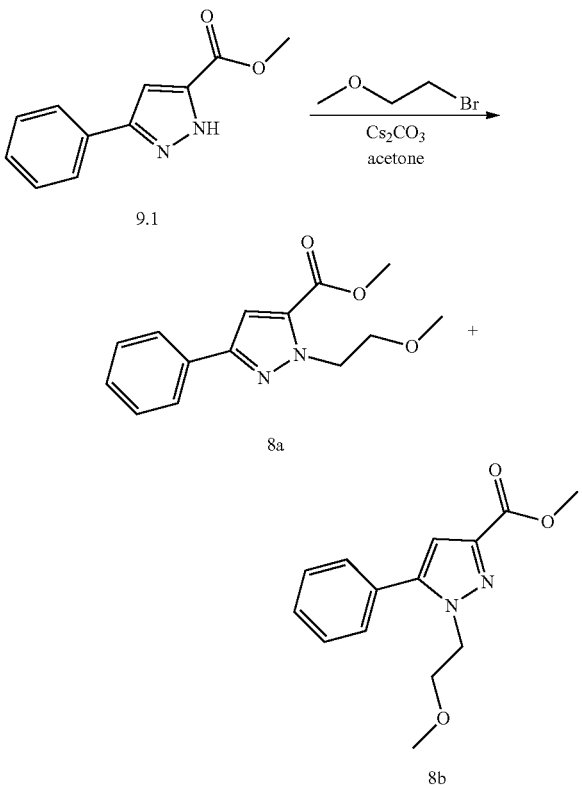

To a solution of methyl 3-phenyl-1H-pyrazole-5-carboxylate 9.1 (250 mg, 1.24 mmol) in commercial anhydrous acetone (30 mL) at RT under $N_2$ was added cesium carbonate at once (806 mg, 2.47 mmol). After 10 min stirring, 2-bromoethyl-methylether (258 mg, 1.85 mmol) was added at once. The reaction mixture was refluxed for 2 h and then allowed to cool down and concentrated, diluted with $CH_2Cl_2$ (50 mL) and washed with water (50 mL). The organic layer was then dried over $MgSO_4$, filtered and evaporated to dryness. The residue was purified on silica gel using $CH_2Cl_2$/MeOH (1% of MeOH) to afford a mixture of 8a alongside with 8b (~10%) as a pale yellow oil. Yield: 359 mg (71%). LCMS: P=100%, ratio 8a/8b=9/1, 8a: rt=4.41 mn, m/z=261; 8b. rt=3.95 mn, m/z=261.

Additional Synthetic Schemes
The synthesis of compounds n° 283, 289, 290, 291, 292 was carried out according to scheme 10
Scheme 10: Synhesis of compounds n° 283, 289, 290, 291, 292
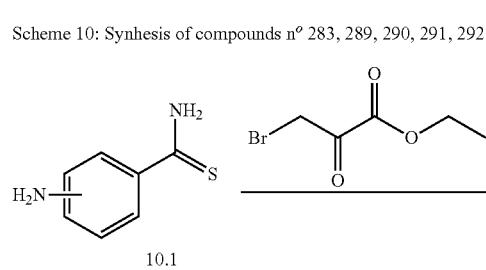
10.1
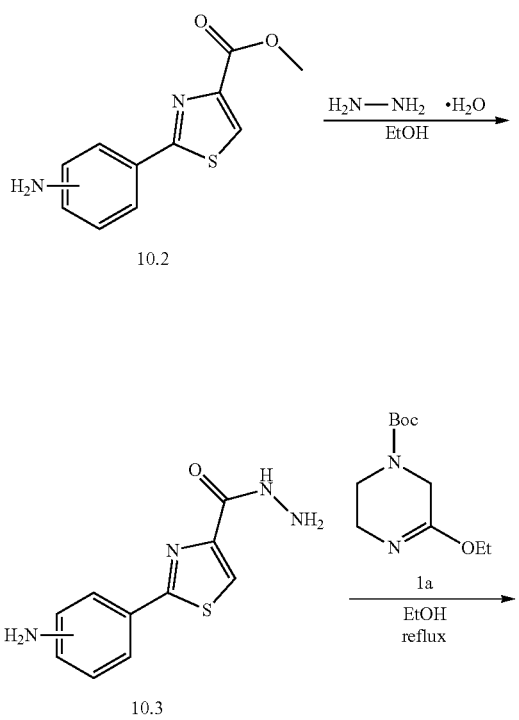
10.2
10.3
10.4
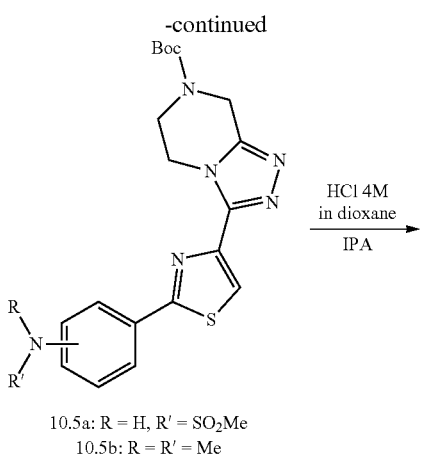
10.5a: R = H, R' = SO₂Me
10.5b: R = R' = Me
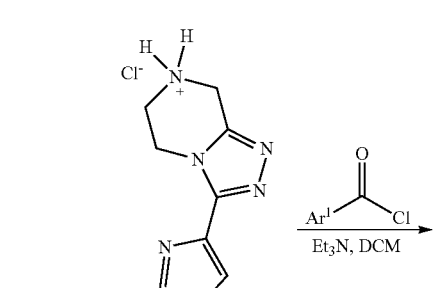
+ 0,1 HCl
10.6a: R = H, R' = SO₂Me
10.6b: R = R' = Me
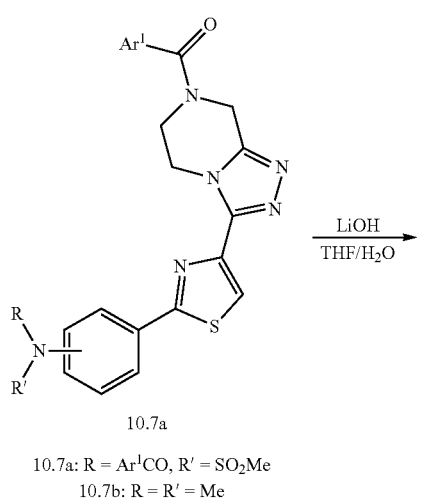
10.7a
10.7a: R = Ar¹CO, R' = SO₂Me
10.7b: R = R' = Me

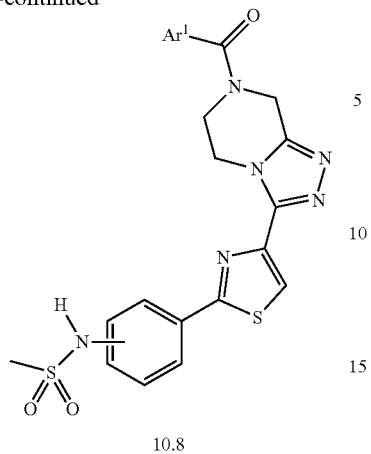

10.8

Thioamide 10.1 is condensed with ethyl 3-bromo-2-oxo-propanoate to yield thiazole ester intermediate 10.2 which was further converted to thiazolylhydrazide 10.3. Condensation of 10.3 with iminoether 1 provided aniline 10.4 which could be further converted to N-methylsulfonylaniline 10.5a or dimethylaniline 10.5b. Boc deprotection followed acylation yielded compounds 10.7a and 10.7b. Di-acylated product 10.7a could be deacylated on the aniline part to provided target compound 10.8.

The synthesis of compounds n° 293 was carried out according to scheme 11

Scheme 11: Synthesis of compound n° 293

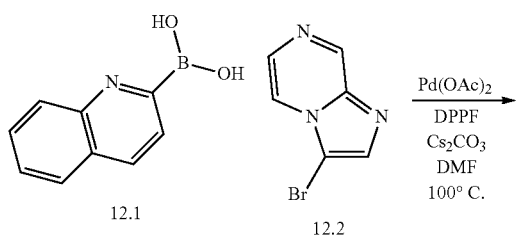

12.1   12.2

Boronic acid 12.1 is reacted with 12.2 using Suzuki coupling to afford 12.3. This latter is reduced by hydrogenation in the presence of Pd/C to furnish 12.4, which is further acylated to provide desired compound n° 293.

Example 1: Synthesis of Compound N° 45

The general procedure used for the synthesis of triazolo-piperazine compounds of the invention is detailed below using the synthesis of compound n° 45: (R)-(4-fluorophenyl)(8-methyl-3-(2-phenylthiazol-4-yl)-5,6-dihydro-[1,2,4]triazolo[4,3-a]pyrazin-7(8H)-yl)methanone Scheme 12: synthesis of (R)-(4-fluorophenyl)(8-methyl-3-(2-phenylthiazol-4-yl)-5,6-dihydro [1,2,4]triazolo[4,3-a]pyrazin-7(8H)-yl methanone (compound n° 45).

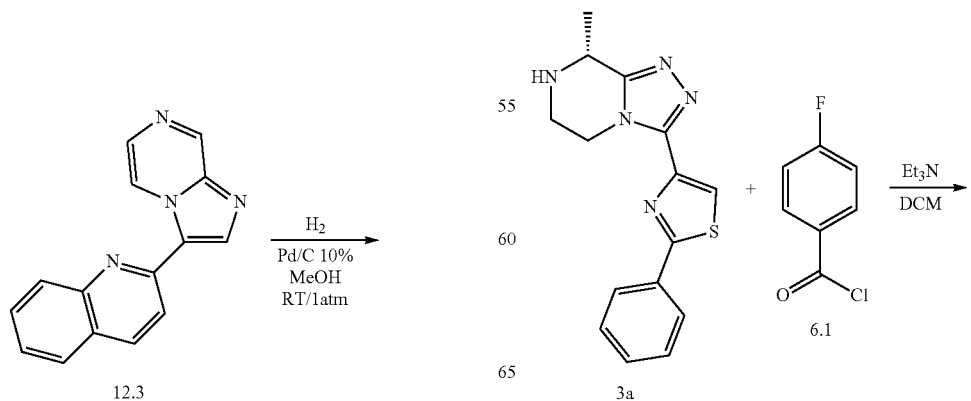

-continued

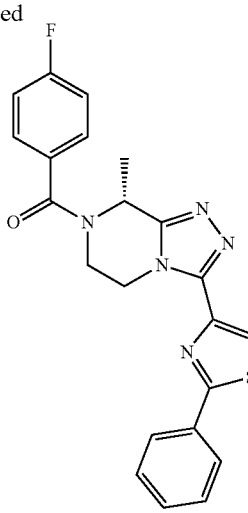

compound n° 45

To a solution of intermediate 3a (80 mg, 0.27 mmol) in 7 mL of DCM there was added Et₃N (68 mg, 0.67 mmol) and then a solution of 4-fluorobenzoyl chloride 6.1 in DCM (43 mg, 0.27 mmol). The solution was left stirring at room temperature for 2 h. The reaction mixture was washed with water, brine, dried over sodium sulfate and approximately ¾ of the volatiles were evaporated. Diethyl ether was added and the precipitate was filtered and dried to yield the title compound. Yield: 68 mg, 60%. LCMS: P=100%, rt=1.96 mn, (M+H)$^+$: 420.1; chiral: 7.22 mn, ee=91%. $^1$HNMR (DMSO-d$^6$): δ: 8.4 ppm (s, 1H), 8.05 ppm (m, 2H), 7.6 ppm (m, 2H), 7.5 ppm (m, 3H), 7.35 ppm (t, 2H), 5.7 ppm (br m, 1H), 4.8 ppm (dd, 1H), 4.3 ppm (m, 1H), 4.1 ppm (br m, 1H), 3.7 ppm (m, 1H), 1.6 ppm (d, 3H).

Examples 2 to 84

The general procedure detailed in example 1 was used for the preparation of compounds in examples 2 to 84 starting from the appropriate intermediates or commercially available reagents. Example n°, compound n°, compound names, triazolopiperazine intermediates 3 and acyl chloride intermediates 4 are listed in Table 2A below.

TABLE 2A

| Example_no | Compound_no | Triazolopiperazine intermediae 3 | Acyl chloride intermediate 4 |
|---|---|---|---|
| 2 | 1 | 3b | 4-fluorobenzoyl chloride |
| 3 | 2 | 3b | 4-chlorobenzoyl chloride |
| 4 | 3 | 3b | 4c |
| 5 | 4 | 3b | 4d |
| 6 | 5 | 3b | 3,4-dichlorobenzoyl chloride |
| 7 | 6 | 3b | 4-phenylbenzoyl chloride |
| 8 | 7 | 3h | 4-fluorobenzoyl chloride |
| 9 | 8 | 3o | 4-fluorobenzoyl chloride |
| 10 | 9 | 3c | 4-fluorobenzoyl chloride |
| 11 | 10 | 3d | 4-fluorobenzoyl chloride |
| 12 | 11 | 3e | 4-fluorobenzoyl chloride |
| 13 | 12 | 3f | 4-fluorobenzoyl chloride |
| 14 | 13 | 3b | 4e |
| 15 | 14 | 3b | 4a |
| 16 | 15 | 3g | 4-fluorobenzoic chloride |
| 17 | 16 | 3b | 4-(4-fluorophenyl)benzoyl chloride |
| 18 | 17 | 3b | 4f |
| 19 | 18 | 3b | 4g |
| 20 | 19 | 3h | 4-phenylbenzoyl chloride |
| 21 | 20 | 3c | 4-phenylbenzoyl chloride |
| 22 | 21 | 3b | 4-(thiophen-2-yl)benzoyl chloride |
| 23 | 22 | 3i | 4-fluorobenzoyl chloride |
| 24 | 23 | 3j | 4-fluorobenzoyl chloride |
| 25 | 24 | 3k | 4-fluorobenzoyl chloride |
| 26 | 25 | 3l | 4-fluorobenzoyl chloride |
| 27 | 26 | 3o | 4-phenylbenzoyl chloride |
| 28 | 27 | 3m | 4-fluorobenzoyl chloride |
| 29 | 28 | 3p | 4-fluorobenzoyl chloride |
| 30 | 29 | 3q | 4-fluorobenzoyl chloride |
| 31 | 30 | 3r | 4-fluorobenzoyl chloride |
| 32 | 31 | 3s | 4-fluorobenzoyl chloride |
| 33 | 32 | 3t | 4-fluorobenzoyl chloride |
| 34 | 33 | 3u | 4-fluorobenzoyl chloride |
| 35 | 34 | 3v | 4-fluorobenzoyl chloride |
| 36 | 35 | 3w | 4-fluorobenzoyl chloride |
| 37 | 36 | 3x | 4-fluorobenzoyl chloride |
| 38 | 37 | 3y | 4-fluorobenzoyl chloride |
| 39 | 38 | 3z | 4-fluorobenzoyl chloride |
| 40 | 39 | 3a1 | 4-fluorobenzoyl chloride |
| 41 | 40 | 3b1 | 4-fluorobenzoyl chloride |
| 42 | 41 | 3c1 | 4-fluorobenzoyl chloride |
| 43 | 42 | 3d1 | 4-fluorobenzoyl chloride |
| 44 | 43 | 3e1 | 4-fluorobenzoyl chloride |
| 45 | 44 | 3f1 | 4-fluorobenzoyl chloride |
| 46 | 46 | 3g1 | 4-phenylbenzoyl chloride |

TABLE 2A-continued

| Example_no | Compound_no | Triazolopiperazine intermediae 3 | Acyl chloride intermediate 4 |
|---|---|---|---|
| 47 | 47 | 3h1 | 4-phenylbenzoyl chloride |
| 48 | 48 | 3i1 | 4-fluorobenzoyl chloride |
| 49 | 49 | 3i1 | 4-fluorobenzoyl chloride |
| 50 | 50 | 3h1 | 4-fluorobenzoyl chloride |
| 51 | 51 | 3j1 | 4-fluorobenzoyl chloride |
| 52 | 52 | 3g1 | 4-fluorobenzoyl chloride |
| 53 | 53 | 3g1 | 4-(4-fluorophenyl)benzoyl chloride |
| 54 | 54 | 3o | 4-(thiophen-2-yl)benzoyl chloride |
| 55 | 55 | 3c | 4-(thiophen-2-yl)benzoyl chloride |
| 56 | 56 | 3g1 | 4-(thiophen-2-yl)benzoyl chloride |
| 57 | 57 | 3k1 | 4-fluorobenzoyl chloride |
| 58 | 58 | 3l1 | 4-fluorobenzoyl chloride |
| 59 | 59 | 3n | 4-fluorobenzoyl chloride |
| 60 | 60 | 3m1 | 4-fluorobenzoyl chloride |
| 61 | 61 | 3n1 | 4-fluorobenzoyl chloride |
| 62 | 62 | 3o1 | 4-(thiophen-2-yl)benzoyl chloride |
| 63 | 63 | 3o | 4-(thiophen-3-yl)benzoyl chloride |
| 64 | 64 | 3o1 | 4-(thiophen-3-yl)benzoyl chloride |
| 65 | 65 | 3n1 | 4-(thiophen-2-yl)benzoyl chloride |
| 66 | 66 | 3l1 | 4-(thiophen-2-yl)benzoyl chloride |
| 67 | 67 | 3l1 | 4-phenylbenzoyl chloride |
| 68 | 68 | 3p1 | 4-fluorobenzoyl chloride |
| 69 | 69 | 3h | 4-(thiophen-2-yl)benzoyl chloride |
| 70 | 70 | 3q1 | 4-fluorobenzoyl chloride |
| 71 | 71 | 3r1 | 4-fluorobenzoyl chloride |
| 72 | 72 | 3s1 | 4-phenylbenzoyl chloride |
| 73 | 73 | 3t | 4-(thiophen-2-yl)benzoyl chloride |
| 74 | 74 | 3t1 | 4-fluorobenzoyl chloride |
| 75 | 75 | 3s1 | 4-fluorobenzoyl chloride |
| 76 | 76 | 3q1 | 4-phenylbenzoyl chloride |
| 77 | 77 | 3u1 | 4-fluorobenzoyl chloride |
| 78 | 78 | 3q1 | 4-(thiophen-2-yl)benzoyl chloride |
| 79 | 79 | 3u1 | 4-phenylbenzoyl chloride |
| 80 | 80 | 3u1 | 4-(thiophen-2-yl)benzoyl chloride |
| 81 | 81 | 3b | 1-naphthoyl chloride |
| 82 | 82 | 3b | 4h converted to acyl chloride |
| 83 | 83 | 3b | 4i converted to acyl chloride |
| 84 | 85 | 3v1 | 4-(thiophen-2-yl)benzoyl chloride |

Example 85 compound n° 87 was synthesized by reacting intermediate 3 h and 4-fluorophenylsulfonyl chloride using well known sulfonylation conditions.

Examples 87 to 111

The general procedure detailed in example 1 was used for the preparation of compounds in examples 87 to 111 starting from the appropriate intermediates or commercially available reagents. Example n°, compound n°, compound names, triazolopiperazine intermediates 3 and carboxylic acidacyl chloride intermediates 4 are listed in table 2B hereunder.

TABLE 2B

| Example_no | Compound_no | Triazolopiperazine intermediate 3 | Acyl chloride intermediate 4 |
|---|---|---|---|
| 87 | 89 | 3h | 4-fluorophenylacetyl chloride |
| 88 | 90 | 3h | 5-phenylpicolinyl chloride |
| 89 | 91 | 3h | 6-phenylnicotinyl chloride |
| 90 | 92 | 3h | 2-phenylpyrimidine-5-carbonyl chloride |
| 91 | 93 | 3h | 4-phenylcyclohexanecarbonyl chloride |
| 92 | 95 | 3h | 3-methylbutanoyl chloride |
| 93 | 96 | 3h | 2-phenylbenzoyl chloride |
| 94 | 98 | 3h | 4-(pyrimidin-5-yl)benzoyl chloride |
| 95 | 100 | 3h | 4-(pyrimidin-2-yl)benzoyl chloride |
| 96 | 101 | 3h | 4-(pyrazin-2-yl)benzoic chloride |
| 97 | 102 | 3h | 4-(pyridazin-3-yl)benzoyl chloride |

TABLE 2B-continued

| Example_no | Compound_no | Triazolopiperazine intermediate 3 | Acyl chloride intermediate 4 |
|---|---|---|---|
| 98 | 103 | 3h | 4'-cyano-[1,1'-biphenyl]-4-carbonyl chloride |
| 99 | 104 | 3h | 4-(2-oxopiperidin-1-yl)benzoyl chloride |
| 100 | 105 | 3h | 4-morpholinobenzoyl chloride |
| 101 | 106 | 3h | 4-(3,5-dimethyl-1H-pyrazol-1-yl)benzoyl chloride |
| 102 | 107 | 3w1 | 4-(thiophen-2-yl)benzoyl chloride |
| 103 | 108 | 3x1 | 4-(thiophen-2-yl)benzoyl chloride |
| 104 | 109 | 3q1 | 3,4-dichlorobenzoyl chloride |
| 105 | 110 | 3q1 | 3,4-difluorobenzoyl chloride |
| 106 | 111 | 3q1 | 3-chloro-4-fluorobenzoyl chloride |
| 107 | 112 | 3q1 | 3-fluoro-4-chlorobenzoyl chloride |
| 108 | 113 | 3q1 | 3,4,5-trifluorobenzoyl chloride |
| 109 | 114 | 3i1 | 4-(thiophen-2-yl)benzoyl chloride |
| 110 | 135 | 3a | 4-(thiophen-2-yl)benzoyl chloride |
| 111 | 136 | 3g1 | 4-(thiophen-2-yl)benzoyl chloride |

It was noted that synthesis from chiral intermediate 3 could lead to compounds with low enantiomeric excess. It could therefore be advantageous to make the synthesis of compounds of invention from racemic building block 3 and perform further purification by chiral preparative HPLC.

Example 112: Synthesis of Compound N° 166

A variant to the general procedure used for the synthesis of triazolopiperazine compounds of the invention is detailed below using the synthesis of compound n° 166: (4-fluorophenyl)(8-methyl-3-(2-phenylthiazol-4-yl)-5,6-dihydro-[1,2,4]triazolo[4,3-a]pyrazin-7(8H)-yl)methanone:

Scheme 13: synthesis of (4-fluorophenyl)(8-methyl-3-(2-phenylthiazol-4-yl)-5,6-dihydro [1,2,4]triazolo[4.3-a]pyrazin-7(8H)-yl)methanone (compound n° 166).

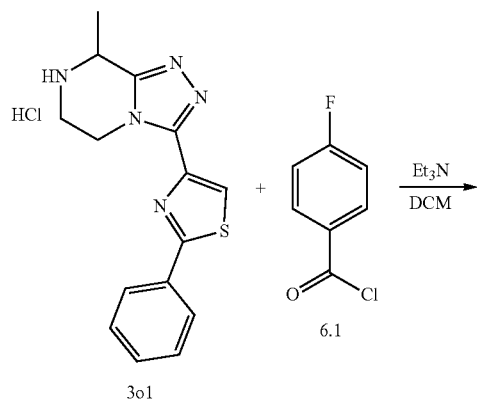

-continued

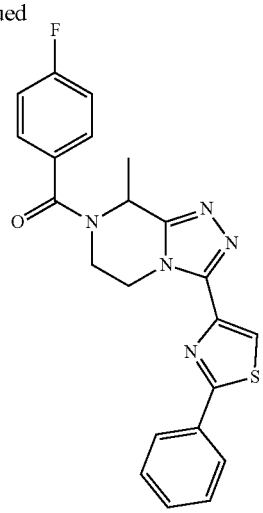

compound n° 166

To a solution of intermediate 3o1 (500 mg, 1.50 mmol) in 20 mL of anhydrous DCM was added 4-fluorobenzoyl chloride 6.1 (261 mg, 1.65 mmol) and Et$_3$N (0.625 mL, 455 mg, 4.49 mmol). The reaction mixture was stirred for 2 h. Thereupon the reaction mixture was washed with water, and the extracted organic layer further washed with brine, dried over sodium sulfate. Thereafter the volatiles were concentrated and diethyl ether was added to precipitate the product. The filtered precipitate was then dried in vacuo. Yield: 630 mg, 100%. LCMS: P=100%, rt=8.2 min, (M+H)$^+$: 420.1. $^1$HNMR (CDCl$_3$): δ: 8.3 ppm (s, 1H), 8.0 ppm (m, 2H), 7.5 ppm (m, 5H), 7.2 ppm (t, 2H), 5.7 ppm (br m, 1H), 5.0 ppm (dd, 1H), 4.4 ppm (m, 1H), 3.5 ppm (m, 1H), 1.6 ppm (d, 3H).

The general procedure variant detailed in example 112 was used for the preparation of compounds in examples 113 to 257 starting from the appropriate intermediates or commercially available reagents.

Example n°, compound n°, compound names, triazolopiperazine intermediates 3 and acyl chloride intermediates 4 are listed in table 2C hereunder.

TABLE 2C

| Example_no | Compound_no | Triazolopiperazine intermediate 3 | Acyl chloride intermediate 4 |
|---|---|---|---|
| 113 | 115 | chiral preparative HPLC of compound no61 | |
| 114 | 118 | chiral preparative HPLC of compound no46 | |
| 115 | 131 | chiral preparative HPLC of compound no49 | |
| 116 | 134 | chiral preparative HPLC of compound no53 | |
| 117 | 144 | chiral preparative HPLC of compound no65 | |
| 118 | 156 | chiral preparative HPLC of compound no80 | |
| 119 | 159 | 3y1 | 4-fluorobenzoyl chloride |
| 120 | 160 | 3z1 | 4-fluorobenzoyl chloride |
| 121 | 161 | 3a2 | 4'-fluoro-[1,1'-biphenyl]-4-carbonyl chloride |
| 122 | 162 | chiral preparative HPLC of compound no61 | |
| 123 | 163 | chiral preparative HPLC of compound no65 | |
| 124 | 164 | chiral preparative HPLC of compound no70 | |
| 125 | 165 | chiral preparative HPLC of compound no80 | |
| 126 | 167 | chiral preparative HPLC of compound no166 | |
| 127 | 168 | chiral preparative HPLC of compound no209 | |
| 128 | 169 | chiral preparative HPLC of compound no209 | |
| 129 | 170 | 3q | 4-(thiophen-2-yl)benzoyl chloride |
| 130 | 171 | 3b2 | 4-(thiophen-2-yl)benzoyl chloride |
| 131 | 172 | 3c2 | 4-fluorobenzoyl chloride |
| 132 | 173 | 3b2 | 4-fluorobenzoyl chloride |
| 133 | 174 | 3c2 | 4-(thiophen-2-yl)benzoyl chloride |
| 134 | 175 | 3d2 | 4-fluorobenzoyl chloride |
| 135 | 176 | 3d2 | 4-(thiophen-2-yl)benzoyl chloride |
| 136 | 177 | 3e2 | 4-(thiophen-2-yl)benzoyl chloride |
| 137 | 178 | 3f2 | 4-fluorobenzoyl chloride |
| 138 | 179 | 3f2 | 4-(thiophen-2-yl)benzoyl chloride |
| 139 | 180 | 3g2 | 4-fluorobenzoyl chloride |
| 140 | 181 | 3g2 | 4-(thiophen-2-yl)benzoyl chloride |
| 141 | 182 | 3g2 | 4-phenylbenzoyl chloride |
| 142 | 183 | 3g2 | 4'-fluoro-[1,1'-biphenyl]-4-carbonyl chloride |
| 143 | 185 | 3h2 | 4-(thiophen-2-yl)benzoyl chloride |
| 144 | 186 | 3h2 | 4-phenylbenzoyl chloride |
| 145 | 187 | 3h2 | 4'-fluoro-[1,1'-biphenyl]-4-carbonyl chloride |
| 146 | 188 | 3i2 | 4-fluorobenzoyl chloride |
| 147 | 189 | 3i2 | 4-(thiophen-2-yl)benzoyl chloride |
| 148 | 190 | 3j2 | 4-fluorobenzoyl chloride |
| 149 | 191 | 3j2 | 4-(thiophen-2-yl)benzoyl chloride |
| 150 | 192 | 3j2 | 4-phenylbenzoyl chloride |
| 151 | 193 | 3k2 | 4-fluorobenzoyl chloride |
| 152 | 194 | 3k2 | 4-(thiophen-2-yl)benzoyl chloride |
| 153 | 195 | 3k2 | 4-phenylbenzoyl chloride |
| 154 | 196 | 3k2 | 4'-fluoro-[1,1'-biphenyl]-4-carbonyl chloride |
| 155 | 198 | 3l2 | 4-(thiophen-2-yl)benzoyl chloride |
| 156 | 199 | 3l2 | 4-phenylbenzoyl chloride |
| 157 | 200 | 3l2 | 4'-fluoro-[1,1'-biphenyl]-4-carbonyl chloride |
| 158 | 201 | 3m2 | 4-fluorobenzoyl chloride |
| 159 | 202 | 3m2 | 4-(thiophen-2-yl)benzoyl chloride |
| 160 | 203 | 3m2 | 4-phenylbenzoyl chloride |
| 161 | 204 | 3d2 | 4-phenylbenzoyl chloride |
| 162 | 205 | 3d2 | 4'-fluoro-[1,1'-biphenyl]-4-carbonyl chloride |
| 163 | 206 | 3n2 | 4-fluorobenzoyl chloride |
| 164 | 207 | 3n2 | 4-(thiophen-2-yl)benzoyl chloride |
| 165 | 208 | 3o2 | 4-fluorobenzoyl chloride |
| 166 | 209 | 3p2 | 4-(thiophen-2-yl)benzoyl chloride |
| 167 | 211 | 3q2 | 4-(thiophen-2-yl)benzoyl chloride |

TABLE 2C-continued

| Example_no | Compound_no | Triazolopiperazine intermediate 3 | Acyl chloride intermediate 4 |
|---|---|---|---|
| 168 | 212 | 3q2 | 4-fluorobenzoyl chloride |
| 169 | 213 | 3r2 | 4-(thiophen-2-yl)benzoyl chloride |
| 170 | 214 | 3r2 | 4-fluorobenzoyl chloride |
| 171 | 215 | 3q1 | 4-(5-methylthiophen-2-yl)benzoyl chloride |
| | | | 4-(5-methylthiophen-2-yl)benzoyl chloride was prepared from a classical Suzuki coupling between 2-bromo-5-methylthiophene and 4-methoxycarbonylphenylboronic acid followed by a saponification and acyl chloride formation |
| 172 | 216 | 3q1 | 4-cyanobenzoyl chloride |
| 173 | 217 | 3c2 | 4-phenylbenzoyl chloride |
| 174 | 218 | 3s2 | 4-fluorobenzoyl chloride |
| 175 | 219 | 3t2 | 4-(thiophen-2-yl)benzoyl chloride |
| 176 | 220 | 3u2 | 4-(thiophen-2-yl)benzoyl chloride |
| 177 | 221 | 3v2 | 4-fluorobenzoyl chloride |
| 178 | 222 | 3w2 | 4-(thiophen-2-yl)benzoyl chloride |
| 179 | 223 | 3x2 | 4'-fluoro-[1,1'-biphenyl]-4-carbonyl chloride |
| 180 | 224 | 3y2 | 4-(thiophen-2-yl)benzoyl chloride |
| 181 | 225 | 3u2 | 4-fluorobenzoyl chloride |
| 182 | 226 | 3z2 | 4-(thiophen-2-yl)benzoyl chloride |
| 183 | 227 | | chiral preparative HPLC of compound no56 |
| 184 | 228 | 3s2 | 4-(thiophen-2-yl)benzoyl chloride |
| 185 | 229 | 3v2 | 4-(thiophen-2-yl)benzoyl chloride |
| 186 | 230 | 3y2 | 4-fluorobenzoyl chloride |
| 187 | 231 | 3b | benzoyl chloride |
| 188 | 232 | 3b | 4-methylbenzoyl chloride |
| 189 | 304 | 3q1 | 4-(2-methylthiophen-3-yl)benzoyl chloride |
| | | | 4-(2-methylthiophen-3-yl)benzoyl chloride was prepared from a classical Suzuki coupling between methyl 4-iodobenzoate & 4,4,5,5-tetramethyl-2-(2-methylthiophen-3-yl)-1,3,2-dioxaborolane followed by a saponification and acyl chloride formation |
| 190 | 233 | | chiral preparative HPLC of compound no304 |
| 191 | 234 | | chiral preparative HPLC of compound no304 |
| 192 | 235 | 3a3 | 4-(thiophen-2-yl)benzoyl chloride |
| 193 | 236 | | Cyanation of compound no213 using the procedure described in WO2008/103500 A1 |
| 194 | 237 | 3a3 | 4-fluorobenzoyl chloride |
| 195 | 238 | 3w2 | 4-fluorobenzoyl chloride |
| 196 | 239 | 3b3 | 4-(thiophen-2-yl)benzoyl chloride |
| 197 | 240 | 3b3 | 4-fluorobenzoyl chloride |
| 198 | 241 | 3c3 | 4-(thiophen-2-yl)benzoyl chloride |
| 199 | 242 | 3c3 | 4-fluorobenzoyl chloride |
| 200 | 244 | 3d3 | 4-fluorobenzoyl chloride |
| 201 | 245 | 3e3 | 4-(thiophen-2-yl)benzoyl chloride |
| 202 | 246 | 3e3 | 4-fluorobenzoyl chloride |
| 203 | 247 | 3f3 | 4-(thiophen-2-yl)benzoyl chloride |
| 204 | 248 | 3g3 | 4-(thiophen-2-yl)benzoyl chloride |
| 205 | 249 | 3g3 | 4-fluorobenzoyl chloride |
| 206 | 250 | 3h3 | 4-(thiophen-2-yl)benzoyl chloride |
| 207 | 251 | 3h3 | 4-fluorobenzoyl chloride |
| 208 | 252 | 3i3 | 4-(thiophen-2-yl)benzoyl chloride |
| 209 | 253 | 3t | 4-(dimethylamino)benzoyl chloride |
| 210 | 254 | 3j3 | 4-(thiophen-2-yl)benzoyl chloride |
| 211 | 255 | 3j3 | 4-fluorobenzoyl chloride |
| 212 | 256 | 3k3 | 4-(thiophen-2-yl)benzoyl chloride |
| 213 | 257 | 3l3 | 4-(thiophen-2-yl)benzoyl chloride |
| 214 | 258 | 3m3 | 4-fluorobenzoyl chloride |

TABLE 2C-continued

| Example_no | Compound_no | Triazolopiperazine intermediate 3 | Acyl chloride intermediate 4 |
|---|---|---|---|
| 215 | 259 | 3k3 | 4-fluorobenzoyl chloride |
| 216 | 260 | 2-(4-fluorophenyl)-4-(5,6,7,8-tetrahydroimidazo[1,5-a]pyrazin-3-yl)thiazole | 4-fluorobenzoyl chloride |
| | | 2-(4-fluorophenyl)-4-(5,6,7,8-tetrahydroimidazo[1,5-a]pyrazin-3-yl)thiazole was synthesized using the procedure described by T.G. Murali Dhar et al. in *Bioorg. Med. Chem. Lett.* 17 (2007) 5019-24 | |
| 217 | 261 | 3n3 | 4-(thiophen-2-yl)benzoyl chloride |
| 218 | 262 | 2o3 | 4-(thiophen-2-yl)benzoyl chloride |
| 219 | 263 | 3l3 | 4-(thiophen-2-yl)benzoyl chloride |
| 220 | 265 | 3p3 | 4-(thiophen-2-yl)benzoyl chloride |
| 221 | 266 | 3q3 | 4-(thiophen-2-yl)benzoyl chloride |
| 222 | 267 | 3r3 | 4-(thiophen-2-yl)benzoyl chloride |
| 223 | 268 | 3q1 | 4-(3-methylthiophen-2-yl)benzoyl chloride |
| | | 4-(3-methylthiophen-2-yl)benzoyl chloride was prepared from a classical Suzuki coupling between methyl 4-iodobenzoate & 4,4,5,5-tetramethyl-2-(3-methylthiophen-2-yl)-1,3,2-dioxaborolane followed by a saponification and acyl chloride formation | |
| 224 | 269 | 3r3 | 4-fluorobenzoyl chloride |
| 225 | 270 | chiral preparative HPLC of compound no268 | |
| 226 | 271 | 3o3 | 4-fluorobenzoyl chloride |
| 227 | 272 | chiral preparative HPLC of compound no268 | |
| 228 | 273 | 3s3 | 4-(thiophen-2-yl)benzoyl chloride |
| 229 | 274 | 3t3 | 4-(thiophen-2-yl)benzoyl chloride |
| 230 | 275 | 3u3 | 4-(thiophen-2-yl)benzoyl chloride |
| 231 | 276 | 3t3 | 4-fluorobenzoyl chloride |
| 232 | 277 | 3v3 | 4-fluorobenzoyl chloride |
| 233 | 278 | 3w3 | 4-fluorobenzoyl chloride |
| 234 | 279 | 3v3 | 4-(thiophen-2-yl)benzoyl chloride |
| 235 | 280 | Compound no262 was alkylated with tert-butyl (2-bromoethyl)carbamate using the same alkylation procedure that is described in General Method H | |
| 236 | 281 | Compound no262 was alkylated with 2-(2-bromoethoxy)tetrahydro-2H-pyran using the same alkylation procedure that is described in General Method H, then the THP group was removed with HCl in dioxane | |
| 237 | 282 | Compound no280 was treated with TFA in DCM (Boc deprotection) | |
| 238 | 283 | According to scheme 10 | |
| 239 | 284 285 | Compound no267 was alkylated with 2-(2-bromoethoxy)tetrahydro-2H-pyran using the same alkylation procedure that is described in General Method H, then the THP group was removed with HCl in dioxane. Chiral preparative HPLC yielded compounds no 284 and 285 | |
| 240 | 286 | 3w3 | 4-phenylbenzoyl chloride |
| 241 | 287 | 3w3 | 4-(thiophen-2-yl)benzoyl chloride |
| 242 | 288 | Compound no275 was reacted with 2,4-difluoro-iodobenzene according to General Method F (C2-arylation described in Org. Lett. 2008, 10 (13), 2909) | |
| 243 | 289 | According to scheme 10 | |
| 244 | 290 | According to scheme 10 | |
| 245 | 291 | According to scheme 10 | |
| 246 | 292 | According to scheme 10 | |
| 247 | 293 | According to scheme 11 | |
| 248 | 294 | 3t | 4c |
| 249 | 295 | 3t | 4h |
| 250 | 296 | 3t | 4a |
| 251 | 297 | 3t | 4i |
| 252 | 298 299 | Compound no267 was alkylated with tert-butyl (2-bromoethyl)carbamate using the same alkylation procedure that is described in General Method H, Chiral preparative HPLC yielded compounds no 284 and 285 | |

TABLE 2C-continued

| Example_no | Compound_no | Triazolopiperazine intermediate 3 | Acyl chloride intermediate 4 |
|---|---|---|---|
| 253 | 300 | 3x3 | 4-(thiophen-2-yl)benzoyl chloride |
| 254 | 301 | 2y3 | 4-(thiophen-2-yl)benzoyl chloride |
| 255 | 302 | Compound no 300 was converted to compound no 302 using the cyanation procedure described in WO2008/103500 A1 | |
| 256 | 303 | Compound no 301 was converted to compound no 303 using the cyanation procedure described in WO2008/103500 A1 | |
| 257 | 243 | 3d3 | 4-(thiophen-2-yl)benzoyl chloride |

BIOLOGY EXAMPLES

COMPETITIVE BINDING ASSAYS

Figure 1:
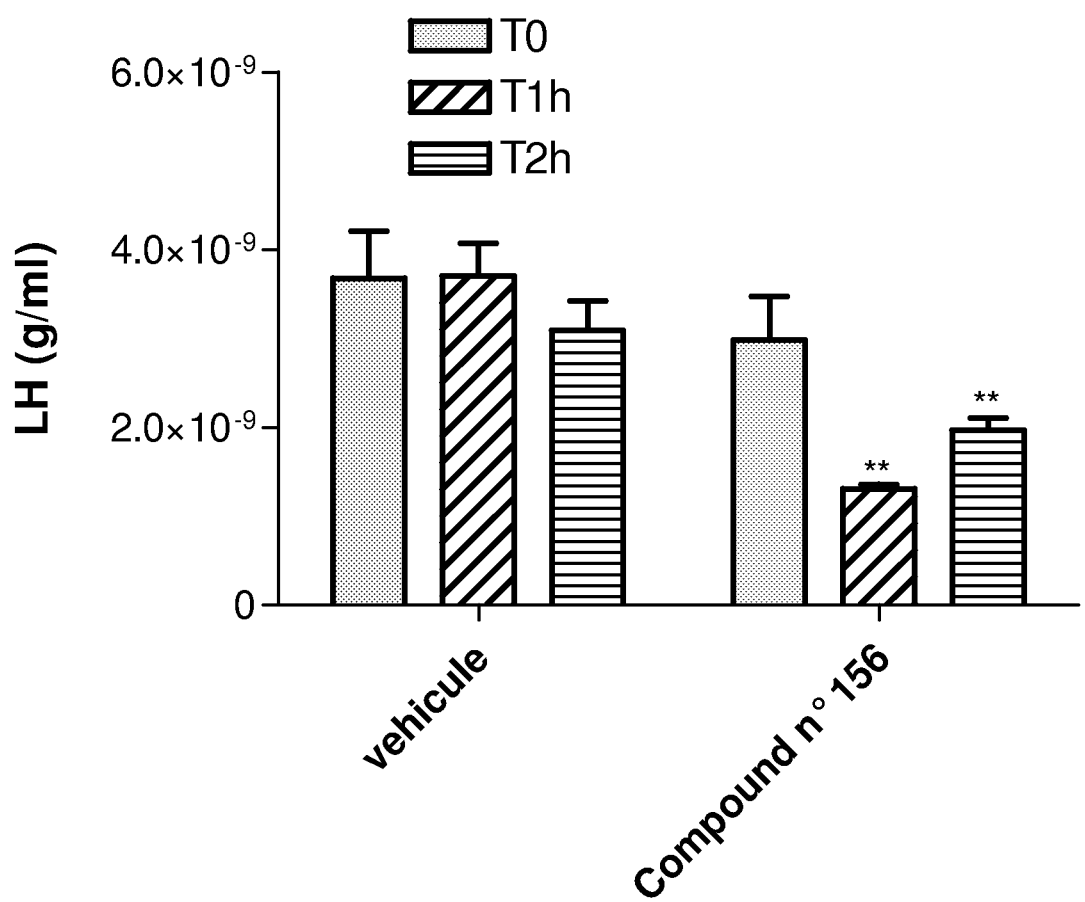
FIG. 1 shows the effects of a single intravenous 10 mg/kg dose of compound n° 156 on LH serum levels in castrated male rats, measured 60 min and 120 min following dosing. LH hormone levels are expressed as means±S.E.M. (**$p<0.001$ vs. baseline, determined by one-Way ANOVA and Dunnett's post hoc).

The affinity of compounds of the invention for the tachykinin receptors was determined by measuring the ability of the compounds of the invention to displace a radiolabeled ligand from its specifics binding site.
$^3$H-SB222200 Binding Competition Assay with Human NK-3 Receptor
The ability of the compounds of the invention to inhibit the binding of the NK-3 receptor selective antagonist SB222200 was assessed by an in vitro radioligand binding assay. Membranes were prepared from Chinese hamster ovary recombinant cells which express the human NK3 receptor. The membranes were incubated with 5 nM $^3$H-SB222200_ (ARC) in a HEPES 25 mM/NaCl 0.1M/CaCl$_2$ 1 mM/MgCl$_2$ 5 Mm/BSA 0.5%/Saponin 10 µg/ml buffer at pH 7.4 and various concentrations of the compounds of the invention. The amount of tritiated SB222200 bound to the receptor was determined after filtration by the quantification of membrane associated radioactivity using the TopCount-NXT reader (Packard). Competition curves were obtained for compounds of the invention and the concentrations of compounds which displaced 50% of bound radioligand (IC$_{50}$) were determined and then apparent inhibition constant Ki values were calculated by the following equation: Ki=IC$_{50}$/(1+[L]/K$_D$) where [L] is the concentration of free radioligand and K$_D$ is its dissociation constant at the receptor, derived from saturation binding experiments (Cheng and Prusoff, 1973) (see results in table 3 below).

In Table 3 biological results obtained using the $^3$H-SB222200 binding competition assay with compounds of the invention are set out in tabulated form. In this table the calculated Ki is given. The Ki value obtained (in accordance with the protocol set forth above) is represented as follows: "+++" means Ki<500 nM; "++" means 500 nM≤Ki≤1 µM; "+" means 1 µM<Ki≤5 µM; "#" means Ki>5 µM.

TABLE 3

| Compound no | Ki range |
|---|---|
| 1 | + |
| 2 | + |
| 3 | + |
| 4 | + |
| 5 | + |
| 6 | + |
| 7 | +++ |
| 8 | +++ |
| 9 | +++ |
| 10 | +++ |
| 11 | +++ |
| 13 | + |
| 14 | + |
| 15 | + |
| 16 | + |
| 17 | + |
| 18 | + |
| 19 | +++ |
| 20 | +++ |
| 21 | +++ |
| 22 | ++ |
| 23 | ++ |
| 24 | +++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |
| 38 | +++ |
| 39 | ++ |
| 40 | +++ |
| 41 | +++ |
| 42 | +++ |
| 43 | + |
| 44 | + |
| 45 | +++ |
| 46 | +++ |

TABLE 3-continued

| Compound no | Ki range |
|---|---|
| 47 | +++ |
| 48 | +++ |
| 49 | +++ |
| 50 | +++ |
| 51 | +++ |
| 52 | +++ |
| 53 | +++ |
| 54 | +++ |
| 55 | +++ |
| 56 | +++ |
| 57 | +++ |
| 58 | +++ |
| 59 | +++ |
| 60 | +++ |
| 61 | +++ |
| 62 | +++ |
| 63 | +++ |
| 64 | +++ |
| 65 | +++ |
| 66 | +++ |
| 67 | +++ |
| 68 | +++ |
| 69 | +++ |
| 70 | +++ |
| 71 | +++ |
| 72 | +++ |
| 73 | +++ |
| 74 | +++ |
| 75 | ++ |
| 76 | +++ |
| 77 | +++ |
| 78 | +++ |
| 79 | +++ |
| 80 | +++ |
| 83 | # |
| 85 | +++ |
| 90 | +++ |
| 91 | +++ |
| 92 | + |
| 93 | + |
| 95 | + |
| 96 | # |
| 103 | + |
| 107 | ++ |
| 108 | ++ |
| 109 | +++ |
| 110 | +++ |
| 111 | +++ |
| 112 | +++ |
| 113 | +++ |
| 114 | +++ |
| 115 | +++ |
| 118 | +++ |
| 131 | +++ |
| 134 | +++ |
| 135 | +++ |
| 136 | +++ |
| 144 | +++ |
| 156 | +++ |
| 159 | # |
| 160 | + |
| 161 | + |
| 162 | +++ |
| 163 | ++ |
| 164 | +++ |
| 165 | +++ |
| 166 | +++ |
| 167 | ++ |
| 168 | +++ |
| 169 | +++ |
| 170 | +++ |
| 171 | +++ |
| 172 | +++ |
| 173 | +++ |
| 174 | +++ |
| 175 | +++ |
| 176 | +++ |
| 177 | +++ |
| 178 | + |
| 179 | +++ |
| 180 | +++ |
| 181 | +++ |
| 182 | +++ |
| 183 | +++ |
| 185 | # |
| 186 | + |
| 187 | + |
| 188 | ++ |
| 189 | +++ |
| 190 | +++ |
| 191 | # |
| 193 | +++ |
| 194 | +++ |
| 195 | +++ |
| 196 | +++ |
| 198 | + |
| 199 | + |
| 200 | ++ |
| 201 | + |
| 202 | +++ |
| 203 | ++ |
| 204 | +++ |
| 205 | ++ |
| 206 | + |
| 207 | +++ |
| 208 | + |
| 209 | +++ |
| 211 | +++ |
| 212 | +++ |
| 213 | +++ |
| 214 | +++ |
| 215 | +++ |
| 216 | +++ |
| 217 | +++ |
| 218 | + |
| 219 | +++ |
| 220 | +++ |
| 221 | ++ |
| 222 | +++ |
| 223 | +++ |
| 224 | +++ |
| 225 | + |
| 226 | # |
| 227 | ++ |
| 228 | +++ |
| 229 | +++ |
| 230 | + |
| 231 | + |
| 232 | + |
| 233 | +++ |
| 234 | +++ |
| 235 | +++ |
| 236 | +++ |
| 238 | +++ |
| 239 | + |
| 240 | ++ |
| 241 | +++ |
| 242 | ++ |
| 244 | ++ |
| 245 | +++ |
| 246 | +++ |
| 247 | +++ |
| 248 | +++ |
| 249 | +++ |
| 250 | ++ |
| 252 | ++ |
| 253 | ++ |
| 254 | +++ |
| 255 | ++ |
| 256 | +++ |
| 257 | +++ |
| 258 | +++ |
| 259 | + |
| 260 | +++ |
| 261 | +++ |
| 262 | +++ |

TABLE 3-continued

| Compound no | Ki range |
| --- | --- |
| 263 | +++ |
| 265 | +++ |
| 266 | +++ |
| 267 | +++ |
| 268 | +++ |
| 269 | ++ |
| 271 | +++ |
| 273 | +++ |
| 274 | ++ |
| 275 | # |
| 276 | # |
| 277 | # |
| 278 | +++ |
| 279 | +++ |
| 280 | +++ |
| 281 | +++ |
| 282 | ++ |
| 283 | ++ |
| 284 | +++ |
| 285 | +++ |
| 286 | +++ |
| 287 | +++ |

[$^{125}$I]-His-MePhe7-Neurokinin B Binding Competition Assay with Rat NK-3 Receptor The affinity of compounds of the invention for the rat NK3 receptor was evaluated in CHO recombinant cells which express the rat NK3 receptor. Membrane suspensions were prepared from these cells. The following radioligand: [$^{125}$I]-His-MePhe7-Neurokinin B (PerkinElmer Cat # NEX285) was used in this assay. Binding assays were performed in a 25 nM HEPES/1 mM CaCl$_2$/5 mM MgCl$_2$/0.5% BSA/10 µg/ml Saponin, at pH 7.4. Binding assays consisted of 25 µl of membrane suspension (approximately 5 µg protein/well in a 96 well plate), 50 µl of compound or reference ligand (MePhe7-Neurokinin B) at increasing concentrations (diluted in assay buffer) and 0.09 nM [$^{125}$I]-His-MePhe7-Neurokinin B. The plate was incubated 60 min at 25° C. in a water bath and then filtered over GF/C filters (Perkin Elmer, 6005174, presoaked in assay buffer without saponine for 2 h at room temperature) with a Filtration unit (Perkin Elmer). The radioactivity retained on the filters was measured by using the TopCount-NXT reader (Packard). Competition curves were obtained for compounds of the invention and the concentrations of compounds which displaced 50% of bound radioligand (IC$_{50}$) were determined and then apparent inhibition constant Ki values were calculated by the following equation: Ki=IC$_{50}$/(1+[L]/K$_D$) where [L] is the concentration of free radioligand and K$_D$ is its dissociation constant at the receptor, derived from saturation binding experiments (Cheng and Prusoff, 1973).

When tested in above described assay, preferred compounds of the invention showed an inhibition constant (Ki) for rat NK-3 receptor <50 nM.

Selectivity Assay

Selectivity of the compounds of the invention was determined over the other human NK receptors, namely NK-1 and NK2 receptors.

Human NK1

The affinity of compounds of the invention for the NK1 receptor was evaluated in CHO recombinant cells which express the human NK1 receptor. Membrane suspensions were prepared from these cells. The following radioligand: [$^3$H] substance P (PerkinElmer Cat # NET111520) was used in this assay. Binding assays were performed in a 50 mM Tris/5 mM MnCl2/150 mM NaCl/0.1% BSA at pH 7.4. Binding assays consisted of 25 µl of membrane suspension (approximately 5 µg of protein/well in a 96 well plate), 50 µl of compound or reference ligand (Substance P) at increasing concentrations (diluted in assay buffer) and 2 nM [$^3$H] substance P. The plate was incubated 60 min at 25° C. in a water bath and then filtered over GF/C filters (Perkin Elmer, 6005174, presoaked in 0.5% PEI for 2 h at room temperature) with a Filtration unit (Perkin Elmer). The radioactivity retained on the filters was measured by using the TopCount-NXT reader (Packard). Competition curves were obtained for compounds of the invention and the concentrations of compounds which displaced 50% of bound radioligand (IC$_{50}$) were determined and then apparent inhibition constant Ki values were calculated by the following equation: Ki=IC$_{50}$/(1+[L]/K$_D$) where [L] is the concentration of free radioligand and K$_D$ is its dissociation constant at the receptor, derived from saturation binding experiments (Cheng and Prusoff, 1973).

Human NK2

The affinity of compounds of the invention for the NK2 receptor was evaluated in CHO recombinant cells which express the human NK2 receptor. Membrane suspensions were prepared from these cells. The following radioligand [$^{125}$I]-Neurokinin A (PerkinElmer Cat # NEX252) was used in this assay. Binding assays were performed in a 25 mM HEPES/1 mM CaCl2/5 mM MgCl2/0.5% BSA/10 µg/ml saponin, at pH 7.4. Binding assays consisted of 25 µl of membrane suspension (approximately 3.75 µg of protein/well in a 96 well plate), 50 µl of compound or reference ligand (Neurokinin A) at increasing concentrations (diluted in assay buffer) and 0.1 nM [$^{125}$I]-Neurokinin A. The plate was incubated 60 min at 25° C. in a water bath and then filtered over GF/C filters (Perkin Elmer, 6005174, presoaked in assay buffer without saponine for 2 h at room temperature) with a Filtration unit (Perkin Elmer). The radioactivity retained on the filters was measured by using the TopCount-NXT reader (Packard). Competition curves were obtained for compounds of the invention and the concentrations of compounds which displaced 50% of bound radioligand (IC$_{50}$) were determined and then apparent inhibition constant Ki values were calculated by the following equation: Ki=IC$_{50}$/(1+[L]/K$_D$) where [L] is the concentration of free radioligand and K$_D$ is its dissociation constant at the receptor, derived from saturation binding experiments (Cheng and Prusoff, 1973).

The compounds of the invention, which were tested in the above NK-1 and NK-2 described assays, demonstrated a low affinity at the human NK-1 and human NK-2 receptors: 100-200 fold shift of the Ki compared to the human NK-3 receptor. Thus, compounds according to the invention have been shown to be selective over NK1 and NK2 receptors.

In Vivo Assay to Assess Compound Activity in Rat

The inhibitory effect of the compounds of the invention in luteinizing hormone (LH) secretion and on circulating steroid levels are determined by the following biological studies.

Castrated Male Rat Model to Assess the Effect of Compound of Invention on Circulating Levels of Luteinizing Hormone (LH).

In humans and rodents, castration is well-precedented to permit heightened, persistent GnRH signaling and consequently elevation of circulating LH. Thus, in this animal model, LH is measured in castrated rats as a marker of test compound inhibition of the GnRH signaling pathway.

Castrated adult male Sprague-Dawley (SD) rats (150-175 g) were purchased from Janvier (St Berthevin, France). All animals were housed 3 per cage in a temperature-controlled room (22±2° C.) and 50±5% relative humidity with a 12 hour light/12 hour dark photoperiod (lights off at 6 h00 pm). The animals were allowed 2 weeks of postoperative recovery prior to study. Animals were handled on a daily basis. Standard diet and tap water were provided ad libitum. Animal cage litters were changed once a week. On the study day, animals were acclimated to the procedure room for a period of one hour prior to the initiation of the experiment.

Compounds of the invention were formulated as 10% DMSO, 10% Cremophore EL, and 80% saline solutions.

After basal sampling (T0) a single dose of compounds of the invention or vehicle was administrated intravenously to rats. Blood was then collected at 60 min and 120 min post dosing. Blood samples were obtained via tail vein bleed, drawn into EDTA-containing tubes and centrifuged immediately. Plasma samples were collected and stored in a −80° C. freezer until assayed. Serum LH levels were determined using radioimmunoassay kit from IDS (Liège, Belgium). Baseline was defined as the initial basal blood sample.

Figure 2:
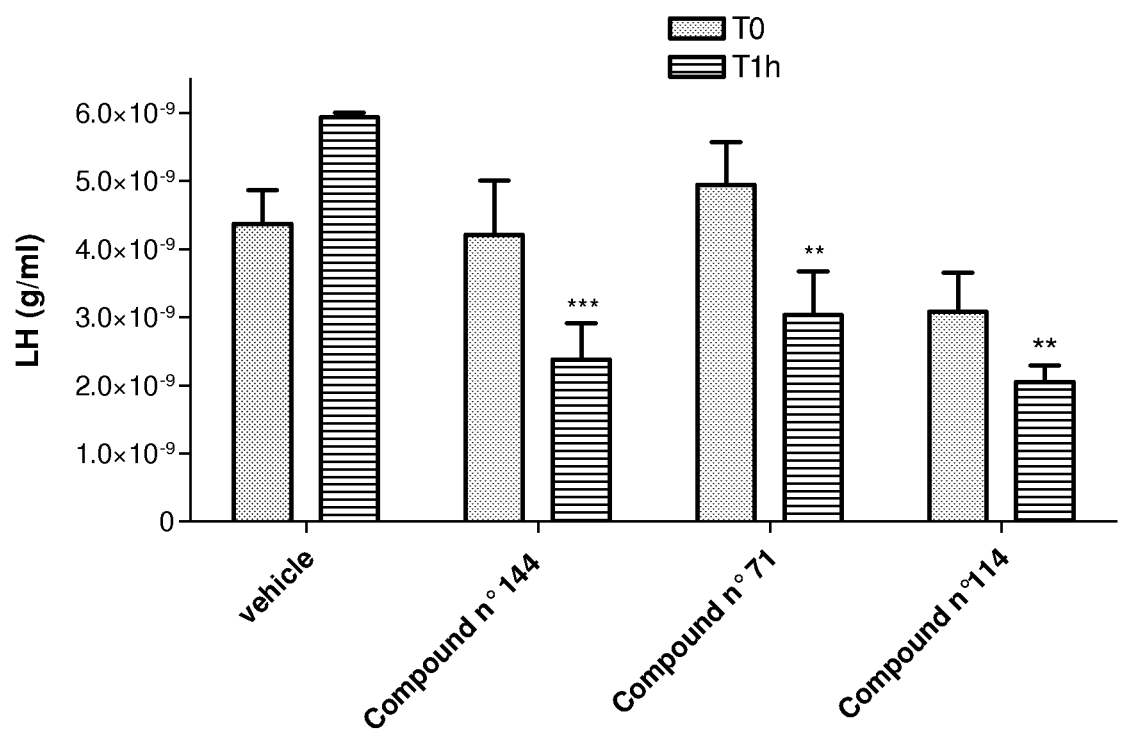
FIG. 2 shows the effects of a single intravenous dose of compound n° 144 (10 mg/kg), compound 71 (15 mg/kg) and compound 114 (20 mg/kg) on LH serum levels in castrated male rats, measured 60 min following dosing. LH hormone levels are expressed as means±S.E.M. (**$p<0.001$ vs. baseline, determined by one-Way ANOVA and Dunnett's post hoc).

When tested in the castrated male rat model described above, the compounds n° 144, 71, 156 and 114 significantly suppressed GnRH-mediated elevation of LH (FIGS. 1 and 2).

This result also shows that the compounds according to the invention pass through the blood-brain barrier and that they are capable of blocking the action of the NK-3 receptors in the CNS. The brain to plasma ratio values (B/P) obtained with the compounds according to the invention were generally greater than 0.1 indicating a significant brain penetration.

Gonad-Intact Adult Male to Assess the Effect of Compounds of the Invention on Circulating Levels of Testosterone.

Gonad-intact adult male Sprague-Dawley (SD) rats (300-385 g N=5/group were single housed in a temperature-controlled room (22±2° C.) and 50±5% relative humidity with a 12 hour light/12 hour dark photoperiod (lights off at 6 h00 pm). Purina rat chow (Ralston Purina Co., St. Louis, Mo.) and tap water were made available to rats, ad libitum. Chronic intracardiac venous cannulae were implanted under sodium pentobarbital anaesthesia (50 mg/kg, i.p.). After surgery, rats were placed directly into isolation test chambers and provided with food and water ad libitum until body weight returned to preoperative levels (a period of at least five days). On the test day, food was removed 1.5 h before the start of sampling and was returned at the end of the experiment. After basal blood sampling, free-moving rats were intravenously injected at time=0 min with either a single dose (20 mg/kg) of compound n° 156 or vehicle. Blood was then collected through a heparinized line at regular intervals up to 420 min and centrifuged immediately. Plasma samples were collected and stored in a −80° C. freezer until assayed. Plasma testosterone levels were determined using a radioimmunoassay kit (Immunotech).

Compound n° 156 was formulated as 40% DMA, 50% PEG400, and 10% sterile water solution.

Figure 3:
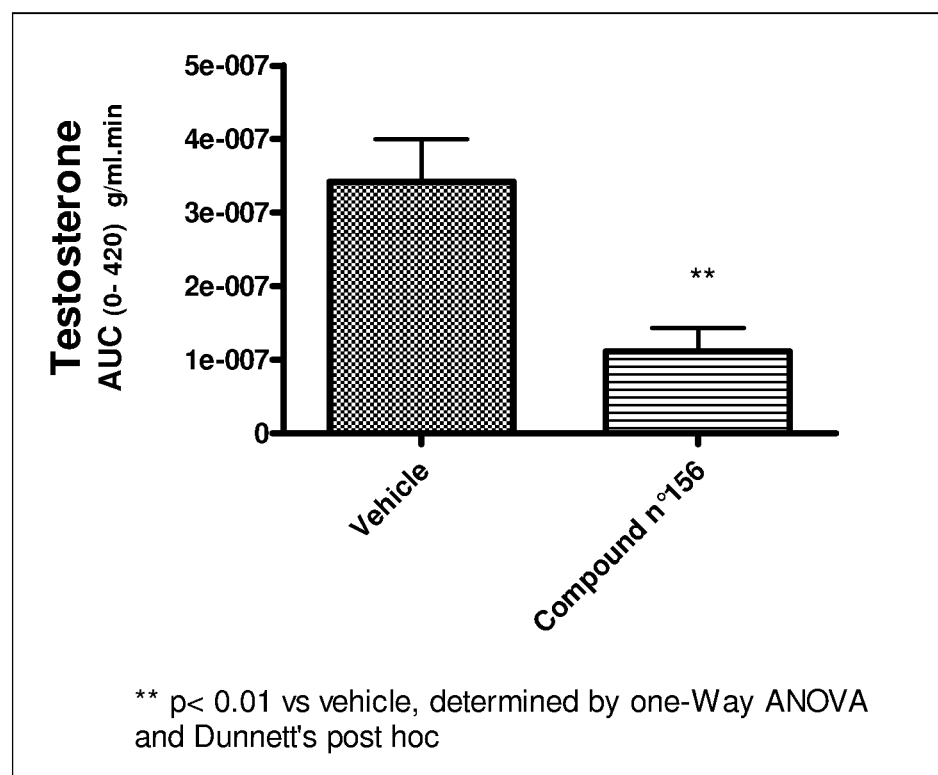
FIG. 3 shows the effect of a single intravenous 20 mg/kg dose of compound n° 156 on testosterone plasma levels in gonad-intact male rats (N=5 rats/group). Plasma testosterone levels are represented as an integrated testosterone response (AUC) over a 420 min period following dosing.

When tested in gonad-intact male rats, compound n° 156 significantly suppressed plasma testosterone levels over the 420 minute test period (FIG. 3).

The invention claimed is:

1. A pharmaceutical composition comprising a compound of formula I:

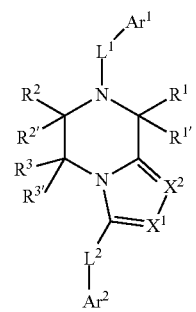

or a pharmaceutically acceptable salt or solvate thereof and at least one pharmaceutically acceptable carrier, diluent, excipient and/or adjuvant, wherein $Ar^1$ is a 5- to 6-membered aryl or heteroaryl group, 3- to 6-membered cycloalkyl group, a 3- to 6-membered heterocyclyl group or a C3-C6 alkyl group, each of the aryl, heteroaryl, cycloalkyl or heterocyclyl groups being optionally substituted by one or more group(s) selected from halo, cyano, alkyl, haloalkyl, cycloalkyl, heteroalkyl, heterocyclyl, aryl, aralkyl, heteroaryl, hydroxyl, alkoxy, haloalkoxy, alkoxyalkoxy, alkylamino, carboxy, alkoxycarbonyl, alkylcarbonyloxy, alkylcarbonylamino, haloalkylcarbonylamino, carbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or two substituents form an alkylenedioxy group or a haloalkylenedioxy group, or two substituents form a cycloalkyl or heterocycloalkyl moiety together with the cycloalkyl or heterocycloalkyl group they are attached to, or fused to the aryl, heteroaryl, cycloalkyl or heterocycloalkyl group may be one or more aryl moiety, each of said substituents being optionally substituted by one or more further substituent(s) selected from halo, cyano, alkyl, haloalkyl, cyclopropyl, alkoxy, haloalkoxy, heterocyclyl, aryl, heteroaryl, aryloxy heteroaryloxy;

$L^1$ is $C_1$-$C_2$ alkylene optionally being substituted by one or more group(s) selected from halo, methyl or ethyl under the condition that $R^{2'}$ together with $R^2$ form an oxo substituent, or $L^1$ is carbonyl or sulfonyl, or $L^1$ is (C=O)—CH$_2$— where the C=O is linked to the piperazine nitrogen and the CH$_2$ to $Ar^1$;

$R^1$ is H, a $C_1$-$C_4$ alkyl, aryl or aralkyl group, each of said alkyl, aryl or aralkyl groups being optionally substituted by one or more group(s) selected from halo or hydroxyl;

$R^{1'}$ is H or a $C_1$-$C_4$ alkyl group;

$R^2$ is H or a $C_1$-$C_4$ alkyl group;

$R^{2'}$ is H or a $C_1$-$C_4$ alkyl group, or, when $L^1$ is $C_1$-$C_2$ alkylene optionally being substituted by one or more group(s) selected from halo, methyl or ethyl, $R^{2'}$ together with $R^2$ form an oxo substituent;

$R^3$ is H or a $C_1$-$C_4$ alkyl group optionally substituted by one hydroxy;

$R^{3'}$ is H or a $C_1$-$C_4$ alkyl group;

$X^1$ and $X^2$ are independently N;

$L^2$ is a single bond or carbonyl, $Ar^2$ is a 5- to 6-membered aryl or heteroaryl group, each of the aryl, or heteroaryl groups being optionally substituted by one or more group(s) selected from halo, cyano, alkyl, hydroxyalkyl, haloalkyl, cycloalkyl, heteroalkyl, heterocyclyl, aryl, heteroaryl, aralkyl, heteroarylalkyl, hydroxyl, alkoxy, haloalkoxy, alkylamino, carboxy, alkoxycarbonyl, alkylcarbonyloxy, alkylcarbonylamino, haloalkylcarbonylamino, acylamino, carbamoyl, alkylcarbamoyl, carbamoylalkyl, carbamoylamino, alkylcarbamoylamino, alkylsulfonyl, haloalkylsulfonyl, arylsulfonylalkyl, sulfamoyl, alkylsulfamoyl, alkylsulfonylamino, haloalkylsulfonylamino, or two substituents form an alkylenedioxy group or a haloalkylenedioxy group, or fused to the aryl or heteroaryl group may be one or more cycloalkyl, aryl, heterocyclyl or heteroaryl moiety, each of said substituents being optionally substituted by one or more further substituent(s) selected from halo, cyano, alkyl, haloalkyl, alkoxy, haloalkoxy, cycloalkyl, heterocyclyl optionally substituted by alkyl, aryl, heteroaryl, hydroxyl, alkoxyalkyl, hydroxyalkoxy, alkylamino, alkylsulfonylamino, alkoxycarbonylamino, aminoalkoxy, or alkoxycarbonylaminoalkoxy;

and wherein, when:

$R^1$, $R^{1'}$, $R^2$, $R^{2'}$, $R^3$, $R^{3'}$ are H, and $L^1$ is carbonyl, and $L^2$ is single bond, and $Ar^1$ is a 6-membered aryl optionally substituted by one or more group(s) selected from halo, cyano, C1-C3 alkyl, C1 haloalkyl, and $Ar^2$ is a 5- to 6-membered aryl or heteroaryl group optionally substituted by one or more group(s) selected from halo, C1-C3 alkyl, hydroxyl, methoxy, or fused to an aryl or heteroaryl group optionally substituted by one or more further halo, C1-C3 alkyl, hydroxyl, methoxy, then, $Ar^1$ is phenyl, 3-halophenyl, 4-halophenyl, 2,3-dichlorophenyl, 2,4-difluorophenyl, 2,4-dichlorophenyl, 2,5-dihalophenyl, 2,6-difluorophenyl, 2,6-dichlorophenyl, 3,4-dihalophenyl, 3,5-dihalophenyl, 3,4,5-trihalophenyl, 2-cyanophenyl, 3-cyanophenyl, 4-cyanophenyl, 2,3-dicyanophenyl, 2,4-dicyanophenyl, 3,5-dicyanophenyl, 3-cyano-4-halophenyl, 4-(C1-C3 alkyl)phenyl, 3,4-di(C1-C3 alkyl)phenyl, 3,5-di(C1-C3 alkyl)phenyl, 4-(C1 haloalkyl)phenyl, and $Ar^2$ is, quinolin-2-yl, isoquinolin-3-yl, 8-haloquinolin-2-yl, benzothiazol-2-yl, 4,5,6,7-tetrahydro-1,3-benzothiazol-2-yl;

with the following provisos:

$Ar^1$ is neither a substituted or unsubstituted pyrazolo[1,5-a]pyridin-2yl nor a substituted or unsubstituted pyrazolo[1,5-a]pyrimidin-2yl moiety.

2. The pharmaceutical composition according to claim 1 comprising a compound of formula Ib

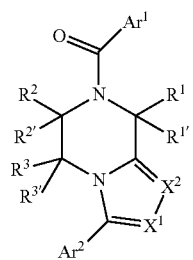

Ib or a pharmaceutically acceptable salt or solvate thereof and at least one pharmaceutically acceptable carrier, diluent, excipient and/or adjuvant.

3. The pharmaceutical composition according to claim 2 comprising a compound of formula Ic

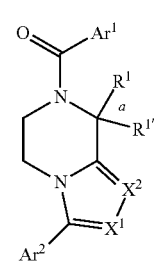

Ic or a pharmaceutically acceptable salt or solvate thereof and at least one pharmaceutically acceptable carrier, diluent, excipient and/or adjuvant, wherein a depicts the bond linking $R^1$ to the piperazine moiety.

4. The pharmaceutical composition according to claim 3 comprising a compound selected from formulae Id-1, Id-2, Id-3 and Id-4

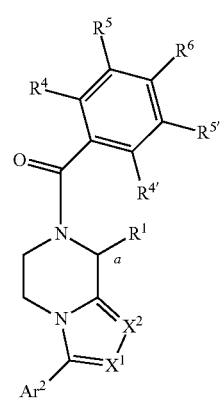

Id-1

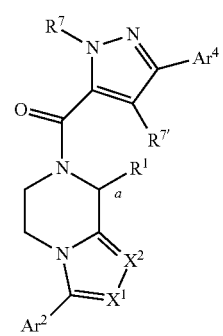

Id-2

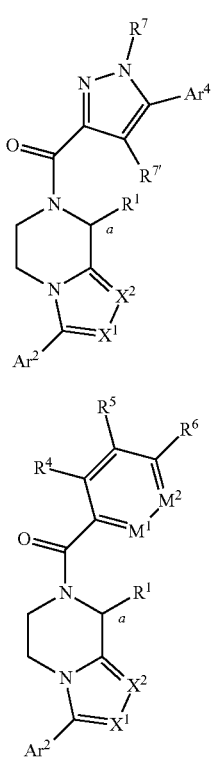

Id-3

Id-4 or a pharmaceutically acceptable salt or solvate thereof and at least one pharmaceutically acceptable carrier, diluent, excipient and/or adjuvant, wherein
  a depicts the bond linking $R^1$ to the piperazine moiety; and
  $R^4$, $R^{4'}$, $R^5$, $R^{5'}$ and $R^6$ are independently selected from H, halo, cyano, alkyl, haloalkyl, C3-C6 cycloalkyl, heteroalkyl, heterocyclyl, aryl, heteroaryl, hydroxyl, alkoxy, haloalkoxy, alkoxyalkoxy, alkylamino, carboxy, alkoxycarbonyl, alkylcarbonyloxy, alkylcarbonylamino, haloalkylcarbonylamino, carbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or $R^5$ together with $R^4$ or $R^6$, or $R^{5'}$ together with $R^{4'}$ or $R^6$ forms an alkylenedioxy group or a haloalkylenedioxy group, or $R^5$ together with $R^4$ or $R^6$, or $R^{5'}$ together with $R^{4'}$ or $R^6$ forms an aryl moiety fused to the phenyl group to which they are attached, each of said substituents being optionally substituted by one or more further substituent(s) selected from halo, cyano, alkyl, haloalkyl, cyclopropyl; and
  $R^7$ is H or methyl; and
  $R^{7'}$ is H or methyl; and
  $Ar^4$ is a cycloalkyl or an aryl group, each of said cycloalkyl or aryl groups being optionally substituted by one or more group(s) selected from halo, alkyl, haloalkyl, cyclopropyl, haloalkoxy, aryloxy; and
  $M^1$ is N or C—$R^{4''}$ wherein $R^{4''}$ is selected from H, halo, cyano, alkyl, haloalkyl, C3-C6 cycloalkyl, heteroalkyl, heterocyclyl, aryl, heteroaryl, hydroxyl, alkoxy, haloalkoxy, alkoxyalkoxy, alkylamino, carboxy, alkoxycarbonyl, alkylcarbonyloxy, alkylcarbonylamino, haloalkylcarbonylamino, carbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, each of said substituents being optionally substituted by one or more further substituent(s) selected from halo, cyano, alkyl, haloalkyl, cyclopropyl; and
  $M^2$ is N or $M^2$ is C—$R^{5''}$ under the condition that $M^1$ is N, wherein $R^{5''}$ is selected from H, halo, cyano, alkyl, haloalkyl, C3-C6 cycloalkyl, heteroalkyl, heterocyclyl, aryl, heteroaryl, hydroxyl, alkoxy, haloalkoxy, alkoxyalkoxy, alkylamino, carboxy, alkoxycarbonyl, alkylcarbonyloxy, alkylcarbonylamino, haloalkylcarbonylamino, carbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or $R^{5''}$ together with $R^6$ forms an alkylenedioxy group or a haloalkylenedioxy group, or an aryl moiety fused to the pyridinyl group to which they are attached, each of said substituents being optionally substituted by one or more further substituent(s) selected from halo, cyano, alkyl, haloalkyl, cyclopropyl; and wherein, in formula Id-1 when:
  $R^1$ is H, and
  $R^4$, $R^{4'}$, $R^5$, $R^{5'}$ and $R^6$ are independently selected from H, halo, cyano, C1-C3 alkyl, C1 haloalkyl, and
  $Ar^2$ is a 5- to 6-membered aryl or heteroaryl group optionally substituted by one or more group(s) selected from halo, C1-C3 alkyl, hydroxyl, alkoxy, or fused to an aryl group optionally substituted by one or more further halo, C1-C3 alkyl, hydroxyl, methoxy
then,
  $R^4$, $R^{4'}$, $R^5$, $R^{5'}$ and $R^6$ are H, or $R^4$, $R^{4'}$, $R^{5'}$, $R^6$ are H and $R^5$ is halo, or $R^4$, $R^{4'}$, $R^5$, $R^{5'}$ are H and $R^6$ is halo, cyano, C1-C3 alkyl, C1 haloalkyl, or $R^{4'}$, $R^{5'}$, $R^6$ are H and $R^4$, $R^5$ are halo, or $R^4$, $R^{4'}$, $R^{5'}$ are H and $R^5$, $R^6$ are independently halo, or $R^4$, $R^{4'}$ are H and $R^5$, $R^{5'}$, $R^6$ are halo, and
  $Ar^2$ is, quinolin-2-yl, isoquinolin-3-yl, 8-haloquinolin-2-yl, benzothiazol-2-yl, 4,5,6,7-tetrahydro-1,3-benzothiazol-2-yl.

5. The pharmaceutical composition according to claim 4 comprising a compound selected from formulae Ie-1, Ie-2 and Ie-3

Ie-1

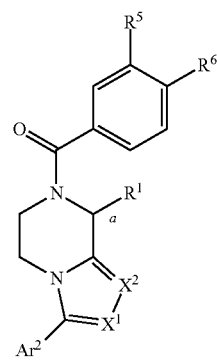

-continued

Ie-2

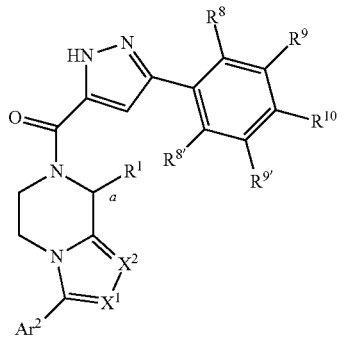

Ie-3

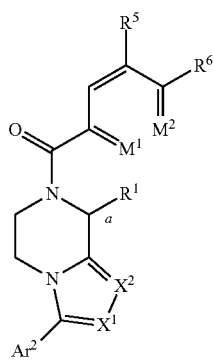

or a pharmaceutically acceptable salt or solvate thereof and at least one pharmaceutically acceptable carrier, diluent, excipient and/or adjuvant, wherein a depicts the bond linking $R^1$ to the piperazine moiety; and $R^5$ and $R^6$ are independently selected from H, halo, cyano, alkyl, cyclopropyl, aryl, heteroaryl, each of said aryl and heteroaryl groups being optionally substituted by one or more group(s) selected from halo, alkyl, cyclopropyl, or $R^5$ and $R^6$ together form a phenyl moiety fused to the phenyl ring they are attached to; and $R^8$, $R^{8'}$, $R^9$, $R^{9'}$ and $R^{10}$ are independently selected from H, halo, haloalkyl, cyclopropyl or haloalkoxy, or $R^8$, $R^{8'}$, $R^9$, $R^{9'}$ are H and $R^{10}$ is phenoxy;

wherein, in formula Ie-1 when:

$R^1$ is H, and $R^5$ and $R^6$ are independently selected from H, halo, cyano, C1-C3 alkyl, and $Ar^2$ is a 5- to 6-membered aryl or heteroaryl group optionally substituted by one or more group(s) selected from halo, C1-C3alkyl, hydroxyl, alkoxy, or fused to an aryl group optionally substituted by one or more further halo, C1-C3 alkyl, hydroxyl, methoxy then, $R^6$ is H and $R^5$ is H, halo, or $R^5$ is H and $R^6$ is halo, cyano, C1-C3 alkyl, C1 haloalkyl, or $R^5$ and $R^6$ are independently halo, and $Ar^2$ is quinolin-2-yl, isoquinolin-3-yl, 8-haloquinolin-2-yl, benzothiazol-2-yl, 4,5,6,7-tetrahydro-1,3-benzothiazol-2-yl.

6. The pharmaceutical composition according to claim 3 comprising a compound selected from formulae If-1, If-2, If-3, If-4, If-5, If-6, If-7 and If-8

If-1

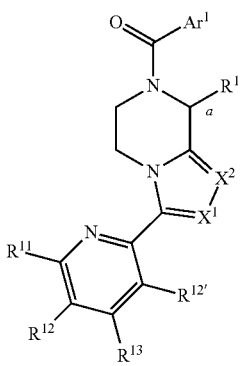

If-2

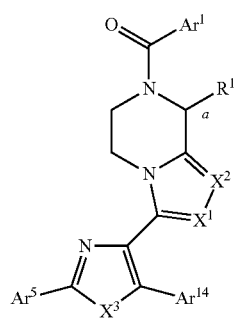

If-3

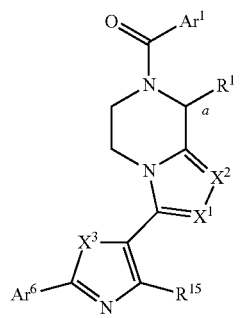

If-4

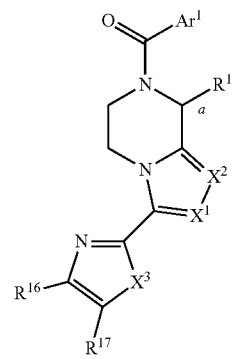

-continued

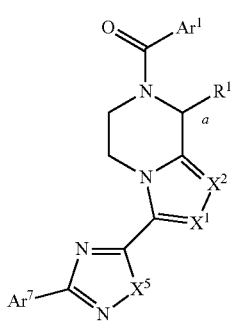
If-5

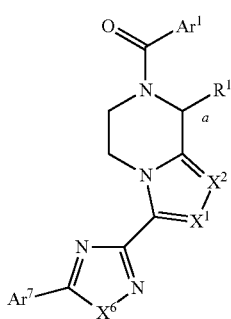
If-6

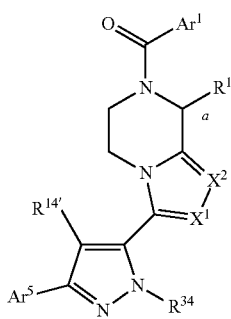
If-7

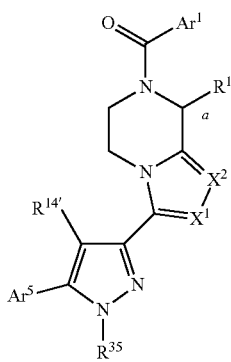
If-8 or a pharmaceutically acceptable salt or solvate thereof and at least one pharmaceutically acceptable carrier, diluent, excipient and/or adjuvant, wherein
  a designates the bond linking $R^1$ to the piperazine moiety; and
  $R^{11}$, $R^{12}$, $R^{12'}$ and $R^{13}$ are independently selected from H, halo, cyano, alkyl, hydroxyalkyl, haloalkyl, C3-C6 cycloalkyl, heteroalkyl, heterocyclyl, aryl, heteroaryl, -hydroxyl, alkoxy, haloalkoxy, alkylamino, carboxy, alkoxycarbonyl, alkylcarbonyloxy, alkylcarbonylamino, haloalkylcarbonylamino, acylamino, carbamoyl, alkylcarbamoyl, carbamoylalkyl, carbamoylamino, alkylcarbamoylamino, alkylsulfonyl, haloalkylsulfonyl, sulfamoyl, alkylsulfamoyl, alkylsulfonylamino, haloalkylsulfonylamino, or $R^{12}$ together with $R^{11}$ or $R^{13}$, or $R^{13}$ together with $R^{12'}$ forms an alkylenedioxy group or a haloalkylenedioxy group, or $R^{12}$ together with $R^{11}$ or $R^{13}$ forms a cycloalkyl, aryl, heterocyclyl or heteroaryl moiety fused to the pyridyl group to which they are attached, each of said groups being optionally substituted by one or more group(s) selected from halo, cyano, alkyl, haloalkyl, cyclopropyl, alkoxy, haloalkoxy or hydroxyl; and $Ar^5$ is a heterocyclyl, aryl, heteroaryl, aralkyl, heteroarylalkyl, or arylsulfonylalkyl group, each of which being optionally substituted by one or more group(s) selected from halo, cyano, alkyl, haloalkyl, cyclopropyl, alkoxy, haloalkoxy, heterocyclyl optionally substituted by alkyl, aryl, hydroxyl, alkoxy, alkoxyalkyl, hydroxyalkoxy, alkylamino, alkylsulfonylamino, aminoalkoxy, or alkoxycarbonylaminoalkoxy; and $X^3$ is O or S; and $R^{14}$ is H or methyl; and $Ar^6$ is a heterocyclyl, aryl or heteroaryl group, each of which being optionally substituted by one or more group(s) selected from halo, cyano, alkyl, haloalkyl, cyclopropyl, alkoxy, haloalkoxy, aryl or hydroxyl; and $R^{15}$ is H or methyl; and $R^{16}$ is a heterocyclyl, aryl or heteroaryl group, each of said groups being optionally substituted by one or more group(s) selected from halo, cyano, alkyl, haloalkyl, cyclopropyl, alkoxy, haloalkoxy or hydroxyl;

$R^{17}$ is H, methyl or $R^{17}$ together with $R^{16}$ forms a cycloalkyl or aryl moiety fused to the thiazolyl group to which they are attached, thus forming a fused ring system, said fused ring system being optionally substituted by one or more group(s) selected from halo, cyano, alkyl, haloalkyl, cyclopropyl, alkoxy, haloalkoxy or hydroxyl; and $X^5$ is O or S, or N—$R^{36}$ wherein $R^{36}$ is H or C1-C3 alkyl; and $Ar^7$ is a heterocyclyl, aryl or heteroaryl group, each of which being optionally substituted by one or more group(s) selected from halo, cyano, alkyl, haloalkyl, cyclopropyl, alkoxy, haloalkoxy, aryl or hydroxyl; and $X^6$ is O, S or N—$R^{36}$ wherein $R^{36'}$ is H or C1-C3 alkyl; and $R^{14'}$ is H or methyl; and $R^{34}$ is H, alkyl, alkoxyalkyl, hydroxyalkyl, alkoxycarbonylaminoalkyl; and $R^{35}$ is H, alkyl, alkoxyalkyl, hydroxyalkyl, alkoxycarbonylaminoalkyl; and wherein,
  in formula If-1 when:
    $R^1$ is H, and
    $Ar^1$ is a 6-membered aryl optionally substituted by one or more group(s) selected from halo, cyano, C1-C3 alkyl, C1-haloalkyl, and
    $R^{11}$, $R^{12}$, $R^{12'}$ and $R^{13}$ are independently selected from H, halo, C1-C3 alkyl, hydroxyl, methoxy, or $R^{12}$ together with $R^{11}$ or $R^{13}$ forms an aryl or heterocyclyl or heteroaryl moiety fused to the pyridyl group to which they are attached and being optionally substituted by one or more group(s)

selected from halo, C1-C3 alkyl, methoxy or hydroxyl,
then,
Ar$^1$ is phenyl, 3-halophenyl, 4-halophenyl, 2,3-dichlorophenyl, 3,4-dihalophenyl, 3,4,5-trihalophenyl, 4-cyanophenyl, 4-(C1-C3 alkyl)phenyl, 4-(C1 haloalkyl)phenyl, and
R$^{11}$, R$^{12}$, R$^{12'}$ and R$^{13}$ together with the pyridyl group they are attached form a quinolin-2-yl, isoquinolin-3-yl or 8-haloquinolin-2-yl moiety; and in formula If-4 when:
R$^1$ is H, and
Ar$^1$ is a 6-membered aryl optionally substituted by one or more group(s) selected from halo, cyano, C1-C3 alkyl, C1-haloalkyl, and
R$^{17}$ together with R$^{16}$ forms a cycloalkyl or aryl moiety fused to the thiazolyl group to which they are attached, thus forming a fused ring system, said fused ring system being optionally substituted by one or more group(s) selected from halo, C1-3 alkyl, methoxy or hydroxyl,
then
Ar$^1$ is phenyl, 3-halophenyl, 4-halophenyl, 2,3-dichlorophenyl, 3,4-dihalophenyl, 3,4,5-trihalophenyl, 4-cyanophenyl, 4-(C1-C3 alkyl)phenyl, 4-(C1 haloalkyl)phenyl, and
R$^{17}$ and R$^{16}$ form together with the thiazolyl group to which they are attached a benzothiazol-2-yl or 4,5,6,7-tetrahydro-1,3-benzothiazol-2-yl moiety.

7. The pharmaceutical composition according to claim 6 comprising a compound selected from formulae Ig-1, Ig-2, Ig-3, Ig-4, Ig-5, Ig-6, Ig-7 and Ig-8

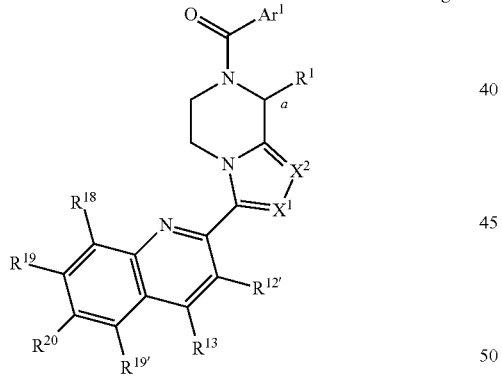

Ig-1

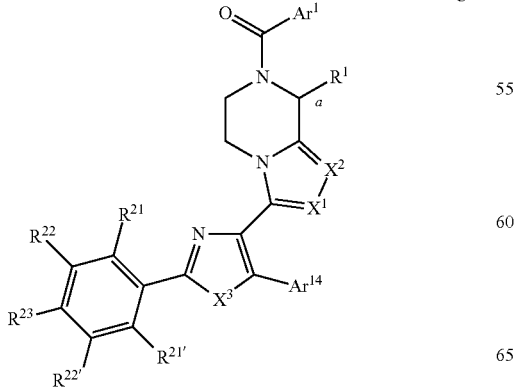

Ig-2

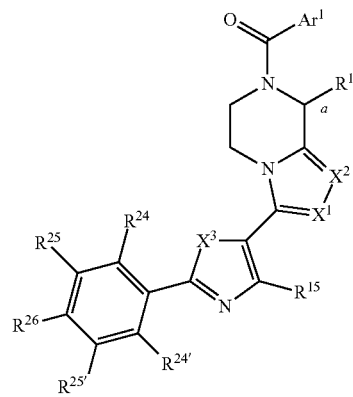

Ig-3

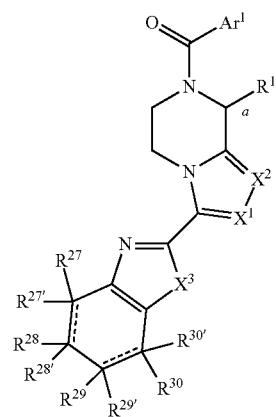

Ig-4

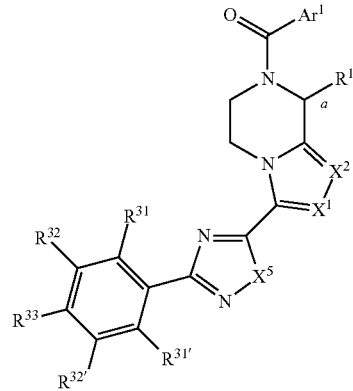

Ig-5

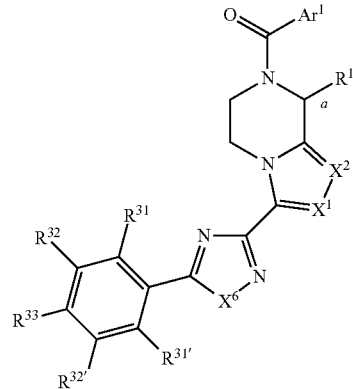

Ig-6

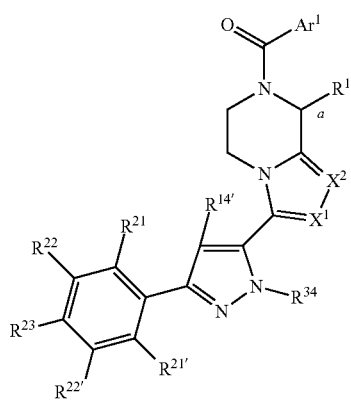

Ig-7

Ig-8 or a pharmaceutically acceptable salt or solvate thereof and at least one pharmaceutically acceptable carrier, diluent, excipient and/or adjuvant, wherein a depicts the bond linking $R^1$ to the piperazine moiety; and $R^{12'}$ and $R^{13}$ are independently selected from H, halo, cyano, alkyl, hydroxyalkyl, haloalkyl, cycloalkyl, heteroalkyl, hydroxyl, alkoxy, haloalkoxy, carboxy, alkoxycarbonyl, alkylcarbonyloxy, alkylcarbonylamino, haloalkylcarbonylamino, acylamino, carbamoyl, alkylcarbamoyl, carbamoylalkyl, carbamoylamino, alkylcarbamoylamino, alkylsulfonyl, haloalkylsulfonyl, sulfamoyl, alkylsulfamoyl, alkylsulfonylamino, haloalkylsulfonylamino, or $R^{13}$ together with $R^{12'}$ forms an alkylenedioxy group or a haloalkylenedioxy group, each of said groups being optionally substituted by one or more group(s) selected from halo, cyano, alkyl, haloalkyl, alkoxy, haloalkoxy, hydroxyl or oxo; and $R^{18}$, $R^{19}$, $R^{19'}$ and $R^{20}$ are independently selected from H, halo, cyano, alkyl, haloalkyl, cyclopropyl, alkoxy, haloalkoxy; and $R^{21}$, $R^{21'}$, $R^{22}$, $R^{22'}$ and $R^{23}$ are independently selected from H, halo, cyano, alkyl, haloalkyl, cyclopropyl, heterocyclyl optionally substituted by alkyl, hydroxyl, alkoxy, haloalkoxy, hydroxyalkoxy, alkylamino, alkylsulfonylamino, aminoalkoxy, alkoxycarbonylaminoalkoxy; and $R^{24}$, $R^{24'}$, $R^{25}$, $R^{25'}$ and $R^{26}$ are independently selected from H, halo haloalkyl, cyclopropyl; and $R^{27}$, $R^{28}$, $R^{29}$ and $R^{30}$ are independently selected from H, halo, cyano, alkyl, haloalkyl, cyclopropyl, alkoxy, haloalkoxy; and $R^{27'}$, $R^{28'}$, $R^{29'}$ and $R^{30'}$ are absent, or $R^{27'}$, $R^{28'}$, $R^{29'}$ and $R^{30'}$ are H under the condition that $R^{28}$, $R^{29}$ and $R^{30}$ are H and that $R^{27}$ is selected from H, chloro or fluoro; and the two bonds represented by the dotted lines in formula Ig-4 are both absent, or both present under the condition that $R^{27'}$, $R^{28'}$, $R^{29'}$ and $R^{30'}$ are absent; and $R^{31}$, $R^{31'}$, $R^{32}$, $R^{32'}$ and $R^{33}$ are independently selected from H, halo, cyano, alkyl, haloalkyl, cyclopropyl, alkoxy, haloalkoxy; and wherein, in formula Ig-1 when:

$R^1$ is H, and $Ar^1$ is a 6-membered aryl optionally substituted by one or more group(s) selected from halo, cyano, C1-C3 alkyl, C1-haloalkyl, and $R^{12'}$, $R^{13}$, $R^{18}$, $R^{19}$, $R^{19'}$ and $R^{20}$ are independently selected from H, halo, C1-3 alkyl, hydroxyl, methoxy, then, $Ar^1$ is phenyl, 3-halophenyl, 4-halophenyl, 2,3-dichlorophenyl, 3,4-dihalophenyl, 3,4,5-trihalophenyl, 4-cyanophenyl, 4-(C1-C3 alkyl)phenyl, 4-(C1 haloalkyl)phenyl, and $R^{12'}$, $R^{13}$, $R^{18}$, $R^{19}$, $R^{19'}$ and $R^{20}$ are H, or $R^{12'}$, $R^{13}$, $R^{19}$, $R^{19'}$, $R^{20}$ are H and $R^{18}$ is fluoro, chloro, and in formula Ig-4 when $R^1$ is H, and $Ar^1$ is a 6-membered aryl optionally substituted by one or more group(s) selected from halo, cyano, C1-C3 alkyl, C1-haloalkyl, and $R^{27}$, $R^{28}$, $R^{29}$ and $R^{30}$ are independently selected from H, halo, C1-3 alkyl, methoxy, and $R^{27'}$, $R^{28'}$, $R^{29'}$ and $R^{30'}$ are absent or H under the condition that $R^{28}$, $R^{29}$ and $R^{30}$ are H and $R^{27}$ is selected from H, chloro or fluoro, then $Ar^1$ is phenyl, 3-halophenyl, 4-halophenyl, 2,3-dichlorophenyl, 3,4-dihalophenyl, 3,4,5-trihalophenyl, 4-cyanophenyl, 4-(C1-C3 alkyl)phenyl, 4-(C1 haloalkyl)phenyl, and $R^{27}$, $R^{28}$, $R^{29}$ and $R^{30}$ are H, and $R^{27'}$, $R^{28'}$, $R^{29'}$ and $R^{30'}$ are absent or H under the condition that $R^{27}$, $R^{28}$, $R^{29}$ and $R^{30}$ are H.

8. The pharmaceutical composition according to claim 6 comprising a compound having formula Ih-2

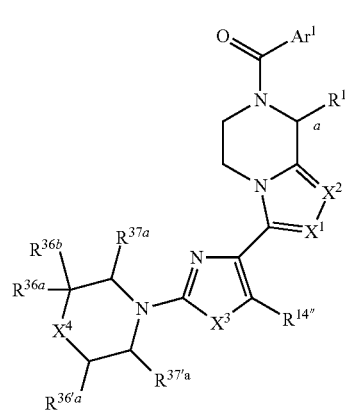

Ih-2 or a pharmaceutically acceptable salt or solvate thereof and at least one pharmaceutically acceptable carrier, diluent, excipient and/or adjuvant, wherein a designates the bond linking R¹ to the piperazine moiety; and R$^{14''}$ is H or methyl; and X$^4$ is O, CH$_2$, CF$_2$, C(CH$_3$)$_2$, N—(C1-C3 alkyl)N-phenyl; and R$^{36a}$, R$^{36b}$, R$^{36'a}$, R$^{37a}$ and R$^{37'a}$ are independently selected from H, C1-C3 alkyl, alkoxyC1-C3 alkyl.

9. The pharmaceutical composition according to claim 3 comprising a compound selected from formulae Ii-1, Ii-2, Ii-3, Ii-4, Ii-5, Ii-6, Ii-7, Ii-8, Ij-1, Ij-2, Ij-3, Ij-4, Ij-5, Ij-6, Ij-7, Ij-8, Ik-1, Ik-2, Ik-3, Ik-4, Ik-5, Ik-6, Ik-7, Ik-8, Ii'-1, Ii'-2, Ii'-3, Ii'-4, Ii'-5, Ii'-6, Ii'-7 and Ii'-8

Ii-1
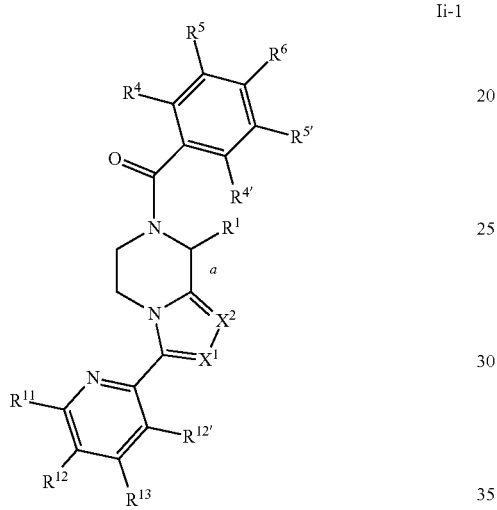

Ii-2
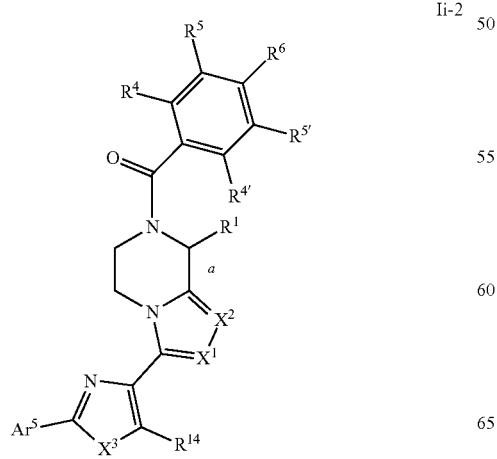

Ii-3
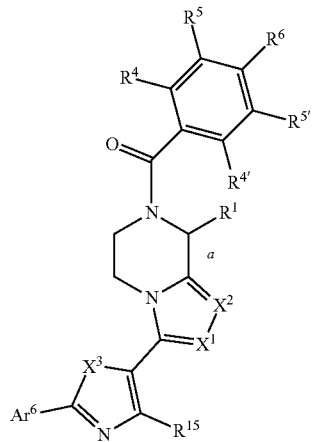

Ii-4
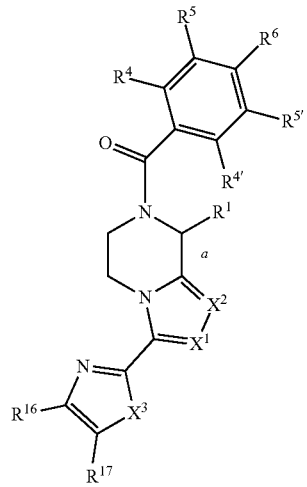

Ii-5
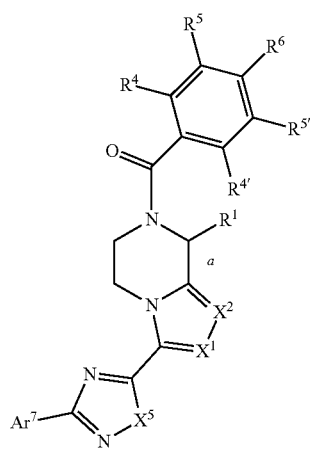

151
-continued
Ii-6
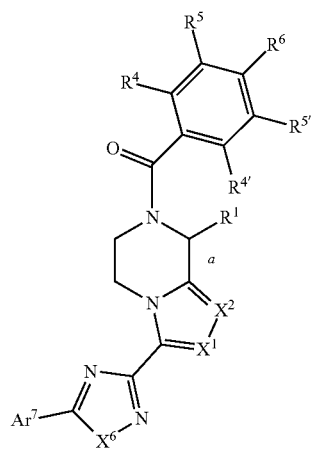
Ii-7
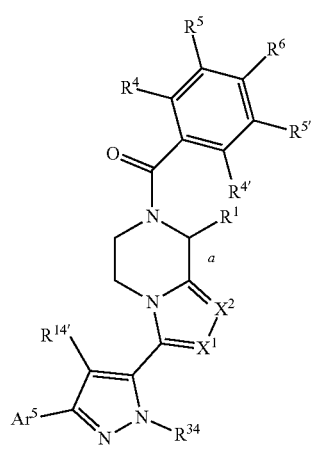
Ii-8
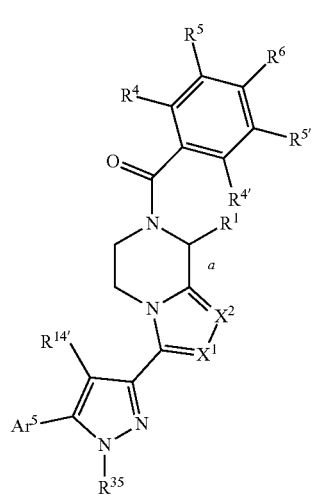
152
-continued
Ij-1
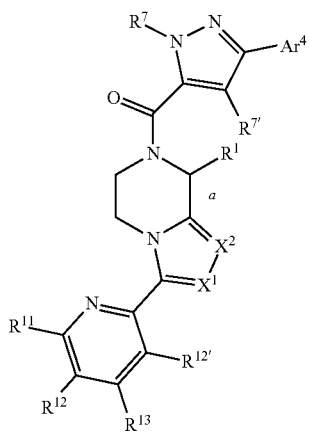
Ij-2
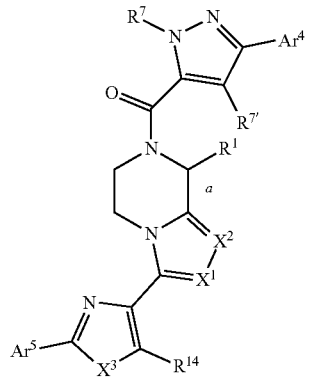
Ij-3
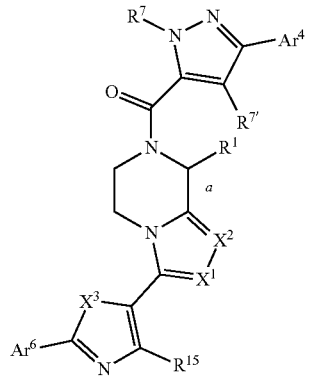
Ij-4
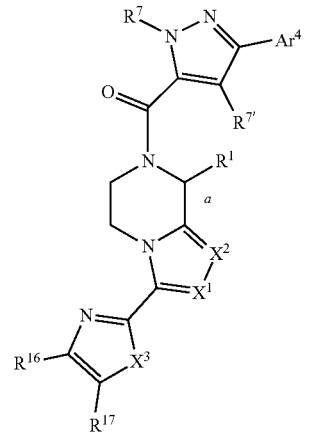

Ij-5
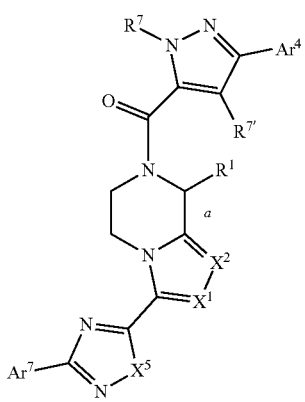
Ij-6
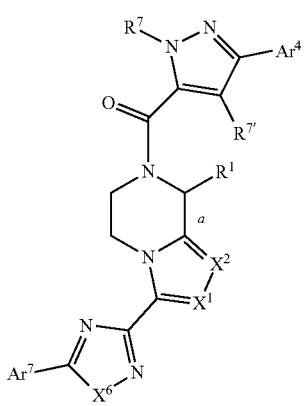
Ij-7
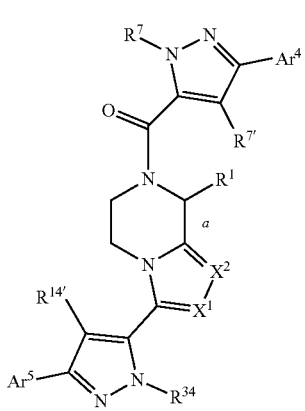
Ij-8
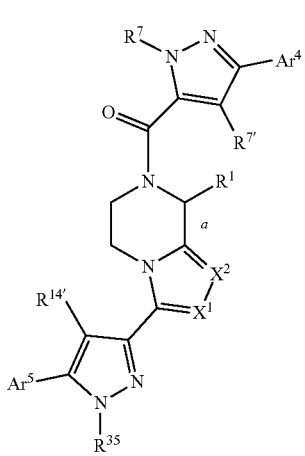
Ik-1
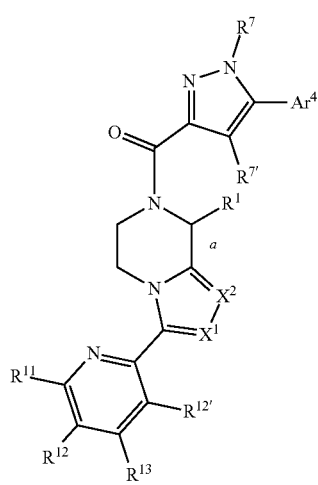
Ik-2
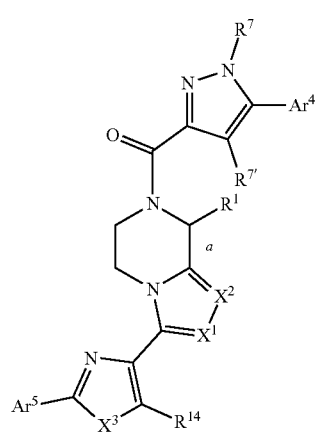
Ik-3
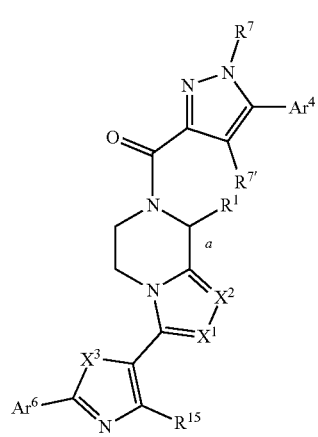

Ik-4
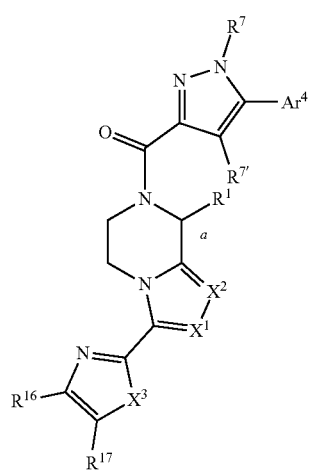
Ik-5
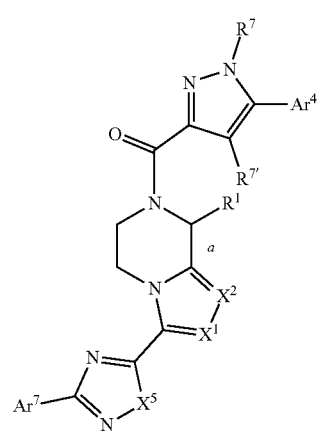
Ik-6
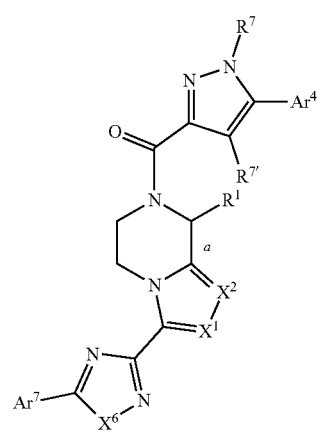
Ik-7
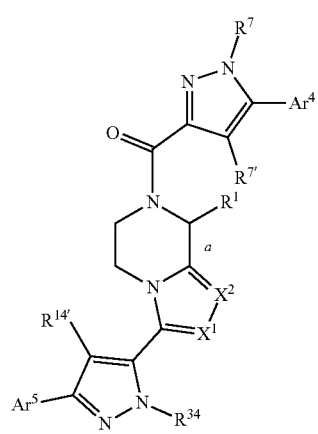
Ik-8
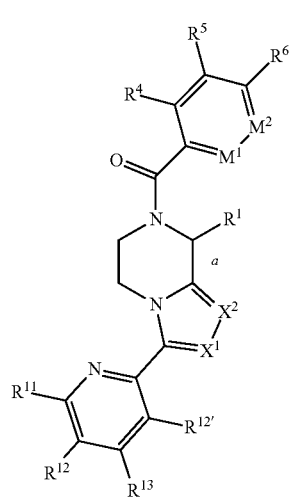
Ii'-1

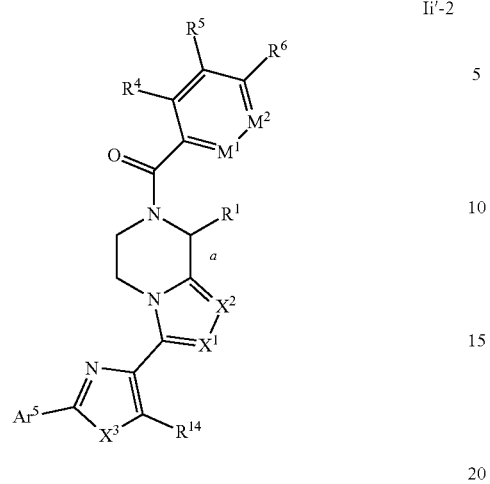
Ii′-2
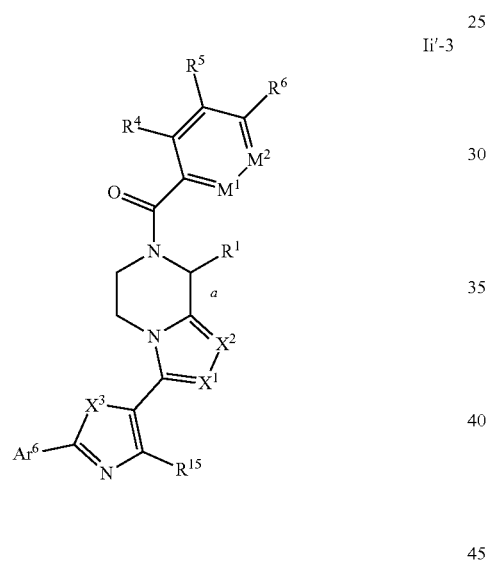
Ii′-3
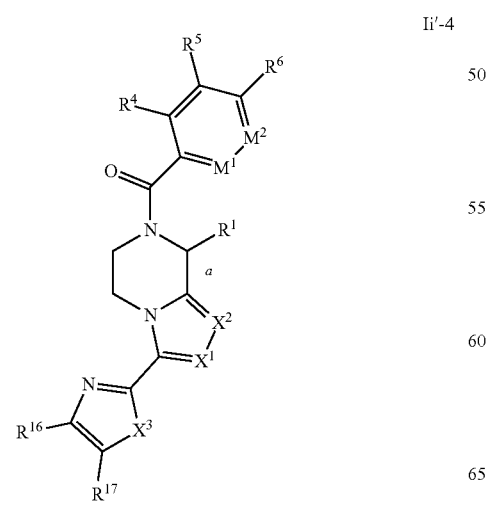
Ii′-4
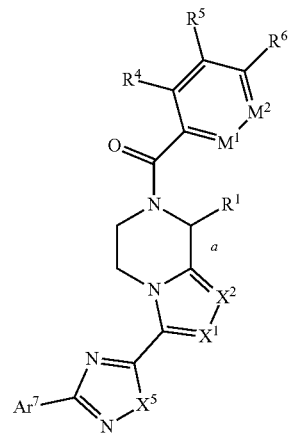
Ii′-5
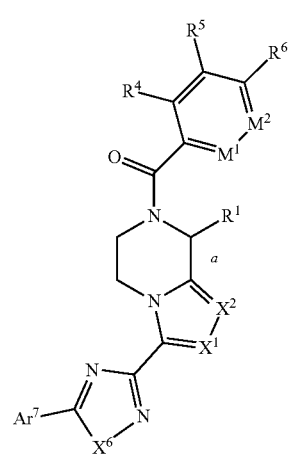
Ii′-6
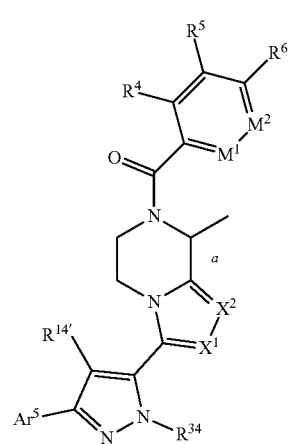
Ii′-7

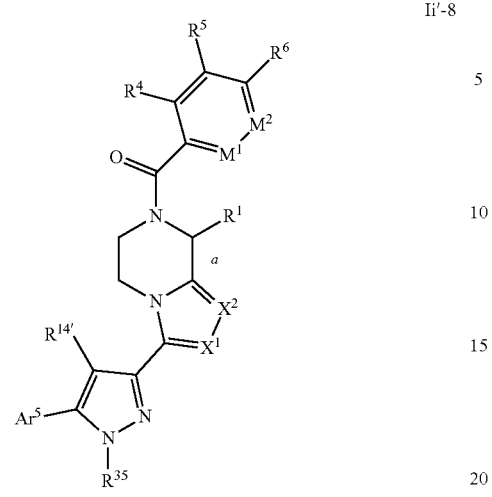

Ii'-8 or a pharmaceutically acceptable salt or solvate thereof and at least one pharmaceutically acceptable carrier, diluent, excipient and/or adjuvant, wherein a depicts the bond linking $R^1$ to the piperazine moiety; and $Ar^4$, $R^4$, $R^{4'}$, $R^5$, $R^{5'}$, $R^6$, $R^7$, $R^{7'}$, $M^1$, $M^2$ are as defined in claim 4; and $Ar^5$, $Ar^6$, $Ar^7$, $R^{11}$, $R^{12}$, $R^{12'}$, $R^{13}$, $R^{14}$, $R^{14'}$, $R^{15}$, $R^{16}$, $R^{17}$, $R^{34}$, $R^{35}$, $X^3$, $X^5$, $X^6$, and are as defined in claim 6.

10. The pharmaceutical composition according to claim 9 comprising a compound selected from formulae Il-1, Il-2, Il-3, Il-4, Il-5, Il-6, Il-7, Il-8, Il'-1, Il'-2, Il'-3, Il'-4, Il'-5, Il'-6, Il'-7, Il'-8

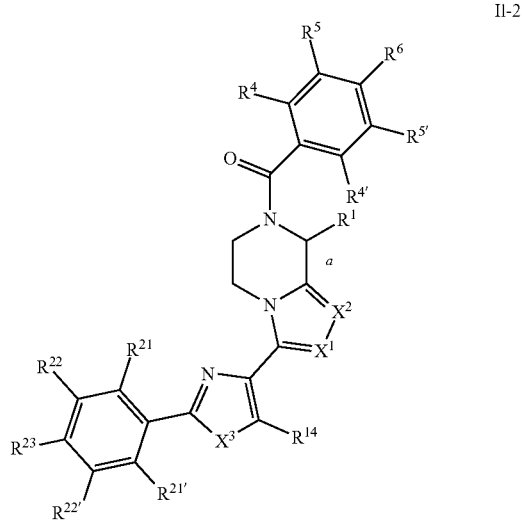

Il-2

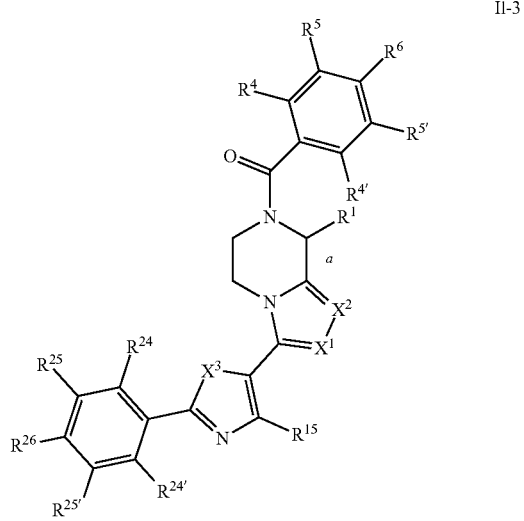

Il-3

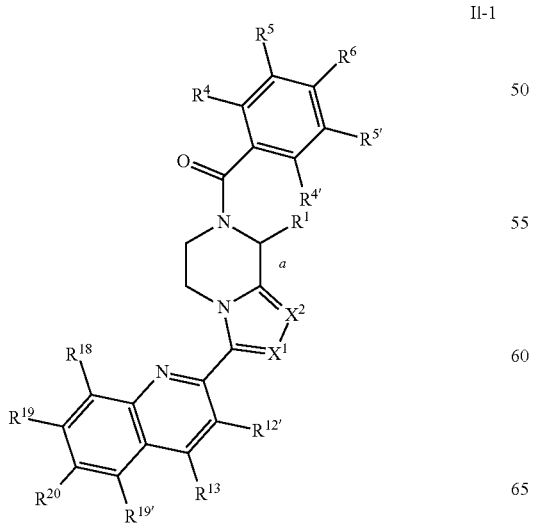

Il-1

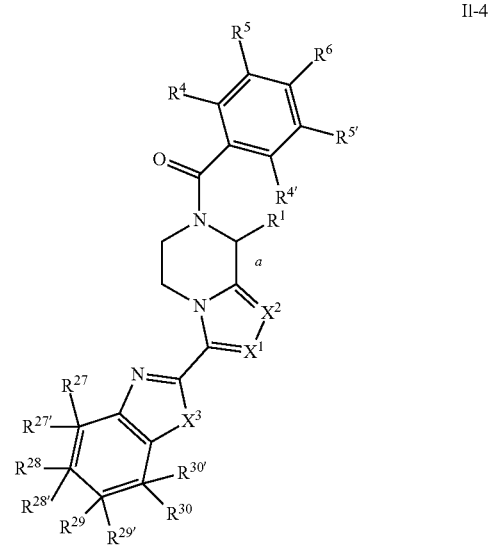

Il-4

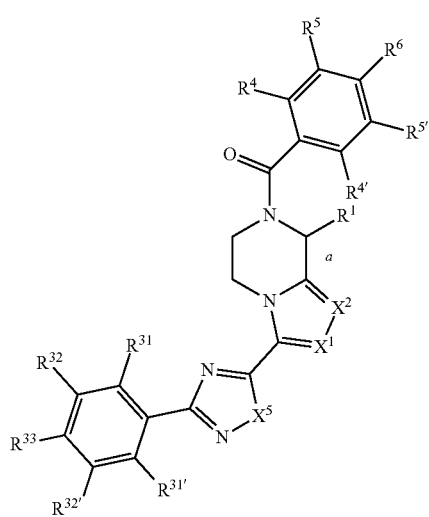
II-5
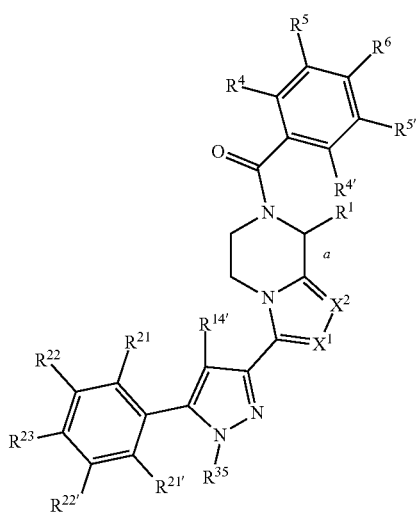
II-8
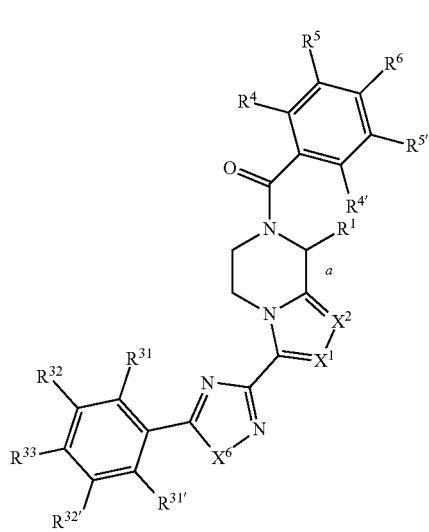
II-6
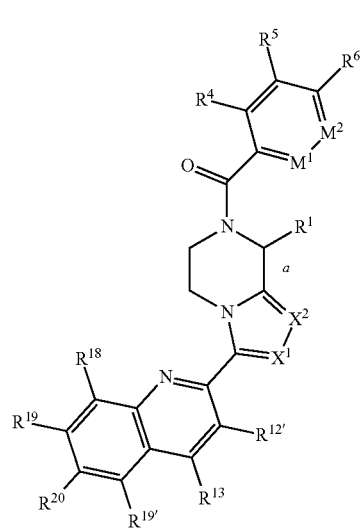
II'-1
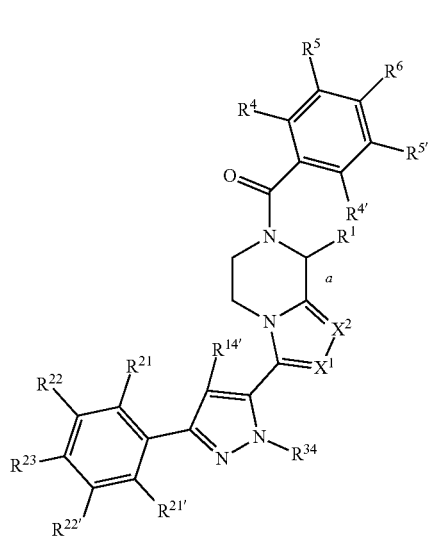
II-7
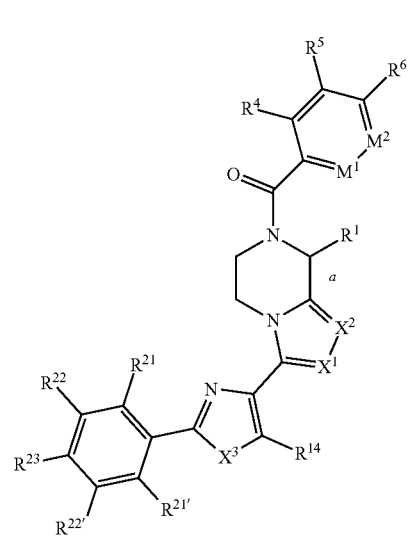
II'-2

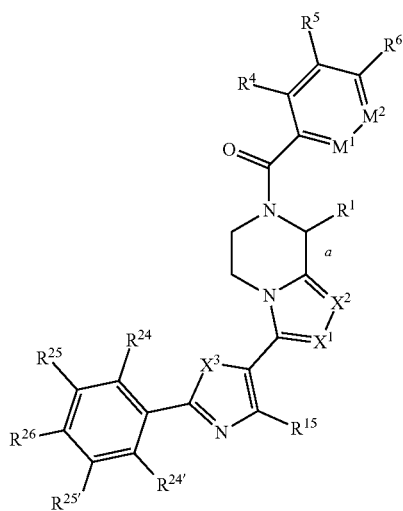
II'-3
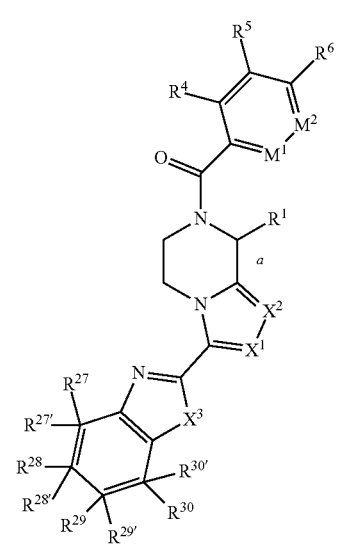
II'-4
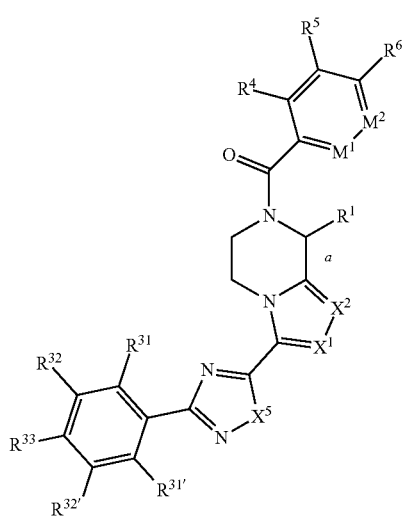
II'-5
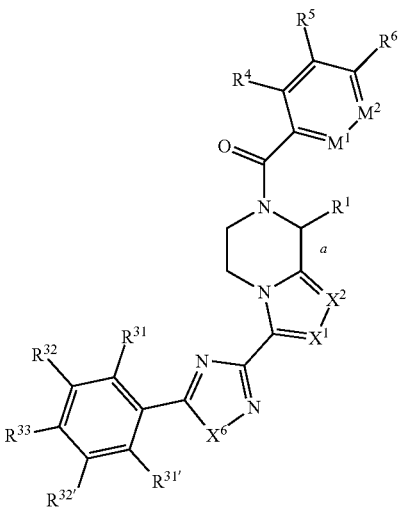
II'-6
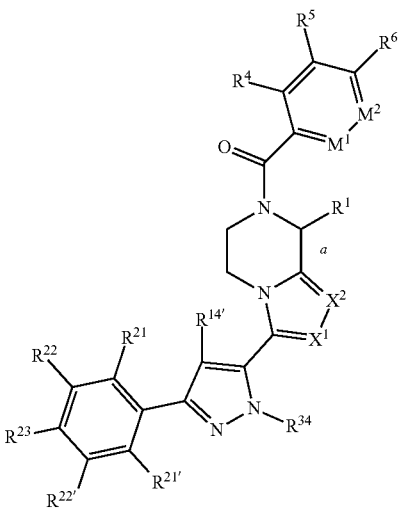
II'-7
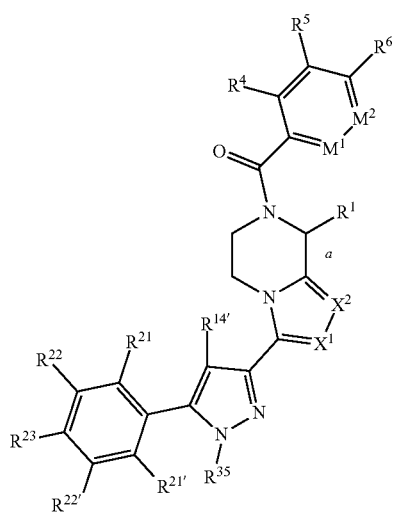
II'-8
or a pharmaceutically acceptable salt or solvate thereof and at least one pharmaceutically acceptable carrier, diluent, excipient and/or adjuvant, wherein:

a depicts the bond linking R¹ to the piperazine moiety; and

R⁴, R⁴', R⁵, R⁵', R⁶, M¹ and M² are as defined in claim 4; and

R¹²', R¹³, R¹⁴, R¹⁴', R¹⁵, R¹⁸, R¹⁹, R¹⁹', R²⁰, R²¹, R²¹', R²², R²²', R²³, R²⁴, R²⁴', R²⁵, R²⁵', R²⁶, R²⁷, R²⁷', R²⁸, R²⁸', R²⁹, R²⁹', R³⁰, R³⁰', R³¹, R³¹', R³², R³²', R³³, R³⁴, R³⁵, X³, X⁵; X⁶; and the two bonds represented by the dotted lines are as defined in claim 7.

11. The pharmaceutical composition according to claim 10 comprising a compound selected from formulae Im-1, Im-2, Im-3, Im-4, Im-5, Im-6, Im-7, Im-8, Im'-1, Im'-2, Im'-3, Im'-4, Im'-5, Im'-6, Im'-7 and Im'-8

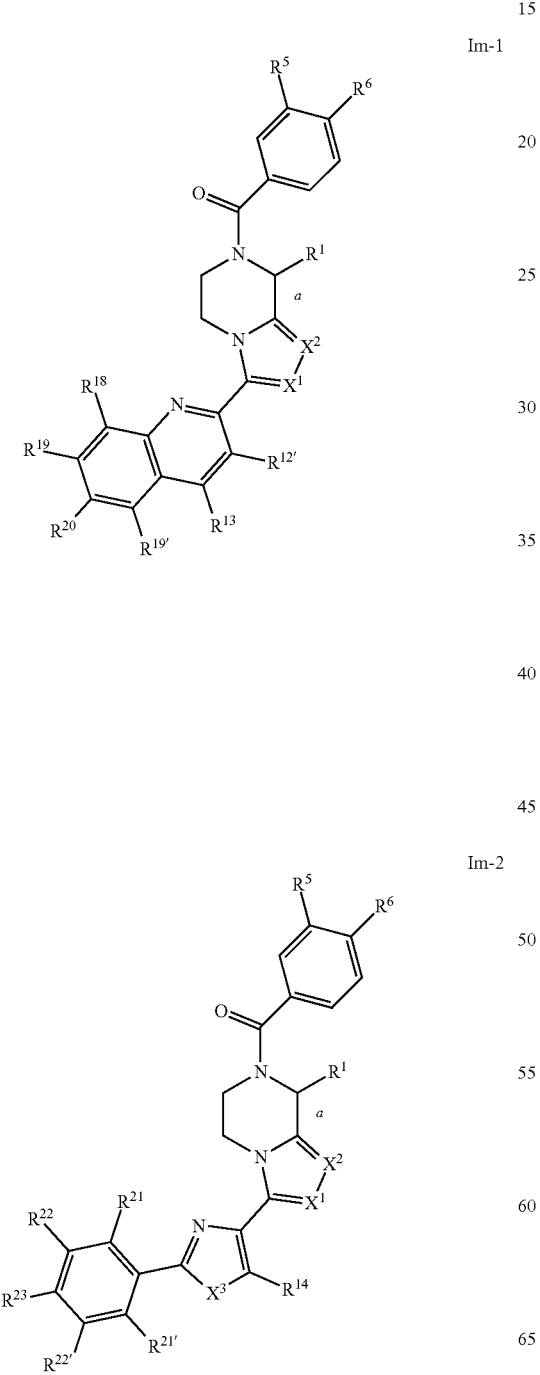

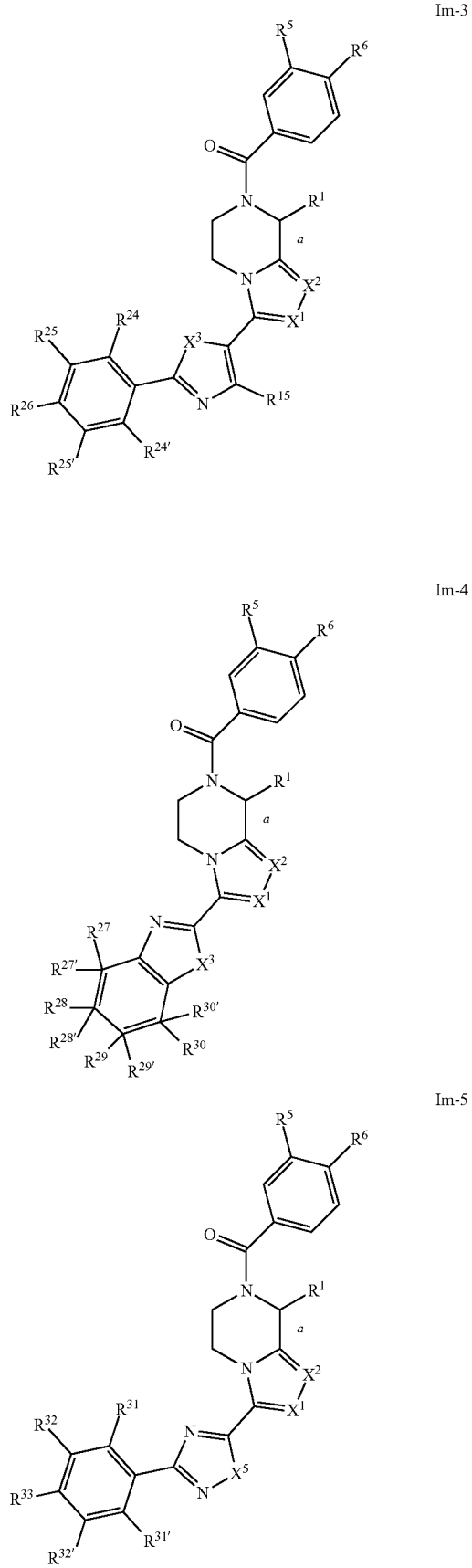

Im-6
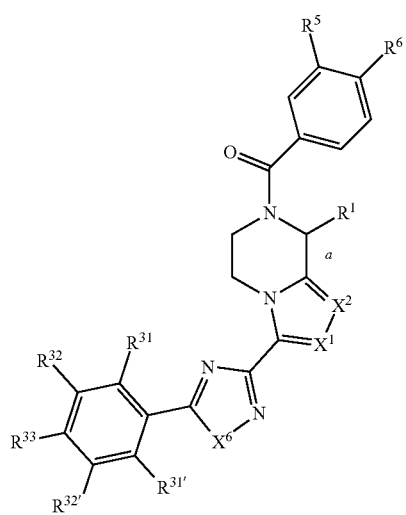
Im-7
Im'-1
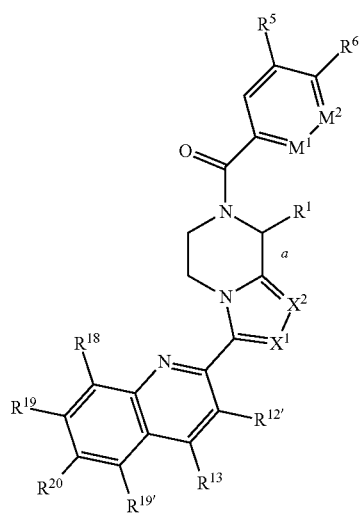
Im'-2
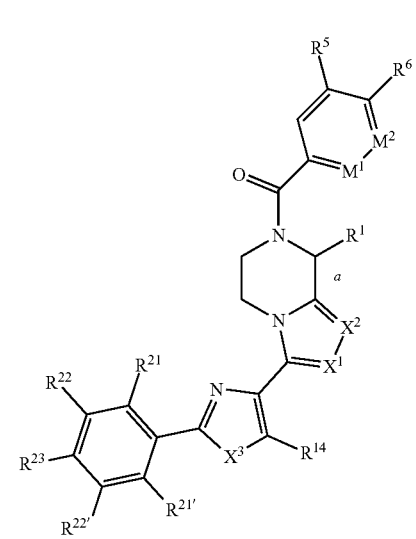
Im-8
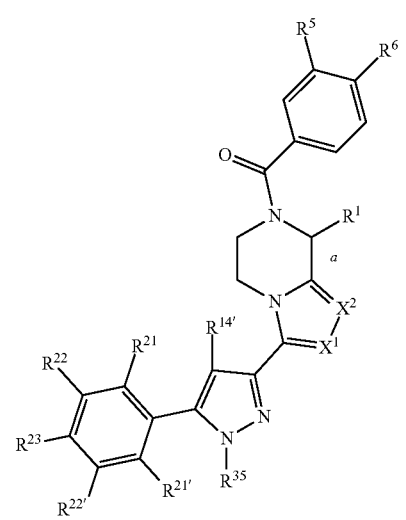
Im'-3
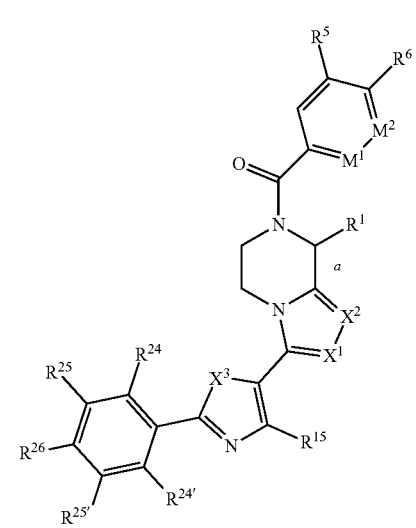

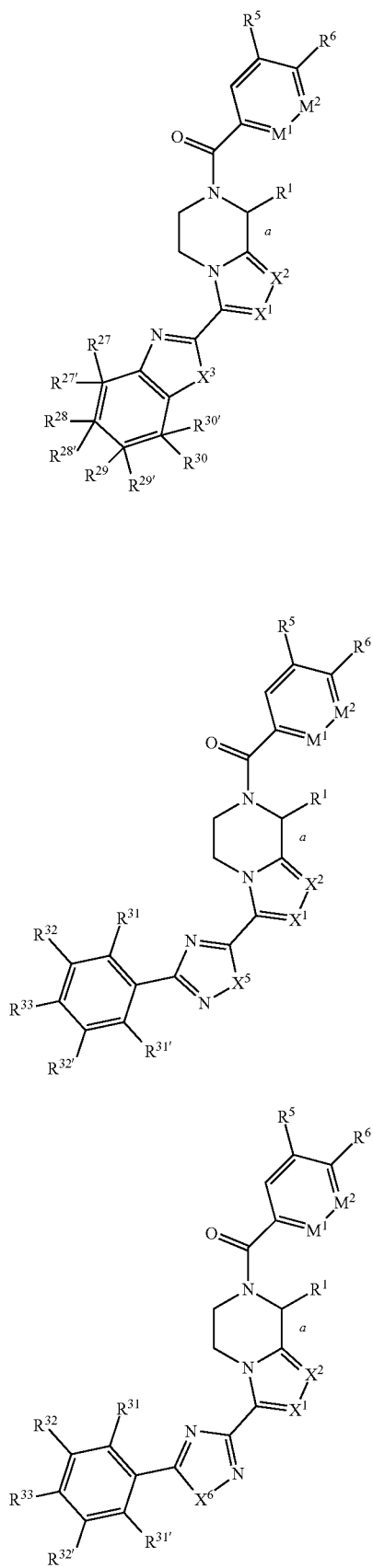
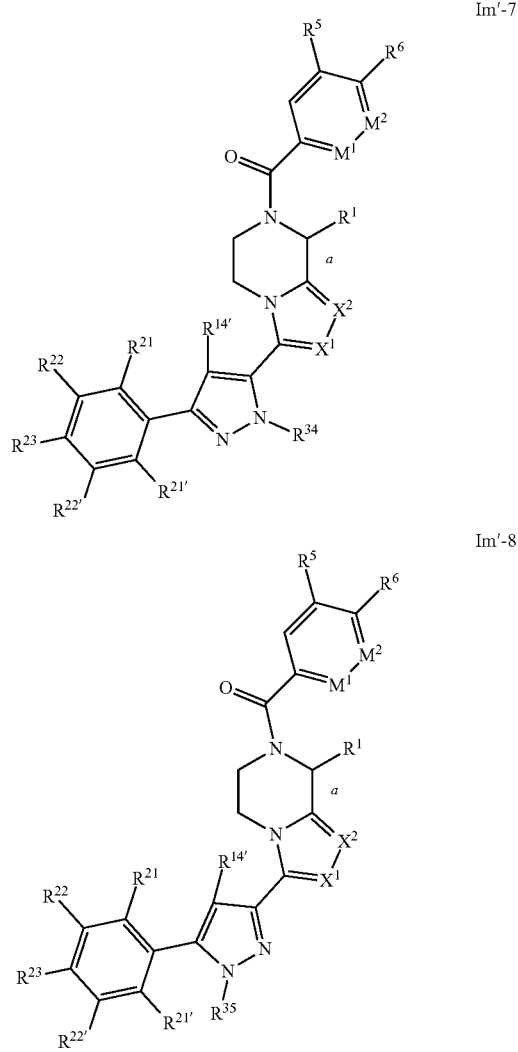

or a pharmaceutically acceptable salt or solvate thereof and at least one pharmaceutically acceptable carrier, diluent, excipient and/or adjuvant, wherein:

a designates the bond linking $R^1$ to the piperazine moiety; and $R^5$, $R^6$, $M^1$ and $M^2$ are as defined in claim 5; and $R^{12'}$, $R^{13}$, $R^{14}$, $R^{14'}$, $R^{15}$, $R^{18}$, $R^{19}$, $R^{19'}$, $R^{20}$, $R^{21}$, $R^{21'}$, $R^{22}$, $R^{22'}$, $R^{23}$, $R^{24}$, $R^{24'}$, $R^{25}$, $R^{25'}$, $R^{26}$, $R^{27}$, $R^{27'}$, $R^{28}$, $R^{28'}$, $R^{29}$, $R^{29'}$, $R^{30}$, $R^{30'}$, $R^{31}$, $R^{31'}$, $R^{32}$, $R^{32'}$, $R^{33}$, $R^{34}$, $R^{35}$, $X^3$, $X^5$, $X^6$; and the two bonds represented by the dotted lines are as defined in claim 7.

12. The pharmaceutical composition according to claim 1 comprising at least one pharmaceutically acceptable carrier, diluent, excipient and/or adjuvant and a compound selected from the group consisting of:

(3-(4-chlorophenyl)-1H-pyrazol-5-yl)(3-(pyridin-2-yl)-5,6-dihydro-[1,2,4]triazolo[4,3-a]pyrazin-7(8H)-yl)methanone;

(3-(3,4-dichlorophenyl)-1H-pyrazol-5-yl)(3-(pyridin-2-yl)-5,6-dihydro-[1,2,4]triazolo[4,3-a]pyrazin-7(8H)-yl)methanone;

[1,1'-biphenyl]-4-yl(3-(pyridin-2-yl)-5,6-dihydro-[1,2,4]triazolo[4,3-a]pyrazin-7(8H)-yl)methanone;

(4-fluorophenyl)(3-(quinolin-2-yl)-5,6-dihydro-[1,2,4]triazolo[4,3-a]pyrazin-7(8H)-yl)methanone;

(4-fluorophenyl)(3-(2-phenylthiazol-4-yl)-5,6-dihydro-[1,2,4]triazolo[4,3-a]pyrazin-7(8H)-yl)methanone;
(4-fluorophenyl)(3-(2-morpholinothiazol-4-yl)-5,6-dihydro-[1,2,4]triazolo[4,3-a]pyrazin-7(8H)-yl)methanone;
(3-(5-chloropyridin-2-yl)-5,6-dihydro-[1,2,4]triazolo[4,3-a]pyrazin-7(8H)-yl)(4-fluorophenyl)methanone;
(4-fluorophenyl)(8-methyl-3-(pyridin-2-yl)-5,6-dihydro-[1,2,4]triazolo[4,3-a]pyrazin-7(8H)-yl)methanone;
(3-(2,4-dichlorophenyl)-1H-pyrazol-5-yl)(3-(pyridin-2-yl)-5,6-dihydro-[1,2,4]triazolo[4,3-a]pyrazin-7(8H)-yl)methanone;
(3-(3,4-dichlorophenyl)-1-methyl-1H-pyrazol-5-yl)(3-(pyridin-2-yl)-5,6-dihydro-[1,2,4]triazolo[4,3-a]pyrazin-7(8H)-yl)methanone;
(4-fluorophenyl)(3-(isoquinolin-3-yl)-5,6-dihydro-[1,2,4]triazolo[4,3-a]pyrazin-7(8H)-yl)methanone;
(4'-fluoro-[1,1'-biphenyl]-4-yl)(3-(pyridin-2-yl)-5,6-dihydro-[1,2,4]triazolo[4,3-a]pyrazin-7(8H)-yl)methanone;
(3-(pyridin-2-yl)-5,6-dihydro-[1,2,4]triazolo[4,3-a]pyrazin-7(8H)-yl)(3-(4-(trifluoromethyl)phenyl)-1H-pyrazol-5-yl)methanone;
(3-(4-phenoxyphenyl)-1H-pyrazol-5-yl)(3-(pyridin-2-yl)-5,6-dihydro-[1,2,4]triazolo[4,3-a]pyrazin-7(8H)-yl)methanone;
[1,1'-biphenyl]-4-yl(3-(quinolin-2-yl)-5,6-dihydro-[1,2,4]triazolo[4,3-a]pyrazin-7(8H)-yl)methanone;
[1,1'-biphenyl]-4-yl(3-(2-morpholinothiazol-4-yl)-5,6-dihydro-[1,2,4]triazolo[4,3-a]pyrazin-7(8H)-yl)methanone;
(3-(pyridin-2-yl)-5,6-dihydro-[1,2,4]triazolo[4,3-a]pyrazin-7(8H)-yl)(4-(thiophen-2-yl)phenyl)methanone;
(4-fluorophenyl)(3-(8-fluoroquinolin-2-yl)-5,6-dihydro-[1,2,4]triazolo[4,3-a]pyrazin-7(8H)-yl)methanone;
(3-(8-chloroquinolin-2-yl)-5,6-dihydro-[1,2,4]triazolo[4,3-a]pyrazin-7(8H)-yl)(4-fluorophenyl)methanone;
(4-fluorophenyl)(3-(2-(4-(trifluoromethyl)phenyl)thiazol-4-yl)-5,6-dihydro-[1,2,4]triazolo[4,3-a]pyrazin-7(8H)-yl)methanone;
(4-fluorophenyl)(3-(6-phenylpyridin-2-yl)-5,6-dihydro-[1,2,4]triazolo[4,3-a]pyrazin-7(8H)-yl)methanone;
[1,1'-biphenyl]-4-yl(3-(2-phenylthiazol-4-yl)-5,6-dihydro-[1,2,4]triazolo[4,3-a]pyrazin-7(8H)-yl)methanone;
(4-fluorophenyl)(3-(4,5,6,7-tetrahydrobenzo[d]thiazol-2-yl)-5,6-dihydro-[1,2,4]triazolo[4,3-a]pyrazin-7(8H)-yl)methanone;
(4-fluorophenyl)(3-(2-(3-(trifluoromethyl)phenyl)thiazol-4-yl)-5,6-dihydro-[1,2,4]triazolo[4,3-a]pyrazin-7(8H)-yl)methanone;
(3-(2-(2,4-difluorophenyl)thiazol-4-yl)-5,6-dihydro-[1,2,4]triazolo[4,3-a]pyrazin-7(8H)-yl)(4-fluorophenyl)methanone;
(3-(2-(2,3-dichlorophenyl)thiazol-4-yl)-5,6-dihydro-[1,2,4]triazolo[4,3-a]pyrazin-7(8H)-yl)(4-fluorophenyl)methanone;
(3-(2-(4-chlorophenyl)thiazol-4-yl)-5,6-dihydro-[1,2,4]triazolo[4,3-a]pyrazin-7(8H)-yl)(4-fluorophenyl)methanone;
(4-fluorophenyl)(3-(2-(4-fluorophenyl)thiazol-4-yl)-5,6-dihydro-[1,2,4]triazolo[4,3-a]pyrazin-7(8H)-yl)methanone;
(4-fluorophenyl)(3-(2-(piperidin-1-yl)thiazol-4-yl)-5,6-dihydro-[1,2,4]triazolo[4,3-a]pyrazin-7(8H)-yl)methanone;
(4-fluorophenyl)(3-(2-(4-phenylpiperazin-1-yl)thiazol-4-yl)-5,6-dihydro-[1,2,4]triazolo[4,3-a]pyrazin-7(8H)-yl)methanone;
(3-(2-(2,4-dichlorophenyl)thiazol-4-yl)-5,6-dihydro-[1,2,4]triazolo[4,3-a]pyrazin-7(8H)-yl)(4-fluorophenyl)methanone;
(3-(2-(3,5-dichlorophenyl)thiazol-4-yl)-5,6-dihydro-[1,2,4]triazolo[4,3-a]pyrazin-7(8H)-yl)(4-fluorophenyl)methanone;
(4-fluorophenyl)(3-(6-(pyrrolidin-1-yl)pyridin-2-yl)-5,6-dihydro-[1,2,4]triazolo[4,3-a]pyrazin-7(8H)-yl)methanone;
(4-fluorophenyl)(3-(6-morpholinopyridin-2-yl)-5,6-dihydro-[1,2,4]triazolo[4,3-a]pyrazin-7(8H)-yl)methanone;
(4-fluorophenyl)(3-(6-(trifluoromethyl)pyridin-2-yl)-5,6-dihydro-[1,2,4]triazolo[4,3-a]pyrazin-7(8H)-yl)methanone;
(3-(2-(3,4-dimethoxyphenyl)thiazol-4-yl)-5,6-dihydro-[1,2,4]triazolo[4,3-a]pyrazin-7(8H)-yl)(4-fluorophenyl)methanone;
(4-fluorophenyl)(8-(4-fluorophenyl)-3-(2-phenylthiazol-4-yl)-5,6-dihydro-[1,2,4]triazolo[4,3-a]pyrazin-7(8H)-yl)methanone;
(3-(2-(3-chlorophenyl)thiazol-4-yl)-5,6-dihydro-[1,2,4]triazolo[4,3-a]pyrazin-7(8H)-yl)(4-fluorophenyl)methanone;
(4-fluorophenyl)(8-isopropyl-3-(2-phenylthiazol-4-yl)-5,6-dihydro-[1,2,4]triazolo[4,3-a]pyrazin-7(8H)-yl)methanone;
(R)-(4-fluorophenyl)(8-methyl-3-(pyridin-2-yl)-5,6-dihydro-[1,2,4]triazolo[4,3-a]pyrazin-7(8H)-yl)methanone;
(R)-(4-fluorophenyl)(8-methyl-3-(2-phenylthiazol-4-yl)-5,6-dihydro-[1,2,4]triazolo[4,3-a]pyrazin-7(8H)-yl)methanone;
[1,1'-biphenyl]-4-yl(8-methyl-3-(2-morpholinothiazol-4-yl)-5,6-dihydro-[1,2,4]triazolo[4,3-a]pyrazin-7(8H)-yl)methanone;
(4-fluorophenyl)(3-(2-phenyloxazol-4-yl)-5,6-dihydro-[1,2,4]triazolo[4,3-a]pyrazin-7(8H)-yl)methanone;
(4-fluorophenyl)(8-methyl-3-(2-phenyloxazol-4-yl)-5,6-dihydro-[1,2,4]triazolo[4,3-a]pyrazin-7(8H)-yl)methanone;
[1,1'-biphenyl]-4-yl(8-methyl-3-(2-phenyloxazol-4-yl)-5,6-dihydro-[1,2,4]triazolo[4,3-a]pyrazin-7(8H)-yl)methanone;
[1,1'-biphenyl]-4-yl(3-(2-phenyloxazol-4-yl)-5,6-dihydro-[1,2,4]triazolo[4,3-a]pyrazin-7(8H)-yl)methanone;
(4-fluorophenyl)(8-(2-hydroxyethyl)-3-(2-phenylthiazol-4-yl)-5,6-dihydro-[1,2,4]triazolo[4,3-a]pyrazin-7(8H)-yl)methanone;
(4-fluorophenyl)(8-methyl-3-(2-morpholinothiazol-4-yl)-5,6-dihydro-[1,2,4]triazolo[4,3-a]pyrazin-7(8H)-yl)methanone;
(4'-fluoro-[1,1'-biphenyl]-4-yl)(8-methyl-3-(2-morpholinothiazol-4-yl)-5,6-dihydro-[1,2,4]triazolo[4,3-a]pyrazin-7(8H)-yl)methanone;
(3-(2-phenylthiazol-4-yl)-5,6-dihydro-[1,2,4]triazolo[4,3-a]pyrazin-7(8H)-yl)(4-(thiophen-2-yl)phenyl)methanone;
(3-(2-morpholinothiazol-4-yl)-5,6-dihydro-[1,2,4]triazolo[4,3-a]pyrazin-7(8H)-yl)(4-(thiophen-2-yl)phenyl)methanone;

(8-methyl-3-(2-morpholinothiazol-4-yl)-5,6-dihydro-[1,2,4]triazolo[4,3-a]pyrazin-7(8H)-yl)(4-(thiophen-2-yl)phenyl)methanone;
(4-fluorophenyl)(3-(4-phenylthiazol-2-yl)-5,6-dihydro-[1,2,4]triazolo[4,3-a]pyrazin-7(8H)-yl)methanone;
(3-(2-(2-chlorophenyl)thiazol-4-yl)-5,6-dihydro-[1,2,4]triazolo[4,3-a]pyrazin-7(8H)-yl)(4-fluorophenyl)methanone;
(3-(benzo[d]thiazol-2-yl)-5,6-dihydro-[1,2,4]triazolo[4,3-a]pyrazin-7(8H)-yl)(4-fluorophenyl)methanone;
(8,8-dimethyl-3-(2-phenylthiazol-4-yl)-5,6-dihydro-[1,2,4]triazolo[4,3-a]pyrazin-7(8H)-yl)(4-fluorophenyl)methanone;
(4-fluorophenyl)(8-methyl-3-(quinolin-2-yl)-5,6-dihydro-[1,2,4]triazolo[4,3-a]pyrazin-7(8H)-yl)methanone;
(8-methyl-3-(2-phenylthiazol-4-yl)-5,6-dihydro-[1,2,4]triazolo[4,3-a]pyrazin-7(8H)-yl)(4-(thiophen-2-yl)phenyl)methanone;
(3-(2-phenylthiazol-4-yl)-5,6-dihydro-[1,2,4]triazolo[4,3-a]pyrazin-7(8H)-yl)(4-(thiophen-3-yl)phenyl)methanone;
(8-methyl-3-(2-phenylthiazol-4-yl)-5,6-dihydro-[1,2,4]triazolo[4,3-a]pyrazin-7(8H)-yl)(4-(thiophen-3-yl)phenyl)methanone;
(8-methyl-3-(quinolin-2-yl)-5,6-dihydro-[1,2,4]triazolo[4,3-a]pyrazin-7(8H)-yl)(4-(thiophen-2-yl)phenyl)methanone;
(3-(2-(2-chlorophenyl)thiazol-4-yl)-5,6-dihydro-[1,2,4]triazolo[4,3-a]pyrazin-7(8H)-yl)(4-(thiophen-2-yl)phenyl)methanone;
[1,1'-biphenyl]-4-yl(3-(2-(2-chlorophenyl)thiazol-4-yl)-5,6-dihydro-[1,2,4]triazolo[4,3-a]pyrazin-7(8H)-yl)methanone;
(R)-(3-(2-(4-chlorophenyl)thiazol-4-yl)-8-methyl-5,6-dihydro-[1,2,4]triazolo[4,3-a]pyrazin-7(8H)-yl)(4-fluorophenyl)methanone;
(3-(quinolin-2-yl)-5,6-dihydro-[1,2,4]triazolo[4,3-a]pyrazin-7(8H)-yl)(4-(thiophen-2-yl)phenyl)methanone;
(4-fluorophenyl)(3-(2-(4-fluorophenyl)thiazol-4-yl)-8-methyl-5,6-dihydro-[1,2,4]triazolo[4,3-a]pyrazin-7(8H)-yl)methanone;
(R)-(4-fluorophenyl)(3-(2-(4-fluorophenyl)thiazol-4-yl)-8-methyl-5,6-dihydro-[1,2,4]triazolo[4,3-a]pyrazin-7(8H)-yl)methanone;
[1,1'-biphenyl]-4-yl(8-methyl-3-(4-methyl-2-phenylthiazol-5-yl)-5,6-dihydro-[1,2,4]triazolo[4,3-a]pyrazin-7(8H)-yl)methanone;
(3-(2-(4-fluorophenyl)thiazol-4-yl)-5,6-dihydro-[1,2,4]triazolo[4,3-a]pyrazin-7(8H)-yl)(4-(thiophen-2-yl)phenyl)methanone;
(3-(2-(2-chlorophenyl)thiazol-4-yl)-8-methyl-5,6-dihydro-[1,2,4]triazolo[4,3-a]pyrazin-7(8H)-yl)(4-fluorophenyl)methanone;
(4-fluorophenyl)(8-methyl-3-(4-methyl-2-phenylthiazol-5-yl)-5,6-dihydro-[1,2,4]triazolo[4,3-a]pyrazin-7(8H)-yl)methanone;
[1,1'-biphenyl]-4-yl(3-(2-(4-fluorophenyl)thiazol-4-yl)-8-methyl-5,6-dihydro-[1,2,4]triazolo[4,3-a]pyrazin-7(8H)-yl)methanone;
(3-(2-(2,4-difluorophenyl)thiazol-4-yl)-8-methyl-5,6-dihydro-[1,2,4]triazolo[4,3-a]pyrazin-7(8H)-yl)(4-fluorophenyl)methanone;
(3-(2-(4-fluorophenyl)thiazol-4-yl)-8-methyl-5,6-dihydro-[1,2,4]triazolo[4,3-a]pyrazin-7(8H)-yl)(4-(thiophen-2-yl)phenyl)methanone;

[1,1'-biphenyl]-4-yl(3-(2-(2,4-difluorophenyl)thiazol-4-yl)-8-methyl-5,6-dihydro-[1,2,4]triazolo[4,3-a]pyrazin-7(8H)-yl)methanone;
(3-(2-(2,4-difluorophenyl)thiazol-4-yl)-8-methyl-5,6-dihydro-[1,2,4]triazolo[4,3-a]pyrazin-7(8H)-yl)(4-(thiophen-2-yl)phenyl)methanone;
naphthalen-1-yl(3-(pyridin-2-yl)-5,6-dihydro-[1,2,4]triazolo[4,3-a]pyrazin-7(8H)-yl)methanone;
(3-(4-chlorophenyl)-1-methyl-1H-pyrazol-5-yl)(3-(pyridin-2-yl)-5,6-dihydro-[1,2,4]triazolo[4,3-a]pyrazin-7(8H)-yl)methanone;
(5-(4-chlorophenyl)-1-methyl-1H-pyrazol-3-yl)(3-(pyridin-2-yl)-5,6-dihydro-[1,2,4]triazolo[4,3-a]pyrazin-7(8H)-yl)methanone;
(8-methyl-3-(5-phenyl-1,2,4-oxadiazol-3-yl)-5,6-dihydro-[1,2,4]triazolo[4,3-a]pyrazin-7(8H)-yl)(4-(thiophen-2-yl)phenyl)methanone;
(8-methyl-3-(3-phenyl-1,2,4-oxadiazol-5-yl)-5,6-dihydro-[1,2,4]triazolo[4,3-a]pyrazin-7(8H)-yl)(4-(thiophen-2-yl)phenyl)methanone;
(R)-(3-(2-(4-fluorophenyl)oxazol-4-yl)-8-methyl-5,6-dihydro-[1,2,4]triazolo[4,3-a]pyrazin-7(8H)-yl)(4-(thiophen-2-yl)phenyl)methanone;
2-(7-((4-fluorophenyl)sulfonyl)-5,6,7,8-tetrahydro-[1,2,4]triazolo[4,3-a]pyrazin-3-yl)quinoline;
2-(4-fluorophenyl)-1-(3-(quinolin-2-yl)-5,6-dihydro-[1,2,4]triazolo[4,3-a]pyrazin-7(8H)-yl)ethanone;
(5-phenylpyridin-2-yl)(3-(quinolin-2-yl)-5,6-dihydro-[1,2,4]triazolo[4,3-a]pyrazin-7(8H)-yl)methanone;
(6-phenylpyridin-3-yl)(3-(quinolin-2-yl)-5,6-dihydro-[1,2,4]triazolo[4,3-a]pyrazin-7(8H)-yl)methanone;
(2-phenylpyrimidin-5-yl)(3-(quinolin-2-yl)-5,6-dihydro-[1,2,4]triazolo[4,3-a]pyrazin-7(8H)-yl)methanone;
(4-phenylcyclohexyl)(3-(quinolin-2-yl)-5,6-dihydro-[1,2,4]triazolo[4,3-a]pyrazin-7(8H)-yl)methanone;
cyclohexyl(3-(quinolin-2-yl)-5,6-dihydro-[1,2,4]triazolo[4,3-a]pyrazin-7(8H)-yl)methanone;
3-methyl-1-(3-(quinolin-2-yl)-5,6-dihydro-[1,2,4]triazolo[4,3-a]pyrazin-7(8H)-yl)butan-1-one;
[1,1'-biphenyl]-2-yl(3-(quinolin-2-yl)-5,6-dihydro-[1,2,4]triazolo[4,3-a]pyrazin-7(8H)-yl)methanone;
(4-(furan-3-yl)phenyl)(3-(quinolin-2-yl)-5,6-dihydro-[1,2,4]triazolo[4,3-a]pyrazin-7(8H)-yl)methanone;
(4-(pyrimidin-5-yl)phenyl)(3-(quinolin-2-yl)-5,6-dihydro-[1,2,4]triazolo[4,3-a]pyrazin-7(8H)-yl)methanone;
(9-methyl-9H-carbazol-2-yl)(3-(quinolin-2-yl)-5,6-dihydro-[1,2,4]triazolo[4,3-a]pyrazin-7(8H)-yl)methanone;
(4-(pyrimidin-2-yl)phenyl)(3-(quinolin-2-yl)-5,6-dihydro-[1,2,4]triazolo[4,3-a]pyrazin-7(8H)-yl)methanone;
(4-(pyrazin-2-yl)phenyl)(3-(quinolin-2-yl)-5,6-dihydro-[1,2,4]triazolo[4,3-a]pyrazin-7(8H)-yl)methanone;
(4-(pyridazin-3-yl)phenyl)(3-(quinolin-2-yl)-5,6-dihydro-[1,2,4]triazolo[4,3-a]pyrazin-7(8H)-yl)methanone;
4'-(3-(quinolin-2-yl)-5,6,7,8-tetrahydro-[1,2,4]triazolo[4,3-a]pyrazine-7-carbonyl)-[1,1'-biphenyl]-4-carbonitrile;
1-(4-(3-(quinolin-2-yl)-5,6,7,8-tetrahydro-[1,2,4]triazolo[4,3-a]pyrazine-7-carbonyl)phenyl)piperidin-2-one;
(4-morpholinophenyl)(3-(quinolin-2-yl)-5,6-dihydro-[1,2,4]triazolo[4,3-a]pyrazin-7(8H)-yl)methanone;
(4-(3,5-dimethyl-1H-pyrazol-1-yl)phenyl)(3-(quinolin-2-yl)-5,6-dihydro-[1,2,4]triazolo[4,3-a]pyrazin-7(8H)-yl)methanone;

(3-(2-(4-fluorophenyl)thiazol-4-yl)-6-methyl-5,6-di-hydro-[1,2,4]triazolo[4,3-a]pyrazin-7(8H)-yl)(4-(thiophen-2-yl)phenyl)methanone;

(3-(2-(4-fluorophenyl)thiazol-4-yl)-5-methyl-5,6-di-hydro-[1,2,4]triazolo[4,3-a]pyrazin-7(8H)-yl)(4-(thiophen-2-yl)phenyl)methanone;

(3,4-dichlorophenyl)(3-(2-(4-fluorophenyl)thiazol-4-yl)-8-methyl-5,6-dihydro-[1,2,4]triazolo[4,3-a]pyrazin-7(8H)-yl)methanone;

(3,4-difluorophenyl)(3-(2-(4-fluorophenyl)thiazol-4-yl)-8-methyl-5,6-dihydro-[1,2,4]triazolo[4,3-a]pyrazin-7(8H)-yl)methanone;

(3-chloro-4-fluorophenyl)(3-(2-(4-fluorophenyl)thiazol-4-yl)-8-methyl-5,6-dihydro-[1,2,4]triazolo[4,3-a]pyrazin-7(8H)-yl)methanone;

(4-chloro-3-fluorophenyl)(3-(2-(4-fluorophenyl)thiazol-4-yl)-8-methyl-5,6-dihydro-[1,2,4]triazolo[4,3-a]pyrazin-7(8H)-yl)methanone;

(3-(2-(4-fluorophenyl)thiazol-4-yl)-8-methyl-5,6-di-hydro-[1,2,4]triazolo[4,3-a]pyrazin-7(8H)-yl)(3,4,5-trifluorophenyl)methanone;

(8-methyl-3-(2-phenyloxazol-4-yl)-5,6-dihydro-[1,2,4]triazolo[4,3-a]pyrazin-7(8H)-yl)(4-(thiophen-2-yl)phenyl)methanone;

(R)-(4-fluorophenyl)(8-methyl-3-(quinolin-2-yl)-5,6-di-hydro-[1,2,4]triazolo[4,3-a]pyrazin-7(8H)-yl)methanone;

(R)-[1,1'-biphenyl]-4-yl(8-methyl-3-(quinolin-2-yl)-5,6-dihydro-[1,2,4]triazolo[4,3-a]pyrazin-7(8H)-yl)methanone;

(R)-[1,1'-biphenyl]-4-yl(8-methyl-3-(2-morpholinothiazol-4-yl)-5,6-dihydro-[1,2,4]triazolo[4,3-a]pyrazin-7(8H)-yl)methanone;

(R)-(4-fluorophenyl)(8-methyl-3-(6-phenylpyridin-2-yl)-5,6-dihydro-[1,2,4]triazolo[4,3-a]pyrazin-7(8H)-yl)methanone;

(R)-[1,1'-biphenyl]-4-yl(8-methyl-3-(2-phenylthiazol-4-yl)-5,6-dihydro-[1,2,4]triazolo[4,3-a]pyrazin-7(8H)-yl)methanone;

(R)-(4-fluorophenyl)(8-methyl-3-(4,5,6,7-tetrahydrobenzo[d]thiazol-2-yl)-5,6-dihydro-[1,2,4]triazolo[4,3-a]pyrazin-7(8H)-yl)methanone;

(R)-(3-(2-(2,4-difluorophenyl)thiazol-4-yl)-8-methyl-5,6-dihydro-[1,2,4]triazolo[4,3-a]pyrazin-7(8H)-yl)(4-fluorophenyl)methanone;

(R)-(3-(2-(2,3-dichlorophenyl)thiazol-4-yl)-8-methyl-5,6-dihydro-[1,2,4]triazolo[4,3-a]pyrazin-7(8H)-yl)(4-fluorophenyl)methanone;

(R)-(4-fluorophenyl)(8-methyl-3-(2-(4-phenylpiperazin-1-yl)thiazol-4-yl)-5,6-dihydro-[1,2,4]triazolo[4,3-a]pyrazin-7(8H)-yl)methanone;

(R)-(3-(2-(2,4-dichlorophenyl)thiazol-4-yl)-8-methyl-5,6-dihydro-[1,2,4]triazolo[4,3-a]pyrazin-7(8H)-yl)(4-fluorophenyl)methanone;

(R)-(3-(2-(3-chlorophenyl)thiazol-4-yl)-8-methyl-5,6-dihydro-[1,2,4]triazolo[4,3-a]pyrazin-7(8H)-yl)(4-fluorophenyl)methanone;

(R)-(4-fluorophenyl)(8-methyl-3-(2-phenyloxazol-4-yl)-5,6-dihydro-[1,2,4]triazolo[4,3-a]pyrazin-7(8H)-yl)methanone;

(R)-[1,1'-biphenyl]-4-yl(8-methyl-3-(2-phenyloxazol-4-yl)-5,6-dihydro-[1,2,4]triazolo[4,3-a]pyrazin-7(8H)-yl)methanone;

(R)-(4-fluorophenyl)(8-(2-hydroxyethyl)-3-(2-phenylthiazol-4-yl)-5,6-dihydro-[1,2,4]triazolo[4,3-a]pyrazin-7(8H)-yl)methanone;

(R)-(4'-fluoro-[1,1'-biphenyl]-4-yl)(8-methyl-3-(2-morpholinothiazol-4-yl)-5,6-dihydro-[1,2,4]triazolo[4,3-a]pyrazin-7(8H)-yl)methanone;

(R)-(8-methyl-3-(2-phenylthiazol-4-yl)-5,6-dihydro-[1,2,4]triazolo[4,3-a]pyrazin-7(8H)-yl)(4-(thiophen-2-yl)phenyl)methanone;

(R)-(8-methyl-3-(2-morpholinothiazol-4-yl)-5,6-dihydro-[1,2,4]triazolo[4,3-a]pyrazin-7(8H)-yl)(4-(thiophen-2-yl)phenyl)methanone;

(R)-(4-fluorophenyl)(8-methyl-3-(4-phenylthiazol-2-yl)-5,6-dihydro-[1,2,4]triazolo[4,3-a]pyrazin-7(8H)-yl)methanone;

(R)-(3-(2-(2-chlorophenyl)thiazol-4-yl)-8-methyl-5,6-di-hydro-[1,2,4]triazolo[4,3-a]pyrazin-7(8H)-yl)(4-fluorophenyl)methanone;

(R)-(8-methyl-3-(2-phenylthiazol-4-yl)-5,6-dihydro-[1,2,4]triazolo[4,3-a]pyrazin-7(8H)-yl)(4-(thiophen-3-yl)phenyl)methanone;

(R)-(8-methyl-3-(quinolin-2-yl)-5,6-dihydro-[1,2,4]triazolo[4,3-a]pyrazin-7(8H)-yl)(4-(thiophen-2-yl)phenyl)methanone;

(R)-(3-(2-(2-chlorophenyl)thiazol-4-yl)-8-methyl-5,6-di-hydro-[1,2,4]triazolo[4,3-a]pyrazin-7(8H)-yl)(4-(thiophen-2-yl)phenyl)methanone;

(R)-[1,1'-biphenyl]-4-yl(3-(2-(2-chlorophenyl)thiazol-4-yl)-8-methyl-5,6-dihydro-[1,2,4]triazolo[4,3-a]pyrazin-7(8H)-yl)methanone;

(R)-[1,1'-biphenyl]-4-yl(8-methyl-3-(4-methyl-2-phenylthiazol-5-yl)-5,6-dihydro-[1,2,4]triazolo[4,3-a]pyrazin-7(8H)-yl)methanone;

(R)-(3-(2-(4-fluorophenyl)thiazol-4-yl)-8-methyl-5,6-di-hydro-[1,2,4]triazolo[4,3-a]pyrazin-7(8H)-yl)(4-(thiophen-2-yl)phenyl)methanone;

(R)-[1,1'-biphenyl]-4-yl(3-(2-(4-fluorophenyl)thiazol-4-yl)-8-methyl-5,6-dihydro-[1,2,4]triazolo[4,3-a]pyrazin-7(8H)-yl)methanone;

(R)-[1,1'-biphenyl]-4-yl(3-(2-(2,4-difluorophenyl)thiazol-4-yl)-8-methyl-5,6-dihydro-[1,2,4]triazolo[4,3-a]pyrazin-7(8H)-yl)methanone;

(R)-(3-(2-(2,4-difluorophenyl)thiazol-4-yl)-8-methyl-5,6-dihydro-[1,2,4]triazolo[4,3-a]pyrazin-7(8H)-yl)(4-(thiophen-2-yl)phenyl)methanone;

(S)-(4-fluorophenyl)(8-methyl-3-(pyridin-2-yl)-5,6-di-hydro-[1,2,4]triazolo[4,3-a]pyrazin-7(8H)-yl)methanone;

(S)-(4-fluorophenyl)(3-(2-(4-fluorophenyl)thiazol-4-yl)-8-methyl-5,6-dihydro-[1,2,4]triazolo[4,3-a]pyrazin-7(8H)-yl)methanone;

(S)-(4'-fluoro-[1,1'-biphenyl]-4-yl)(8-methyl-3-(2-morpholinothiazol-4-yl)-5,6-dihydro-[1,2,4]triazolo[4,3-a]pyrazin-7(8H)-yl)methanone;

(S)-(4-fluorophenyl)(8-methyl-3-(quinolin-2-yl)-5,6-di-hydro-[1,2,4]triazolo[4,3-a]pyrazin-7(8H)-yl)methanone;

(S)-(8-methyl-3-(quinolin-2-yl)-5,6-dihydro-[1,2,4]triazolo[4,3-a]pyrazin-7(8H)-yl)(4-(thiophen-2-yl)phenyl)methanone;

(S)-(4-fluorophenyl)(3-(2-(4-fluorophenyl)thiazol-4-yl)-8-methyl-5,6-dihydro-[1,2,4]triazolo[4,3-a]pyrazin-7(8H)-yl)methanone;

(S)-(3-(2-(2,4-difluorophenyl)thiazol-4-yl)-8-methyl-5,6-dihydro-[1,2,4]triazolo[4,3-a]pyrazin-7(8H)-yl)(4-(thiophen-2-yl)phenyl)methanone;

(4-fluorophenyl)(8-methyl-3-(2-phenylthiazol-4-yl)-5,6-dihydro-[1,2,4]triazolo[4,3-a]pyrazin-7(8H)-yl)methanone;

(S)-(4-fluorophenyl)(8-methyl-3-(2-phenylthiazol-4-yl)-5,6-dihydro-[1,2,4]triazolo[4,3-a]pyrazin-7(8H)-yl)methanone;

(S)-(3-(3-(4-fluorophenyl)-1,2,4-oxadiazol-5-yl)-8-methyl-5,6-dihydro-[1,2,4]triazolo[4,3-a]pyrazin-7(8H)-yl)(4-(thiophen-2-yl)phenyl)methanone;

(R)-(3-(3-(4-fluorophenyl)-1,2,4-oxadiazol-5-yl)-8-methyl-5,6-dihydro-[1,2,4]triazolo[4,3-a]pyrazin-7(8H)-yl)(4-(thiophen-2-yl)phenyl)methanone;

(3-(2-(2,4-difluorophenyl)thiazol-4-yl)-5,6-dihydro-[1,2,4]triazolo[4,3-a]pyrazin-7(8H)-yl)(4-(thiophen-2-yl)phenyl)methanone;

(3-(5-phenyl-1,2,4-oxadiazol-3-yl)-5,6-dihydro-[1,2,4]triazolo[4,3-a]pyrazin-7(8H)-yl)(4-(thiophen-2-yl)phenyl)methanone;

(4-fluorophenyl)(3-(3-phenyl-1,2,4-oxadiazol-5-yl)-5,6-dihydro-[1,2,4]triazolo[4,3-a]pyrazin-7(8H)-yl)methanone;

(4-fluorophenyl)(3-(5-phenyl-1,2,4-oxadiazol-3-yl)-5,6-dihydro-[1,2,4]triazolo[4,3-a]pyrazin-7(8H)-yl)methanone;

(3-(3-phenyl-1,2,4-oxadiazol-5-yl)-5,6-dihydro-[1,2,4]triazolo[4,3-a]pyrazin-7(8H)-yl)(4-(thiophen-2-yl)phenyl)methanone;

(4-fluorophenyl)(3-(3-(4-fluorophenyl)-1,2,4-oxadiazol-5-yl)-5,6-dihydro-[1,2,4]triazolo[4,3-a]pyrazin-7(8H)-yl)methanone;

(3-(3-(4-fluorophenyl)-1,2,4-oxadiazol-5-yl)-5,6-dihydro-[1,2,4]triazolo[4,3-a]pyrazin-7(8H)-yl)(4-(thiophen-2-yl)phenyl)methanone;

(3-(3-(2,4-difluorophenyl)-1,2,4-oxadiazol-5-yl)-5,6-dihydro-[1,2,4]triazolo[4,3-a]pyrazin-7(8H)-yl)(4-(thiophen-2-yl)phenyl)methanone;

(4-fluorophenyl)(3-(5-phenyl-1H-1,2,4-triazol-3-yl)-5,6-dihydro-[1,2,4]triazolo[4,3-a]pyrazin-7(8H)-yl)methanone;

(3-(5-phenyl-1H-1,2,4-triazol-3-yl)-5,6-dihydro-[1,2,4]triazolo[4,3-a]pyrazin-7(8H)-yl)(4-(thiophen-2-yl)phenyl)methanone;

(4-fluorophenyl)(3-(2-(2-fluorophenyl)thiazol-4-yl)-5,6-dihydro-[1,2,4]triazolo[4,3-a]pyrazin-7(8H)-yl)methanone;

(3-(2-(2-fluorophenyl)thiazol-4-yl)-5,6-dihydro-[1,2,4]triazolo[4,3-a]pyrazin-7(8H)-yl)(4-(thiophen-2-yl)phenyl)methanone;

[1,1'-biphenyl]-4-yl(3-(2-(2-fluorophenyl)thiazol-4-yl)-5,6-dihydro-[1,2,4]triazolo[4,3-a]pyrazin-7(8H)-yl)methanone;

(4'-fluoro-[1,1'-biphenyl]-4-yl)(3-(2-(2-fluorophenyl)thiazol-4-yl)-5,6-dihydro-[1,2,4]triazolo[4,3-a]pyrazin-7(8H)-yl)methanone;

(3-(3-(2,4-difluorophenyl)-1,2,4-oxadiazol-5-yl)-5,6-dihydro-[1,2,4]triazolo[4,3-a]pyrazin-7(8H)-yl)(4-(thiophen-2-yl)phenyl)methanone;

[1,1'-biphenyl]-4-yl(3-(2-((4,5-dichloro-1H-imidazol-1-yl)methyl)thiazol-4-yl)-5,6-dihydro-[1,2,4]triazolo[4,3-a]pyrazin-7(8H)-yl)methanone;

(3-(2-((4,5-dichloro-1H-imidazol-1-yl)methyl)thiazol-4-yl)-5,6-dihydro-[1,2,4]triazolo[4,3-a]pyrazin-7(8H)-yl)(4'-fluoro-[1,1'-biphenyl]-4-yl)methanone;

(3-(2-(4-chlorobenzyl)thiazol-4-yl)-5,6-dihydro-[1,2,4]triazolo[4,3-a]pyrazin-7(8H)-yl)(4-fluorophenyl)methanone;

(3-(2-(4-chlorobenzyl)thiazol-4-yl)-5,6-dihydro-[1,2,4]triazolo[4,3-a]pyrazin-7(8H)-yl)(4-(thiophen-2-yl)phenyl)methanone;

(4-fluorophenyl)(3-(2-(p-tolyl)thiazol-4-yl)-5,6-dihydro-[1,2,4]triazolo[4,3-a]pyrazin-7(8H)-yl)methanone;

(4-(thiophen-2-yl)phenyl)(3-(2-(p-tolyl)thiazol-4-yl)-5,6-dihydro-[1,2,4]triazolo[4,3-a]pyrazin-7(8H)-yl)methanone;

[1,1'-biphenyl]-4-yl(3-(2-(p-tolyl)thiazol-4-yl)-5,6-dihydro-[1,2,4]triazolo[4,3-a]pyrazin-7(8H)-yl)methanone;

(4-fluorophenyl)(3-(2-(thiophen-2-yl)thiazol-4-yl)-5,6-dihydro-[1,2,4]triazolo[4,3-a]pyrazin-7(8H)-yl)methanone;

(4-(thiophen-2-yl)phenyl)(3-(2-(thiophen-2-yl)thiazol-4-yl)-5,6-dihydro-[1,2,4]triazolo[4,3-a]pyrazin-7(8H)-yl)methanone;

[1,1'-biphenyl]-4-yl(3-(2-(thiophen-2-yl)thiazol-4-yl)-5,6-dihydro-[1,2,4]triazolo[4,3-a]pyrazin-7(8H)-yl)methanone;

(4'-fluoro-[1,1'-biphenyl]-4-yl)(3-(2-(thiophen-2-yl)thiazol-4-yl)-5,6-dihydro-[1,2,4]triazolo[4,3-a]pyrazin-7(8H)-yl)methanone;

(3-(2-(((4-chlorophenyl)sulfonyl)methyl)thiazol-4-yl)-5,6-dihydro-[1,2,4]triazolo[4,3-a]pyrazin-7(8H)-yl)(4-(thiophen-2-yl)phenyl)methanone;

[1,1'-biphenyl]-4-yl(3-(2-(((4-chlorophenyl)sulfonyl)methyl)thiazol-4-yl)-5,6-dihydro-[1,2,4]triazolo[4,3-a]pyrazin-7(8H)-yl)methanone;

(3-(2-(((4-chlorophenyl)sulfonyl)methyl)thiazol-4-yl)-5,6-dihydro-[1,2,4]triazolo[4,3-a]pyrazin-7(8H)-yl)(4'-fluoro-[1,1'-biphenyl]-4-yl)methanone;

(4-fluorophenyl)(3-(2-(2-methoxyphenyl)thiazol-4-yl)-5,6-dihydro-[1,2,4]triazolo[4,3-a]pyrazin-7(8H)-yl)methanone;

(3-(2-(2-methoxyphenyl)thiazol-4-yl)-5,6-dihydro-[1,2,4]triazolo[4,3-a]pyrazin-7(8H)-yl)(4-(thiophen-2-yl)phenyl)methanone;

[1,1'-biphenyl]-4-yl(3-(2-(2-methoxyphenyl)thiazol-4-yl)-5,6-dihydro-[1,2,4]triazolo[4,3-a]pyrazin-7(8H)-yl)methanone;

[1,1'-biphenyl]-4-yl(3-(3-(4-fluorophenyl)-1,2,4-oxadiazol-5-yl)-5,6-dihydro-[1,2,4]triazolo[4,3-a]pyrazin-7(8H)-yl)methanone;

(4'-fluoro-[1,1'-biphenyl]-4-yl)(3-(3-(4-fluorophenyl)-1,2,4-oxadiazol-5-yl)-5,6-dihydro-[1,2,4]triazolo[4,3-a]pyrazin-7(8H)-yl)methanone;

(4-fluorophenyl)(3-(2-(3-fluorophenyl)thiazol-4-yl)-5,6-dihydro-[1,2,4]triazolo[4,3-a]pyrazin-7(8H)-yl)methanone;

(3-(2-(3-fluorophenyl)thiazol-4-yl)-5,6-dihydro-[1,2,4]triazolo[4,3-a]pyrazin-7(8H)-yl)(4-(thiophen-2-yl)phenyl)methanone;

(3-(3-(4-fluorophenyl)-1,2,4-oxadiazol-5-yl)-8-methyl-5,6-dihydro-[1,2,4]triazolo[4,3-a]pyrazin-7(8H)-yl)(4-(thiophen-2-yl)phenyl)methanone;

(3-(3-phenyl-1,2,4-thiadiazol-5-yl)-5,6-dihydro-[1,2,4]triazolo[4,3-a]pyrazin-7(8H)-yl)(4-(thiophen-2-yl)phenyl)methanone;

(4-fluorophenyl)(3-(3-phenyl-1,2,4-thiadiazol-5-yl)-5,6-dihydro-[1,2,4]triazolo[4,3-a]pyrazin-7(8H)-yl)methanone;

(3-(2-(4-bromophenyl)thiazol-4-yl)-5,6-dihydro-[1,2,4]triazolo[4,3-a]pyrazin-7(8H)-yl)(4-(thiophen-2-yl)phenyl)methanone;

(3-(2-(4-bromophenyl)thiazol-4-yl)-5,6-dihydro-[1,2,4]triazolo[4,3-a]pyrazin-7(8H)-yl)(4-fluorophenyl)methanone;

(3-(2-(4-fluorophenyl)thiazol-4-yl)-8-methyl-5,6-di-hydro-[1,2,4]triazolo[4,3-a]pyrazin-7(8H)-yl)(4-(5-methylthiophen-2-yl)phenyl)methanone;

4-(3-(2-(4-fluorophenyl)thiazol-4-yl)-8-methyl-5,6,7,8-tetrahydro-[1,2,4]triazolo[4,3-a]pyrazine-7-carbonyl)benzonitrile;

[1,1'-biphenyl]-4-yl(3-(3-phenyl-1,2,4-oxadiazol-5-yl)-5,6-dihydro-[1,2,4]triazolo[4,3-a]pyrazin-7(8H)-yl)methanone;

(4-fluorophenyl)(3-(2-(pyridin-4-yl)thiazol-4-yl)-5,6-di-hydro-[1,2,4]triazolo[4,3-a]pyrazin-7(8H)-yl)methanone;

(3-(2-(quinolin-2-yl)thiazol-4-yl)-5,6-dihydro-[1,2,4]triazolo[4,3-a]pyrazin-7(8H)-yl)(4-(thiophen-2-yl)phenyl)methanone;

(3-(1-methyl-3-phenyl-1H-pyrazol-5-yl)-5,6-dihydro-[1,2,4]triazolo[4,3-a]pyrazin-7(8H)-yl)(4-(thiophen-2-yl)phenyl)methanone;

(3-(2-(4-(dimethylamino)phenyl)thiazol-4-yl)-5,6-di-hydro-[1,2,4]triazolo[4,3-a]pyrazin-7(8H)-yl)(4-fluorophenyl)methanone;

(3-(1-methyl-5-phenyl-1H-pyrazol-3-yl)-5,6-dihydro-[1,2,4]triazolo[4,3-a]pyrazin-7(8H)-yl)(4-(thiophen-2-yl)phenyl)methanone;

(4'-fluoro-[1,1'-biphenyl]-4-yl)(3-(3-phenyl-1,2,4-oxadi-azol-5-yl)-5,6-dihydro-[1,2,4]triazolo[4,3-a]pyrazin-7(8H)-yl)methanone;

(3-(2-(pyridin-2-yl)thiazol-4-yl)-5,6-dihydro-[1,2,4]tri-azolo[4,3-a]pyrazin-7(8H)-yl)(4-(thiophen-2-yl)phe-nyl)methanone;

(4-fluorophenyl)(3-(1-methyl-3-phenyl-1H-pyrazol-5-yl)-5,6-dihydro-[1,2,4]triazolo[4,3-a]pyrazin-7(8H)-yl)methanone;

(3-(2-(pyrimidin-2-yl)thiazol-4-yl)-5,6-dihydro-[1,2,4]triazolo[4,3-a]pyrazin-7(8H)-yl)(4-(thiophen-2-yl)phe-nyl)methanone;

(S)-(8-methyl-3-(2-morpholinothiazol-4-yl)-5,6-dihydro-[1,2,4]triazolo[4,3-a]pyrazin-7(8H)-yl)(4-(thiophen-2-yl)phenyl)methanone;

(3-(2-(pyridin-4-yl)thiazol-4-yl)-5,6-dihydro-[1,2,4]tri-azolo[4,3-a]pyrazin-7(8H)-yl)(4-(thiophen-2-yl)phe-nyl)methanone;

(3-(2-(4-(dimethylamino)phenyl)thiazol-4-yl)-5,6-di-hydro-[1,2,4]triazolo[4,3-a]pyrazin-7(8H)-yl)(4-(thio-phen-2-yl)phenyl)methanone;

(4-fluorophenyl)(3-(2-(pyridin-2-yl)thiazol-4-yl)-5,6-di-hydro-[1,2,4]triazolo[4,3-a]pyrazin-7(8H)-yl)metha-none;

(S)-(3-(2-(4-fluorophenyl)thiazol-4-yl)-8-methyl-5,6-di-hydro-[1,2,4]triazolo[4,3-a]pyrazin-7(8H)-yl)(4-(2-methylthiophen-3-yl)phenyl)methanone;

(R)-(3-(2-(4-fluorophenyl)thiazol-4-yl)-8-methyl-5,6-di-hydro-[1,2,4]triazolo[4,3-a]pyrazin-7(8H)-yl)(4-(2-methylthiophen-3-yl)phenyl)methanone;

(3-(2-(pyrazin-2-yl)thiazol-4-yl)-5,6-dihydro-[1,2,4]tri-azolo[4,3-a]pyrazin-7(8H)-yl)(4-(thiophen-2-yl)phe-nyl)methanone;

4-(4-(7-(4-(thiophen-2-yl)benzoyl)-5,6,7,8-tetrahydro-[1,2,4]triazolo[4,3-a]pyrazin-3-yl)thiazol-2-yl)benzoni-trile;

(4-fluorophenyl)(3-(2-(pyrazin-2-yl)thiazol-4-yl)-5,6-di-hydro-[1,2,4]triazolo[4,3-a]pyrazin-7(8H)-yl)metha-none;

(4-fluorophenyl)(3-(1-methyl-5-phenyl-1H-pyrazol-3-yl)-5,6-dihydro-[1,2,4]triazolo[4,3-a]pyrazin-7(8H)-yl)methanone;

(3-(2-(4-morpholinophenyl)thiazol-4-yl)-5,6-dihydro-[1,2,4]triazolo[4,3-a]pyrazin-7(8H)-yl)(4-(thiophen-2-yl)phenyl)methanone;

(4-fluorophenyl)(3-(2-(4-morpholinophenyl)thiazol-4-yl)-5,6-dihydro-[1,2,4]triazolo[4,3-a]pyrazin-7(8H)-yl)methanone;

(3-(2-(4-(4-methylpiperazin-1-yl)phenyl)thiazol-4-yl)-5,6-dihydro-[1,2,4]triazolo[4,3-a]pyrazin-7(8H)-yl)(4-(thiophen-2-yl)phenyl)methanone;

(4-fluorophenyl)(3-(2-(4-(4-methylpiperazin-1-yl)phe-nyl)thiazol-4-yl)-5,6-dihydro-[1,2,4]triazolo[4,3-a]pyrazin-7(8H)-yl)methanone;

(3-(2-(4-(piperidin-1-yl)phenyl)thiazol-4-yl)-5,6-di-hydro-[1,2,4]triazolo[4,3-a]pyrazin-7(8H)-yl)(4-(thio-phen-2-yl)phenyl)methanone;

(4-fluorophenyl)(3-(2-(4-(piperidin-1-yl)phenyl)thiazol-4-yl)-5,6-dihydro-[1,2,4]triazolo[4,3-a]pyrazin-7(8H)-yl)methanone;

(3-(2-(4-(pyrrolidin-1-yl)phenyl)thiazol-4-yl)-5,6-di-hydro-[1,2,4]triazolo[4,3-a]pyrazin-7(8H)-yl)(4-(thio-phen-2-yl)phenyl)methanone;

(4-fluorophenyl)(3-(2-(4-(pyrrolidin-1-yl)phenyl)thiazol-4-yl)-5,6-dihydro-[1,2,4]triazolo[4,3-a]pyrazin-7(8H)-yl)methanone;

(3-(2-(piperidin-1-yl)thiazol-4-yl)-5,6-dihydro-[1,2,4]tri-azolo[4,3-a]pyrazin-7(8H)-yl)(4-(thiophen-2-yl)phe-nyl)methanone;

(3-(2-(pyrrolidin-1-yl)thiazol-4-yl)-5,6-dihydro-[1,2,4]triazolo[4,3-a]pyrazin-7(8H)-yl)(4-(thiophen-2-yl)phe-nyl)methanone;

(4-fluorophenyl)(3-(2-(pyrrolidin-1-yl)thiazol-4-yl)-5,6-dihydro-[1,2,4]triazolo[4,3-a]pyrazin-7(8H)-yl)metha-none;

(3-(2-(4-methylpiperazin-1-yl)thiazol-4-yl)-5,6-dihydro-[1,2,4]triazolo[4,3-a]pyrazin-7(8H)-yl)(4-(thiophen-2-yl)phenyl)methanone;

(4-fluorophenyl)(3-(2-(4-methylpiperazin-1-yl)thiazol-4-yl)-5,6-dihydro-[1,2,4]triazolo[4,3-a]pyrazin-7(8H)-yl)methanone;

(3-(1-methyl-2-phenyl-1H-imidazol-4-yl)-5,6-dihydro-[1,2,4]triazolo[4,3-a]pyrazin-7(8H)-yl)(4-(thiophen-2-yl)phenyl)methanone;

(4-(dimethylamino)phenyl)(3-(2-(4-fluorophenyl)thiazol-4-yl)-5,6-dihydro-[1,2,4]triazolo[4,3-a]pyrazin-7(8H)-yl)methanone;

(3-(1-(2-methoxyethyl)-3-phenyl-1H-pyrazol-5-yl)-5,6-dihydro-[1,2,4]triazolo[4,3-a]pyrazin-7(8H)-yl)(4-(thiophen-2-yl)phenyl)methanone;

(4-fluorophenyl)(3-(1-(2-methoxyethyl)-3-phenyl-1H-pyrazol-5-yl)-5,6-dihydro-[1,2,4]triazolo[4,3-a]pyrazin-7(8H)-yl)methanone;

(3-(2-isobutylthiazol-4-yl)-5,6-dihydro-[1,2,4]triazolo[4,3-a]pyrazin-7(8H)-yl)(4-(thiophen-2-yl)phenyl)metha-none;

(3-(2-(2-(2-methoxyethyl)morpholino)thiazol-4-yl)-5,6-dihydro-[1,2,4]triazolo[4,3-a]pyrazin-7(8H)-yl)(4-(thiophen-2-yl)phenyl)methanone;

(3-(2-(4,4-difluoropiperidin-1-yl)thiazol-4-yl)-5,6-di-hydro-[1,2,4]triazolo[4,3-a]pyrazin-7(8H)-yl)(4-fluo-rophenyl)methanone;

(3-(2-(2,5-dimethylmorpholino)thiazol-4-yl)-5,6-di-hydro-[1,2,4]triazolo[4,3-a]pyrazin-7(8H)-yl)(4-(thio-phen-2-yl)phenyl)methanone;

(3-(2-(2-hydroxyphenyl)thiazol-4-yl)-5,6-dihydro-[1,2,4]triazolo[4,3-a]pyrazin-7(8H)-yl)(4-(thiophen-2-yl)phe-nyl)methanone;

(3-(2-(4,4-difluoropiperidin-1-yl)thiazol-4-yl)-5,6-dihydro-[1,2,4]triazolo[4,3-a]pyrazin-7(8H)-yl)(4-(thiophen-2-yl)phenyl)methanone;
(3-(2-(2,6-dimethylmorpholino)thiazol-4-yl)-5,6-dihydro-[1,2,4]triazolo[4,3-a]pyrazin-7(8H)-yl)(4-(thiophen-2-yl)phenyl)methanone;
(3-(2-(2,2-dimethylmorpholino)thiazol-4-yl)-5,6-dihydro-[1,2,4]triazolo[4,3-a]pyrazin-7(8H)-yl)(4-(thiophen-2-yl)phenyl)methanone;
(3-(3-phenyl-1H-pyrazol-5-yl)-5,6-dihydro-[1,2,4]triazolo[4,3-a]pyrazin-7(8H)-yl)(4-(thiophen-2-yl)phenyl)methanone;
(3-(2-(4-fluorophenyl)thiazol-4-yl)-8-methyl-5,6-dihydro-[1,2,4]triazolo[4,3-a]pyrazin-7(8H)-yl)(4-(3-methylthiophen-2-yl)phenyl)methanone;
(4-fluorophenyl)(3-(3-phenyl-1H-pyrazol-5-yl)-5,6-dihydro-[1,2,4]triazolo[4,3-a]pyrazin-7(8H)-yl)methanone;
(R)-(3-(2-(4-fluorophenyl)thiazol-4-yl)-8-methyl-5,6-dihydro-[1,2,4]triazolo[4,3-a]pyrazin-7(8H)-yl)(4-(3-methylthiophen-2-yl)phenyl)methanone;
(4-fluorophenyl)(3-(2-(2-hydroxyphenyl)thiazol-4-yl)-5,6-dihydro-[1,2,4]triazolo[4,3-a]pyrazin-7(8H)-yl)methanone;
(S)-(3-(2-(4-fluorophenyl)thiazol-4-yl)-8-methyl-5,6-dihydro-[1,2,4]triazolo[4,3-a]pyrazin-7(8H)-yl)(4-(3-methylthiophen-2-yl)phenyl)methanone;
(3-(2-(2-methylmorpholino)thiazol-4-yl)-5,6-dihydro-[1,2,4]triazolo[4,3-a]pyrazin-7(8H)-yl)(4-(thiophen-2-yl)phenyl)methanone;
(3-(2-(4,4-dimethylpiperidin-1-yl)thiazol-4-yl)-5,6-dihydro-[1,2,4]triazolo[4,3-a]pyrazin-7(8H)-yl)(4-(thiophen-2-yl)phenyl)methanone;
(3-(5-methylthiazol-4-yl)-5,6-dihydro-[1,2,4]triazolo[4,3-a]pyrazin-7(8H)-yl)(4-(thiophen-2-yl)phenyl)methanone;
(3-(2-(4,4-dimethylpiperidin-1-yl)thiazol-4-yl)-5,6-dihydro-[1,2,4]triazolo[4,3-a]pyrazin-7(8H)-yl)(4-fluorophenyl)methanone;
(4-fluorophenyl)(3-(2-(2-(methoxymethyl)piperidin-1-yl)thiazol-4-yl)-5,6-dihydro-[1,2,4]triazolo[4,3-a]pyrazin-7(8H)-yl)methanone;
(4-fluorophenyl)(8-methyl-3-(6-methylpyridin-2-yl)-5,6-dihydro-[1,2,4]triazolo[4,3-a]pyrazin-7(8H)-yl)methanone;
(3-(2-(2-(methoxymethyl)piperidin-1-yl)thiazol-4-yl)-5,6-dihydro-[1,2,4]triazolo[4,3-a]pyrazin-7(8H)-yl)(4-(thiophen-2-yl)phenyl)methanone;
tert-butyl (2-(2-(4-(7-(4-(thiophen-2-yl)benzoyl)-5,6,7,8-tetrahydro-[1,2,4]triazolo[4,3-a]pyrazin-3-yl)thiazol-2-yl)phenoxy)ethyl)carbamate;
(3-(2-(2-(2-hydroxyethoxy)phenyl)thiazol-4-yl)-5,6-dihydro-[1,2,4]triazolo[4,3-a]pyrazin-7(8H)-yl)(4-(thiophen-2-yl)phenyl)methanone;
(3-(2-(2-(2-aminoethoxy)phenyl)thiazol-4-yl)-5,6-dihydro-[1,2,4]triazolo[4,3-a]pyrazin-7(8H)-yl)(4-(thiophen-2-yl)phenyl)methanone;
N-(4-(4-(7-(4-(thiophen-2-yl)benzoyl)-5,6,7,8-tetrahydro-[1,2,4]triazolo[4,3-a]pyrazin-3-yl)thiazol-2-yl)phenyl)methanesulfonamide;
(3-(1-(2-hydroxyethyl)-3-phenyl-1H-pyrazol-5-yl)-5,6-dihydro-[1,2,4]triazolo[4,3-a]pyrazin-7(8H)-yl)(4-(thiophen-2-yl)phenyl)methanone;
(3-(1-(2-hydroxyethyl)-5-phenyl-1H-pyrazol-3-yl)-5,6-dihydro-[1,2,4]triazolo[4,3-a]pyrazin-7(8H)-yl)(4-(thiophen-2-yl)phenyl)methanone;
[1,1'-biphenyl]-4-yl(8-methyl-3-(6-methylpyridin-2-yl)-5,6-dihydro-[1,2,4]triazolo[4,3-a]pyrazin-7(8H)-yl)methanone;
(8-methyl-3-(6-methylpyridin-2-yl)-5,6-dihydro-[1,2,4]triazolo[4,3-a]pyrazin-7(8H)-yl)(4-(thiophen-2-yl)phenyl)methanone;
(3-(2-(2,4-difluorophenyl)-5-methylthiazol-4-yl)-5,6-dihydro-[1,2,4]triazolo[4,3-a]pyrazin-7(8H)-yl)(4-(thiophen-2-yl)phenyl)methanone;
(3-(2-(3-(dimethylamino)phenyl)thiazol-4-yl)-5,6-dihydro-[1,2,4]triazolo[4,3-a]pyrazin-7(8H)-yl)(4-(thiophen-2-yl)phenyl)methanone;
(3-(2-(3-(dimethylamino)phenyl)thiazol-4-yl)-5,6-dihydro-[1,2,4]triazolo[4,3-a]pyrazin-7(8H)-yl)(4-fluorophenyl)methanone;
N-(3-(4-(7-(4-(thiophen-2-yl)benzoyl)-5,6,7,8-tetrahydro-[1,2,4]triazolo[4,3-a]pyrazin-3-yl)thiazol-2-yl)phenyl)methanesulfonamide;
N-(2-(4-(7-(4-(thiophen-2-yl)benzoyl)-5,6,7,8-tetrahydro-[1,2,4]triazolo[4,3-a]pyrazin-3-yl)thiazol-2-yl)phenyl)methanesulfonamide;
(3-(4-chlorophenyl)-1H-pyrazol-5-yl)(3-(2-(4-fluorophenyl)thiazol-4-yl)-5,6-dihydro-[1,2,4]triazolo[4,3-a]pyrazin-7(8H)-yl)methanone;
(3-(4-chlorophenyl)-1-methyl-1H-pyrazol-5-yl)(3-(2-(4-fluorophenyl)thiazol-4-yl)-5,6-dihydro-[1,2,4]triazolo[4,3-a]pyrazin-7(8H)-yl)methanone;
(3-(3,4-dichlorophenyl)-1-methyl-1H-pyrazol-5-yl)(3-(2-(4-fluorophenyl)thiazol-4-yl)-5,6-dihydro-[1,2,4]triazolo[4,3-a]pyrazin-7(8H)-yl)methanone;
(5-(4-chlorophenyl)-1-methyl-1H-pyrazol-3-yl)(3-(2-(4-fluorophenyl)thiazol-4-yl)-5,6-dihydro-[1,2,4]triazolo[4,3-a]pyrazin-7(8H)-yl)methanone;
tert-butyl (2-(3-phenyl-5-(7-(4-(thiophen-2-yl)benzoyl)-5,6,7,8-tetrahydro-[1,2,4]triazolo[4,3-a]pyrazin-3-yl)-1H-pyrazol-1-yl)ethyl)carbamate;
tert-butyl (2-(5-phenyl-3-(7-(4-(thiophen-2-yl)benzoyl)-5,6,7,8-tetrahydro-[1,2,4]triazolo[4,3-a]pyrazin-3-yl)-1H-pyrazol-1-yl)ethyl)carbamate;
(3-(2-(2-bromophenyl)thiazol-4-yl)-5,6-dihydro-[1,2,4]triazolo[4,3-a]pyrazin-7(8H)-yl)(4-(thiophen-2-yl)phenyl)methanone;
(3-(2-(3-bromophenyl)thiazol-4-yl)-5,6-dihydro-[1,2,4]triazolo[4,3-a]pyrazin-7(8H)-yl)(4-(thiophen-2-yl)phenyl)methanone;
2-(4-(7-(4-(thiophen-2-yl)benzoyl)-5,6,7,8-tetrahydro-[1,2,4]triazolo[4,3-a]pyrazin-3-yl)thiazol-2-yl)benzonitrile;
3-(4-(7-(4-(thiophen-2-yl)benzoyl)-5,6,7,8-tetrahydro-[1,2,4]triazolo[4,3-a]pyrazin-3-yl)thiazol-2-yl)benzonitrile;
(3-(2-(4-fluorophenyl)thiazol-4-yl)-8-methyl-5,6-dihydro-[1,2,4]triazolo[4,3-a]pyrazin-7(8H)-;
methylthiophen-3-yl)phenyl)methanone;
and pharmaceutically acceptable salts and solvates thereof.

* * * * *